US011674187B2

(12) United States Patent
Banchereau et al.

(10) Patent No.: US 11,674,187 B2
(45) Date of Patent: Jun. 13, 2023

(54) BREAST CANCER SPLICE VARIANTS

(71) Applicant: The Jackson Laboratory, Bar Harbor, ME (US)

(72) Inventors: Jacques Banchereau, Farmington, CT (US); Diogo Fernando Troggian Veiga, Farmington, CT (US); Anne Deslattes Mays, Farmington, CT (US); Saman Zeeshan, Farmington, CT (US); Anna Karolina Palucka, Avon, CT (US)

(73) Assignee: The Jackson Laboratory, Bar Harbor, ME (US)

( * ) Notice: Subject to any disclaimer, the term of this patent is extended or adjusted under 35 U.S.C. 154(b) by 24 days.

(21) Appl. No.: 17/253,974

(22) PCT Filed: Jun. 28, 2019

(86) PCT No.: PCT/US2019/039794

§ 371 (c)(1),
(2) Date: Dec. 18, 2020

(87) PCT Pub. No.: WO2020/006394

PCT Pub. Date: Jan. 2, 2020

(65) Prior Publication Data

US 2021/0254176 A1 Aug. 19, 2021

Related U.S. Application Data

(60) Provisional application No. 62/818,582, filed on Mar. 14, 2019, provisional application No. 62/692,121, filed on Jun. 29, 2018.

(51) Int. Cl.
*C12Q 1/6886* (2018.01)

(52) U.S. Cl.
CPC ..... *C12Q 1/6886* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2006/0292572 | A1 | 12/2006 | Stuart et al. |
| 2011/0136123 | A1 | 6/2011 | Klinck et al. |
| 2012/0028252 | A1 | 2/2012 | Nistico et al. |
| 2016/0231312 | A1 | 8/2016 | Nistico et al. |

FOREIGN PATENT DOCUMENTS

| | | | | |
|---|---|---|---|---|
| WO | WO 2014/036743 | A1 | 3/2014 | |
| WO | WO-2016168371 | A1 * | 10/2016 | ............. G16B 20/00 |

OTHER PUBLICATIONS

International Search Report and Written Opinion for International Patent Application No. PCT/US2019/039794 dated Nov. 15, 2019.
International Preliminary Report on Patentability for International Patent Application No. PCT/US2019/039794 dated Jan. 7, 2021.
GenBank Accession No. NG_051578.1, "*Homo sapiens* ENAH actin regulator (ENAH), RefSeqGene on chromosome 1," Aug. 24, 2019, 43 pages.
Huddleston et al. Reconstructing complex regions of genomes using long-read sequencing technology. Genome Res. Apr. 2014;24(4):688-96. doi: 10.1101/gr.168450.113. Epub Jan. 13, 2014.
Rhoads et al. PacBio Sequencing and Its Applications. Genomics Proteomics Bioinformatics. Oct. 2015;13(5):278-89. doi: 10.1016/j.gpb.2015.08.002. Epub Nov. 2, 2015.
Urbanelli et al. Characterization of human Enah gene. Biochimica et Biophysica Acta. Jan.-Feb. 2006;1759(1-2):99-107. doi: 10.1016/j.bbaexp.2006.01.001. Epub Jan. 25, 2006.
Partial Supplementary European Search Report, dated Mar. 22, 2022 for European Application No. 19824946.8.
Extended European Search Report, dated Jun. 24, 2022 for European Application No. 19824946.8.
Genbank Submission; NIH/NCBI, Accession No. CX755313. No Author Listed, Jan. 11, 2011. 2 pages.
Kahn et al., Early diagnostic value of survivin and its alternative splice variants in breast cancer. BMC Cancer. Mar. 12, 2014;14:176. doi: 10.1186/1471-2407-14-176.
Veiga et al., A comprehensive long-read isoform analysis platform and sequencing resource for breast cancer. Sci Adv. Jan. 21, 2022;8(3):eabg6711. doi: 10.1126/sciadv.abg6711. Epub Jan. 19, 2022.

* cited by examiner

*Primary Examiner* — Katherine D Salmon
(74) *Attorney, Agent, or Firm* — Wolf, Greenfield & Sacks, P.C.

(57) ABSTRACT

Provided herein, in some embodiments, are methods, compositions, and systems for identifying alternatively spliced tumor-specific exon inclusion and exclusion events that can be used for survival prognosis.

6 Claims, 108 Drawing Sheets

Specification includes a Sequence Listing.

BREAST CANCER SPLICE VARIANTS

RELATED APPLICATIONS

This application is a national stage filing under 35 U.S.C. § 371 of international application number PCT/US2019/039794, filed Jun. 28, 2019, which claims the benefit under 35 U.S.C. § 119(e) of U.S. provisional application No. 62/692,121, filed Jun. 29, 2018, and U.S. provisional application No. 62/818,582, filed Mar. 14, 2019, each of which is incorporated by reference herein in its entirety.

BACKGROUND

Breast cancer survival rates indicate what portion of people with the same type and stage of breast cancer are still alive a certain amount of time (e.g., 5 years) after they are diagnosed. The extensive heterogeneity of breast cancer, however, complicates a precise assessment of prognosis, making therapeutic decisions difficult and treatments inappropriate in some cases.

SUMMARY

Provided herein, in some aspects, is a molecular profiling platform that may be used, for example, to identify exon splicing events (e.g., exon inclusion or exon exclusion) that are specific to breast cancer and can be used for survival prognosis. Alternative splicing is a biological phenomenon that increases protein diversity. In one type of alternative splicing, referred to as "exon skipping," exons are either spliced out of the transcript based on cellular conditions or are not spliced out but instead remain in the transcript and are "skipped" over. Exon skipping events are regulated by RNA-binding proteins (RPBs) and the spliceosome complex. A common metric for evaluating the extent of exon skipping is percent spliced in (PSI or ψ), which represents the percentage of transcripts that include a specific exon or splice site.

Prior approaches for analyzing cancer tissue samples separately analyzed a group of normal samples (non-cancerous samples) and a group of cancer samples (samples known to be cancerous) to generate two distributions. Data in the non-overlapping parts of the two distributions would be analyzed to assess the differences between the two groups of samples. Due to the heterogeneity of the biological data, where alternative splicing can occur for reasons other than having cancer (e.g., exon skipping can occur naturally for non-cancerous (normal) healthy patients), the conventional "two-distribution" approach is not well suited to identifying exon skipping events that are predictive of cancer.

The present disclosure provides, in some aspects, methods that combine the analysis (e.g., PSI values) determined for normal and cancer tissue samples and analyze the combined input using a probabilistic model (GMM) to identify subpopulations (clusters) within the overall population that can be further analyzed to assess whether they are cancer-specific. Some of the data described herein is based on an analysis of ~9300 normal and tumor samples from The Cancer Genome Atlas (TCGA), which identified ~67,000 exon skipping events. From this data, a subset of exon splicing events (e.g., exon inclusion or exon exclusion) specific to breast cancer was identified.

In some aspects, the present disclosure provides a method comprising assaying nucleic acids of a sample for the presence or absence of a target exon comprising a nucleotide sequence of any one of SEQ ID NOS: 22-24, 26-36, 38-40, 73-75, 77-79, 82-100, 102-104. In some embodiments, the target exon comprises a nucleotide sequence of any one of SEQ ID NOS: 27, 98, 102, or 104.

In other aspects, the present disclosure provides a method comprising assaying nucleic acids of a sample for the presence or absence of at least 2 target exons, wherein each target exon comprises a nucleotide sequence of any one of SEQ ID NOS: 23, 27, 35, 85, 88, 89, 98, 101, 102, or 104. In some embodiments, each target exon comprises a nucleotide sequence of any one of SEQ ID NOS: 27, 98, 101, 102, or 104.

In yet other aspects, the present disclosure provides a method comprising assaying nucleic acids of a sample for the presence or absence of at least 3 target exons, wherein each target exon comprises a nucleotide sequence of any one of SEQ ID NOS: 21, 23, 27, 30, 31, 32, 35, 36, 39, 85, 87-89, 91, 94, 98, or 101-104.

In still further aspects, the present disclosure provide a method comprising assaying nucleic acids of a sample for the presence or absence of at least 8 different target exons, wherein each target exon comprises a nucleotide sequence of any one of SEQ ID NOs: 21-40 or 73-104.

In some embodiments, the sample is a breast tissue sample. For example, the sample may be obtained from a subject suspect of having, at risk of, or diagnosed with breast cancer. In some embodiments, the subject is a female subject.

In some embodiments, the nucleic acids comprise messenger ribonucleic acid (mRNA), or complementary deoxyribonucleic acid (cDNA) synthesized from mRNA obtained from the sample.

In some embodiments, the methods further comprise detecting the presence of a target exon comprising a nucleotide sequence of any one of SEQ ID NOs: 24, 28, 31, 33, and/or 38 or the absence of a target exon comprising a nucleotide sequence of any one of SEQ ID NOs: 82, 87 and/or 91, and assigning a favorable survival prognosis to the sample. In some embodiments, the methods further comprise detecting the presence of a target exon comprising a nucleotide sequence of any one of SEQ ID NOs: 21-23, 25-27, 29, 30, 32, and/or 34-40 or the absence of a target exon comprising a nucleotide sequence of any one of SEQ ID NOs: 73-81, 83-86, 88-90, and/or 92-104, and assigning an unfavorable survival prognosis to the sample.

Also provided herein are complementary deoxyribonucleic acids (cDNAs) comprising a nucleotide sequence of any one of SEQ ID NOs: 1-20 or 105-136. In some embodiments, the cDNAs comprise a nucleotide sequence of any one of SEQ ID NOs: 22-24, 27-34, 36, 38, or 40. Compositions comprising the cDNAs are also contemplated herein. In some embodiments, the compositions further comprise a probe or pair of primers that binds the cDNA. Some compositions of the present disclosure comprise (a) a messenger ribonucleic acid (mRNA) comprising a nucleotide sequence of any one of SEQ ID NOs: 1-20 or 105-136 and (b) a probe or a pair of primers that binds a nucleotide sequence of any one of SEQ ID NOs: 1-20 or 105-136. In some embodiments, the probe or primer comprises a detectable label.

Further provided herein are kits comprising a molecule that can detect the presence or absence of a target exon comprising a nucleotide sequence of any one of SEQ ID NOS: 22-24, 26-36, 38-40, 73-75, 77-79, 82-100, 102-104, and a detection reagent selected from buffers, salts, polymerases, and deoxyribonucleotide triphosphates (dNTPs). In some embodiments, the molecule comprise a probe or primer that bind a nucleic acid comprising a nucleotide sequence of any one of SEQ ID NOS: 22-24, 26-36, 38-40, 73-75, 77-79, 82-100, 102-104.

Also provided herein are kits comprising: (a) molecules that can detect the presence or absence of at least 2 target exons, wherein each target exon comprises a nucleotide sequence of any one of SEQ ID NOS: 23, 27, 35, 85, 88, 89, 98, 101, 102, or 104, (b) molecules that can detect the presence or absence of at least 3 target exons, wherein each target exon comprises a nucleotide sequence of any one of SEQ ID NOS: 21, 23, 27, 30, 31, 32, 35, 36, 39, 85, 87-89, 91, 94, 98, or 101-104, or (c) molecules that can detect the presence or absence of at least 8 different target exons, wherein each target exon comprises a nucleotide sequence of any one of SEQ ID NOs: 21-40 or 73-104, and a detection reagent selected from buffers, salts, polymerases, and deoxyribonucleotide triphosphates (dNTPs). In some embodiments, at least one of the probes and/or primers comprises a detectable label.

BRIEF DESCRIPTION OF THE DRAWINGS

The GMM analysis showed 4 distinct clusters (subpopulations). The x-axis indicates the exon PSI (ψ) level within samples, and y-axis denotes the number of samples in a normalized density scale. Shading indicates the cluster assignment of each sample.

DETAILED DESCRIPTION

Figure 1A:
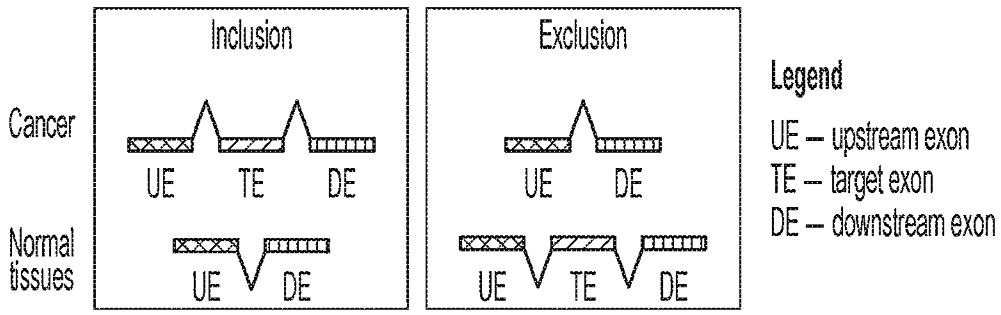
FIG. 1A: Alternative splicing leads to target exon inclusion or exon exclusion in cancer patients when compared to normal tissues.

Alternative splicing is a key mechanism of biological diversity in eukaryotes because it allows multiple mRNA isoforms to be transcribed and translated from a single gene. The human genome includes more than 20,000 genes; however, more than 95% of multi-exonic pre-mRNAs are alternatively spliced to generate nearly 200,000 isoforms. The alternative splicing isoforms translated into proteins can have distinct or even opposing functions. Alternative splicing is involved in a wide range of biological processes, including immune cell maturation and processing.

Studies examining the cancer transcriptome have enabled unprecedented insight into cancer cell heterogeneity and generated novel classifications. This progress has not yet fully translated into clinical benefit. Isoforms as well as alterations in alternative splicing are associated with numerous diseases and can contribute to cancer malignancy by regulating the expression of oncogenes and tumor suppressors. Aberrant alternative splicing profiles can arise in cancer due to mutations at the splice sites or splicing-regulatory elements, but can also reflect changes in splicing regulators. Recurrent mutations in core splicing machinery are found in myeloid leukemia, as well as in sporadic mutations in lung and breast cancer, suggesting that alternative alterations play a key role in tumorigenesis. Alterations in alternative splicing result in the generation of a repertoire of novel isoforms in tumors that, together with fusion molecules, can be viewed as another class of neoantigens.

Provided herein, in some aspects, are methods that comprise assaying a sample for a particular cancer isoform including or excluding a particular exon. In some embodiments, a sample is assayed for multiple exon inclusion or exon exclusion isoforms as provided herein. The data provided by the present disclosure demonstrates that at least one of fifty-two different exon inclusion or exon exclusion isoforms can be detected in ~91% of all breast cancer samples tested.

Methods of Detection

Some aspects of the present disclosure comprise assaying a sample for (the presence or absence of) a nucleic acid (e.g., an exon inclusion event or an exon exclusion event) comprising a nucleotide sequence (e.g., an exon) of any one of SEQ ID NOS: 21-40 and 105-136. It should be understood that the phrase "assaying a sample for a nucleic acid comprising a nucleotide sequence of SEQ ID NO: X" encompasses assaying a sample for the presence or absence of a nucleic acid that includes the full length nucleotide sequence identified by SEQ ID NO: X (all nucleotides of SEQ ID NO: X); and the phrase also includes assaying a sample for the presence or absence of a nucleic acid that includes a fragment of the nucleotide sequence identified by SEQ ID NO: X. The length of the fragment is not limited and may be, for example, at least 50, at least 60, at least 70, at least 80, at least 90, or at least 100 nucleotides.

In some embodiments, the methods comprise assaying a sample for a nucleic acid comprising the nucleotide sequence of SEQ ID NO: 21. In some embodiments, the methods comprise assaying a sample for a nucleic acid comprising the nucleotide sequence of SEQ ID NO: 22. In some embodiments, the methods comprise assaying a sample for a nucleic acid comprising the nucleotide sequence of SEQ ID NO: 23. In some embodiments, the methods comprise assaying a sample for a nucleic acid comprising the nucleotide sequence of SEQ ID NO: 24. In some embodiments, the methods comprise assaying a sample for a nucleic acid comprising the nucleotide sequence of SEQ ID NO: 25. In some embodiments, the methods comprise assaying a sample for a nucleic acid comprising the nucleotide sequence of SEQ ID NO: 26. In some embodiments, the methods comprise assaying a sample for a nucleic acid comprising the nucleotide sequence of SEQ ID NO: 27. In some embodiments, the methods comprise assaying a sample for a nucleic acid comprising the nucleotide sequence of SEQ ID NO: 28. In some embodiments, the methods comprise assaying a sample for a nucleic acid comprising the nucleotide sequence of SEQ ID NO: 29. In some embodiments, the methods comprise assaying a sample for a nucleic acid comprising the nucleotide sequence of SEQ ID NO: 30. In some embodiments, the methods comprise assaying a sample for a nucleic acid comprising the nucleotide sequence of SEQ ID NO: 31. In some embodiments, the methods comprise assaying a sample for a nucleic acid comprising the nucleotide sequence of SEQ ID NO: 32. In some embodiments, the methods comprise assaying a sample for a nucleic acid comprising the nucleotide sequence of SEQ ID NO: 33. In some embodiments, the methods comprise assaying a sample for a nucleic acid comprising the nucleotide sequence of SEQ ID NO: 34. In some embodiments, the methods comprise assaying a sample for a nucleic acid comprising the nucleotide sequence of SEQ ID NO: 35. In some embodiments, the methods comprise assaying a sample for a nucleic acid comprising the nucleotide sequence of SEQ ID NO: 36. In some embodiments, the methods comprise assaying a sample for a nucleic acid comprising the nucleotide sequence of SEQ ID NO: 37. In some embodiments, the methods comprise assaying a sample for a nucleic acid comprising the nucleotide sequence of SEQ ID NO: 38. In some embodiments, the methods comprise assaying a sample for a nucleic acid comprising the nucleotide sequence of SEQ ID NO: 39. In some embodiments, the methods comprise assaying a sample for a nucleic acid comprising the nucleotide sequence of SEQ ID NO: 40. In some embodiments, the methods comprise assaying a sample for a nucleic acid comprising the nucleotide sequence of SEQ ID NO: 105. In some embodiments, the methods comprise assaying a sample for a nucleic acid comprising the nucleotide sequence of SEQ ID NO: 106. In some embodiments, the methods comprise assaying a sample for a nucleic acid comprising the nucleotide sequence of SEQ ID NO: 107. In some embodiments, the methods comprise assaying a sample for a nucleic acid comprising the nucleotide sequence of SEQ ID NO: 108. In some embodiments, the methods comprise assaying a sample for a nucleic acid comprising the nucleotide sequence of SEQ ID NO: 109. In some embodiments, the methods comprise assaying a sample for a nucleic acid comprising the nucleotide sequence of SEQ ID NO: 110. In some embodiments, the methods comprise assaying a sample for a nucleic acid comprising the nucleotide sequence of SEQ ID NO: 111. In some embodiments, the methods comprise assaying a sample for a nucleic acid comprising the nucleotide sequence of SEQ ID NO: 112. In some embodiments, the methods comprise assaying a sample for a nucleic acid comprising the nucleotide sequence of SEQ ID NO: 113. In some embodiments, the methods comprise assaying a sample for a nucleic acid comprising the nucleotide sequence of SEQ ID NO: 114. In some embodiments, the methods comprise assaying a sample for a nucleic acid comprising the nucleotide sequence of SEQ ID NO: 115. In some embodiments, the methods comprise assaying a sample for a nucleic acid comprising the nucleotide sequence of SEQ ID NO: 116. In some embodiments, the methods comprise assaying a sample for a nucleic acid comprising the nucleotide sequence of SEQ ID NO: 117. In some embodiments, the methods comprise assaying a sample for a nucleic acid comprising the nucleotide sequence of SEQ ID NO: 118. In some embodiments, the methods comprise assaying a sample for a nucleic acid comprising the nucleotide sequence of SEQ ID NO: 119. In some embodiments, the methods comprise assaying a sample for a nucleic acid comprising the nucleotide sequence of SEQ ID NO: 120. In some embodiments, the methods comprise assaying a sample for a nucleic acid comprising the nucleotide sequence of SEQ ID NO: 121. In some embodiments, the methods comprise assaying a sample for a nucleic acid comprising the nucleotide sequence of SEQ ID NO: 122. In some embodiments, the methods comprise assaying a sample for a nucleic acid comprising the nucleotide sequence of SEQ ID NO: 123. In some embodiments, the methods comprise assaying a sample for a nucleic acid comprising the nucleotide sequence of SEQ ID NO: 124. In some embodiments, the methods comprise assaying a sample for a nucleic acid comprising the nucleotide sequence of SEQ ID NO: 125. In some embodiments, the methods comprise assaying a sample for a nucleic acid comprising the nucleotide sequence of SEQ ID NO: 126. In some embodiments, the methods comprise assaying a sample for a nucleic acid comprising the nucleotide sequence of SEQ ID NO: 127. In some embodiments, the methods comprise assaying a sample for a nucleic acid comprising the nucleotide sequence of SEQ ID NO: 128. In some embodiments, the methods comprise assaying a sample for a nucleic acid comprising the nucleotide sequence of SEQ ID NO: 129. In some embodiments, the methods comprise assaying a sample for a nucleic acid comprising the nucleotide sequence of SEQ ID NO: 130. In some embodiments, the methods comprise assaying a sample for a nucleic acid comprising the nucleotide sequence of SEQ ID NO: 131. In some embodiments, the methods comprise assaying a sample for a nucleic acid comprising the nucleotide sequence of SEQ ID NO: 132. In some embodiments, the methods comprise assaying a sample for a nucleic acid comprising the nucleotide sequence of SEQ ID NO: 133. In some embodiments, the methods comprise assaying a sample for a nucleic acid comprising the nucleotide sequence of SEQ ID NO: 134. In some embodiments, the methods comprise assaying a sample for a nucleic acid comprising the nucleotide sequence of SEQ ID NO: 135. In some embodiments, the methods comprise assaying a sample for a nucleic acid comprising the nucleotide sequence of SEQ ID NO: 136.

In some embodiments, methods of the present disclosure comprise assaying a sample for a (at least one) nucleic acid comprising a nucleotide sequence of any one of SEQ ID NOS: 22-24, 27-34, 36, 38, or 40. In some embodiments, the methods further comprise assaying the sample for a nucleic acid comprising a nucleotide sequence of any one of SEQ ID NOS: 21, 25, 26, 35, 37, or 39.

In some embodiments, methods of the present disclosure comprise assaying the sample for a nucleic acid comprising a nucleotide sequence of SEQ ID NO: 21, a nucleic acid comprising a nucleotide sequence of SEQ ID NO: 22, a nucleic acid comprising a nucleotide sequence of SEQ ID NO: 23, a nucleic acid comprising a nucleotide sequence of SEQ ID NO: 24, a nucleic acid comprising a nucleotide sequence of SEQ ID NO: 25, a nucleic acid comprising a nucleotide sequence of SEQ ID NO: 26, a nucleic acid comprising a nucleotide sequence of SEQ ID NO: 27, a nucleic acid comprising a nucleotide sequence of SEQ ID NO: 28, a nucleic acid comprising a nucleotide sequence of SEQ ID NO: 29, a nucleic acid comprising a nucleotide sequence of SEQ ID NO: 30, a nucleic acid comprising a nucleotide sequence of SEQ ID NO: 31, a nucleic acid comprising a nucleotide sequence of SEQ ID NO: 32, a nucleic acid comprising a nucleotide sequence of SEQ ID NO: 33, a nucleic acid comprising a nucleotide sequence of SEQ ID NO: 34, a nucleic acid comprising a nucleotide sequence of SEQ ID NO: 35, a nucleic acid comprising a nucleotide sequence of SEQ ID NO: 36, a nucleic acid comprising a nucleotide sequence of SEQ ID NO: 37, a nucleic acid comprising a nucleotide sequence of SEQ ID NO: 38, a nucleic acid comprising a nucleotide sequence of SEQ ID NO: 39, a nucleic acid comprising a nucleotide sequence of SEQ ID NO: 40, a nucleic acid comprising a nucleotide sequence of SEQ ID NO: 105, a nucleic acid comprising a nucleotide sequence of SEQ ID NO: 106, a nucleic acid comprising a nucleotide sequence of SEQ ID NO: 107, a nucleic acid comprising a nucleotide sequence of SEQ ID NO: 108, a nucleic acid comprising a nucleotide sequence of SEQ ID NO: 109, a nucleic acid comprising a nucleotide sequence of SEQ ID NO: 110, a nucleic acid comprising a nucleotide sequence of SEQ ID NO: 111, a nucleic acid comprising a nucleotide sequence of SEQ ID NO: 112, a nucleic acid comprising a nucleotide sequence of SEQ ID NO: 113, a nucleic acid comprising a nucleotide sequence of SEQ ID NO: 114, a nucleic acid comprising a nucleotide sequence of SEQ ID NO: 115, a nucleic acid comprising a nucleotide sequence of SEQ ID NO: 116, a nucleic acid comprising a nucleotide sequence of SEQ ID NO: 117, a nucleic acid comprising a nucleotide sequence of SEQ ID NO: 118, a nucleic acid comprising a nucleotide sequence of SEQ ID NO: 119, a nucleic acid comprising a nucleotide sequence of SEQ ID NO: 120, a nucleic acid comprising a nucleotide sequence of SEQ ID NO: 121, a nucleic acid comprising a nucleotide sequence of SEQ ID NO: 122, a nucleic acid comprising a nucleotide sequence of SEQ ID NO: 123, a nucleic acid comprising a nucleotide sequence of SEQ ID NO: 124, a nucleic acid comprising a nucleotide sequence of SEQ ID NO: 125, a nucleic acid comprising a nucleotide sequence of SEQ ID NO: 126, a nucleic acid comprising a nucleotide sequence of SEQ ID NO: 127, a nucleic acid comprising a nucleotide sequence of SEQ ID NO: 128, a nucleic acid comprising a nucleotide sequence of SEQ ID NO: 129, a nucleic acid comprising a nucleotide sequence of SEQ ID NO: 130, a nucleic acid comprising a nucleotide sequence of SEQ ID NO: 131, a nucleic acid comprising a nucleotide sequence of SEQ ID NO: 132, a nucleic acid comprising a nucleotide sequence of SEQ ID NO: 133, a nucleic acid comprising a nucleotide sequence of SEQ ID NO: 134, a nucleic acid comprising a nucleotide sequence of SEQ ID NO: 135, a nucleic acid comprising a nucleotide sequence of SEQ ID NO: 136.

In some embodiments, the methods of the present disclosure comprise assaying the sample for 2 (or at least 2) of the 52 exons (selected from exons comprising a nucleotide sequence of any one of SEQ ID NOS: 21-40 and 105-136). In some embodiments, the methods of the present disclosure comprise assaying the sample for 3 (or at least 3) of the 52 exons. In some embodiments, the methods of the present disclosure comprise assaying the sample for 4 (or at least 4) of the 52 exons. In some embodiments, the methods of the present disclosure comprise assaying the sample for 5 (or at least 5) of the 52 exons. In some embodiments, the methods of the present disclosure comprise assaying the sample for 6 (or at least 7) of the 52 exons. In some embodiments, the methods of the present disclosure comprise assaying the sample for 7 (or at least 7) of the 52 exons. In some embodiments, the methods of the present disclosure comprise assaying the sample for 8 (or at least 8) of the 52 exons. In some embodiments, the methods of the present disclosure comprise assaying the sample for 9 (or at least 9) of the 52 exons. In some embodiments, the methods of the present disclosure comprise assaying the sample for 10 (or at least 10) of the 52 exons. In some embodiments, the methods of the present disclosure comprise assaying the sample for 11 (or at least 11) of the 52 exons. In some embodiments, the methods of the present disclosure comprise assaying the sample for 12 (or at least 12) of the 52 exons. In some embodiments, the methods of the present disclosure comprise assaying the sample for 13 (or at least 13) of the 52 exons. In some embodiments, the methods of the present disclosure comprise assaying the sample for 14 (or at least 14) of the 52 exons. In some embodiments, the methods of the present disclosure comprise assaying the sample for 15 (or at least 15) of the 52 exons. In some embodiments, the methods of the present disclosure comprise assaying the sample for 16 (or at least 16) of the 52 exons. In some embodiments, the methods of the present disclosure comprise assaying the sample for 17 (or at least 17) of the 52 exons. In some embodiments, the methods of the present disclosure comprise assaying the sample for 18 (or at least 18) of the 52 exons. In some embodiments, the methods of the present disclosure comprise assaying the sample for 19 (or at least 19) of the 52 exons. In some embodiments, the methods of the present disclosure comprise assaying the sample for 20 (or at least 20) of the 52 exons. In some embodiments, the methods of the present disclosure comprise assaying the sample for 21 (or at least 21) of the 52 exons. In some embodiments, the methods of the present disclosure comprise assaying the sample for 22 (or at least 22) of the 52 exons. In some embodiments, the methods of the present disclosure comprise assaying the sample for 23 (or at least 23) of the 52 exons. In some embodiments, the methods of the present disclosure comprise assaying the sample for 24 (or at least 24) of the 52 exons. In some embodiments, the methods of the present disclosure comprise assaying the sample for 25 (or at least 25) of the 52 exons. In some embodiments, the methods of the present disclosure comprise assaying the sample for 26 (or at least 26) of the 52 exons. In some embodiments, the methods of the present disclosure comprise assaying the sample for 27 (or at least 27) of the 52 exons. In some embodiments, the methods of the present disclosure comprise assaying the sample for 28 (or at least 28) of the 52 exons. In some embodiments, the methods of the present disclosure comprise assaying the sample for 29 (or at least 29) of the 52 exons. In some embodiments, the methods of the present disclosure comprise assaying the sample for 30 (or at least 30) of the 52 exons. In some embodiments, the methods of the present disclosure comprise assaying the sample for 31 (or at least 31) of the 52 exons. In some embodiments, the methods of the present disclosure comprise assaying the sample for 32 (or at least 32) of the 52 exons. In some embodiments, the methods of the present disclosure comprise assaying the sample for 33 (or at least 33) of the 52 exons. In some embodiments, the methods of the present disclosure comprise assaying the sample for 34 (or at least 34) of the 52 exons. In some embodiments, the methods of the present disclosure comprise assaying the sample for 35 (or at least 35) of the 52 exons. In some embodiments, the methods of the present disclosure comprise assaying the sample for 36 (or at least 36) of the 52 exons. In some embodiments, the methods of the present disclosure comprise assaying the sample for 37 (or at least 37) of the 52 exons. In some embodiments, the methods of the present disclosure comprise assaying the sample for 38 (or at least 38) of the 52 exons. In some embodiments, the methods of the present disclosure comprise assaying the sample for 39 (or at least 39) of the 52 exons. In some embodiments, the methods of the present disclosure comprise assaying the sample for 40 (or at least 40) of the 52 exons. In some embodiments, the methods of the present disclosure comprise assaying the sample for 41 (or at least 41) of the 52 exons. In some embodiments, the methods of the present disclosure comprise assaying the sample for 42 (or at least 42) of the 52 exons. In some embodiments, the methods of the present disclosure comprise assaying the sample for 43 (or at least 43) of the 52 exons. In some embodiments, the methods of the present disclosure comprise assaying the sample for 44 (or at least 44) of the 52 exons. In some embodiments, the methods of the present disclosure comprise assaying the sample for 45 (or at least 45) of the 52 exons. In some embodiments, the methods of the present disclosure comprise assaying the sample for 46 (or at least 46) of the 52 exons. In some embodiments, the methods of the present disclosure comprise assaying the sample for 47 (or at least 47) of the 52 exons. In some embodiments, the methods of the present disclosure comprise assaying the sample for 48 (or at least 48) of the 52 exons. In some embodiments, the methods of the present disclosure comprise assaying the sample for 49 (or at least 49) of the 52 exons. In some embodiments, the methods of the present disclosure comprise assaying the sample for 50 (or at least 50) of the 52 exons. In some embodiments, the methods of the present disclosure comprise assaying the sample for 51 (or at least 51) of the 52 exons. In some embodiments, the methods of the present disclosure comprise assaying the sample for 52 exons.

It should be understood that a method "comprising assaying the sample for fifty-two (52) exon splicing isoforms (e.g., exon inclusion or exon exclusion, each comprising a different nucleotide sequence of SEQ ID NOS: 21-40 and 105-136" is a method that comprises assaying for all 52 isoforms provided in Table 1, Table 2 and Table 3.

Not every sample will have more than one exon splicing isoform (e.g., exon inclusion or exon exclusion) of the present disclosure. In many embodiments, only one of the exon splicing isoforms of the present disclosure will be detected in a sample. Nonetheless, a sample may be assayed for one or more (e.g., 1 to 52) of the 52 exon splicing isoforms. For example, a single sample may include only the exon splicing isoform comprising the sequence of SEQ ID NO:1 or SEQ ID NO: 21. All 52 or a subset of the 52 (less than 52) of the exon splicing isoforms of Table 1, Table 2, and Table 3 may be assayed in order to detect that exon splicing isoform comprising the sequence of SEQ ID NO:1 or SEQ ID NO: 21

It should also be understood that the step of "assaying for an exon splicing isoform(s) (e.g., exon inclusion or exon exclusion)" or "assaying for a nucleic acid" encompasses assaying for mRNA comprising the exon splicing isoform(s) or assaying for complementary DNA (cDNA) comprising the exon splicing isoform(s) (e.g., comprising the sequence of any one of SEQ ID NOS: 21-40 and 105-136). As is known in the art, cDNA is synthesized from mRNA.

Examples of Nucleic Acid Detection Assays

There are many different known methods for assaying a sample for the presence or absence of a particular nucleotide sequence, any of which may be used in accordance with the present disclosure. For example, standard polymerase chain reaction (PCR) methods (e.g., reverse transcription PCR (RT-PCR)) may be performed using mRNA obtained from a sample. In RT-PCR, the RNA template is first converted into a complementary DNA (cDNA) using a reverse transcriptase. The cDNA is then used as a template for exponential amplification using PCR. Thus, kits provided herein may include any one or more reagents used in a PCR such as, for example, primers or probes that bind to a particular nucleic acid comprising an exon splicing event (e.g., exon inclusion or exon exclusion), polymerases, buffers, deoxyribonucleotide triphosphates (dNTPs), and salts.

In some embodiments, an Archer® FusionPlex® assay is used to assay for a nucleotide sequence (e.g., exon). This assay may include using custom designed probes with and an Anchored Multiplexed PCR (AMP™) following by next generation sequencing (NGS) (e.g., with an Illumina® platform). Thus, kits provided herein may include any one or more reagents used in a Archer® FusionPlex® assay.

In other embodiments, targeted sequencing using long-read sequencing technology (e.g., PacBio®, built on Single Molecule, Real-Time (SMRT) Sequencing technology) is used to assay for a nucleotide sequence (e.g., exon). Thus, kits provided herein may include any one or more reagents used in a long-read sequencing technology.

In other embodiments, Droplet Digital™ PCR (ddPCR™) (BioRad®) is used to assay for a nucleotide sequence (e.g., exon). For example, combinations of primers and probes may be designed to detect selected exon splicing isoforms in single cell suspension or in cells isolated from frozen tumor tissues, e.g., using Laser Capture Microdissection. More than one isoform may be detected in the single cell, for example. Thus, kits provided herein may include any one or more reagents used in a Droplet Digital™ PCR (ddPCR™) assay.

In yet other embodiments, ViewRNA™ In Situ Hybridization (ISH) (Thermo Fisher Scientific) may be used to assay for a nucleotide sequence (e.g., exon). For example, splice junction probes may be designed to enable specific detection of the exon splicing isoforms of the present disclosure in tissue sections (e.g., breast cancer tissue sections) through Fluorescent In Situ Hybridization (FISH).

More than one isoform may be detected in the same cell, for example. Thus, kits provided herein may include any one or more reagents used in an ISH assay.

In still other embodiments, nCounter® technology (nanoString™) is used to assay for a nucleotide sequence (e.g., exon). For example, the nCounter® Analysis System utilizes a novel digital barcode technology for direct multiplexed measurement of analytes and offers high levels of precision and sensitivity (<1 copy per cell). The technology uses molecular "barcodes" and single molecule imaging for the direct hybridization and detection of hundreds of unique transcripts in a single reaction. Each color-coded barcode is attached to a single target-specific probe corresponding to an analyte (e.g., exon) of interest. Combined together with invariant controls, the probes form a multiplexed CodeSet. Thus, kits provided herein may include any one or more reagents used in a nCounter® assay or other nanoString™ nucleic acid detection assay.

Other nucleic acid detection methods may be used.

Probes

Some aspects of the present disclosure comprise assaying a sample for the presence or absence of a nucleic acid (e.g., an exon inclusion event) comprising a nucleotide sequence of any one of SEQ ID NOS: 1-20, each of which include an exon inclusion event as well as a sequence directly upstream from and a sequence directly downstream from the exon inclusion event (any one of SEQ ID NOS: 21-40). Some aspects of the present disclosure comprise assaying a sample for the presence or absence of a nucleic acid (e.g., an exon exclusion event) comprising a nucleotide sequence of any one of SEQ ID NOS: 105-136, each of which include an exon exclusion event as well as a sequence directly upstream from and a sequence directly downstream from the exon exclusion event (any one of SEQ ID NOS: 41-72).

A probe is a synthetic (non-naturally-occurring) nucleic acid that is wholly or partially complementary to and thus binds to a nucleic acid of interest (e.g., a nucleic acid comprising or comprised within a nucleotide sequence of any one of SEQ ID NOS: 1-20, 21-40, 41-72, or 105-136). In some embodiments, a probe comprises DNA. In some embodiments, a probe comprises RNA. In some embodiments, a probe comprise DNA and RNA. It should be understood that the term "probe" encompasses "primer," which, as is known in the art, is a synthetic nucleic acid (e.g., DNA) used as a starting point for nucleic acid (e.g., DNA) synthesis. The length of a probe may vary, depending on the nucleic acid detection assay being used. For example, a probe may have a length of at least 15, at least 18, at least 20, at least 25, at least 30, at least 40, at least 50, at least 60, at least 70, at least 80, at least 90, or at least 100 nucleotides. In some embodiments, a probe has a length of 15 to 30 nucleotides, 15 to 50 nucleotides, or 15 to 100 nucleotides. Depending on the application, a probe may be longer than 100 nucleotides.

In some embodiments, one or more probe is designed to bind directly to an exon (e.g., exon inclusion event or exon exclusion event) of any one of SEQ ID NOS: 21-40 and 105-136. The probe may bind, for example, to a 5' region, a central region, or a 3' region of an exon.

In some embodiments, one or more probe is designed to bind to a nucleotide sequence directly upstream (5') from an exon of any one of SEQ ID NOS: 21-40 and 105-136. In other embodiments, one or more probe is designed to bind to nucleotide sequence directly downstream (3') from an exon of any one of SEQ ID NOS: 21-40 and 105-136. In some embodiments, a first probe (e.g., primer) of a pair of probes is designed to bind to nucleotide sequence directly upstream (5') from an exon of any one of SEQ ID NOS: 21-40 and 105-136, and a second probe (e.g., primer) of the pair of probes is designed to bind to nucleotide sequence directly downstream (3') from an exon of any one of SEQ ID NOS: 21-40 and 105-136 such that the pair of probes flank the exon.

In some embodiments, one or more probe is designed to bind to an exon junction. An exon junction comprises (a) nucleotide sequence that includes a 5' region of an exon (e.g., of any one of SEQ ID NOS: 21-40 and 105-136) and nucleotide sequence directly upstream from the 5' region of the exon, or (b) nucleotide sequence that includes a 3' region of an exon (e.g., of any one of SEQ ID NOS: 21-40 and 105-136) and nucleotide sequence directly downstream from the 3' region of the exon. Table 6 provides examples of cDNA sequences that include exon inclusion events (underlined) as well as sequences directly upstream from and downstream from the exon inclusion event. Any one or more probe may be designed to bind to any region of a nucleotide sequence of Table 6 (SEQ ID NOS: 1-20), e.g., for the purpose of detecting (e.g., amplifying or labeling) the nucleotide sequence in a sample. Table 7 provides examples of cDNA sequences that include exon exclusion events (underlined) as well as sequences directly upstream from and downstream from the exon exclusion event. Any one or more probe may be designed to bind to any region of a nucleotide sequence of Table 7 (SEQ ID NOS: 41-72), e.g., for the purpose of detecting (e.g., amplifying or labeling) the nucleotide sequence in a sample.

Tissue Samples

In some embodiments, the mRNA is obtained from a biological sample. Biological samples include tissue samples or fluid samples. Non-limiting examples of tissue samples include blood samples and breast tissue samples. Non-limiting examples of fluid samples include cerebrospinal fluid (CSF) samples and urine samples.

In some embodiments, the mRNA is obtained from a breast tissue sample. The breast tissue sample, in some embodiments, is obtained from a female subject (e.g., human female subject), although it may alternatively be obtained from a male subject (e.g., human male subject).

In some embodiments, the sample is obtained from a subject diagnosed with a cancer, such as breast cancer. For example, the subject may have, may be at risk of having, or may be suspected of having a cancer of a breast duct, breast lobule, or breast tissue in between the duct and lobule. Non-limiting examples of breast cancer that may be sampled include ductal carcinoma in situ, invasive ductal carcinoma, tubular carcinoma of the breast, medullary carcinoma of the breast, mucinous carcinoma of the breast, papillary carcinoma of the breast, cribriform carcinoma of the breast, invasive lobular carcinoma, inflammatory breast cancer, Paget's disease of the nipple, Phyllodes tumors of the breast, metastatic breast cancer, and triple negative breast cancer (TNBC).

Applications

Methods of the present disclosure, in some embodiments, comprise assigning a favorable prognosis or unfavorable prognosis to a cancer patient, based on the presence of a nucleic acid in the sample (e.g., an exon inclusion event or an exon exclusion) comprising a nucleotide sequence (e.g., an exon) of any one of SEQ ID NOS: 21-40 and 105-136. Thus, in some embodiments, methods herein comprise obtaining a sample from a subject, assaying the sample for a nucleic acid comprising a nucleotide sequence of any one of SEQ ID NOS: 21-40 and 105-136, and assigning a favorable prognosis or unfavorable prognosis to the sample/ patient (e.g., breast tissue sample) (see, e.g., Table 4 or Table 5). In some embodiments, a nucleic acid comprising a nucleotide sequence of any one of SEQ ID NOS: 21-40 or 105-136 is detected in the sample obtained from the patient.

In some embodiments, a favorable prognosis is assigned to the sample when a nucleic acid comprising a nucleotide sequence of any one of SEQ ID NOS: 24, 28, 31, 33, 38, 114, 119, or 123 is detected. In some embodiments, a favorable prognosis is an at least 70% probability of surviving at least 2000 days. In some embodiments, a favorable prognosis is an at least 75% probability of surviving at least 2000 days. In some embodiments, a favorable prognosis is an at least 70% probability of surviving at least 4000 days. In some embodiments, a favorable prognosis is an at least 75% probability of surviving at least 4000 days.

In other embodiments, an unfavorable prognosis is assigned to the sample when a nucleic acid comprising a nucleotide sequence of any one of SEQ ID NOS: 21-27, 29, 30, 32, 34-37, 39, 40, 105-113, 115-118, 120-122, or 124-136 is detected. In some embodiments, an unfavorable prognosis is an at least 75% probability of surviving less than 2000 days.

Additional Embodiments

1. A complementary deoxyribonucleic acid (cDNA) comprising a nucleotide sequence of any one of SEQ ID NOS: 22-24, 27-34, 36, 38, or 40.

2. A composition comprising the cDNA of paragraph 1.

3. A composition comprising at least two cDNAs of paragraph 1.

4. The composition of paragraph 2 or 3 further comprising a cDNA comprising a nucleotide sequence of any one of SEQ ID NOS: 21, 25, 26, 35, 37, or 39.

5. The composition of paragraph 2 or 4 comprising a nucleic acid comprising a nucleotide sequence of SEQ ID NO: 21, a nucleic acid comprising a nucleotide sequence of SEQ ID NO: 22, a nucleic acid comprising a nucleotide sequence of SEQ ID NO: 23, a nucleic acid comprising a nucleotide sequence of SEQ ID NO: 24, a nucleic acid comprising a nucleotide sequence of SEQ ID NO: 25, a nucleic acid comprising a nucleotide sequence of SEQ ID NO: 26, a nucleic acid comprising a nucleotide sequence of SEQ ID NO: 27, a nucleic acid comprising a nucleotide sequence of SEQ ID NO: 28, a nucleic acid comprising a nucleotide sequence of SEQ ID NO: 29, a nucleic acid comprising a nucleotide sequence of SEQ ID NO: 30, a nucleic acid comprising a nucleotide sequence of SEQ ID NO: 31, a nucleic acid comprising a nucleotide sequence of SEQ ID NO: 32, a nucleic acid comprising a nucleotide sequence of SEQ ID NO: 33, a nucleic acid comprising a nucleotide sequence of SEQ ID NO: 34, a nucleic acid comprising a nucleotide sequence of SEQ ID NO: 35, a nucleic acid comprising a nucleotide sequence of SEQ ID NO: 36, a nucleic acid comprising a nucleotide sequence of SEQ ID NO: 37, a nucleic acid comprising a nucleotide sequence of SEQ ID NO: 38, a nucleic acid comprising a nucleotide sequence of SEQ ID NO: 39, and a nucleic acid comprising a nucleotide sequence of SEQ ID NO: 40.

6. The composition of paragraph 2 further comprising a probe that binds to the cDNA, or a pair of primers that bind to the cDNA.

7. The composition of any one of paragraphs 2-6, wherein the cDNA is synthesized from messenger ribonucleic acid (mRNA) obtained from a tissue sample, optionally a breast tissue sample.

8. The composition of paragraph 7, wherein the breast tissue sample is obtained from a female subject.

9. The composition of paragraph 7 or 8, wherein the sample is obtained from a subject diagnosed with a cancer.

10. The composition of paragraph 7 or 8, wherein the sample is obtained from a subject at risk of having a cancer or suspected of having a cancer.

11. A method comprising assaying a sample for a nucleic acid comprising a nucleotide sequence of any one of SEQ ID NOS: 22-24, 27-34, 36, 38, or 40.

12. The method of paragraph 11 further comprising assaying the sample for a nucleic acid comprising a nucleotide sequence of any one of SEQ ID NOS: 21, 25, 26, 35, 37, or 39.

13. The method of paragraph 11 comprising assaying the sample for a nucleic acid comprising a nucleotide sequence of SEQ ID NO: 21, a nucleic acid comprising a nucleotide sequence of SEQ ID NO: 22, a nucleic acid comprising a nucleotide sequence of SEQ ID NO: 23, a nucleic acid comprising a nucleotide sequence of SEQ ID NO: 24, a nucleic acid comprising a nucleotide sequence of SEQ ID NO: 25, a nucleic acid comprising a nucleotide sequence of SEQ ID NO: 26, a nucleic acid comprising a nucleotide sequence of SEQ ID NO: 27, a nucleic acid comprising a nucleotide sequence of SEQ ID NO: 28, a nucleic acid comprising a nucleotide sequence of SEQ ID NO: 29, a nucleic acid comprising a nucleotide sequence of SEQ ID NO: 30, a nucleic acid comprising a nucleotide sequence of SEQ ID NO: 31, a nucleic acid comprising a nucleotide sequence of SEQ ID NO: 32, a nucleic acid comprising a nucleotide sequence of SEQ ID NO: 33, a nucleic acid comprising a nucleotide sequence of SEQ ID NO: 34, a nucleic acid comprising a nucleotide sequence of SEQ ID NO: 35, a nucleic acid comprising a nucleotide sequence of SEQ ID NO: 36, a nucleic acid comprising a nucleotide sequence of SEQ ID NO: 37, a nucleic acid comprising a nucleotide sequence of SEQ ID NO: 38, a nucleic acid comprising a nucleotide sequence of SEQ ID NO: 39, and a nucleic acid comprising a nucleotide sequence of SEQ ID NO: 40.

14. The method of any one of paragraphs 11-13, wherein the nucleic acid is a messenger ribonucleic acid (mRNA), optionally obtained from a breast tissue sample.

15. The method of any one of paragraphs 11-13, wherein the nucleic acid is a complementary deoxyribonucleic acid (cDNA) synthesized from mRNA obtained from a breast tissue sample.

16. The method of paragraph 14 or 15, wherein the breast tissue sample is obtained from a female subject.

17. The method of any one of paragraphs 14-16, wherein the breast tissue sample is obtained from a subject diagnosed with a cancer.

18. The method of any one of paragraphs 14-16, wherein the breast tissue sample is obtained from a subject at risk of having a cancer or suspected of having a cancer.

19. The method of any one of paragraphs 11-18 further comprising detecting a nucleic acid comprising a nucleotide sequence of any one of SEQ ID NOS: 21-40.

20. The method of any one of paragraphs 11-19, wherein the nucleic acid is a mRNA.

21. The method of any one of paragraphs 11-19, wherein the nucleic acid is a cDNA.

22. The method of any one of paragraphs 19-21 further comprising assigning to the subject from whom the sample was obtained a favorable prognosis or an unfavorable prognosis.

23. The method of paragraph 22, wherein a favorable prognosis is assigned to the subject from whom the sample was obtained if a nucleic acid comprising a nucleotide sequence of any one of SEQ ID NOS: 24, 28, 21, 33, or 38 is detected.

24. The method of paragraph 22, wherein an unfavorable prognosis is assigned to the subject from whom the sample was obtained if a nucleic acid comprising a nucleotide sequence of any one of SEQ ID NOS: 21-27, 29, 30, 32, 34-37, 39, or 40 is detected.

25. A method comprising:

obtaining a sample from a subject;

assaying the sample for a nucleic acid comprising a nucleotide sequence of any one of SEQ ID NOS: 21-40; and assigning a favorable prognosis or unfavorable prognosis to the subject.

26. The method of paragraph 25 further comprising detecting in the sample a nucleic acid comprising a nucleotide sequence of any one of SEQ ID NOS: 21-40.

27. The method of paragraph 26, wherein the sample is a breast tissue sample.

28. The method of any one of paragraphs 25-27, wherein the assaying step comprising assaying the sample for a nucleic acid comprising a nucleotide sequence of SEQ ID NO: 21, a nucleic acid comprising a nucleotide sequence of SEQ ID NO: 22, a nucleic acid comprising a nucleotide sequence of SEQ ID NO: 23, a nucleic acid comprising a nucleotide sequence of SEQ ID NO: 24, a nucleic acid comprising a nucleotide sequence of SEQ ID NO: 25, a nucleic acid comprising a nucleotide sequence of SEQ ID NO: 26, a nucleic acid comprising a nucleotide sequence of SEQ ID NO: 27, a nucleic acid comprising a nucleotide sequence of SEQ ID NO: 28, a nucleic acid comprising a nucleotide sequence of SEQ ID NO: 29, a nucleic acid comprising a nucleotide sequence of SEQ ID NO: 30, a nucleic acid comprising a nucleotide sequence of SEQ ID NO: 31, a nucleic acid comprising a nucleotide sequence of SEQ ID NO: 32, a nucleic acid comprising a nucleotide sequence of SEQ ID NO: 33, a nucleic acid comprising a nucleotide sequence of SEQ ID NO: 34, a nucleic acid comprising a nucleotide sequence of SEQ ID NO: 35, a nucleic acid comprising a nucleotide sequence of SEQ ID NO: 36, a nucleic acid comprising a nucleotide sequence of SEQ ID NO: 37, a nucleic acid comprising a nucleotide sequence of SEQ ID NO: 38, a nucleic acid comprising a nucleotide sequence of SEQ ID NO: 39, and a nucleic acid comprising a nucleotide sequence of SEQ ID NO: 40.

28. The method of any one of paragraphs 25-27, wherein a favorable prognosis is assigned to the subject from whom the sample was obtained if a nucleic acid comprising a nucleotide sequence of any one of SEQ ID NOS: 24, 28, 21, 33, or 38 is detected.

29. The method of any one of paragraphs 25-27, wherein an unfavorable prognosis is assigned to the subject from whom the sample was obtained if a nucleic acid comprising a nucleotide sequence of any one of SEQ ID NOS: 21-27, 29, 30, 32, 34-37, 39, or 40 is detected.

30. A kit comprising: a probe comprising a nucleotide sequence complementary to a nucleotide sequence of any one of SEQ ID NOS: 1-20; and at least one reagent for detecting a nucleic acid selected from buffers, salts, polymerases, and deoxyribonucleotide triphosphates (dNTPs).

31. A kit comprising:

a probe comprising a nucleotide sequence complementary to a nucleotide sequence of SEQ ID NO: 1, a probe comprising a nucleotide sequence complementary to a nucleotide sequence of SEQ ID NO: 2, a probe comprising a nucleotide sequence complementary to a nucleotide sequence of SEQ ID NO: 3, a probe comprising a nucleotide sequence complementary to a nucleotide sequence of SEQ ID NO: 4, a probe comprising a nucleotide sequence complementary to a nucleotide sequence of SEQ ID NO: 5, a probe comprising a nucleotide sequence complementary to a nucleotide sequence of SEQ ID NO: 6, a probe comprising a nucleotide sequence complementary to a nucleotide sequence of SEQ ID NO: 7, a probe comprising a nucleotide sequence complementary to a nucleotide sequence of SEQ ID NO: 8, a probe comprising a nucleotide sequence complementary to a nucleotide sequence of SEQ ID NO: 9, a probe comprising a nucleotide sequence complementary to a nucleotide sequence of SEQ ID NO: 10, a probe comprising a nucleotide sequence complementary to a nucleotide sequence of SEQ ID NO: 11, a probe comprising a nucleotide sequence complementary to a nucleotide sequence of SEQ ID NO: 12, a probe comprising a nucleotide sequence complementary to a nucleotide sequence of SEQ ID NO: 13, a probe comprising a nucleotide sequence complementary to a nucleotide sequence of SEQ ID NO: 14, a probe comprising a nucleotide sequence complementary to a nucleotide sequence of SEQ ID NO: 15, a probe comprising a nucleotide sequence complementary to a nucleotide sequence of SEQ ID NO: 16, a probe comprising a nucleotide sequence complementary to a nucleotide sequence of SEQ ID NO: 17, a probe comprising a nucleotide sequence complementary to a nucleotide sequence of SEQ ID NO: 18, a probe comprising a nucleotide sequence complementary to a nucleotide sequence of SEQ ID NO: 19, and a probe comprising a nucleotide sequence complementary to a nucleotide sequence of SEQ ID NO: 20.

32. A kit comprising:

a probe comprising a nucleotide sequence complementary to a nucleotide sequence of SEQ ID NO: 21, a probe comprising a nucleotide sequence complementary to a nucleotide sequence of SEQ ID NO: 22, a probe comprising a nucleotide sequence complementary to a nucleotide sequence of SEQ ID NO: 23, a probe comprising a nucleotide sequence complementary to a nucleotide sequence of SEQ ID NO: 24, a probe comprising a nucleotide sequence complementary to a nucleotide sequence of SEQ ID NO: 25, a probe comprising a nucleotide sequence complementary to a nucleotide sequence of SEQ ID NO: 26, a probe comprising a nucleotide sequence complementary to a nucleotide sequence of SEQ ID NO: 27, a probe comprising a nucleotide sequence complementary to a nucleotide sequence of SEQ ID NO: 28, a probe comprising a nucleotide sequence complementary to a nucleotide sequence of SEQ ID NO: 29, a probe comprising a nucleotide sequence complementary to a nucleotide sequence of SEQ ID NO: 30, a probe comprising a nucleotide sequence complementary to a nucleotide sequence of SEQ ID NO: 31, a probe comprising a nucleotide sequence complementary to a nucleotide sequence of SEQ ID NO: 32, a probe comprising a nucleotide sequence complementary to a nucleotide sequence of SEQ ID NO: 33, a probe comprising a nucleotide sequence complementary to a nucleotide sequence of SEQ ID NO: 34, a probe comprising a nucleotide sequence complementary to a nucleotide sequence of SEQ ID NO: 35, a probe comprising a nucleotide sequence complementary to a nucleotide sequence of SEQ ID NO: 36, a probe comprising a nucleotide sequence complementary to a nucleotide sequence of SEQ ID NO: 37, a probe comprising a nucleotide sequence complementary to a nucleotide sequence of SEQ ID NO: 38, a probe comprising a nucleotide sequence complementary to a nucleotide sequence of SEQ ID NO: 39, and a probe comprising a nucleotide sequence complementary to a nucleotide sequence of SEQ ID NO: 40.

33. The kit of paragraph 31 or 32, wherein the kit further comprises at least one reagent for detecting a nucleic acid selected from buffers, salts, polymerases, and deoxyribonucleotide triphosphates (dNTPs).

EXAMPLES

Example 1

Alternative splicing is a biological phenomenon that increases transcript and protein diversity. In one type of alternative splicing, referred to as "exon skipping," exons are either spliced "in" or spliced "out" of the transcript based on cellular conditions (FIG. 55).

Due to alternative splicing, different transcript isoforms (exon configurations) of the same gene might be expressed in tumor and normal samples. Therefore, even though a gene is expressed in both tumor and normal tissues, transcripts might harbor an exon configuration that is distinctive to cancer.

A conventional approach for identification of cancer biomarkers is based on gene expression. Researchers aim to detect whether a gene is specifically expressed in tumors using microarrays or RNA sequencing. We took a splicing-based approach rather than a gene-based approach to identify cancer biomarkers.

Methods

To identify splicing biomarkers in cancer, we took the steps outlined below, i.e., (i) Transcript sequencing, (ii) TCGA analysis, and (iii) Clustering analysis using a novel methodology to identify splicing-based biomarkers.

Sequencing: Long read sequencing using PacBio® Single Molecule Real Time Sequencing (SMRT) technology. This technology is capable of sequencing full-length cDNA transcripts without the need of cDNA fragmentation, and therefore can be used to directly infer the connectivity of exons in transcripts without the need of computational reconstruction. We used this technology to sequence transcripts in 81 cancer and tumor samples. We obtained 298K transcripts corresponding to ~14K genes, yielding a median of 8 isoforms per gene. This represents a ~2-fold increase over the public human reference transcriptome (Gencode version 25) for those set of genes. This set of transcripts is called PacBio® Transcriptome.

Data Analysis Step 1, TCGA analysis: Quantification of exon skipping events in a large cohort of breast cancer patients available from TCGA using the PacBio® Transcriptome as background. The aim of the step is to compute percent spliced-in (PSI) for exons undergoing alternative splicing. This step was performed using the rMATS software. rMATS identified 67,255 skipping events in the PacBio® transcriptome, and computed the PSI levels for each of those exons across all samples (n=1,748, including 1,111 breast cancer tumors and 637 normal). Given the size of the TCGA sequencing data, this step was performed using the ISB Cancer Genomics Cloud (Google Cloud) platform.

Data Analysis Step 2, Clustering: Apply a methodology of the present disclosure called ts3 (Tumor Specific Splice Site Detection) to find exons that are included (e.g., spliced in) and excluded (spliced out) only in cancer (FIG. 55). This is accomplished by using a clustering approach based on GMM.

Results

We applied our methodology based on Gaussian mixture modeling to identify exon splicing events specific to breast cancer patients from the TCGA cohort. As a result, we identified 20 exon inclusion events (spliced "in" exons) that are specifically expressed in cancer and have prognosis power. These exon inclusion events have the following properties:

- Target exon has increased PSI levels (expression) compared to normal tissues ($PSI_{tumor}-PSI_{normal}>10\%$),
- Target exon is low or absent in normal tissues ($PSI_{normal}<5\%$),
- Splicing event is reliably detected in at least 30 breast cancer patients (coverage of at least 10 RNA-Seq reads in each patient),
- Patients harboring these exon inclusion events have favorable or unfavorable survival prognosis ($p<0.05$, logrank test).

We also identified 32 exon exclusion events (spliced "out" exons) that are specific to breast cancer and have prognosis power. These exon exclusion events have the following properties:

- Target exon has decreased PSI levels (expression) compared to normal tissues ($PSI_{tumor}-PSI_{normal}>-10\%$),
- Target exon is high in normal tissues ($PSI_{normal}>95\%$),
- Splicing event is reliably detected in at least 30 breast cancer patients (coverage of at least 10 RNA-Seq reads in each patient),
- Patients harboring these exon exclusion events have favorable or unfavorable survival prognosis ($p<0.05$, logrank test).

Because they are specific to cancer, these exon events are referred to as "exon inclusion biomarkers or exon exclusion biomarkers."

The exon splicing sequences were identified using long read SMRT PacBio® sequencing (see, e.g., Rhoads A et al. Genomics Proteomics Bioinformatics 2015; 13: 278-289, and Huddleston J et al. Genome Research 2014; 24: 688-696).

We found 2 types of exon splicing biomarkers, with favorable and unfavorable prognosis. Table 1 indicates that 15 exon inclusion events have unfavorable prognosis (worse outcome, lower survival time), and 5 exon inclusion events have favorable prognosis (better outcome, increased survival time). Table 2 indicates that 29 exon exclusion events have unfavorable prognosis, and 3 exon exclusion events have favorable prognosis.

TABLE 1

Exon inclusion biomarkers associated with breast cancer survival

| Splicing Event ID | Gene | Expression Prognosis | EXON SEQ ID NO: |
|---|---|---|---|
| 1446 | CCDC115 | Unfavorable | 21 |
| 4322 | WDR45B | Favorable | 28 |
| 5134 | PLEKHA6 | Unfavorable | 32 |
| 5696 | TTC3 | Unfavorable | 34 |
| 6785 | SPATS2 | Unfavorable | 39 |
| 8742 | DHRS11 | Unfavorable | 40 |
| 13343 | ENAH | Unfavorable | 22 |
| 15088 | POLI | Unfavorable | 23 |
| 16864 | PLXNB1 | Favorable | 24 |
| 21181 | SH3GLB1 | Unfavorable | 25 |
| 34793 | TCF25 | Unfavorable | 26 |
| 42420 | PRR5-ARHGAP8 | Unfavorable | 27 |
| 44438 | VPS29 | Unfavorable | 29 |
| 48175 | E4F1 | Unfavorable | 30 |
| 49765 | TEN1-CDK3 | Favorable | 31 |
| 56552 | GNAZ | Favorable | 33 |
| 57139 | RNF8 | Unfavorable | 35 |

TABLE 1-continued

Exon inclusion biomarkers associated with breast cancer survival

| Splicing Event ID | Gene | Expression Prognosis | EXON SEQ ID NO: |
|---|---|---|---|
| 57874 | ZDHHC13 | Unfavorable | 36 |
| 60615 | SH3GLB2 | Unfavorable | 37 |
| 62560 | ITFG1 | Favorable | 38 |

TABLE 2

Exon exclusion biomarkers associated with breast cancer survival

| Splicing Event ID | Gene | Expression Prognosis | EXON SEQ ID NO: |
|---|---|---|---|
| 1506 | CENPK | Unfavorable | 73 |
| 2098 | METTL5 | Unfavorable | 74 |
| 2242 | PLA2R1 | Unfavorable | 75 |
| 7106 | RHOH | Unfavorable | 76 |
| 7108 | RHOH | Unfavorable | 77 |
| 9442 | QPRT | Unfavorable | 78 |
| 10439 | IL17RB | Unfavorable | 79 |
| 11685 | STAU1 | Unfavorable | 80 |
| 13451 | LYRM1 | Unfavorable | 81 |
| 14574 | PPARG | Favorable | 82 |
| 16269 | BORCS8-MEF2B | Unfavorable | 83 |
| 16833 | ENOSF1 | Unfavorable | 84 |
| 16929 | DHRS4-AS1 | Unfavorable | 85 |
| 16943 | NDUFV2 | Unfavorable | 86 |
| 18745 | FER1L4 | Favorable | 87 |
| 19824 | PHF14 | Unfavorable | 88 |
| 19828 | PHF14 | Unfavorable | 89 |
| 21024 | BCL2L13 | Unfavorable | 90 |
| 22227 | SELENBP1 | Favorable | 91 |
| 24742 | LINC00630 | Unfavorable | 92 |
| 27194 | CTBP2 | Unfavorable | 93 |
| 30244 | SLC52A2 | Unfavorable | 94 |
| 33377 | SLC38A1 | Unfavorable | 95 |
| 40521 | FAM65A | Unfavorable | 96 |
| 41168 | USP25 | Unfavorable | 97 |
| 45885 | HMOX2 | Unfavorable | 98 |
| 50148 | MKRN2OS | Unfavorable | 99 |
| 52249 | ATP8A2P1 | Unfavorable | 100 |
| 53188 | HIBCH | Unfavorable | 101 |
| 58853 | SLC35C2 | Unfavorable | 102 |
| 59314 | TRIM5 | Unfavorable | 103 |
| 60239 | HSD17B6 | Unfavorable | 104 |

Figure 1B:
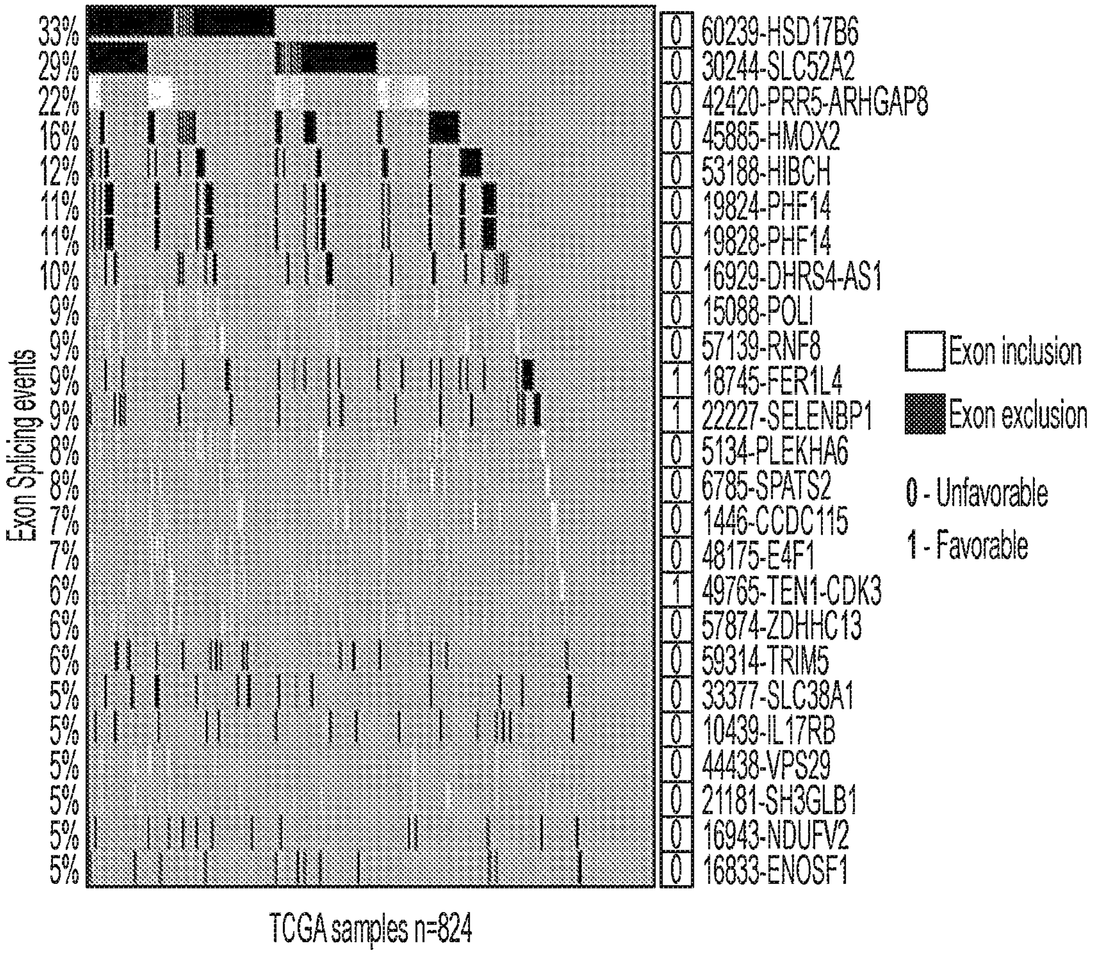
FIG. 1B: Frequency of exon splicing events (e.g., exon inclusion and exon exclusion) in TCGA patients. In total, 20 exon inclusion events and 32 exon exclusion events that are breast cancer specific and associated to survival were detected using the novel Gaussian mixture modeling (GMM) clustering approach. The table indicates the presence or absence of the 52 exon splicing events (rows) across 824 breast cancer patients in TCGA (columns). Exon splicing events are ordered by frequency. Unfavorable and favorable prognosis are shown, respectively.
Figure 1B:
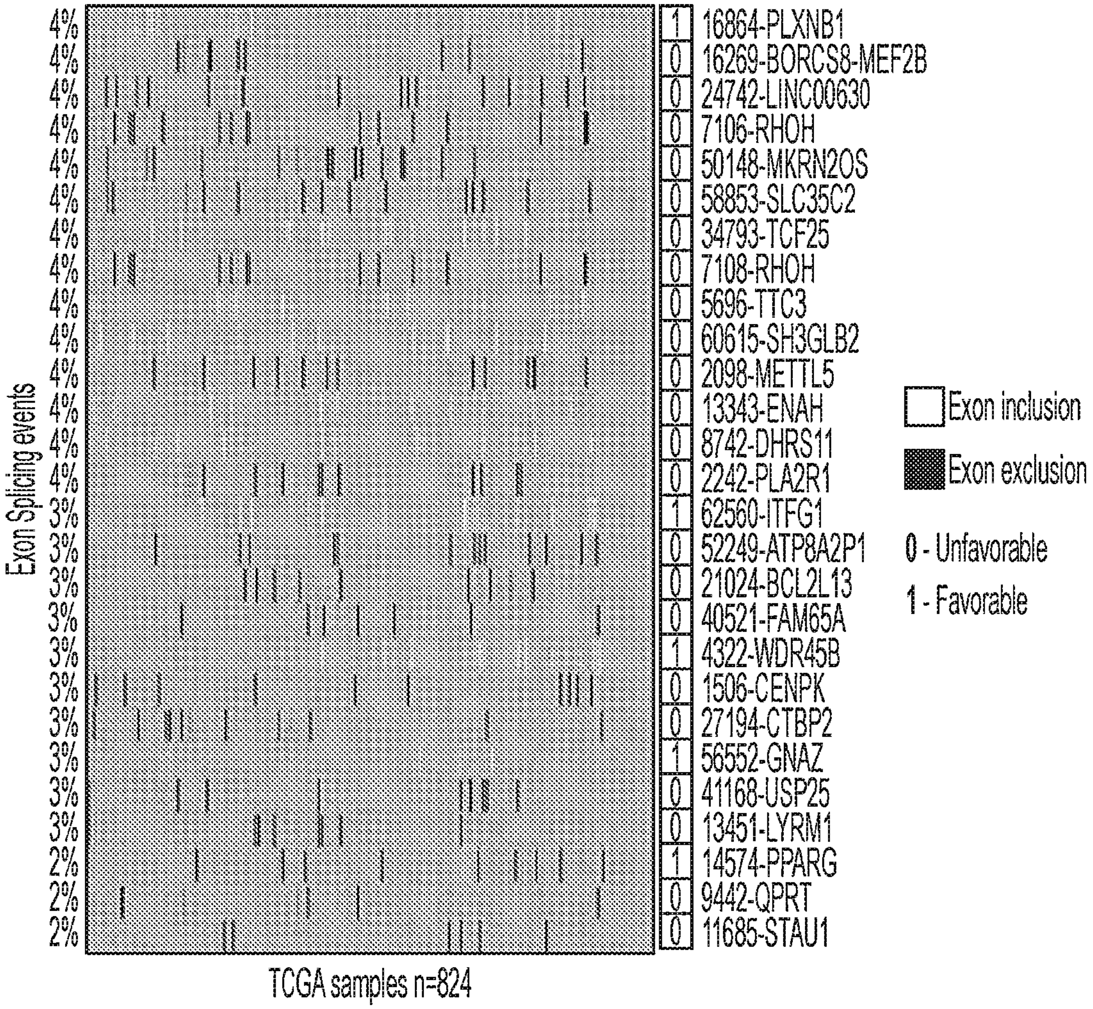

FIG. 1 shows the detection of the 52 exon inclusion or exon exclusion biomarkers in The Cancer Genome Atlas (TCGA) patients. Inclusion biomarkers are depicted in white, and exclusion biomarkers are depicted in black.

Biomarkers with favorable prognosis are denoted "1", while biomarkers with unfavorable prognosis are denoted "0". These biomarkers are detected in 2-33% of patients. For instance, the splicing event 42420 affecting the PRR5-ARHGAP8 gene is present in 22% of patients, while the biomarker 15088-POL1 is present is 9% of patients. Also, 91.5% patients have at least one biomarker (754 out of 824 patients).

Figure 2A:
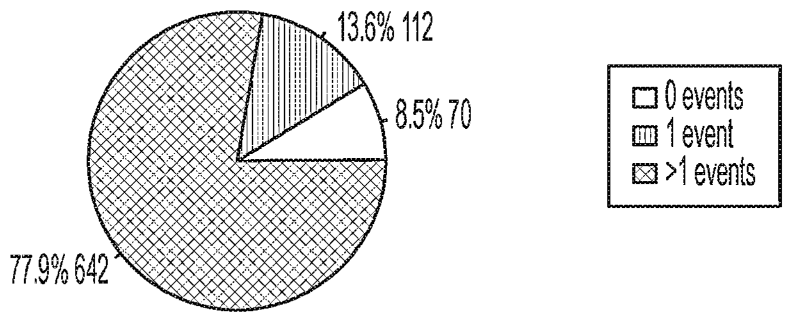
FIG. 2A: Frequency (%) of detection for the list of 52-exon splicing events in the TCGA cohort with survival information (n=824, above).

FIG. 2A shows that 8.5% (70 patients) have no exon inclusion biomarkers predictors of survival, 13.6% (112 patients) have exactly one exon biomarker predictor of survival, and 77.9% (642 patients) have more than one exon inclusion biomarker predictor of survival.

Figure 2B:
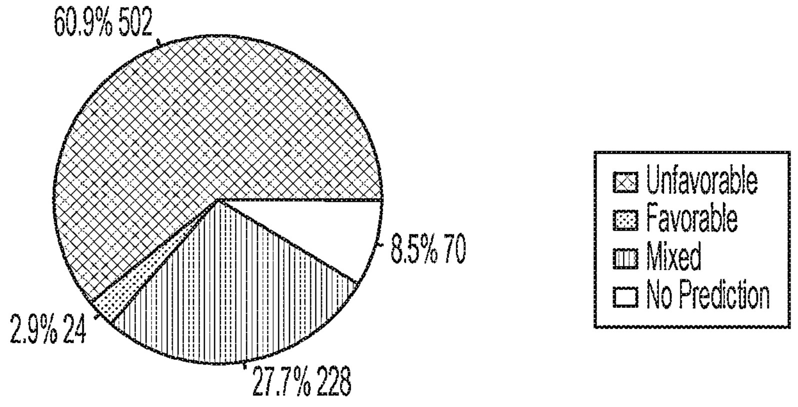
FIG. 2B: Type of exon splicing biomarker detected in patients using the 52-exon splicing biomarker panel.

In terms of exon biomarkers detection, breast cancer TCGA patients can be divided in four groups, (i) unfavorable biomarkers only (60.9% or 502 patients), (ii) favorable biomarkers only (2.9% or 24 patients), and (iii) mixed unfavorable and favorable biomarkers (27.7% or 228 patients), and (iv) no detected biomarkers (8.5% or 70 patients) (FIG. 2B).

Therefore, while it is common to detect more than one biomarker in the patient, we observed that patients tend to have the same type of exon splicing biomarker (all unfavorable or all favorable). Additional work is ongoing to devise a strategy to utilize these exon biomarkers in the clinical

Example Application: Use of 52-Exon Splicing Biomarker Panel for Prognosis

We classified patients into different groups based on the outcome (unfavorable, favorable, mixed, no prediction) and number of exon splicing biomarkers (exactly one event, more than one event). The classification is available in the Table 3. For instant, unfavorable prognosis was ascertained to 11.9% of patient (exactly one event).

TABLE 3

Exon Splicing Biomarker Outcome

| Prediction Outcome | Number of exon splicing biomarkers | Number of patients | Percent Total |
|---|---|---|---|
| Unfavorable | 1 event | 98 | 11.9% |
| Unfavorable | >1 event | 40 | 49% |
| Favorable | 1 event | 14 | 1.7% |
| Favorable | >1 event | 10 | 1.2% |
| Mixed | >1 event | 228 | 27.7% |
| No prediction | 0 event | 70 | 8.5% |

TABLE 4

Genomic Location of Exon Inclusion Biomarkers

| Splicing event id | Gene | Chr | Strand | Exon Target¶ | Exon Upstream¶ | Exon Downstream¶ | RefSeq* | Gencode v.28* |
|---|---|---|---|---|---|---|---|---|
| 13343 | ENAH | chr1 | – | 225595208-225595329 | 225567249-225567414 | 225600208-225600362 | No | No |
| 1446 | CCDC115 | chr2 | – | 130339560-130339701 | 130338250-130339232 | 130340908-130341039 | Yes | Yes |
| 15088 | POLI | chr18 | + | 54272095-54272242 | 54271360-54271485 | 54273926-54274090 | No | No |
| 16864 | PLXNB1 | chr3 | – | 48413458-48413537 | 48413069-48413169 | 48413670-48413818 | No | No |
| 21181 | SH3GLB1 | chr1 | + | 86728403-86728489 | 86724313-86724405 | 86734602-86734691 | Yes | Yes |
| 34793 | TCF25 | chr16 | + | 89878461-89878627 | 89873578-89873859 | 89883351-89883512 | No | Yes |
| 42420 | PRR5-ARHGAP8 | chr22 | + | 44809006-44811304 | 44808307-44808438 | 44814672-44814758 | No | No |

TABLE 4-continued

Genomic Location of Exon Inclusion Biomarkers

| Splicing event id | Gene | Chr | Strand | Exon Target¶ | Exon Upstream¶ | Exon Downstream¶ | RefSeq* | Gencode v.28* |
|---|---|---|---|---|---|---|---|---|
| 4322 | WDR45B | chr17 | − | 82625587-82625762 | 82625389-82625483 | 82627204-82627291 | No | No |
| 44438 | VPS29 | chr12 | − | 110498820-110499546 | 110496012-110496203 | 110502049-110502108 | No | No |
| 48175 | E4F1 | chr16 | + | 2226229-2226317 | 2223591-2223770 | 2228372-2228523 | No | No |
| 49765 | TEN1-CDK3 | chr17 | + | 75985173-75985288 | 75979275-75979511 | 75986187-75986284 | No | No |
| 5134 | PLEKHA6 | chr1 | − | 204271248-204271374 | 204268208-204268312 | 204273626-204273740 | No | No |
| 56552 | GNAZ | chr22 | + | 23122192-23122702 | 23095706-23096418 | 23123087-23125026 | No | No |
| 5696 | TTC3 | chr21 | + | 37075936-37076066 | 37073269-37073364 | 37108392-37108446 | No | No |
| 57139 | RNF8 | chr6 | + | 37359183-37359342 | 37354012-37354275 | 37360446-37360574 | No | Yes |
| 57874 | ZDHHC13 | chr11 | + | 19124904-19125180 | 19117150-19117276 | 19142978-19143123 | No | No |
| 60615 | SH3GLB2 | chr9 | − | 129009453-129009467 | 129009106-129009346 | 129009771-129009871 | Yes | Yes |
| 62560 | ITFG1 | chr16 | − | 47450354-47450453 | 47428804-47428898 | 47451396-47451470 | No | No |
| 6785 | SPATS2 | chr12 | + | 49441730-49441816 | 49371228-49371290 | 49460770-49461037 | No | Yes |
| 8742 | DHRS11 | chr17 | + | 36593449-36593616 | 36591903-36592156 | 36594971-36595180 | No | No |

¶Human genome build hg38

*Yes: there exists a transcript harboring 3 exons (target, upstream and downstream), as well as transcript harboring 2 exons (upstream and downstream) reported in the database

TABLE 5

Genomic Location of Exon Exclusion Biomarkers

| Splicing event id | Gene | Chr | Strand | Exon Target¶ | Exon Upstream¶ | Exon Downstream¶ | RefSeq* | Gencode v.28* |
|---|---|---|---|---|---|---|---|---|
| 1506 | CENPK | chr5 | − | 65528919-65529017 | 65528452-65528578 | 65529117-65529199 | No | Yes |
| 2098 | METTL5 | chr2 | − | 169815477-169815528 | 169811764-169812506 | 169819561-169819643 | No | No |
| 2242 | PLA2R1 | chr2 | − | 159955698-159955828 | 159955199-159955346 | 159956510-159956627 | No | No |
| 7106 | RHOH | chr4 | + | 40197101-40197300 | 40193489-40193812 | 40242714-40242834 | Yes | Yes |
| 7108 | RHOH | chr4 | + | 40197121-40197300 | 40193545-40193812 | 40242714-40242834 | No | No |
| 9442 | QPRT | chr16 | + | 29695172-29695199 | 29694664-29695096 | 29696996-29697127 | No | No |
| 10439 | IL17RB | chr3 | + | 53855294-53855341 | 53852871-53852997 | 53856844-53856986 | No | No |
| 11685 | STAU1 | chr20 | − | 49174195-49174269 | 49153933-49154071 | 49188116-49188357 | Yes | Yes |
| 13451 | LYRM1 | chr16 | + | 20915556-20915714 | 20902486-20902717 | 20920122-20920214 | Yes | Yes |
| 14574 | PPARG | chr3 | + | 12416704-12417154 | 12405882-12406081 | 12433898-12434577 | No | Yes |
| 16269 | BORCS8-MEF2B | chr19 | − | 19180686-19180761 | 19150682-19150764 | 19182573-19182683 | No | Yes |
| 16833 | ENOSF1 | chr18 | − | 691204-691276 | 690549-690631 | 693882-693908 | No | No |
| 16929 | DHRS4-AS1 | chr14 | − | 23953774-23954033 | 23940393-23941158 | 23954748-23955082 | No | No |
| 16943 | NDUFV2 | chr18 | + | 9115528-9115902 | 9103092-9103433 | 9117838-9117903 | No | No |
| 18745 | FER1L4 | chr20 | − | 35560163-35560364 | 35559341-35559627 | 35560540-35560638 | No | No |
| 19824 | PHF14 | chr7 | + | 11061791-11061852 | 11051612-11051780 | 11061964-11063404 | No | No |
| 19828 | PHF14 | chr7 | + | 11061791-11061851 | 11051612-11051780 | 11061964-11062085 | No | No |
| 21024 | BCL2L13 | chr22 | + | 17696141-17696210 | 17683214-17683321 | 17726677-17729133 | No | No |

TABLE 5-continued

| Genomic Location of Exon Exclusion Biomarkers | | | | | | | | |
|---|---|---|---|---|---|---|---|---|
| Splicing event id | Gene | Chr | Strand | Exon Target¶ | Exon Upstream¶ | Exon Downstream¶ | RefSeq* | Gencode v.28* |
| 22227 | SELENBP1 | chr1 | − | 151369004-151369189 | 151368199-151368319 | 151369713-151369769 | No | No |
| 24742 | LINC00630 | chrX | + | 102816992-102817082 | 102770352-102770420 | 102825993-102826169 | No | No |
| 27194 | CTBP2 | chr10 | − | 125133512-125133612 | 125038997-125039155 | 125162581-125162780 | No | No |
| 30244 | SLC52A2 | chr8 | + | 144357251-144357602 | 144354661-144354690 | 144359184-144359423 | No | No |
| 33377 | SLC38A1 | chr12 | − | 46196725-46196871 | 46194651-46196276 | 46197720-46197817 | No | No |
| 40521 | FAM65A | chr16 | + | 67544956-67545117 | 67544695-67544830 | 67545376-67545534 | No | No |
| 41168 | USP25 | chr21 | + | 15777904-15778027 | 15766002-15766141 | 15791502-15791664 | No | No |
| 45885 | HMOX2 | chr16 | + | 4483637-4483754 | 4474771-4474847 | 4505484-4505610 | No | No |
| 50148 | MKRN2OS | chr3 | − | 12543180-12543229 | 12541860-12542022 | 12545247-12545524 | No | No |
| 52249 | ATP8A2P1 | chr10 | + | 37248118-37248396 | 37242758-37242847 | 37261864-37261925 | No | No |
| 53188 | HIBCH | chr2 | − | 190208880-190208913 | 190204635-190205232 | 190212956-190213075 | Yes | Yes |
| 58853 | SLC35C2 | chr20 | − | 46355802-46355865 | 46355073-46355241 | 46356574-46356637 | No | No |
| 59314 | TRIM5 | chr11 | − | 5709135-5709255 | 5679761-5680238 | 5937401-5937505 | No | No |
| 60239 | HSD17B6 | chr12 | + | 56763198-56763414 | 56752180-56752318 | 56773834-56774165 | No | Yes |

¶Human genome build hg38

*Yes: there exists a transcript harboring 3 exons (target, upstream and downstream), as well as transcript harboring 2 exons (upstream and downstream) reported in the database

Example 2

Figure 3A:
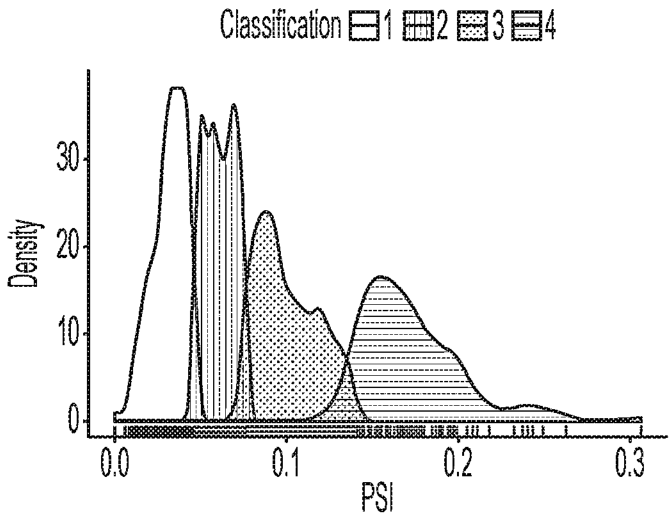
FIG. 3A: GMM analysis of mixed normal and breast cancer samples for the splicing event 1446 (CCDC115 gene). The GMM analysis showed 4 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 54A:
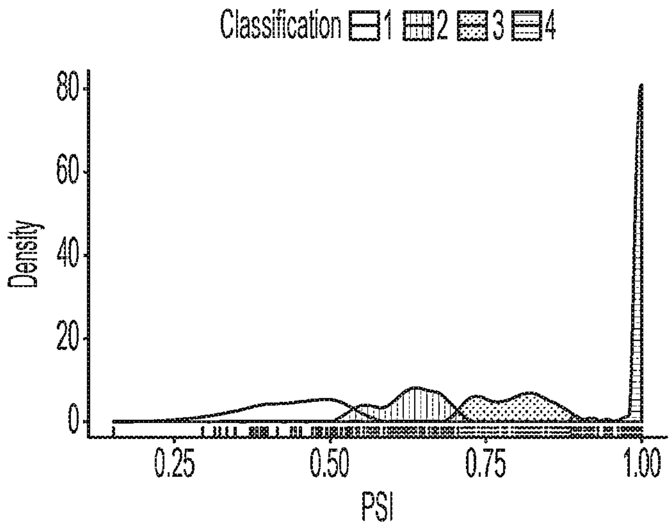
FIG. 54A: GMM analysis of mixed normal and breast cancer samples for the splicing event 60239 (HSD17B6 gene). The GMM analysis showed 4 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 54B:
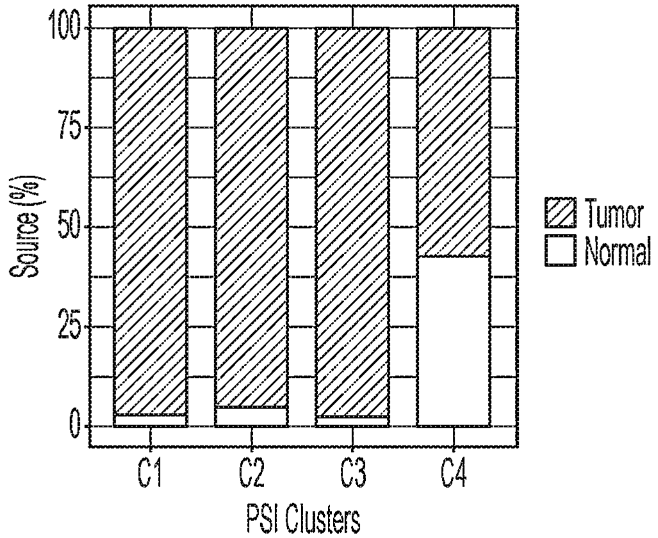
FIG. 54B: Frequency (%) of tumor and normal samples across the 4 clusters identified for the splicing event 60239 (HSD17B6 gene). Clusters 1-4 are composed mostly of breast cancer samples.
Figure 54C:
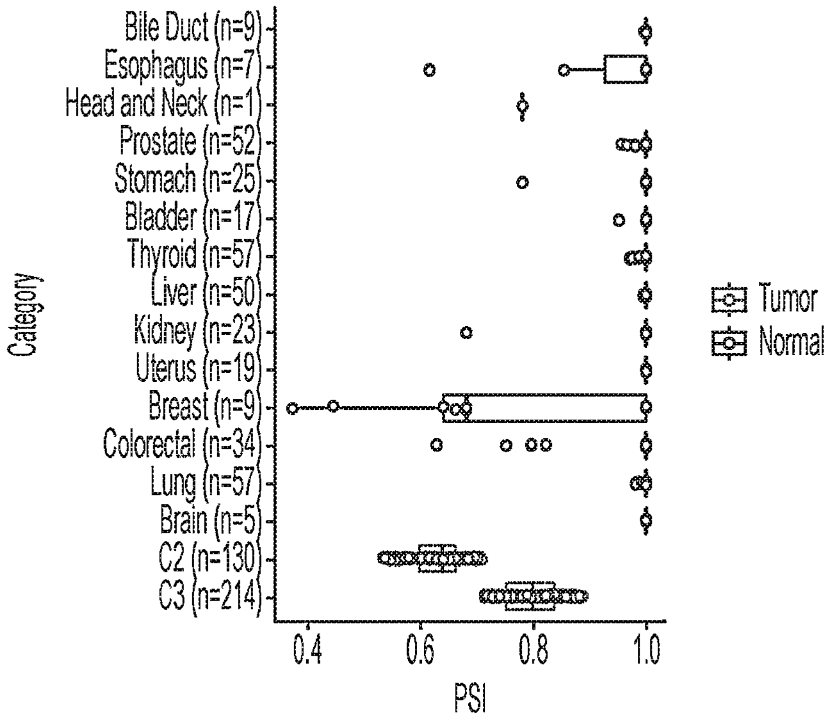
FIG. 54C: Exon splicing levels (PSI) for tumor specific clusters C2 and C3 and normal tissues in TCGA. This analysis indicates that the target exon is expressed in 130 breast cancer patients in cluster C2 and 214 breast cancer patients in cluster C3 while being very low or absent in normal tissues except breast.
Figure 54D:
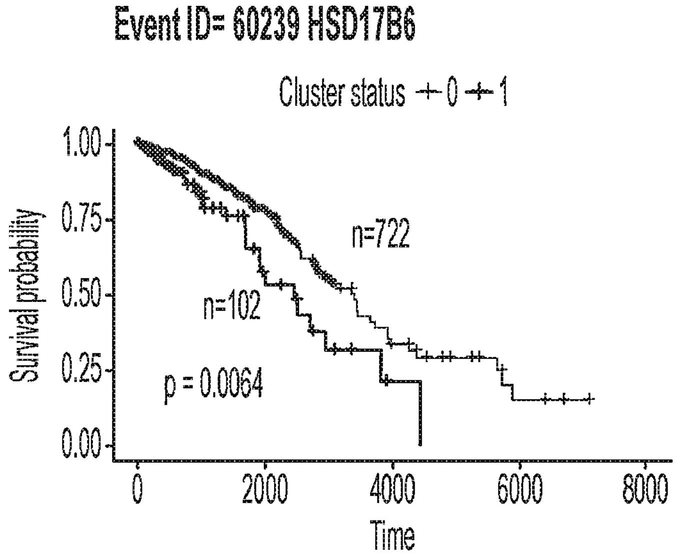
FIG. 54D: Survival analysis of breast cancer patients in cluster C1 versus the remaining breast cancer patients in TCGA. This analysis indicates that patients in C1 (expressing the target exon) have a worse overall survival (shorter survival time, days).

In this example, we analyzed the splicing events listed in Table 4 and Table 5 (see FIGS. 3A-54D). The expression (expressed as PSI) of these target exons varies substantially across cancer and normal samples (see, e.g., FIG. 3A, varying from 0 (0% inclusion) to 0.3 (30% inclusion)).

Visual inspection of data suggests the existence of a subpopulation of samples in which the target exon is included, or "spliced-in". This subpopulation (classification "4" samples in FIG. 3A) was formally detected using a clustering methodology called GMM. The GMM analysis of splicing event 1446 (CCDC115) generated 4 subpopulations of samples (clusters).

Figure 3B:
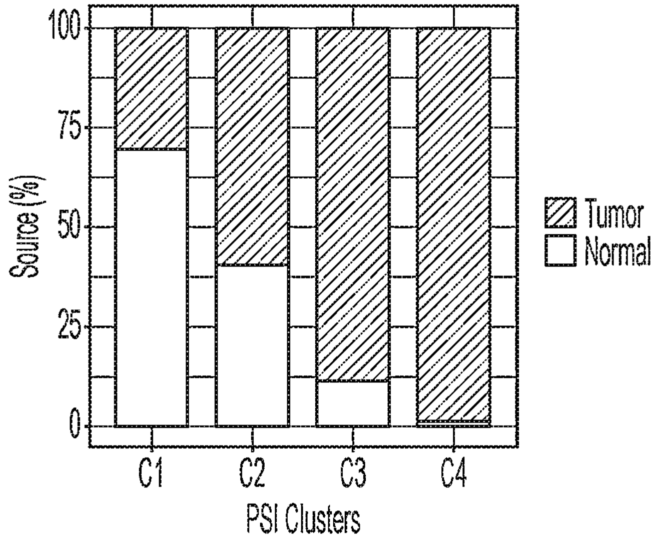
FIG. 3B: Frequency (%) of tumor and normal samples across the 4 clusters identified for the splicing event 1446 (CCDC115 gene). Cluster 4 is composed mostly of breast cancer samples.
Figure 3C:
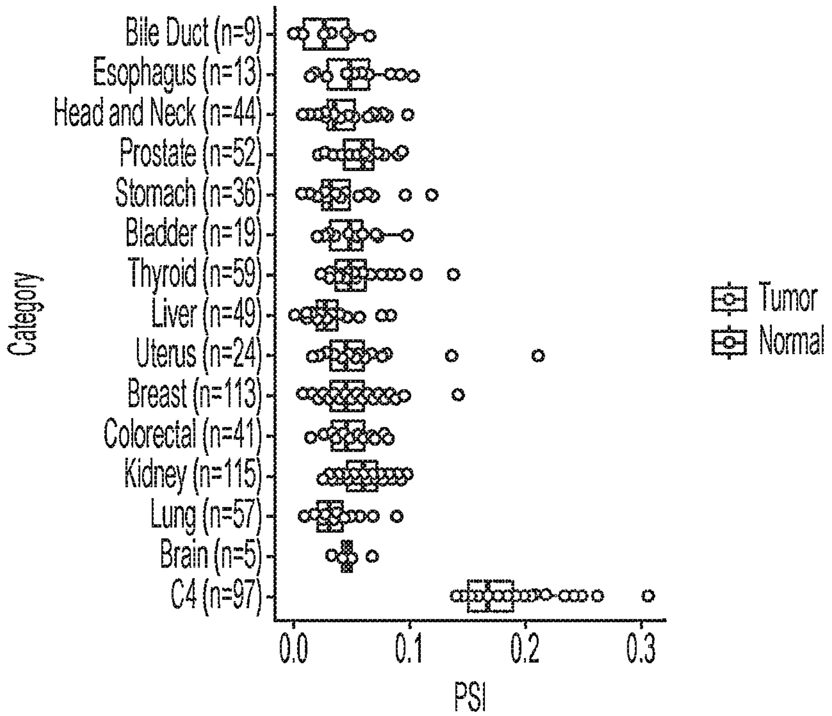
FIG. 3C: Exon levels (PSI) for tumor specific cluster C4 and normal tissues in TCGA. This analysis indicates that the target exon (also referred to herein as an "alternative exon") is expressed in 97 breast cancer patients in cluster C4, while very low or absent in normal tissues.

Nonetheless, only one of the clusters (e.g., C4 of FIGS. 3A and 3B) qualifies as a tumor specific cluster, because it has the following properties:

- cluster C4 contains more than >90% of tumor samples (see FIG. 3B);
- cluster C4 has >10% increase expression (PSI) compared to normal ($PSI_{tumor}$−$PSI_{normal}$>10%), see FIG. 3C; and
- the exon inclusion event is very low or absent expression in normal tissues ($PSI_{normal}$<5%), see FIG. 3C.

Figure 3D:
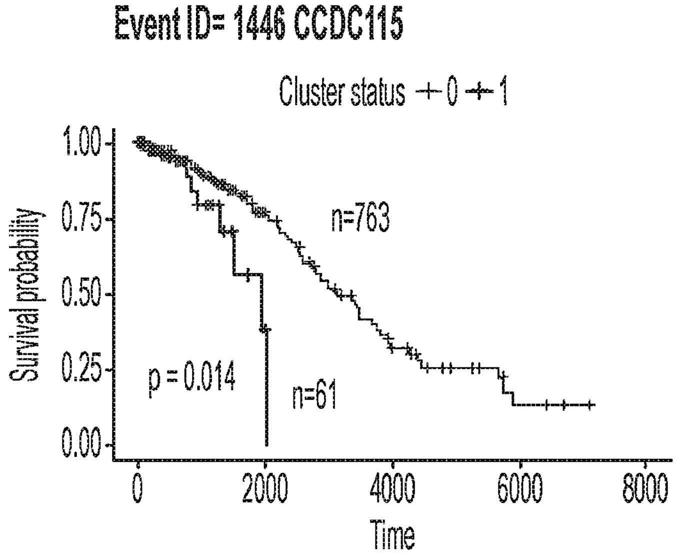
FIG. 3D: Survival analysis of breast cancer patients in cluster C4 versus the remaining breast cancer patients in TCGA. This analysis indicates that patients in C4 (expressing the target exon) have a worse overall survival (shorter survival time, days).
Figure 4A:
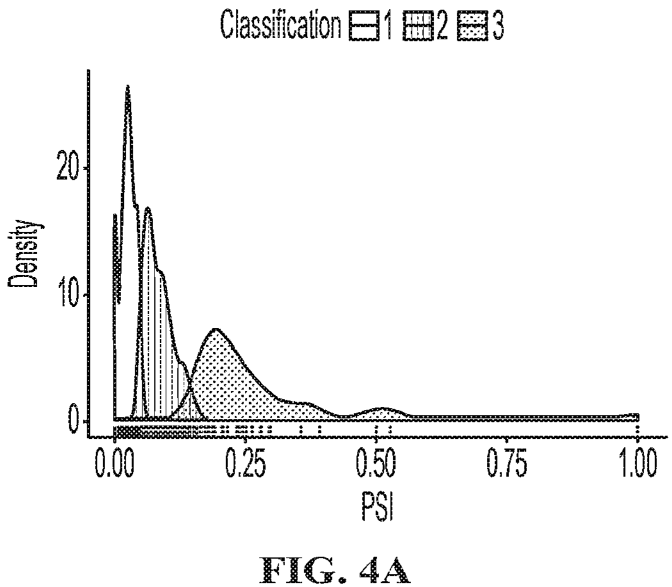
FIG. 4A: GMM analysis of mixed normal and breast cancer samples for the splicing event 13343 (ENAH gene). The GMM analysis showed 3 distinct clusters (subpopulations). The x-axis indicates the exon PSI (ψ) level within samples, and y-axis denotes the number of samples in a normalized density scale. Shading indicates the cluster assignment of each sample.
Figure 4B:
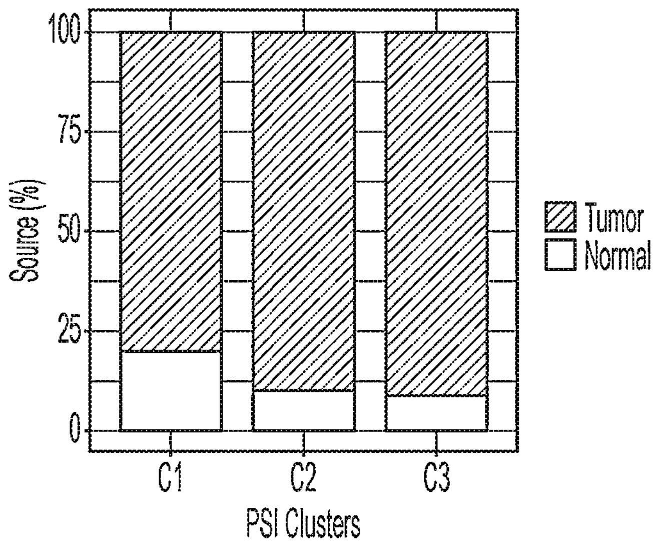
FIG. 4B: Frequency (%) of tumor and normal samples across the 3 clusters identified for the splicing event 13343 (ENAH gene). Cluster 3 is composed mostly of breast cancer samples.
Figure 4C:
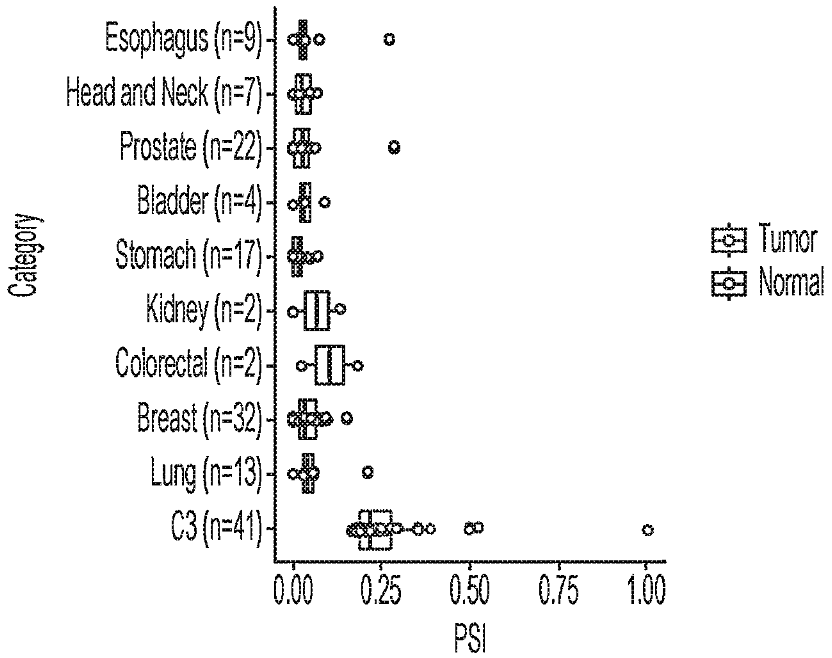
FIG. 4C: Exon splicing levels (PSI) for tumor specific cluster C3 and normal tissues in TCGA. This analysis indicates that the target exon is expressed in 41 breast cancer patients in cluster C3, while very low or absent in normal tissues.
Figure 4D:
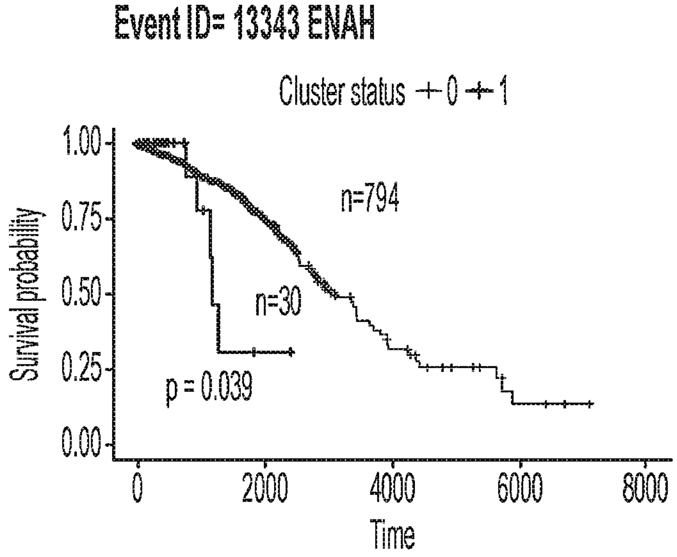
FIG. 4D: Survival analysis of breast cancer patients in cluster C3 versus the remaining breast cancer patients in TCGA. This analysis indicates that patients in C3 (expressing the target exon) have a worse overall survival (shorter survival time, days).
Figure 5A:
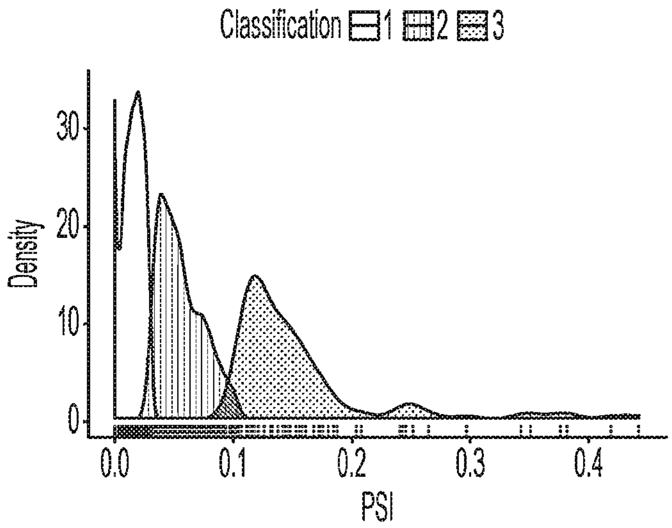
FIG. 5A: GMM analysis of mixed normal and breast cancer samples for the splicing event 15088 (POLI gene). The GMM analysis showed 3 distinct clusters (subpopulations). The x-axis indicates the exon PSI (ψ) level within samples, and y-axis denotes the number of samples in a normalized density scale. Shading indicates the cluster assignment of each sample.
Figure 5B:
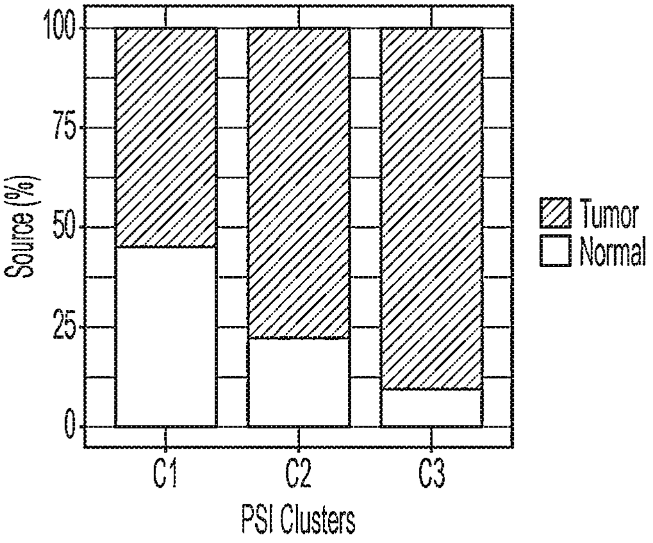
FIG. 5B: Frequency (%) of tumor and normal samples across the 3 clusters identified for the splicing event 15088 (POLI gene). Cluster 3 is composed mostly of breast cancer samples.
Figure 5C:
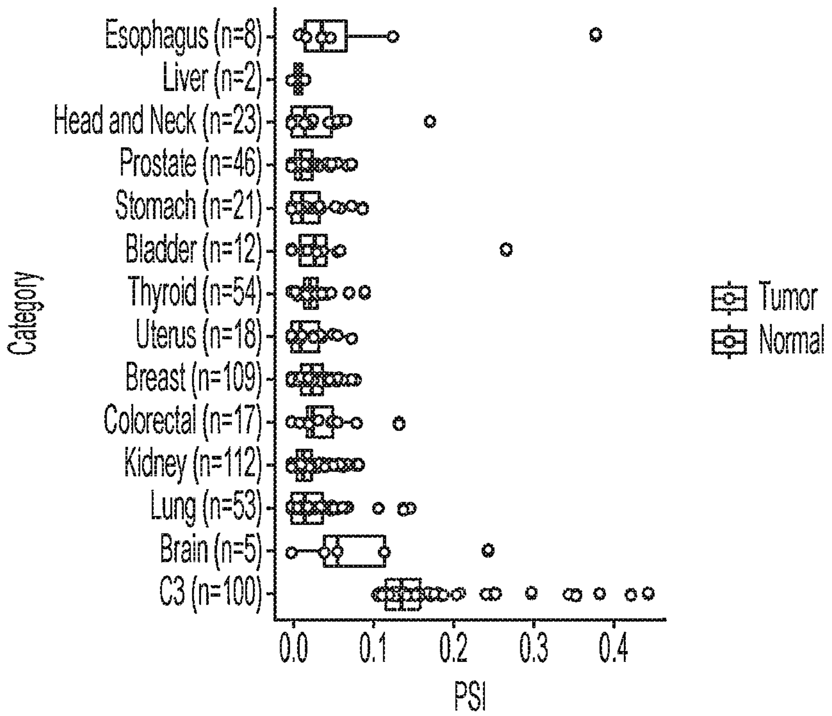
FIG. 5C: Exon splicing levels (PSI) for tumor specific cluster C3 and normal tissues in TCGA. This analysis indicates that the target exon is expressed in 100 breast cancer patients in cluster C3, while very low or absent in normal tissues.
Figure 5D:
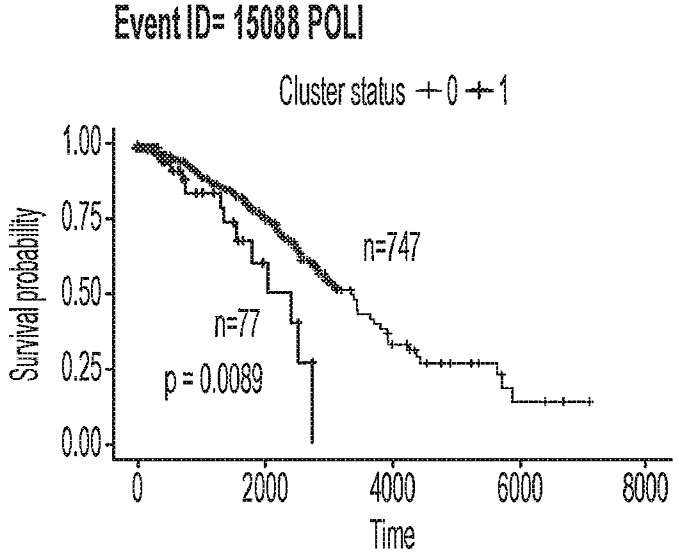
FIG. 5D: Survival analysis of breast cancer patients in cluster C3 versus the remaining breast cancer patients in TCGA. This analysis indicates that patients in C3 (expressing the exon) have a worse overall survival (shorter survival time, days).
Figure 6A:
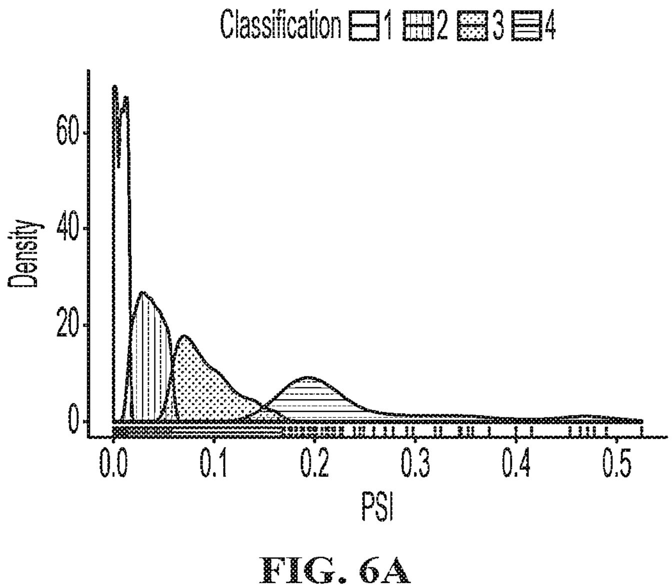
FIG. 6A: GMM analysis of mixed normal and breast cancer samples for the splicing event 16864 (PLXNB1 gene). The GMM analysis showed 4 distinct clusters (subpopulations). The x-axis indicates the exon PSI (ψ) level within samples, and y-axis denotes the number of samples in a normalized density scale. Shading indicates the cluster assignment of each sample.
Figure 6B:
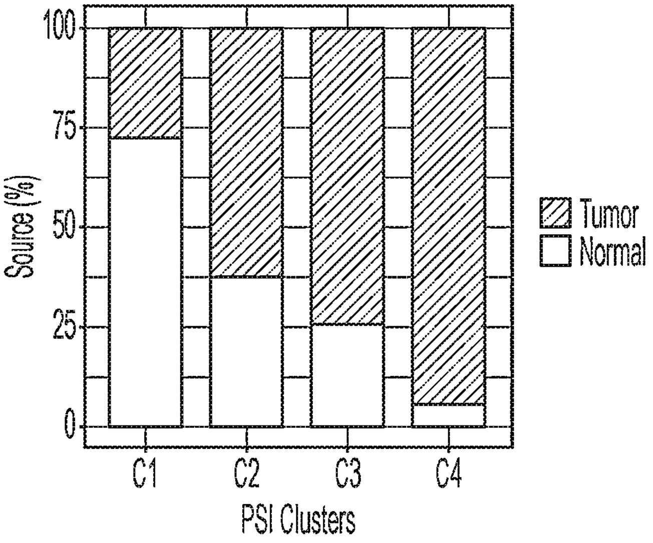
FIG. 6B: Frequency (%) of tumor and normal samples across the 4 clusters identified for the splicing event 16864 (PLXNB1 gene). Cluster 4 is composed mostly of breast cancer samples.
Figure 6C:
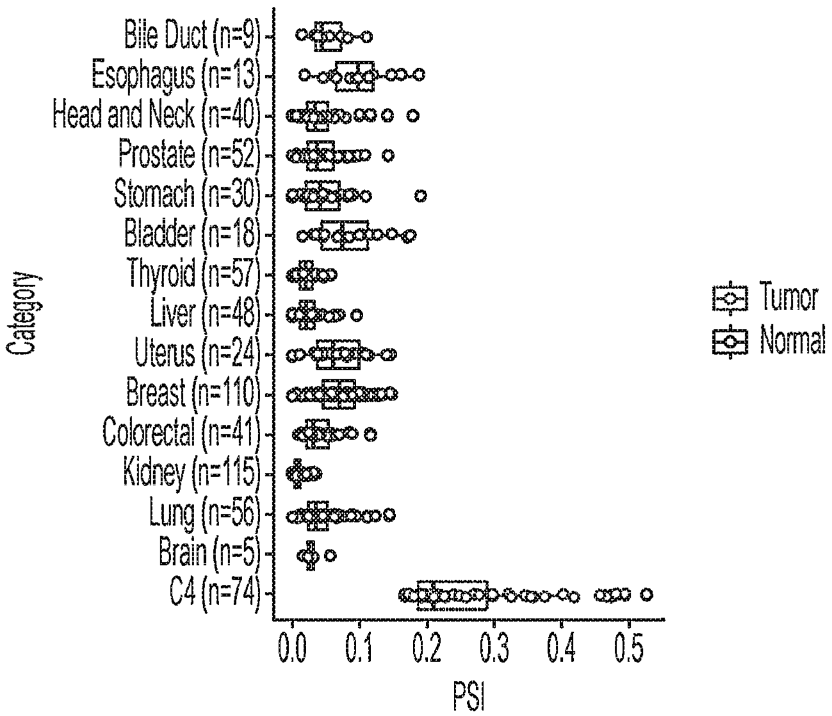
FIG. 6C: Exon splicing levels (PSI) for tumor specific cluster C4 and normal tissues in TCGA. This analysis indicates that the target exon is expressed in 74 breast cancer patients in cluster C4, while very low or absent in normal tissues.
Figure 6D:
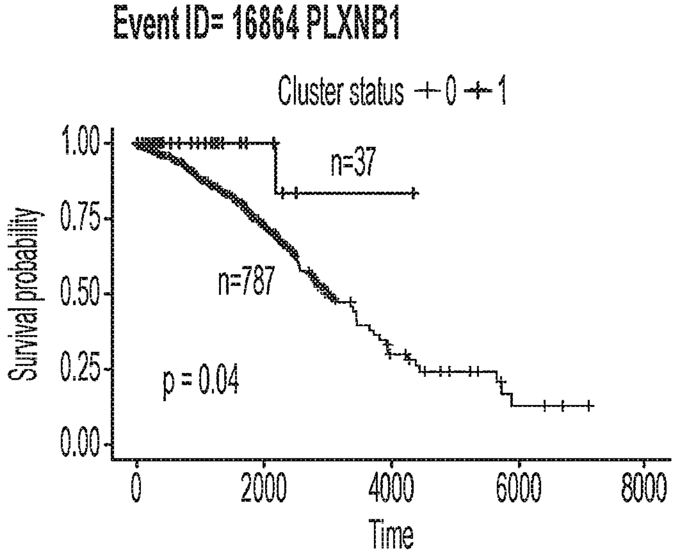
FIG. 6D: Survival analysis of breast cancer patients in cluster C4 versus the remaining breast cancer patients in TCGA. This analysis indicates that patients in C4 (expressing the target exon) have a better overall survival (longer survival time, days).
Figure 7A:
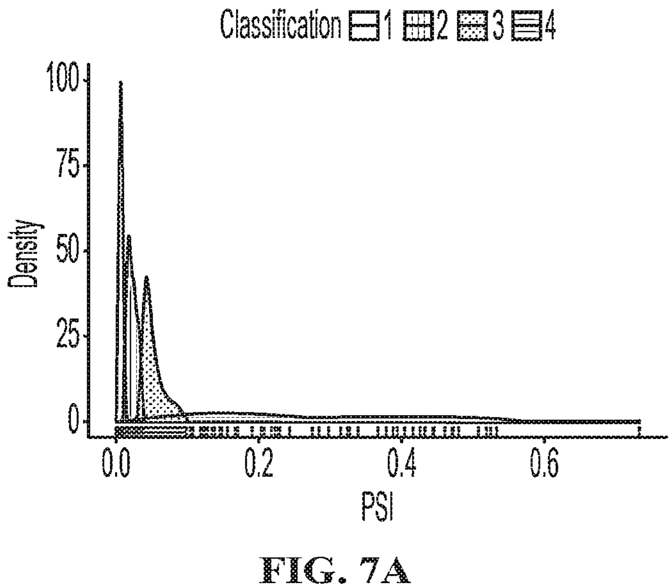
FIG. 7A: GMM analysis of mixed normal and breast cancer samples for the splicing event 21181 (SH3GLB1 gene). The GMM analysis showed 4 distinct clusters (subpopulations). The x-axis indicates the exon PSI (ψ) level within samples, and y-axis denotes the number of samples in a normalized density scale. Shading indicates the cluster assignment of each sample.
Figure 7B:
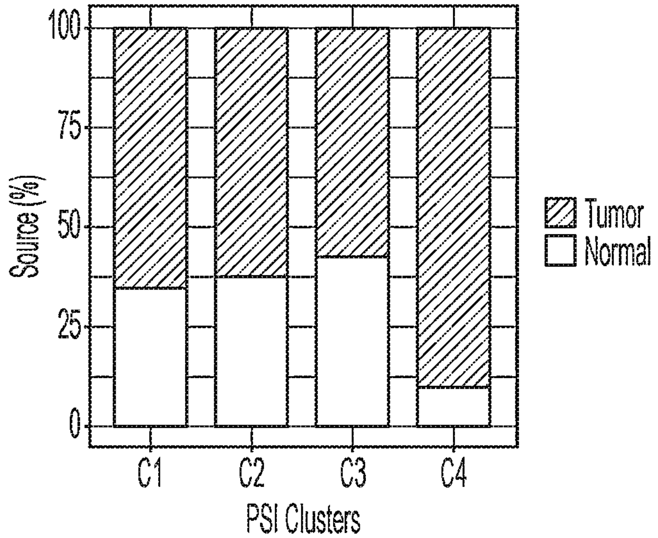
FIG. 7B: Frequency (%) of tumor and normal samples across the 4 clusters identified for the splicing event 21181 (SH3GLB1 gene). Cluster 4 is composed mostly of breast cancer samples.
Figure 7C:
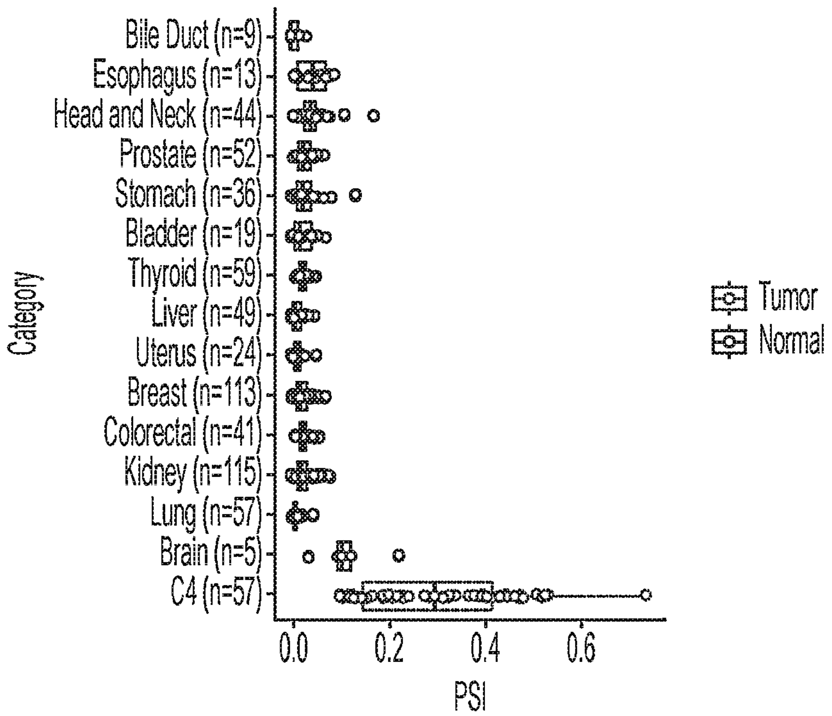
FIG. 7C: Exon splicing levels (PSI) for tumor specific cluster C4 and normal tissues in TCGA. This analysis indicates that the target exon is expressed in 57 breast cancer patients in cluster C4, while very low or absent in normal tissues.
Figure 7D:
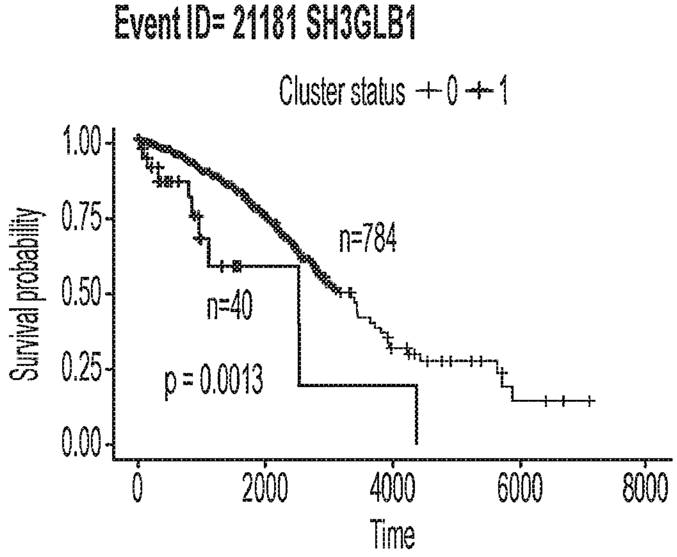
FIG. 7D: Survival analysis of breast cancer patients in cluster C4 versus the remaining breast cancer patients in TCGA. This analysis indicates that patients in C4 (expressing the target exon) have a worse overall survival (shorter survival time, days).
Figure 8A:
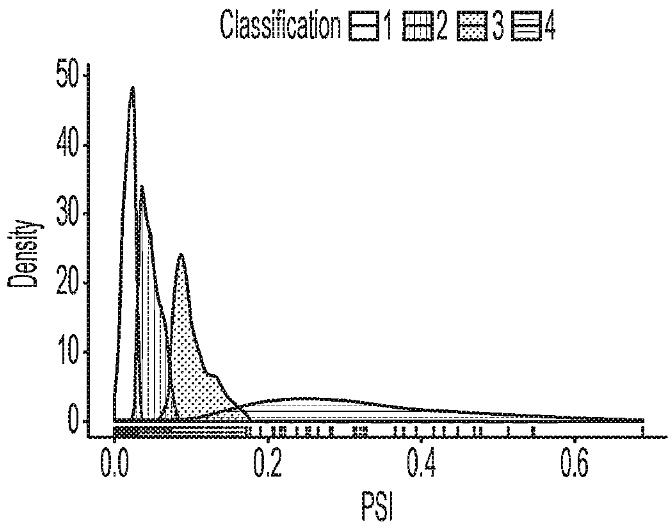
FIG. 8A: GMM analysis of mixed normal and breast cancer samples for the splicing event 34793 (TCF25 gene). The GMM analysis showed 4 distinct clusters (subpopulations). The x-axis indicates the exon PSI (ψ) level within samples, and y-axis denotes the number of samples in a normalized density scale. Shading indicates the cluster assignment of each sample.
Figure 8B:
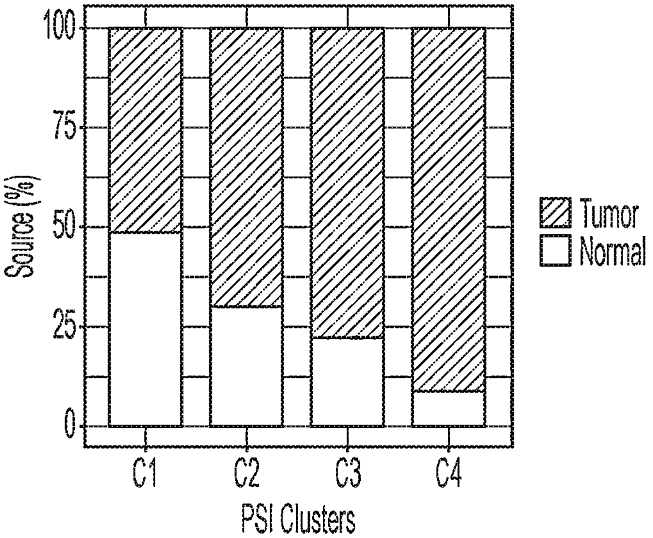
FIG. 8B: Frequency (%) of tumor and normal samples across the 4 clusters identified for the splicing event 34793 (TCF25 gene). Cluster 4 is composed mostly of breast cancer samples.
Figure 8C:
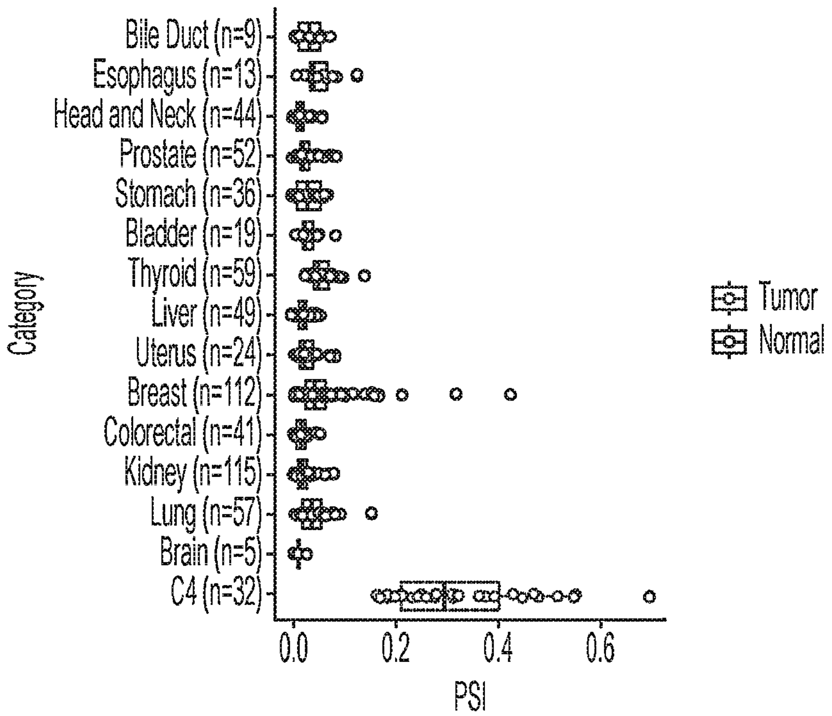
FIG. 8C: Exon splicing levels (PSI) for tumor specific cluster C4 and normal tissues in TCGA. This analysis indicates that the target exon is expressed in 32 breast cancer patients in cluster C4, while very low or absent in normal tissues.
Figure 8D:
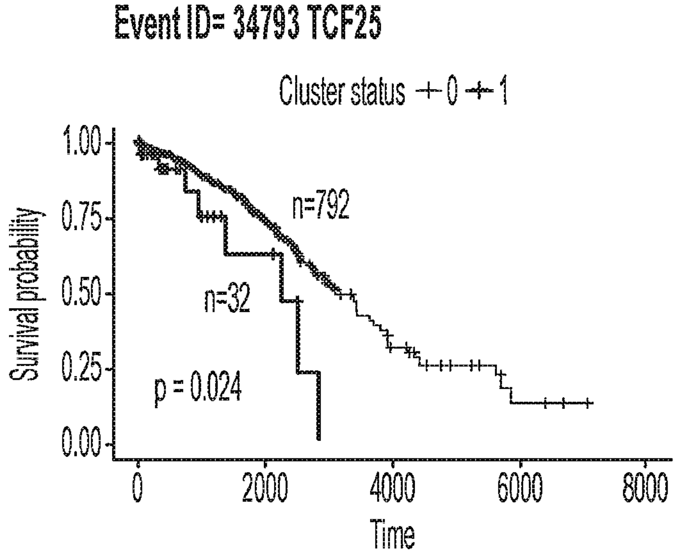
FIG. 8D: Survival analysis of breast cancer patients in cluster C4 versus the remaining breast cancer patients in TCGA. This analysis indicates that patients in C4 (expressing the target exon) have a worse overall survival (shorter survival time, days).
Figure 9A:
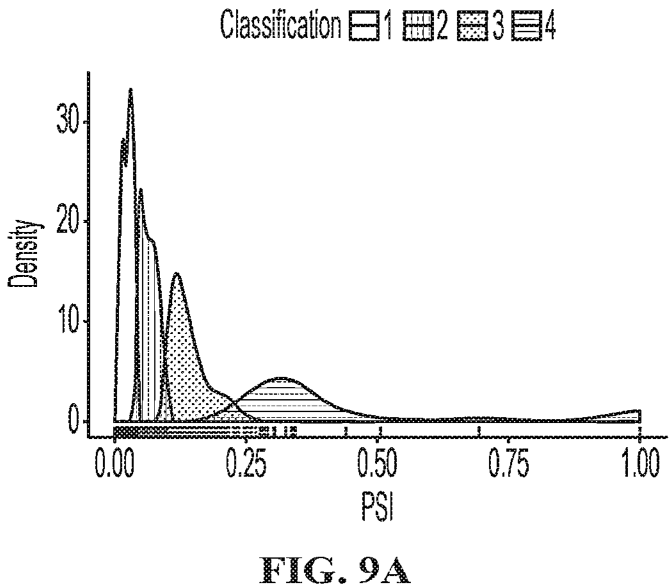
FIG. 9A: GMM analysis of mixed normal and breast cancer samples for the splicing event 42420 (PRR5-ARHGAP8 gene). The GMM analysis showed 4 distinct clusters (subpopulations). The x-axis indicates the exon PSI (ψ) level within samples, and y-axis denotes the number of samples in a normalized density scale. Shading indicates the cluster assignment of each sample.
Figure 9B:
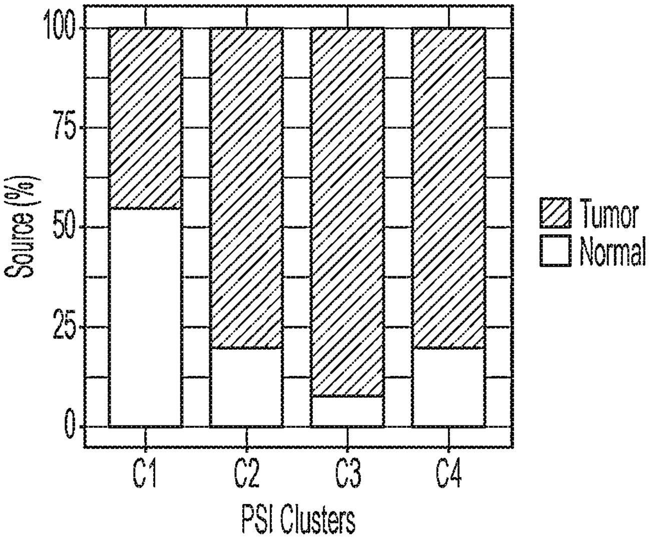
FIG. 9B: Frequency (%) of tumor and normal samples across the 4 clusters identified for the splicing event 42420 (PRR5-ARHGAP8 gene). Cluster 3 is composed mostly of breast cancer samples.
Figure 9C:
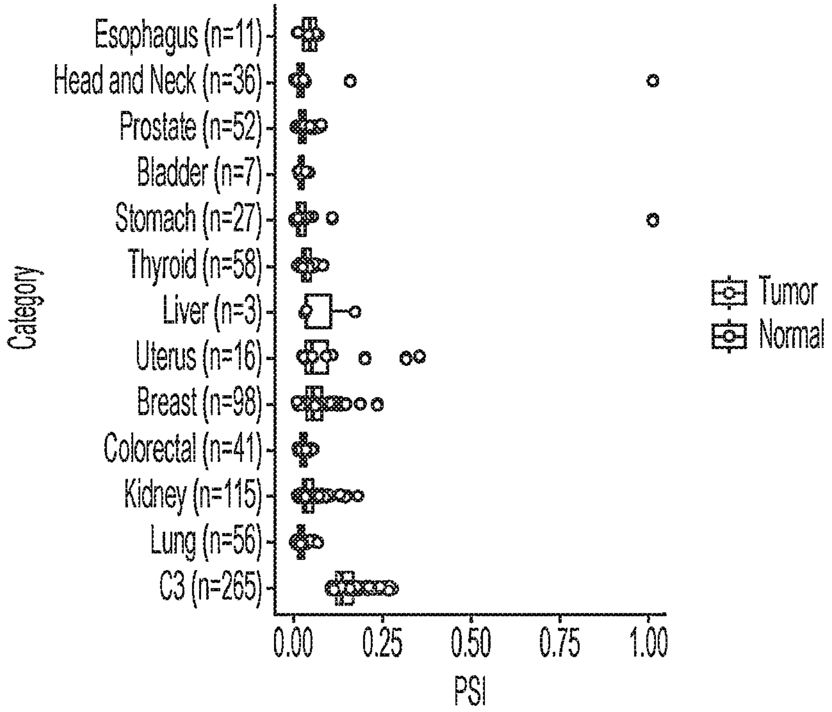
FIG. 9C: Exon splicing levels (PSI) for tumor specific cluster C3 and normal tissues in TCGA. This analysis indicates that the target exon is expressed in 265 breast cancer patients in cluster C3, while very low or absent in normal tissues.
Figure 9D:
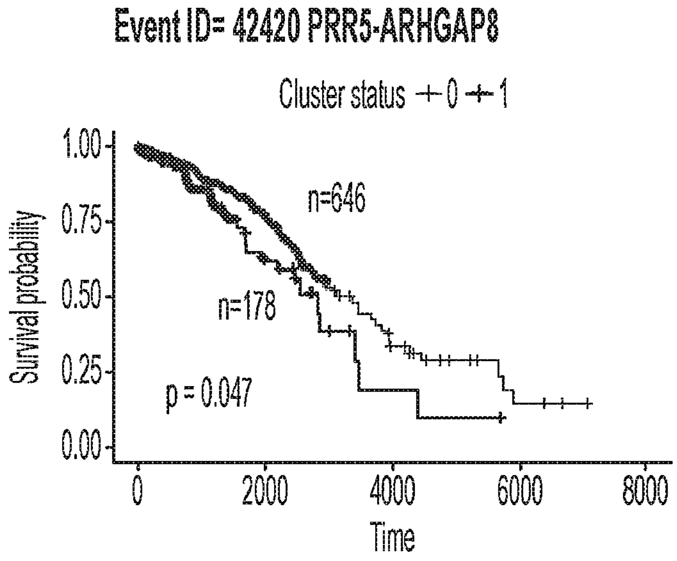
FIG. 9D: Survival analysis of breast cancer patients in cluster C3 versus the remaining breast cancer patients in TCGA. This analysis indicates that patients in C3 (expressing the target exon) have a worse overall survival (shorter survival time, days).
Figure 10A:
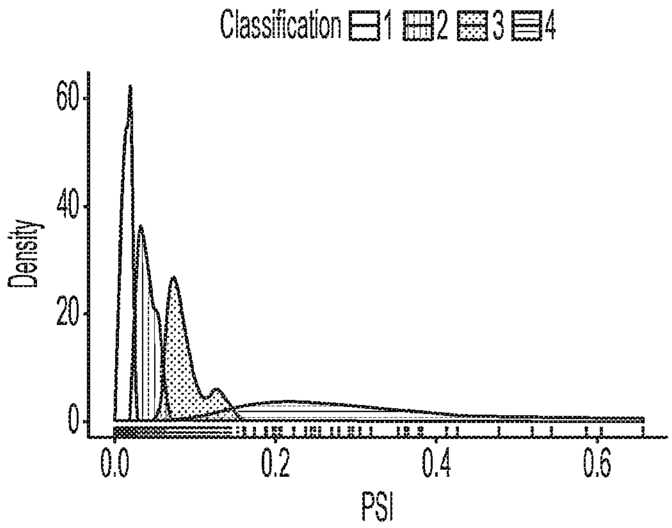
FIG. 10A: GMM analysis of mixed normal and breast cancer samples for the splicing event 4322 (WDR45B gene). The GMM analysis showed 4 distinct clusters (subpopulations). The x-axis indicates the exon PSI (ψ) level within samples, and y-axis denotes the number of samples in a normalized density scale. Shading indicates the cluster assignment of each sample.
Figure 10B:
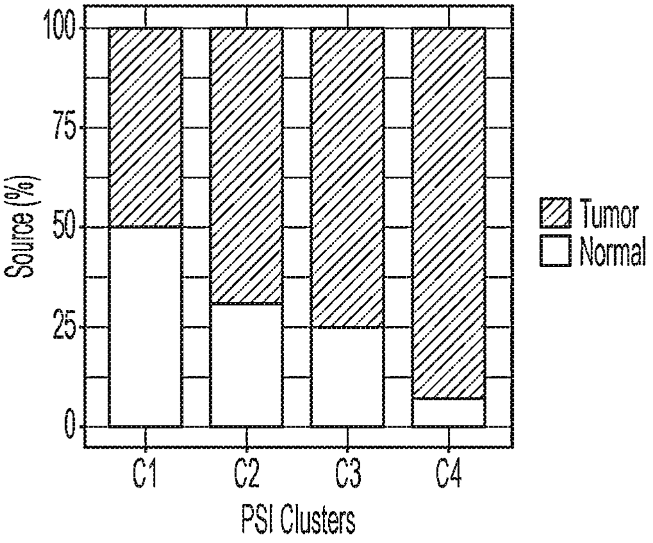
FIG. 10B: Frequency (%) of tumor and normal samples across the 4 clusters identified for the splicing event 4322 (WDR45B gene). Cluster 4 is composed mostly of breast cancer samples.
Figure 10C:
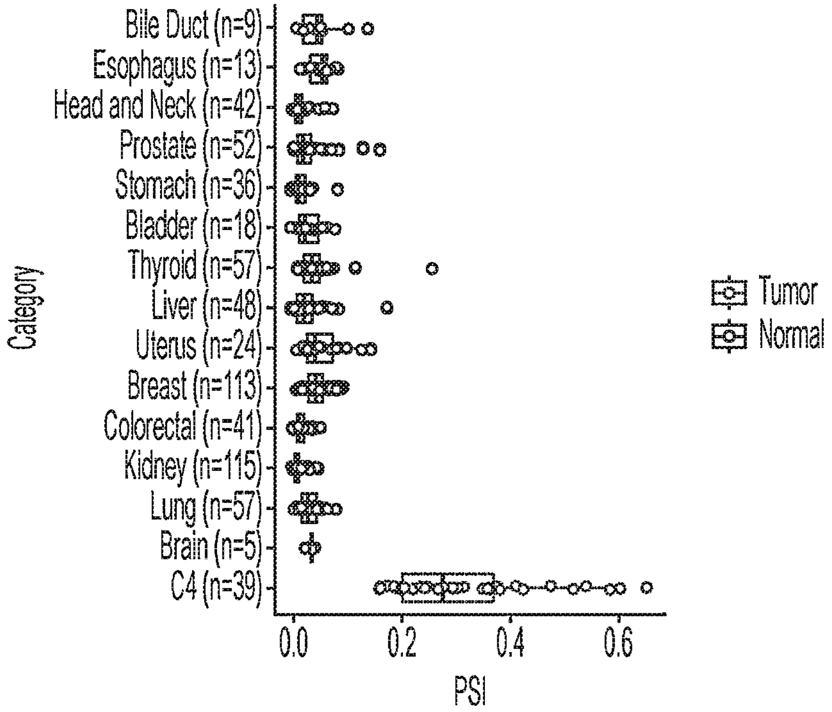
FIG. 10C: Exon splicing levels (PSI) for tumor specific cluster C4 and normal tissues in TCGA. This analysis indicates that the target exon is expressed in 39 breast cancer patients in cluster C4, while very low or absent in normal tissues.
Figure 10D:
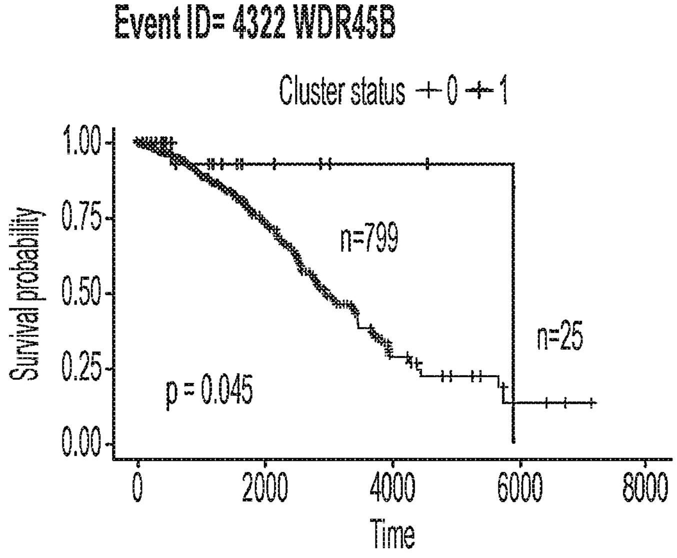
FIG. 10D: Survival analysis of breast cancer patients in cluster C4 versus the remaining breast cancer patients in TCGA. This analysis indicates that patients in C4 (expressing the target exon) have a better overall survival (longer survival time, days).
Figure 11A:
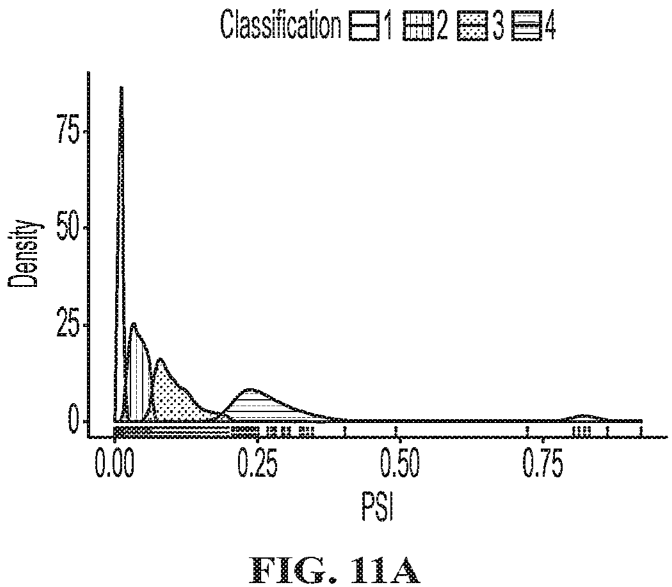
FIG. 11A: GMM analysis of mixed normal and breast cancer samples for the splicing event 44438 (VPS29 gene). The GMM analysis showed 4 distinct clusters (subpopulations). The x-axis indicates the exon PSI (ψ) level within samples, and y-axis denotes the number of samples in a normalized density scale. Shading indicates the cluster assignment of each sample.
Figure 11B:
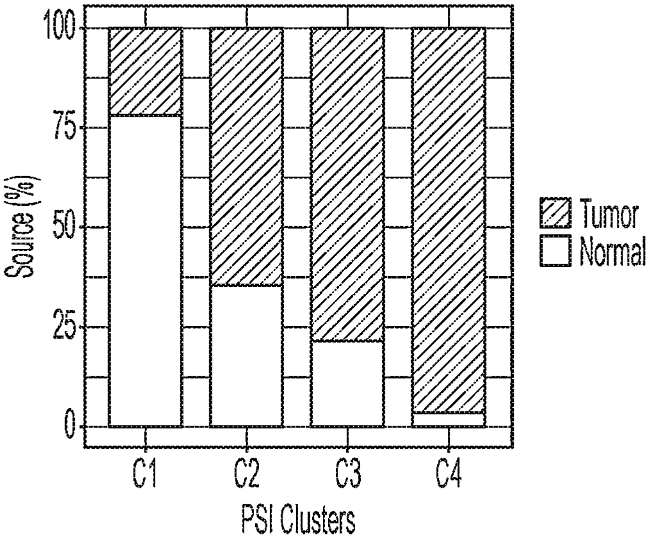
FIG. 11B: Frequency (%) of tumor and normal samples across the 4 clusters identified for the splicing event 44438 (VPS29 gene). Cluster 4 is composed mostly of breast cancer samples.
Figure 11C:
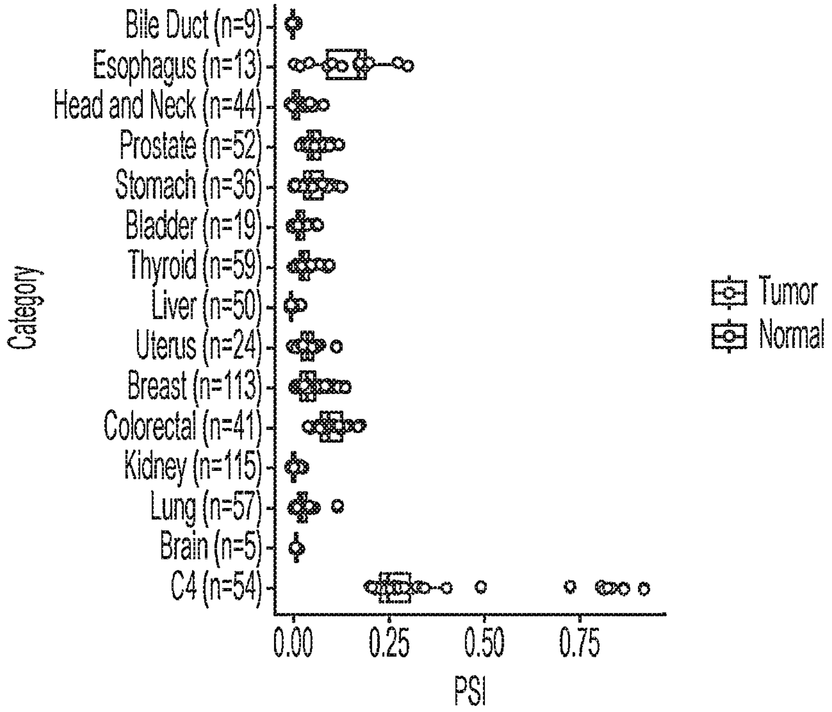
FIG. 11C: Exon splicing levels (PSI) for tumor specific cluster C4 and normal tissues in TCGA. This analysis indicates that the target exon is expressed in 54 breast cancer patients in cluster C4, while very low or absent in normal tissues.
Figure 11D:
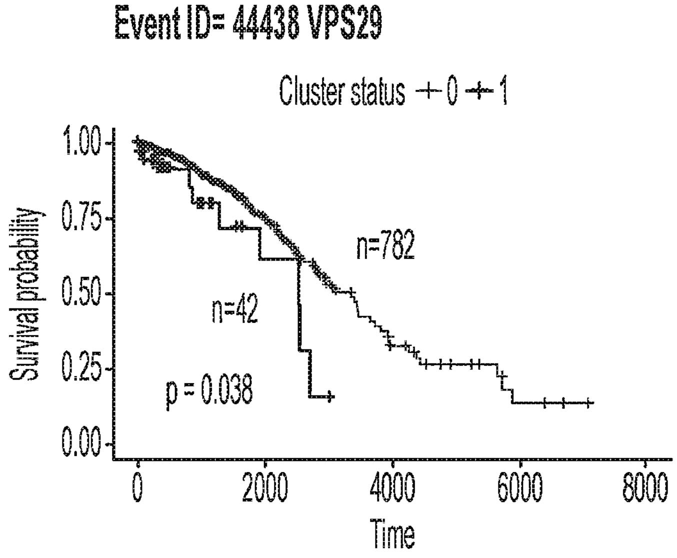
FIG. 11D: Survival analysis of breast cancer patients in cluster C4 versus the remaining breast cancer patients in TCGA. This analysis indicates that patients in C4 (expressing the target exon) have a worse overall survival (shorter survival time, days).
Figure 12A:
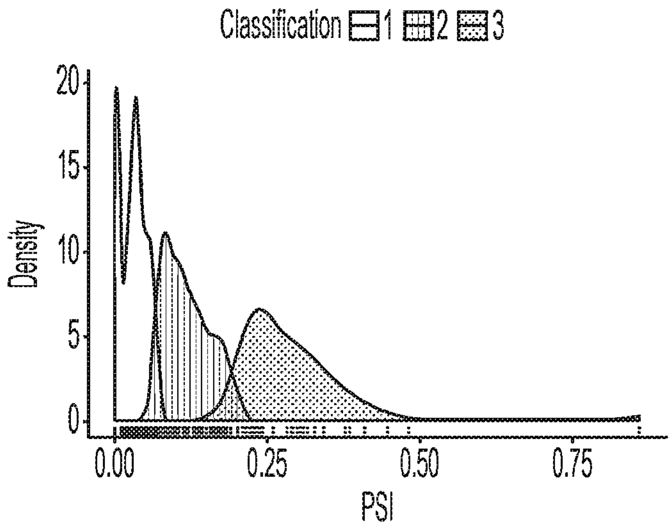
FIG. 12A: GMM analysis of mixed normal and breast cancer samples for the splicing event 48175 (E4F1 gene). The GMM analysis showed 3 distinct clusters (subpopulations). The x-axis indicates the exon PSI (ψ) level within samples, and y-axis denotes the number of samples in a normalized density scale. Shading indicates the cluster assignment of each sample.
Figure 12B:
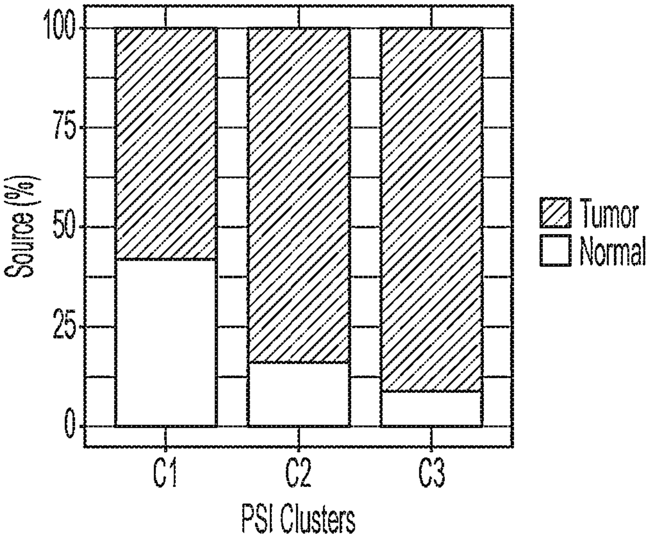
FIG. 12B: Frequency (%) of tumor and normal samples across the 3 clusters identified for the splicing event 48175 (E4F1 gene). Cluster 3 is composed mostly of breast cancer samples.
Figure 12C:
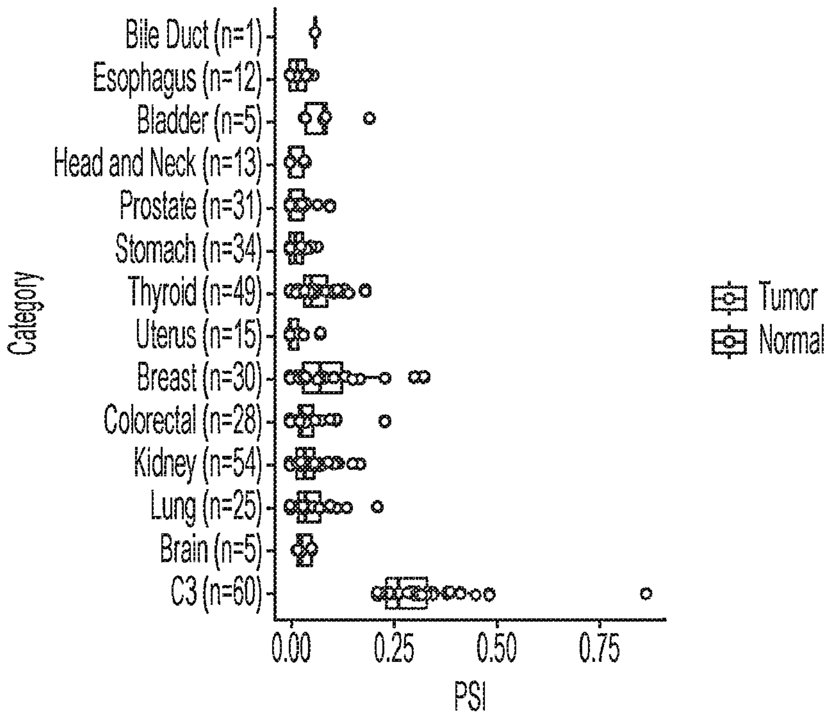
FIG. 12C: Exon splicing levels (PSI) for tumor specific cluster C3 and normal tissues in TCGA. This analysis indicates that the target exon is expressed in 60 breast cancer patients in cluster C3, while very low or absent in normal tissues.
Figure 12D:
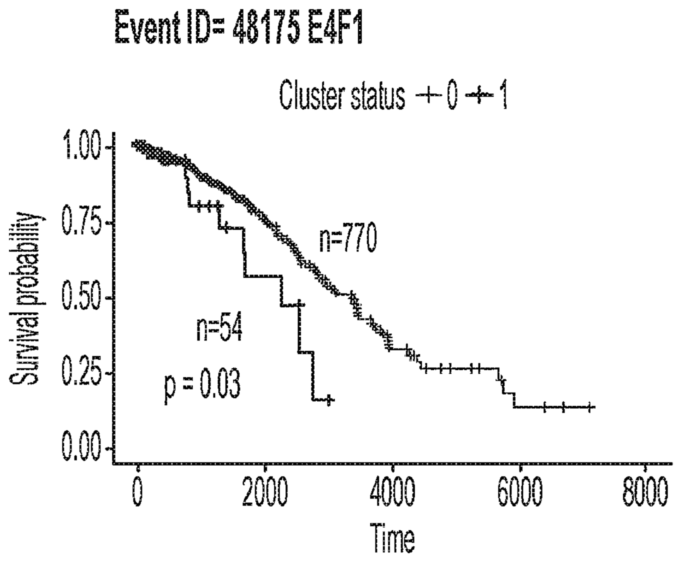
FIG. 12D: Survival analysis of breast cancer patients in cluster C3 versus the remaining breast cancer patients in TCGA. This analysis indicates that patients in C3 (expressing the target exon) have a worse overall survival (shorter survival time, days).
Figure 13A:
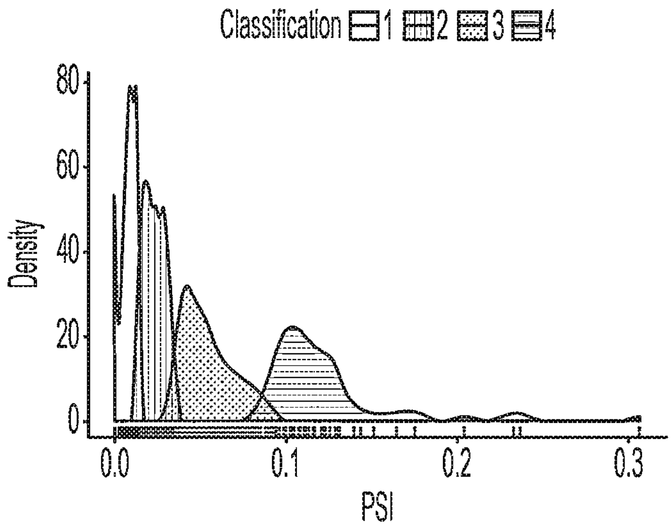
FIG. 13A: GMM analysis of mixed normal and breast cancer samples for the splicing event 49765 (TEN1-CDK3 gene). The GMM analysis showed 4 distinct clusters (subpopulations). The x-axis indicates the exon PSI (ψ) level within samples, and y-axis denotes the number of samples in a normalized density scale. Shading indicates the cluster assignment of each sample.
Figure 13B:
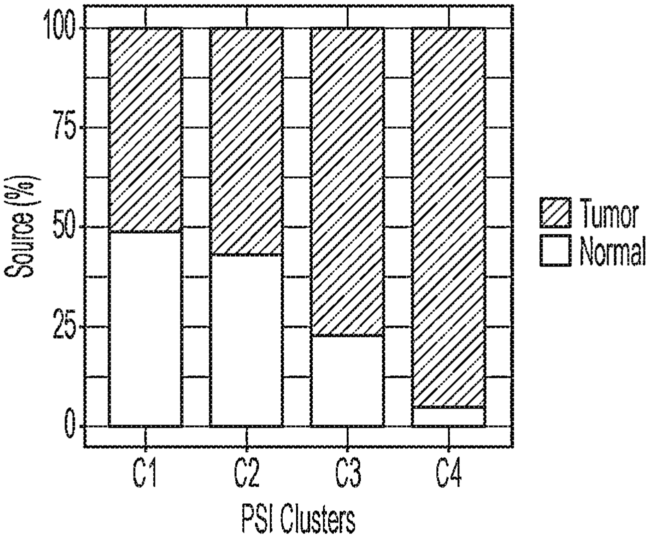
FIG. 13B: Frequency (%) of tumor and normal samples across the 4 clusters identified for the splicing event 49765 (TEN1-CDK3 gene). Cluster 4 is composed mostly of breast cancer samples.
Figure 13C:
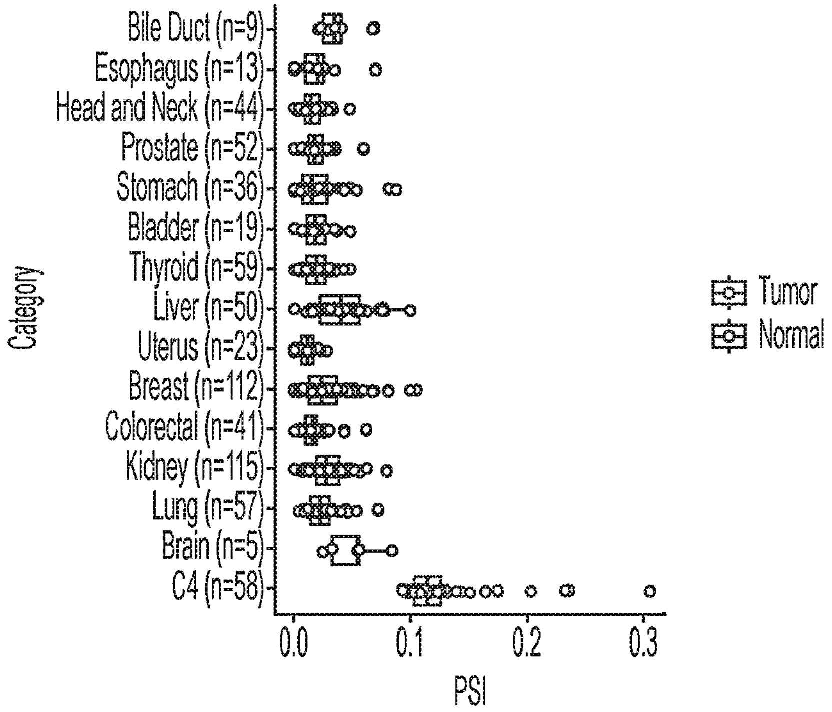
FIG. 13C: Exon splicing levels (PSI) for tumor specific cluster C4 and normal tissues in TCGA. This analysis indicates that the target exon is expressed in 58 breast cancer patients in cluster C4, while very low or absent in normal tissues.
Figure 13D:
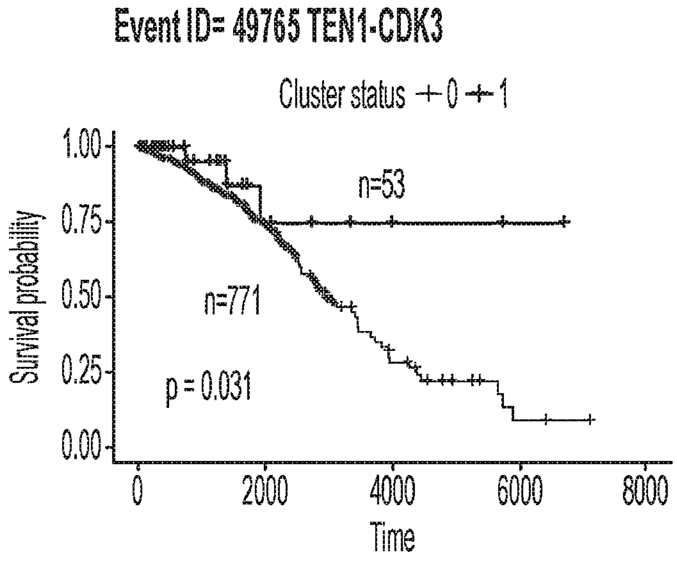
FIG. 13D: Survival analysis of breast cancer patients in cluster C4 versus the remaining breast cancer patients in TCGA. This analysis indicates that patients in C4 (expressing the target exon) have a better overall survival (longer survival time, days).
Figure 14A:
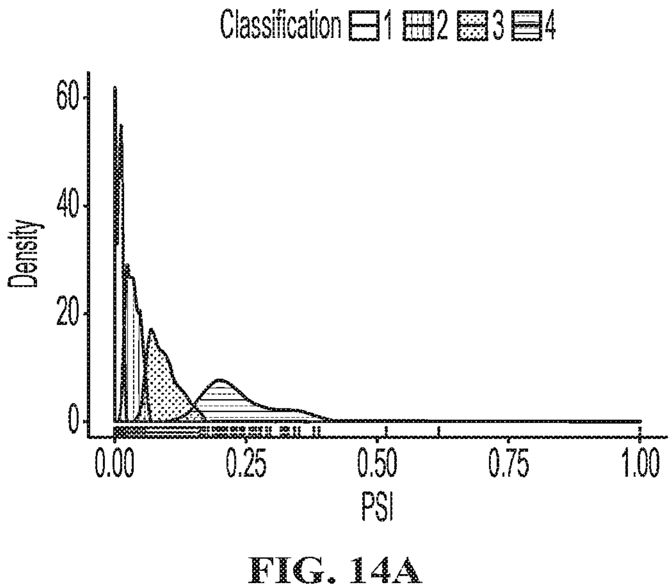
FIG. 14A: GMM analysis of mixed normal and breast cancer samples for the splicing event 5134 (PLEKHA6 gene). The GMM analysis showed 4 distinct clusters (subpopulations). The x-axis indicates the exon PSI (ψ) level within samples, and y-axis denotes the number of samples in a normalized density scale. Shading indicates the cluster assignment of each sample.
Figure 14B:
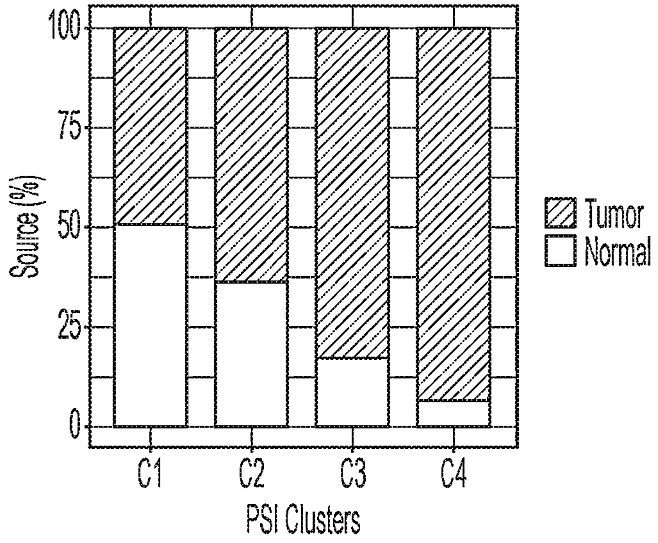
FIG. 14B: Frequency (%) of tumor and normal samples across the 4 clusters identified for the splicing event 5134 (PLEKHA6 gene). Cluster 4 is composed mostly of breast cancer samples.
Figure 14C:
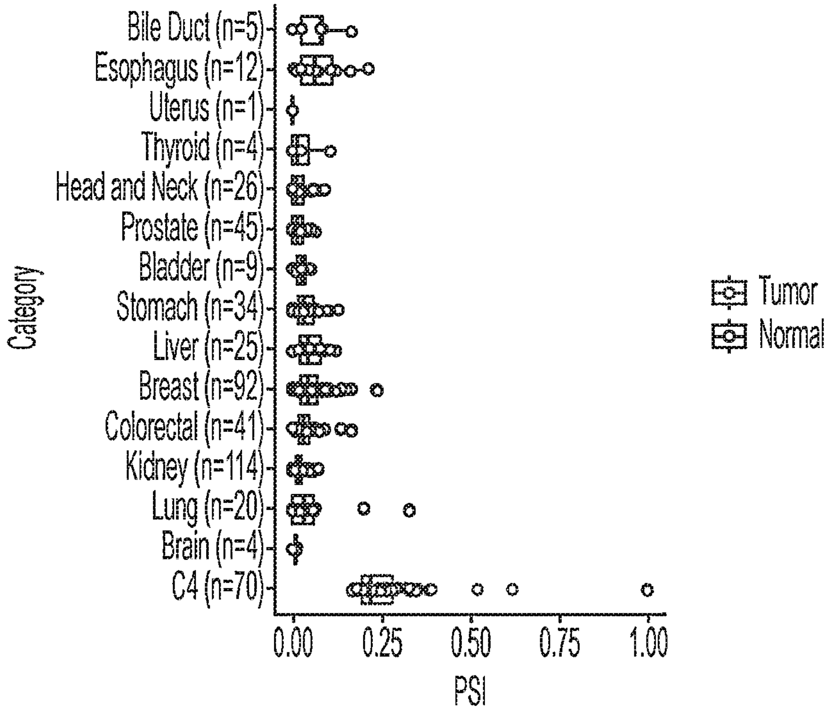
FIG. 14C: Exon splicing levels (PSI) for tumor specific cluster C4 and normal tissues in TCGA. This analysis indicates that the target exon is expressed in 70 breast cancer patients in cluster C4, while very low or absent in normal tissues.
Figure 14D:
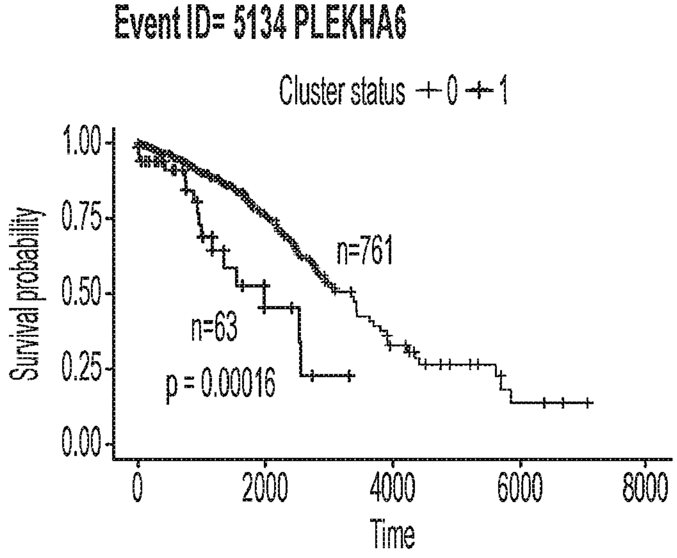
FIG. 14D: Survival analysis of breast cancer patients in cluster C4 versus the remaining breast cancer patients in TCGA. This analysis indicates that patients in C4 (expressing the target exon) have a worse overall survival (shorter survival time, days).
Figure 15A:
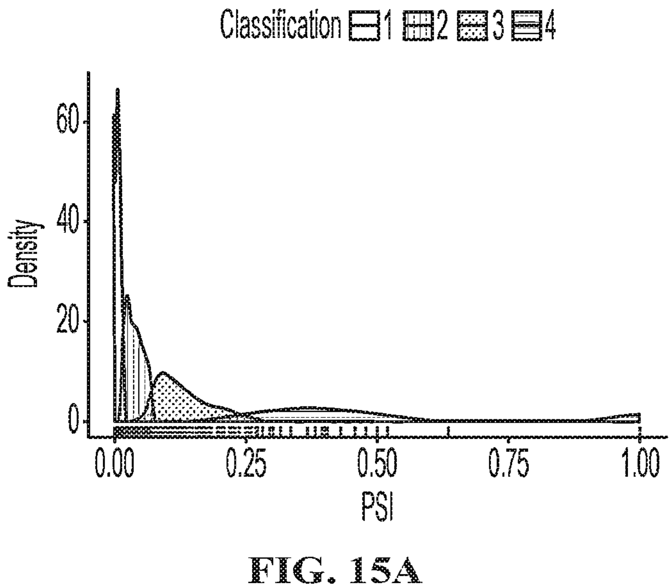
FIG. 15A: GMM analysis of mixed normal and breast cancer samples for the splicing event 56552 (GNAZ gene).
Figure 15B:
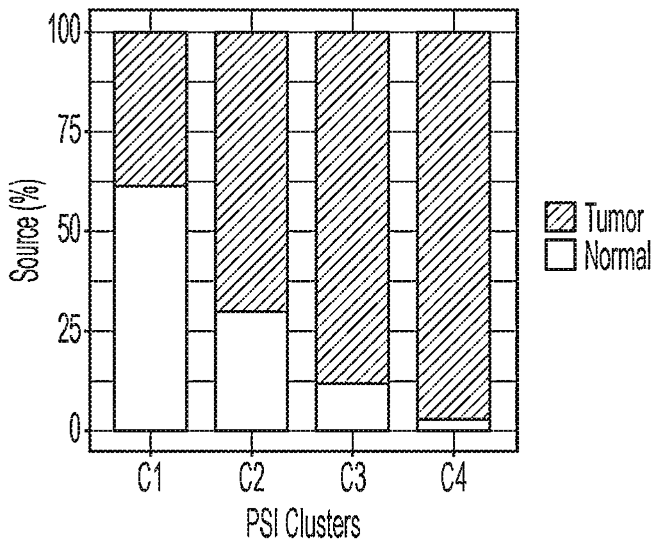
FIG. 15B: Frequency (%) of tumor and normal samples across the 4 clusters identified for the splicing event 56552 (GNAZ gene). Cluster 4 is composed mostly of breast cancer samples.
Figure 15C:
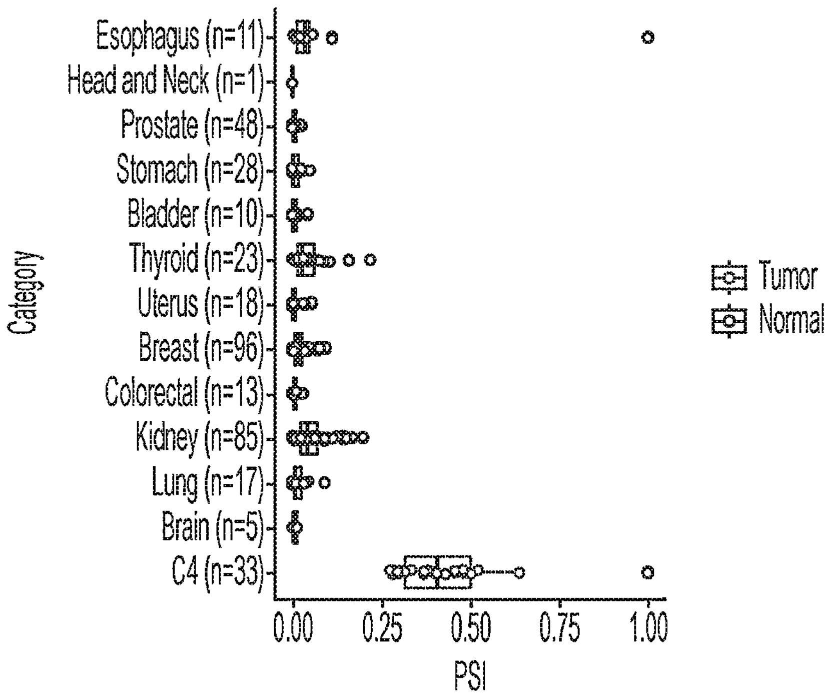
FIG. 15C: Exon splicing levels (PSI) for tumor specific cluster C4 and normal tissues in TCGA. This analysis indicates that the target exon is expressed in 33 breast cancer patients in cluster C4, while very low or absent in normal tissues.
Figure 15D:
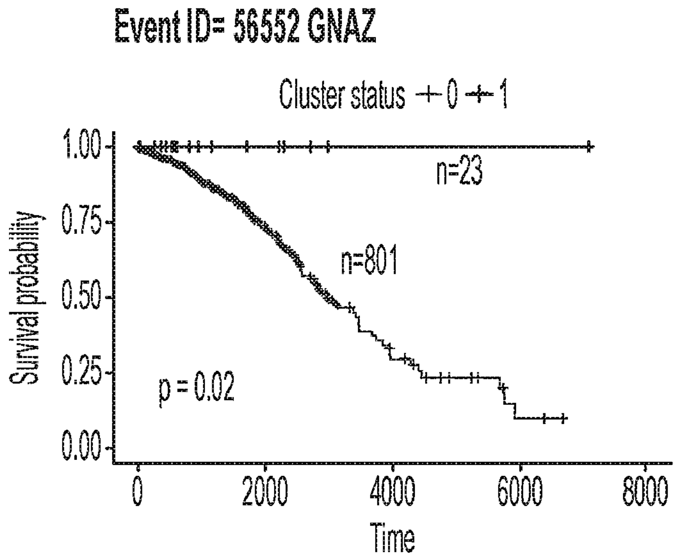
FIG. 15D: Survival analysis of breast cancer patients in cluster C4 versus the remaining breast cancer patients in TCGA. This analysis indicates that patients in C4 (expressing the target exon) have a better overall survival (longer survival time, days).
Figure 16A:
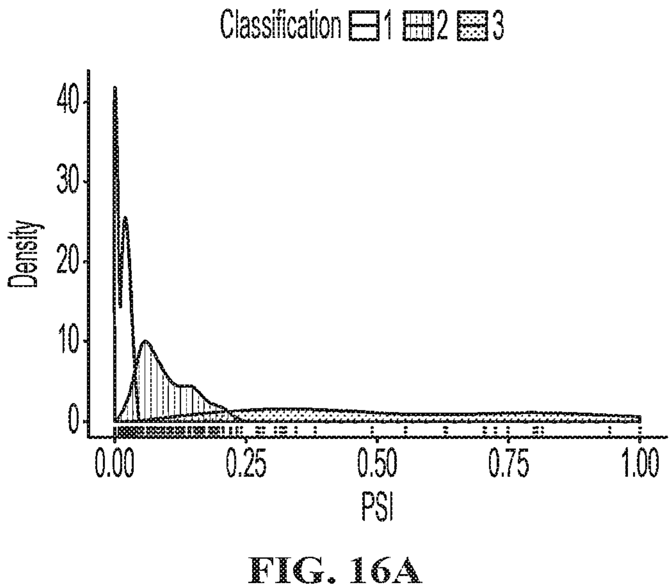
FIG. 16A: GMM analysis of mixed normal and breast cancer samples for the splicing event 5696 (TTC3 gene). The GMM analysis showed 3 distinct clusters (subpopulations). The x-axis indicates the exon PSI (ψ) level within samples, and y-axis denotes the number of samples in a normalized density scale. Shading indicates the cluster assignment of each sample.
Figure 16B:
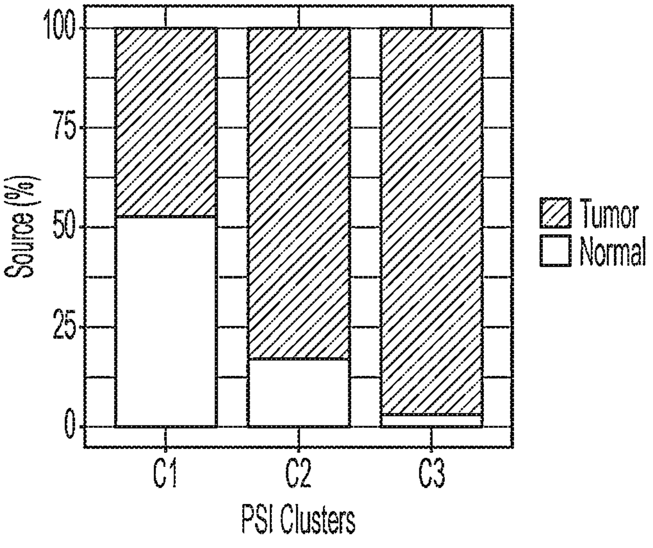
FIG. 16B: Frequency (%) of tumor and normal samples across the 3 clusters identified for the splicing event 5696 (TTC3 gene). Cluster 3 is composed mostly of breast cancer samples.
Figure 16C:
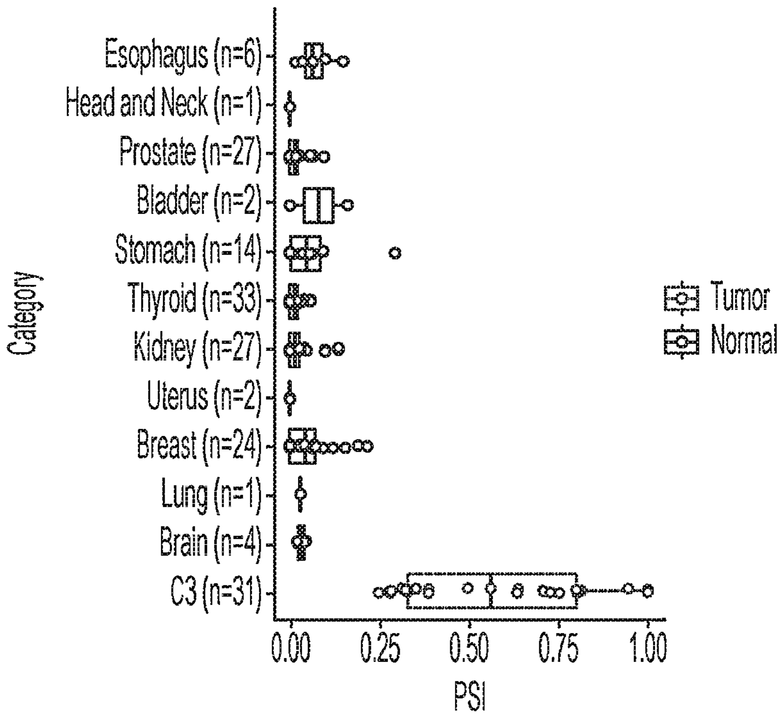
FIG. 16C: Exon splicing levels (PSI) for tumor specific cluster C3 and normal tissues in TCGA. This analysis indicates that the target exon is expressed in 31 breast cancer patients in cluster C3, while very low or absent in normal tissues.
Figure 16D:
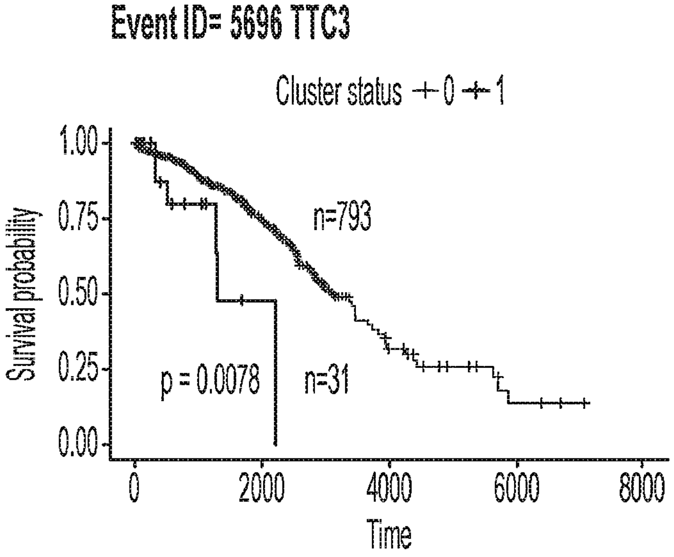
FIG. 16D: Survival analysis of breast cancer patients in cluster C3 versus the remaining breast cancer patients in TCGA. This analysis indicates that patients in C3 (expressing the target exon) have a worse overall survival (shorter survival time, days).
Figure 17A:
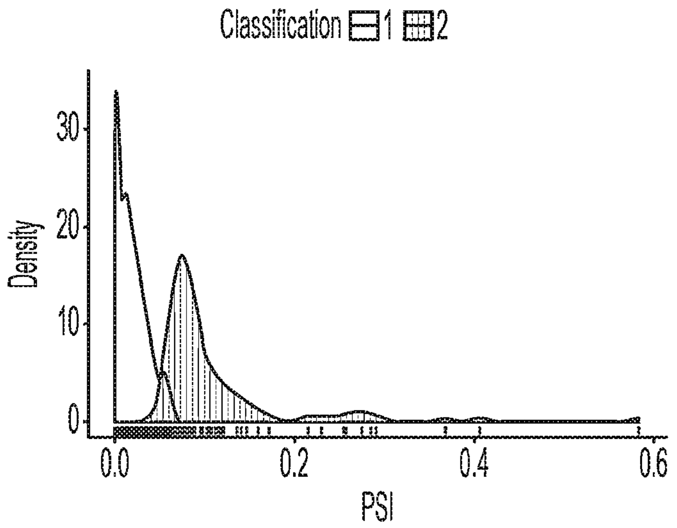
FIG. 17A: GMM analysis of mixed normal and breast cancer samples for the splicing event 57139 (RNF8 gene). The GMM analysis showed 2 distinct clusters (subpopulations). The x-axis indicates the exon PSI (ψ) level within samples, and y-axis denotes the number of samples in a normalized density scale. Shading indicates the cluster assignment of each sample.
Figure 17B:
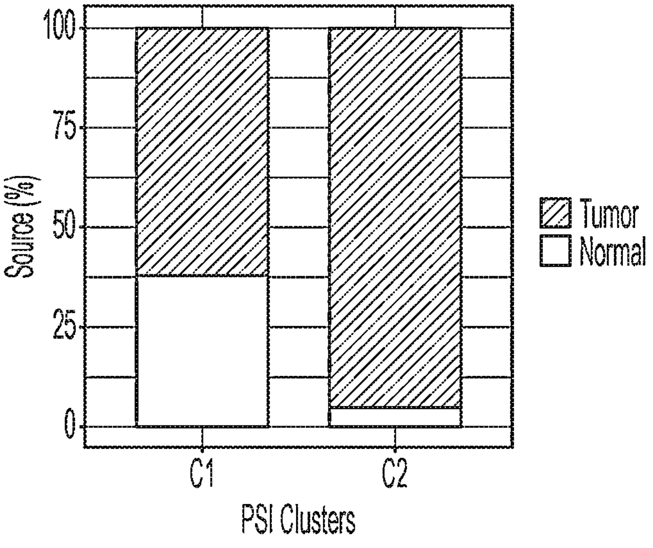
FIG. 17B: Frequency (%) of tumor and normal samples across the 2 clusters identified for the splicing event 57139 (RNF8 gene). Cluster 2 is composed mostly of breast cancer samples.
Figure 17C:
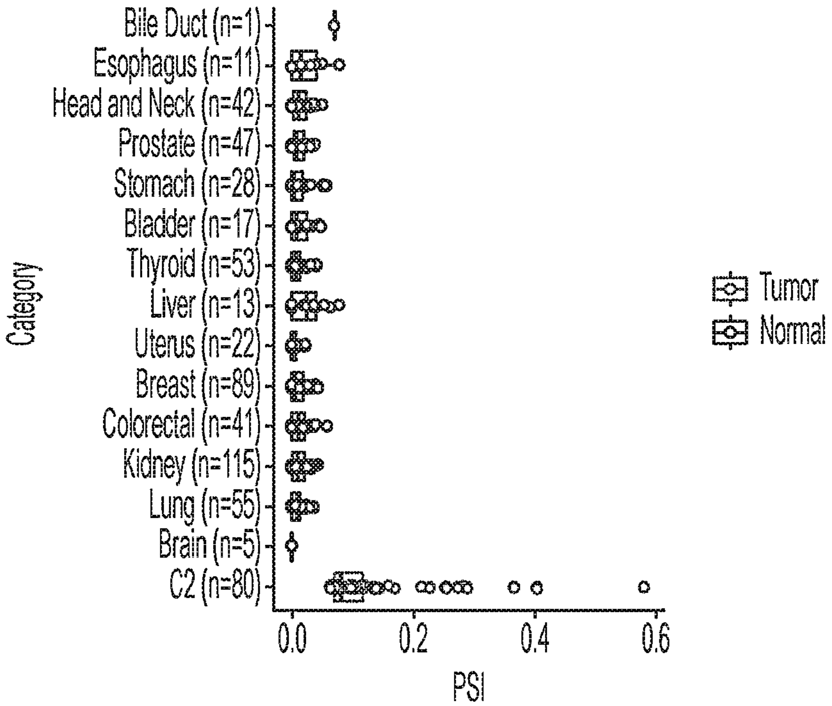
FIG. 17C: Exon splicing levels (PSI) for tumor specific cluster C2 and normal tissues in TCGA. This analysis indicates that the target exon is expressed in 80 breast cancer patients in cluster C2, while very low or absent in normal tissues.
Figure 17D:
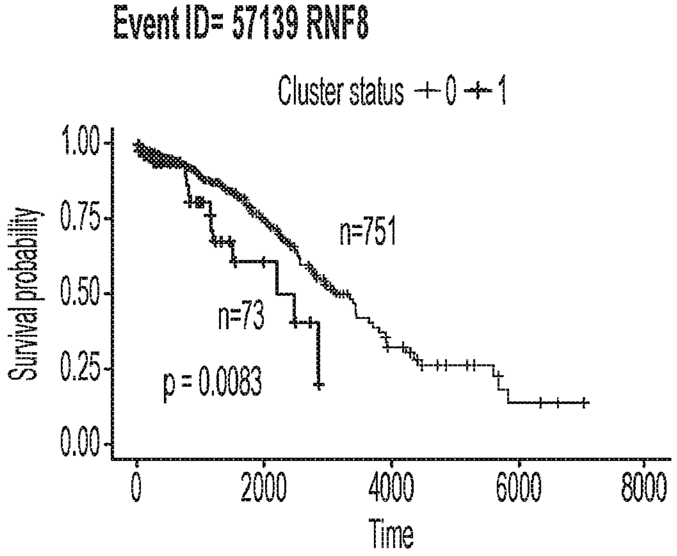
FIG. 17D: Survival analysis of breast cancer patients in cluster C2 versus the remaining breast cancer patients in TCGA. This analysis indicates that patients in C2 (expressing the target exon) have a worse overall survival (shorter survival time, days).
Figure 18A:
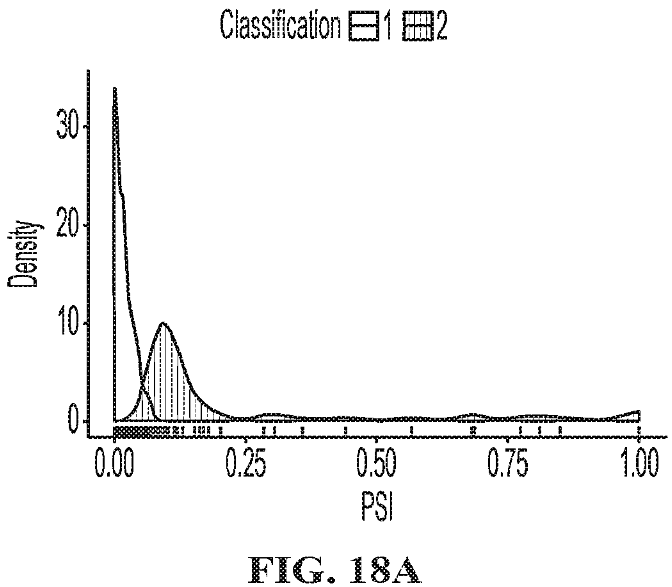
FIG. 18A: GMM analysis of mixed normal and breast cancer samples for the splicing event 57874 (ZDHHC13 gene). The GMM analysis showed 2 distinct clusters (subpopulations). The x-axis indicates the exon PSI (ψ) level within samples, and y-axis denotes the number of samples in a normalized density scale. Shading indicates the cluster assignment of each sample.
Figure 18B:
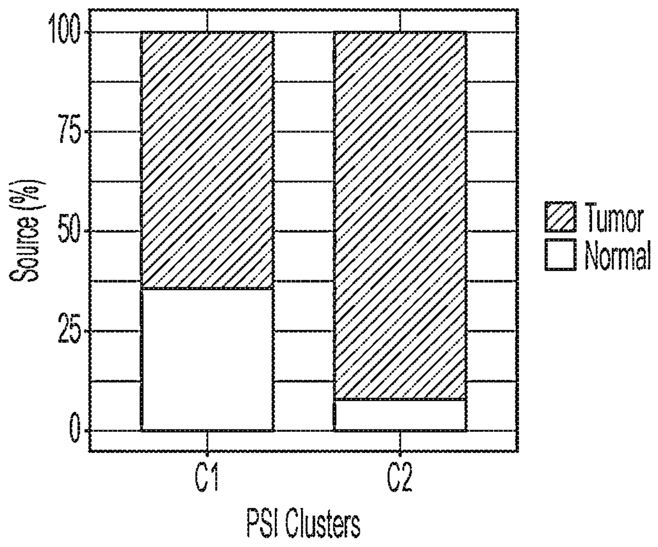
FIG. 18B: Frequency (%) of tumor and normal samples across the 2 clusters identified for the splicing event 57874 (ZDHHC13 gene). Cluster 2 is composed mostly of breast cancer samples.
Figure 18C:
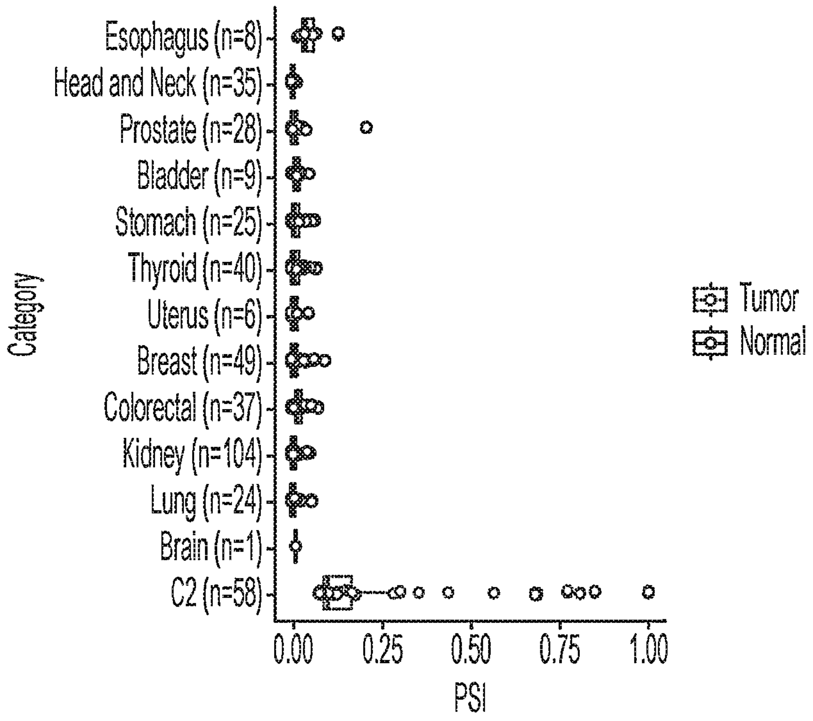
FIG. 18C: Exon splicing levels (PSI) for tumor specific cluster C2 and normal tissues in TCGA. This analysis indicates that the target exon is expressed in 58 breast cancer patients in cluster C2, while very low or absent in normal tissues.
Figure 18D:
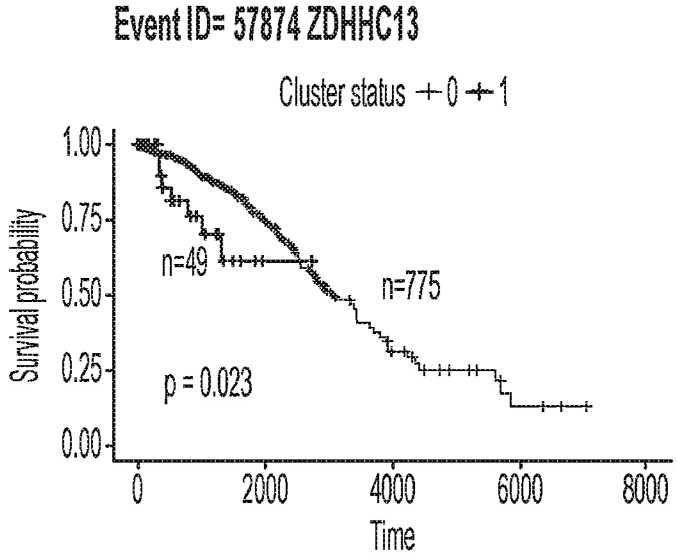
FIG. 18D: Survival analysis of breast cancer patients in cluster C2 versus the remaining breast cancer patients in TCGA. This analysis indicates that patients in C2 (expressing the target exon) have a worse overall survival (shorter survival time, days).
Figure 19A:
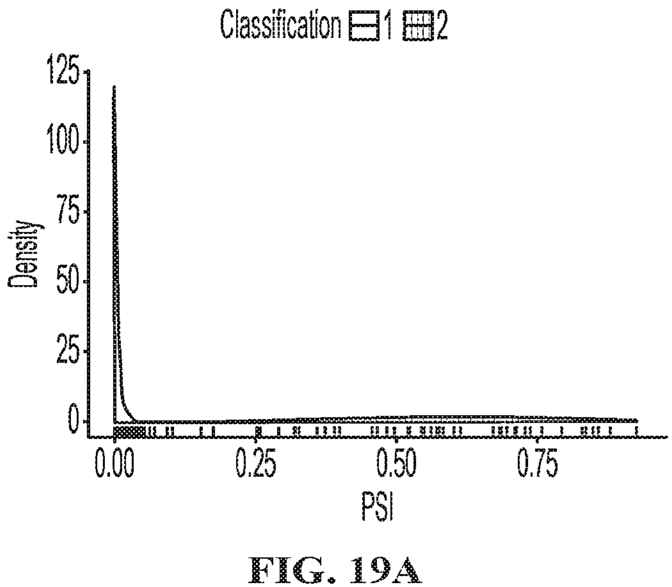
FIG. 19A: GMM analysis of mixed normal and breast cancer samples for the splicing event 60615 (SH3GLB2 gene). The GMM analysis showed 2 distinct clusters (subpopulations). The x-axis indicates the exon PSI (ψ) level within samples, and y-axis denotes the number of samples in a normalized density scale. Shading indicates the cluster assignment of each sample.
Figure 19B:
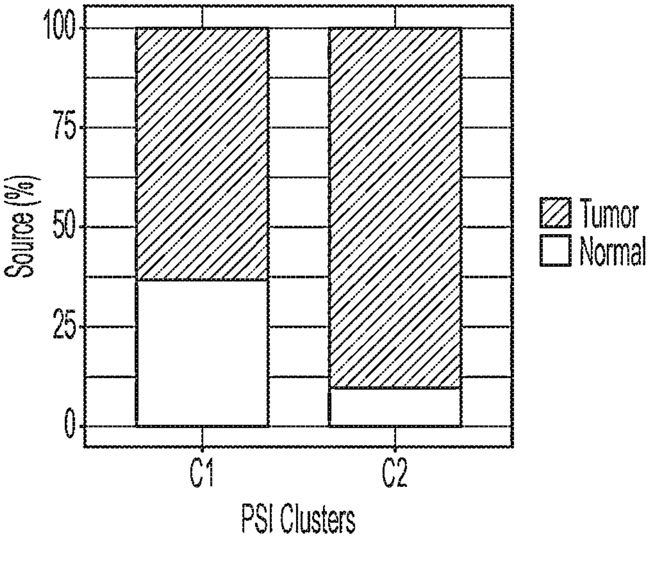
FIG. 19B: Frequency (%) of tumor and normal samples across the 2 clusters identified for the splicing event 60615 (SH3GLB2 gene). Cluster 2 is composed mostly of breast cancer samples.
Figure 19C:
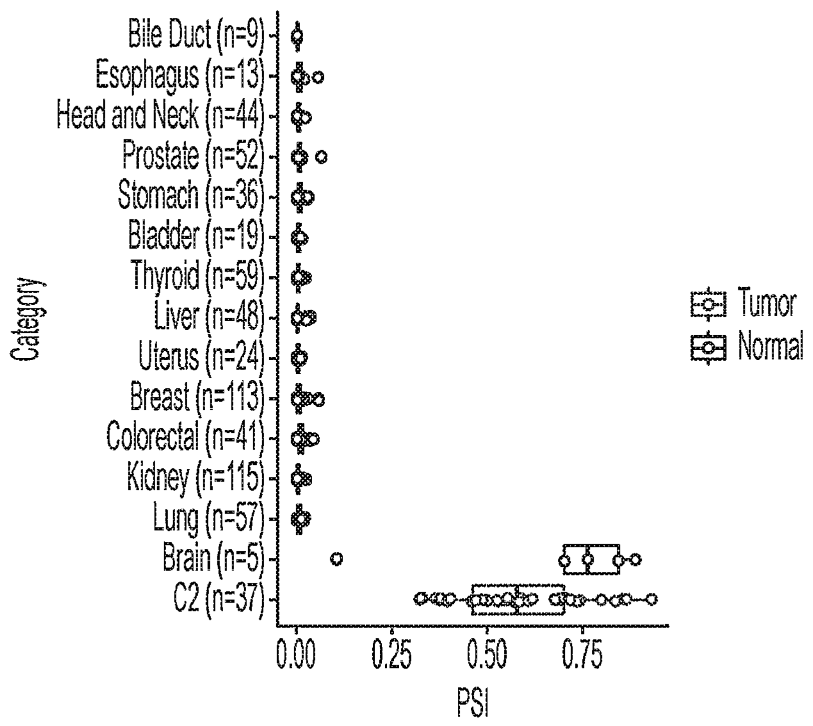
FIG. 19C: Exon splicing levels (PSI) for tumor specific cluster C2 and normal tissues in TCGA. This analysis indicates that the target exon is expressed in 37 breast cancer patients in cluster C2, while very low or absent in normal tissues.
Figure 19D:
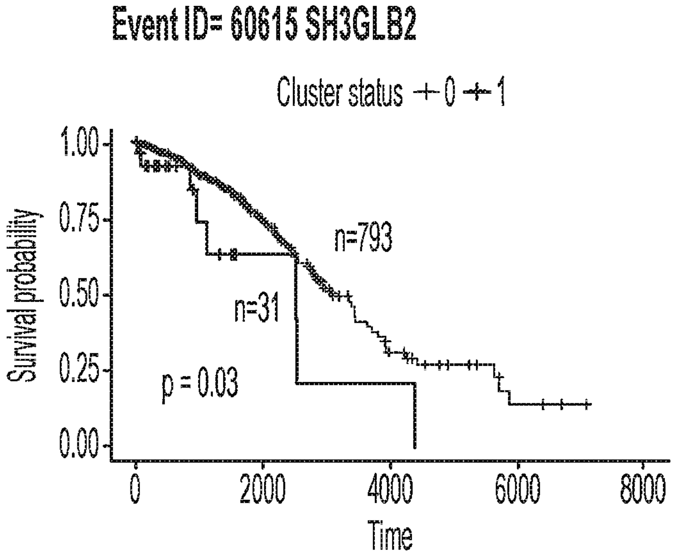
FIG. 19D: Survival analysis of breast cancer patients in cluster C2 versus the remaining breast cancer patients in TCGA. This analysis indicates that patients in C2 (expressing the target exon) have a worse overall survival (shorter survival time, days).
Figure 20A:
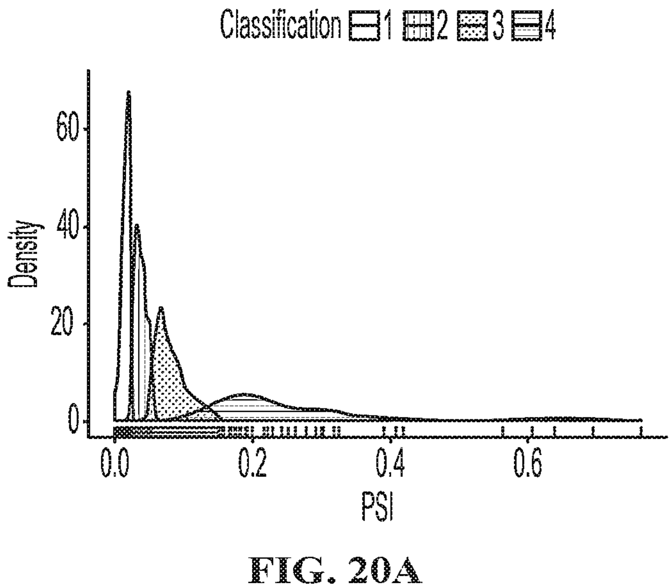
FIG. 20A: GMM analysis of mixed normal and breast cancer samples for the splicing event 62560 (ITFG1 gene). The GMM analysis showed 4 distinct clusters (subpopulations). The x-axis indicates the exon PSI (ψ) level within samples, and y-axis denotes the number of samples in a normalized density scale. Shading indicate the cluster assignment of each sample.
Figure 20B:
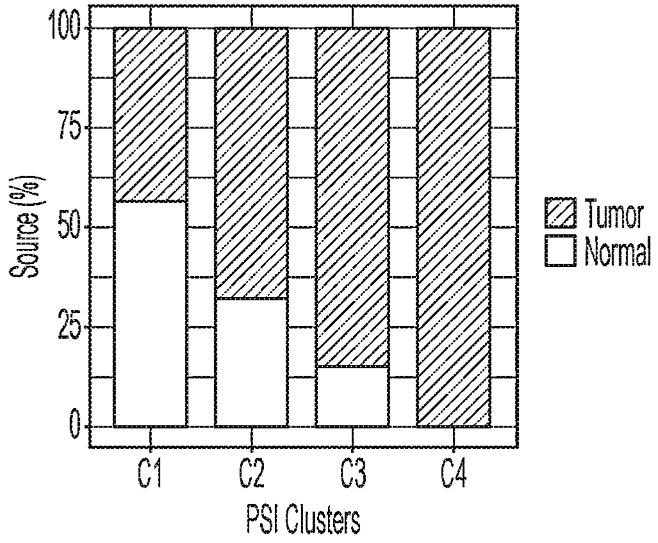
FIG. 20B: Frequency (%) of tumor and normal samples across the 4 clusters identified for the splicing event 62560 (ITFG1 gene). Cluster 4 is composed mostly of breast cancer samples.
Figure 20C:
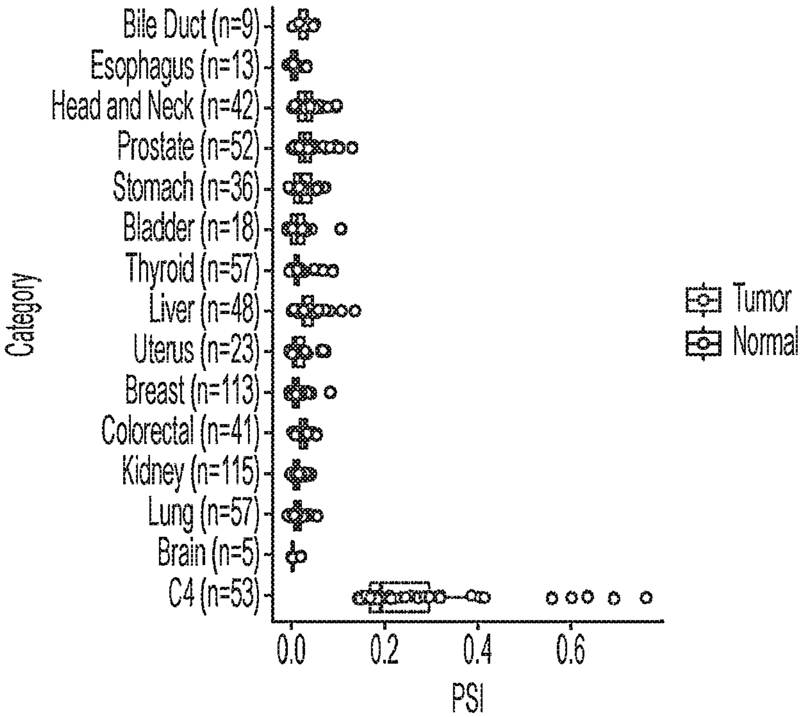
FIG. 20C: Exon splicing levels (PSI) for tumor specific cluster C4 and normal tissues in TCGA. This analysis indicates that the target exon is expressed in 53 breast cancer patients in cluster C4, while very low or absent in normal tissues.
Figure 20D:
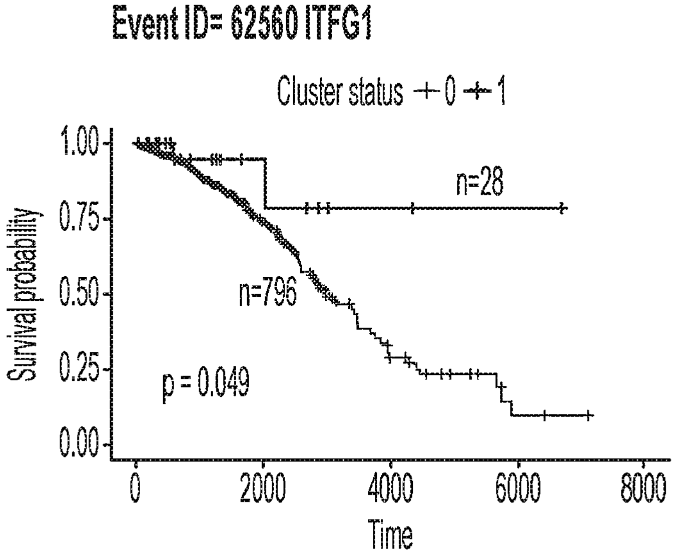
FIG. 20D: Survival analysis of breast cancer patients in cluster C4 versus the remaining breast cancer patients in TCGA. This analysis indicates that patients in C4 (expressing the target exon) have a better overall survival (longer survival time, days).
Figure 21A:
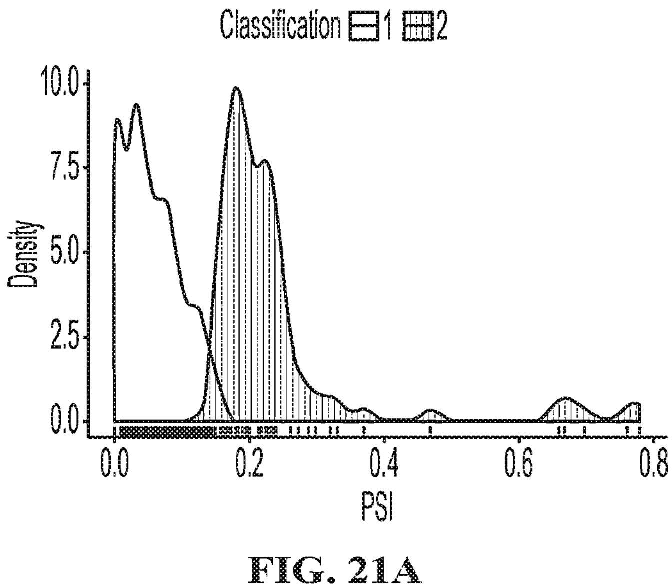
FIG. 21A: GMM analysis of mixed normal and breast cancer samples for the splicing event 6785 (SPATS2 gene). The GMM analysis showed 2 distinct clusters (subpopulations). The x-axis indicates the exon PSI (ψ) level within samples, and y-axis denotes the number of samples in a normalized density scale. Shading indicates the cluster assignment of each sample.
Figure 21B:
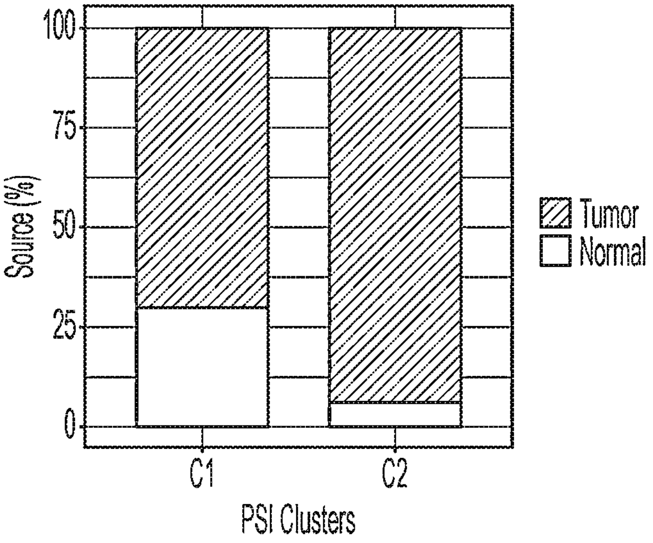
FIG. 21B: Frequency (%) of tumor and normal samples across the 2 clusters identified for the splicing event 6785 (SPATS2 gene). Cluster 2 is composed mostly of breast cancer samples.
Figure 21C:
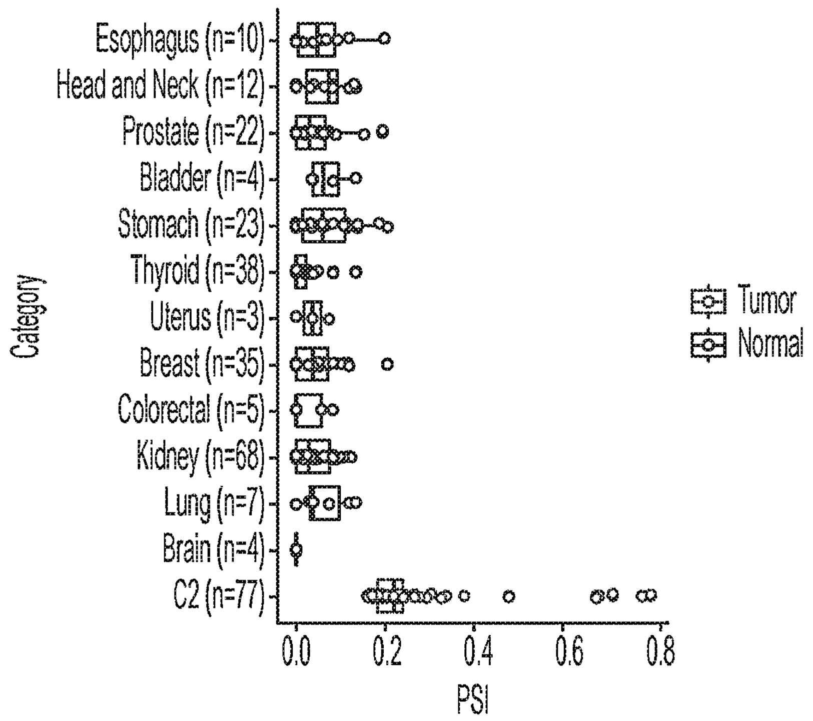
FIG. 21C: Exon splicing levels (PSI) for tumor specific cluster C2 and normal tissues in TCGA. This analysis indicates that the target exon is expressed in 77 breast cancer patients in cluster C2, while very low or absent in normal tissues.
Figure 21D:
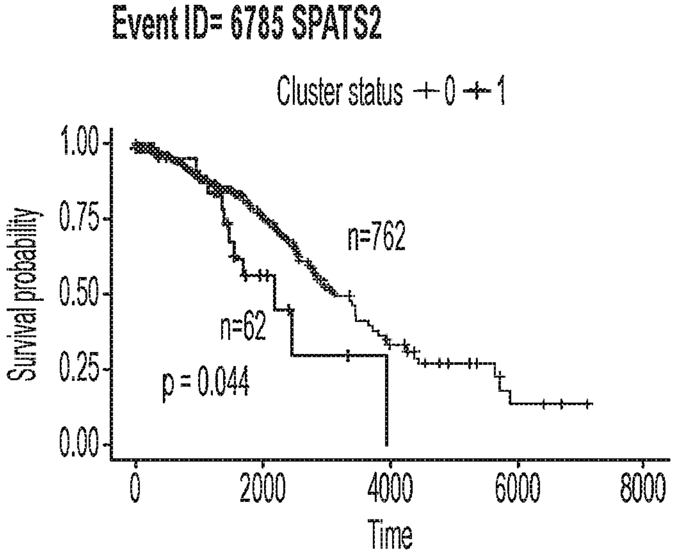
FIG. 21D: Survival analysis of breast cancer patients in cluster C2 versus the remaining breast cancer patients in TCGA. This analysis indicates that patients in C2 (expressing the target exon) have a worse overall survival (shorter survival time, days).
Figure 22A:
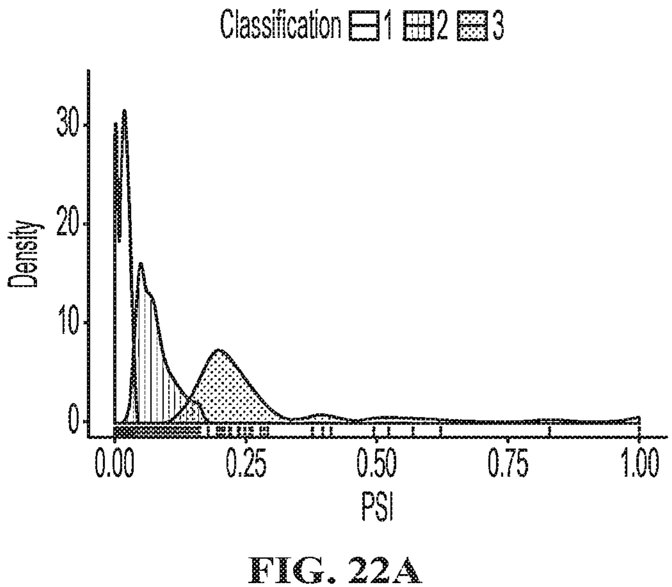
FIG. 22A: GMM analysis of mixed normal and breast cancer samples for the splicing event 8742 (DHRS11 gene). The GMM analysis showed 3 distinct clusters (subpopulations). The x-axis indicates the exon PSI (ψ) level within samples, and y-axis denotes the number of samples in a normalized density scale. Shading indicates the cluster assignment of each sample.
Figure 22B:
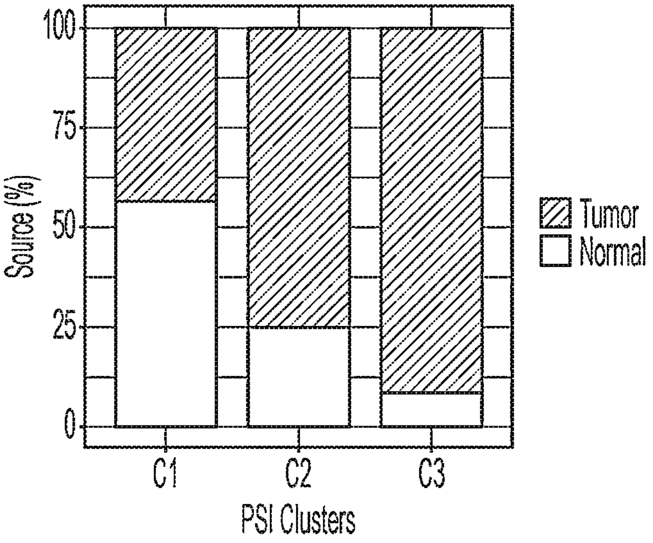
FIG. 22B: Frequency (%) of tumor and normal samples across the 3 clusters identified for the splicing event 8742 (DHRS11 gene). Cluster 3 is composed mostly of breast cancer samples.
Figure 22C:
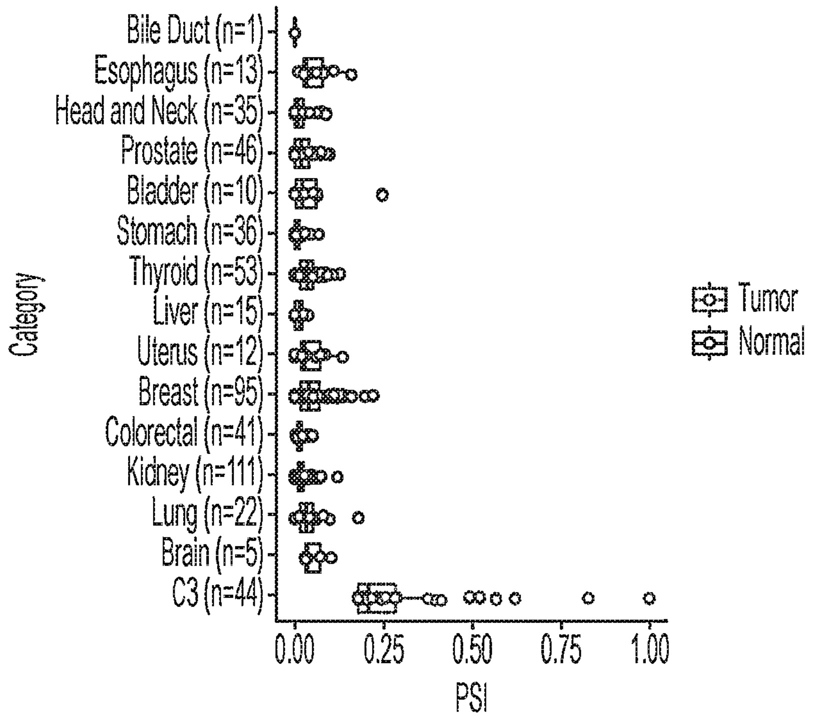
FIG. 22C: Exon splicing levels (PSI) for tumor specific cluster C3 and normal tissues in TCGA. This analysis indicates that the target exon is expressed in 44 breast cancer patients in cluster C3, while very low or absent in normal tissues.
Figure 22D:
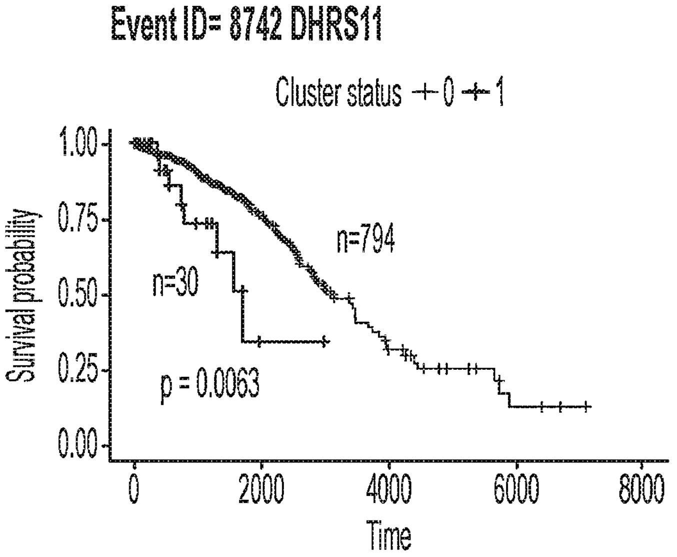
FIG. 22D: Survival analysis of breast cancer patients in cluster C3 versus the remaining breast cancer patients in TCGA. This analysis indicates that patients in C3 (expressing the target exon) have a worse overall survival (shorter survival time, days).

The cluster C4 contains 97 breast cancer patients out of 824 analyzed, which means that the exon inclusion event was detected in ~12% of TCGA breast cancer patients. Moreover, survival analysis of breast cancer patients in cluster C4 versus the remaining breast cancer patients in TCGA indicates that patients in C4 (expressing the targeting exon) have a worse overall survival (FIG. 3D). Therefore, the exon inclusion event 1446 (CCDC115) is (i) specific to breast cancer, (ii) is detected in a subpopulation of breast cancer patients, and (iii) is associated to unfavorable overall survival.

Figure 23A:
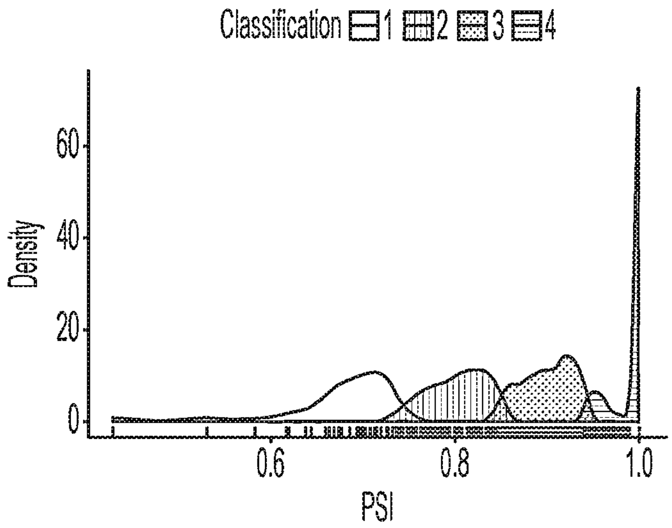
FIG. 23A: GMM analysis of mixed normal and breast cancer samples for the splicing event 1506 (CENPK gene). The GMM analysis showed 4 distinct clusters (subpopulations). The x-axis indicates the exon percent spliced in (PSI, ψ) level within samples, and y-axis denotes the number of samples in a normalized density scale. Shading indicates the cluster assignment of each sample.

Furthermore, the expression (expressed as PSI) of a different target exon varies substantially across cancer and normal samples (see, e.g., FIG. 23A, varying from 0 (0% exclusion) to 1.0 (100% inclusion)).

Visual inspection of data suggests the existence of a subpopulation of samples in which the target exon is excluded, or "spliced-out". This subpopulation (classification "4" samples in FIG. 23A) was formally detected using a clustering methodology called GMM. The GMM analysis of splicing event 1506 (CENPK) generated 4 subpopulations of samples (clusters).

Figure 23B:
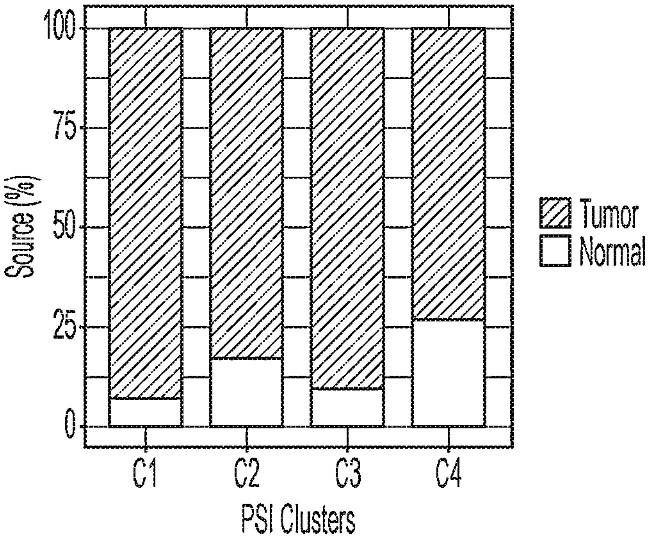
FIG. 23B: Frequency (%) of tumor and normal samples across the 4 clusters identified for the splicing event 1506 (CENPK gene). Clusters 1-4 are composed mostly of breast cancer samples.
Figure 23C:
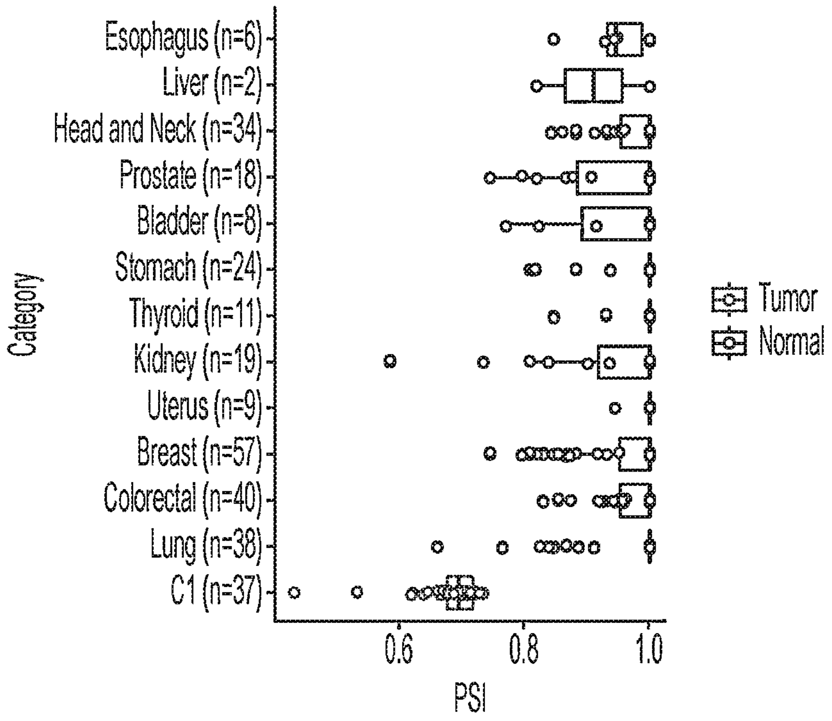
FIG. 23C: Exon splicing levels (PSI) for tumor specific cluster C1 and normal tissues in TCGA. This analysis indicates that the target exon is expressed in 37 breast cancer patients in cluster C1, while very low or absent in normal tissues.

Nonetheless, only two of the clusters (e.g., C1 and C3 of FIGS. 23A and 23B) qualifies as a tumor specific cluster, because it has the following properties:

- clusters C1 and C3 contains more than >90% of tumor samples (see FIG. 23B);
- cluster C1 has >10% increase expression (PSI) compared to normal ($PSI_{tumor}$−$PSI_{normal}$>10%), see FIG. 23C; and
- the exon exclusion event is very low or absent expression in normal tissues ($PSI_{normal}$<5%), see FIG. 23C.

Figure 23D:
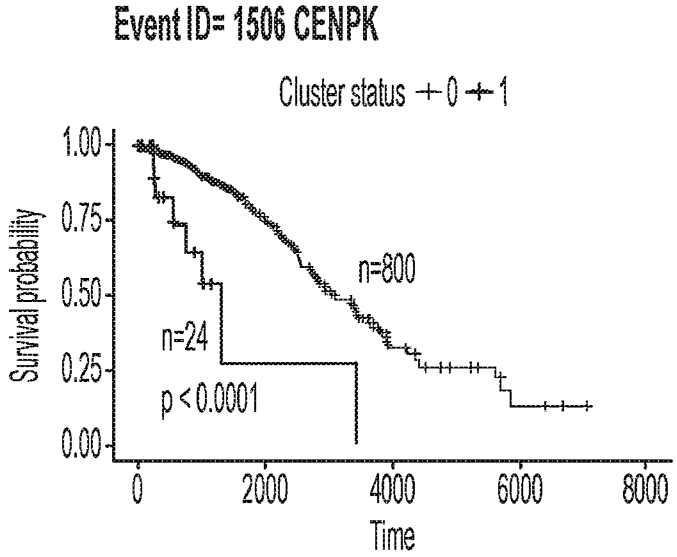
FIG. 23D: Survival analysis of breast cancer patients in cluster C1 versus the remaining breast cancer patients in TCGA. This analysis indicates that patients in C1 (expressing the target exon) have a worse overall survival (shorter survival time, days).
Figure 24A:
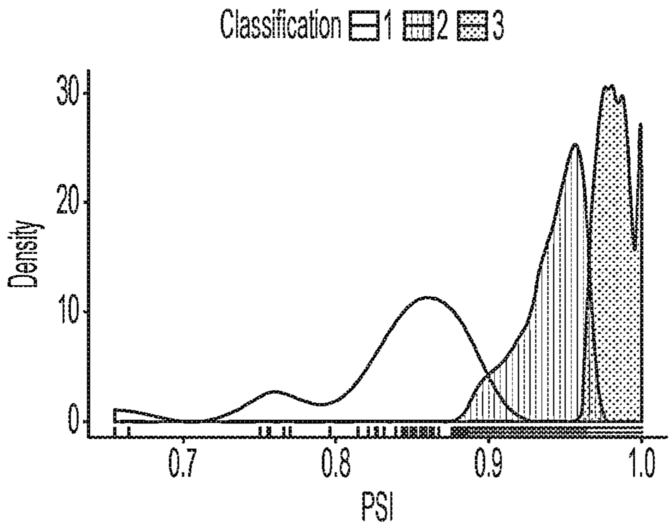
FIG. 24A: GMM analysis of mixed normal and breast cancer samples for the splicing event 2098 (METTL5 gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 24B:
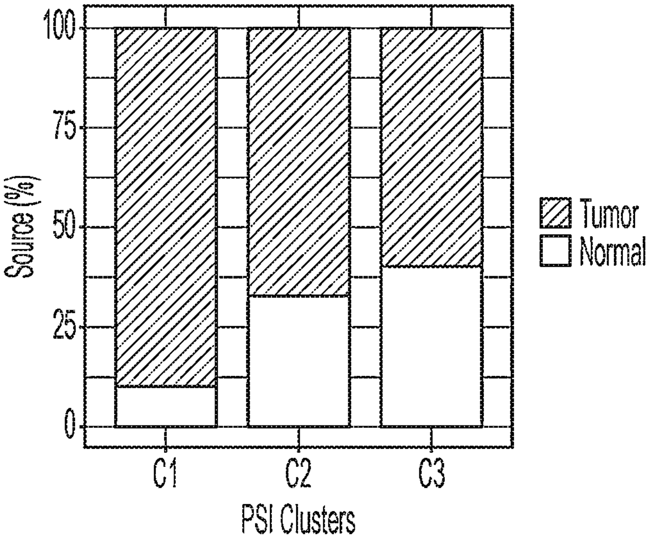
FIG. 24B: Frequency (%) of tumor and normal samples across the 3 clusters identified for the splicing event 2098 (METTL5 gene). Clusters 1-3 are composed mostly of breast cancer samples.
Figure 24C:
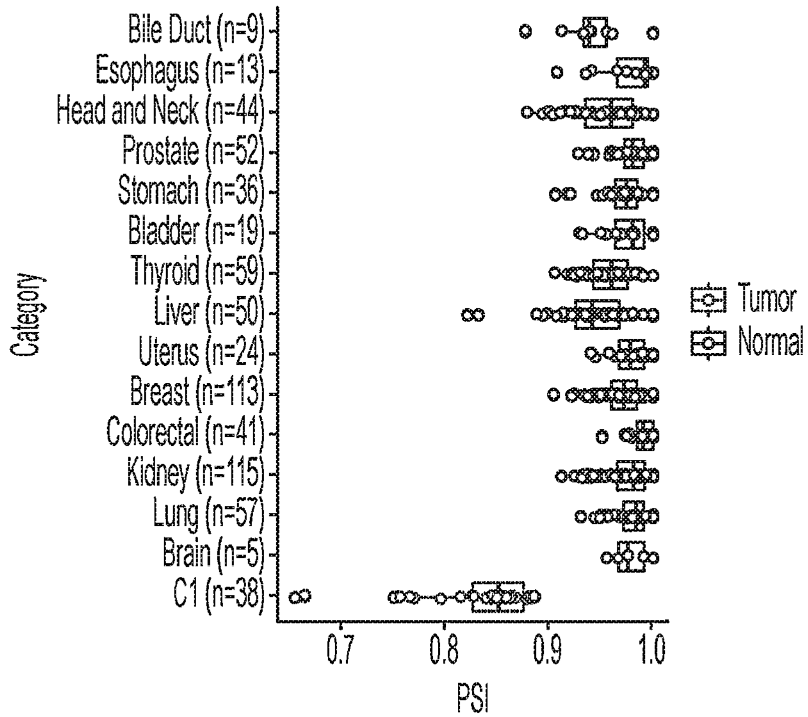
FIG. 24C: Exon splicing levels (PSI) for tumor specific cluster C1 and normal tissues in TCGA. This analysis indicates that the target exon is expressed in 38 breast cancer patients in cluster C1, while very low or absent in normal tissues.
Figure 24D:
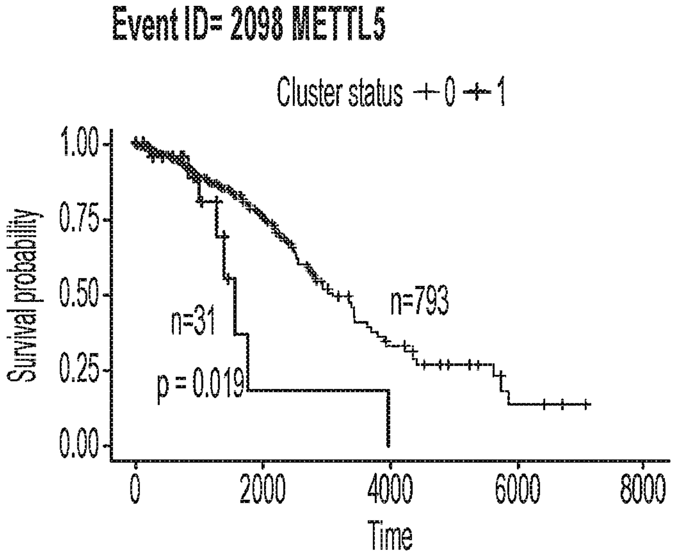
FIG. 24D: Survival analysis of breast cancer patients in cluster C1 versus the remaining breast cancer patients in TCGA. This analysis indicates that patients in C1 (expressing the target exon) have a worse overall survival (shorter survival time, days).
Figure 25A:
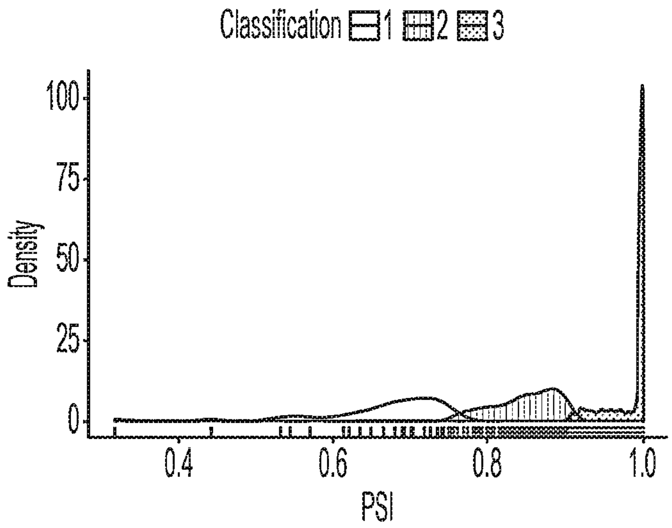
FIG. 25A: GMM analysis of mixed normal and breast cancer samples for the splicing event 2242 (PLA2R1 gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 25B:
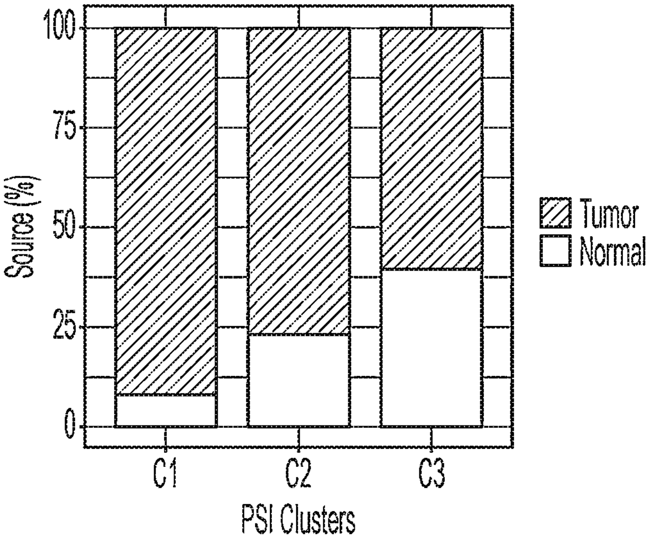
FIG. 25B: Frequency (%) of tumor and normal samples across the 3 clusters identified for the splicing event 2242 (PLA2R1 gene). Clusters 1-3 are composed mostly of breast cancer samples.
Figure 25C:
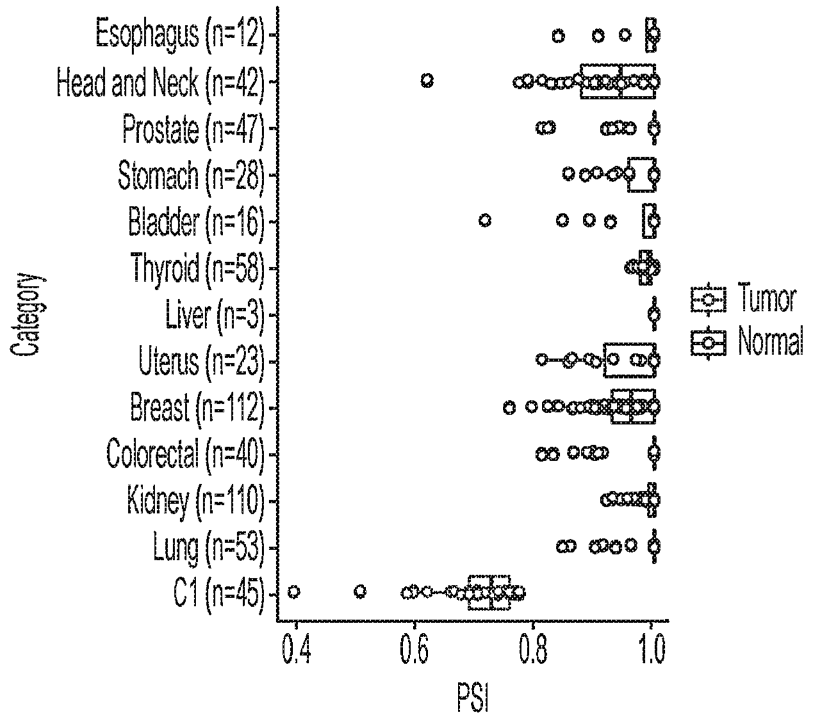
FIG. 25C: Exon splicing levels (PSI) for tumor specific cluster C1 and normal tissues in TCGA. This analysis indicates that the target exon is expressed in 45 breast cancer patients in cluster C1, while very low or absent in normal tissues.
Figure 25D:
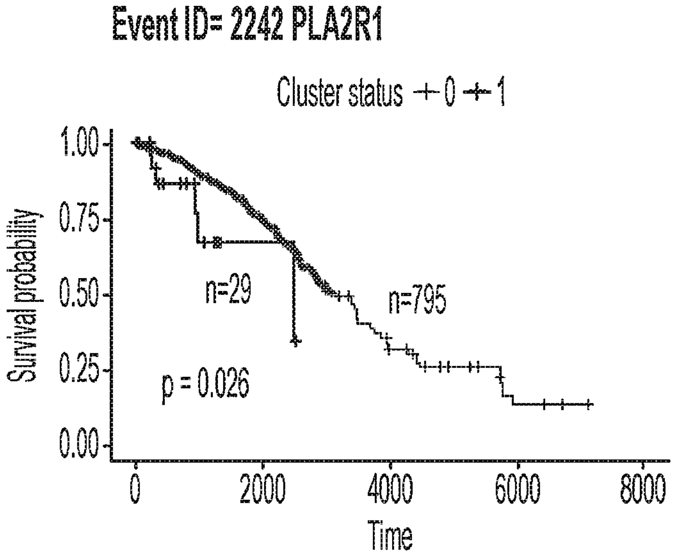
FIG. 25D: Survival analysis of breast cancer patients in cluster C1 versus the remaining breast cancer patients in TCGA. This analysis indicates that patients in C1 (expressing the target exon) have a worse overall survival (shorter survival time, days).
Figure 26A:
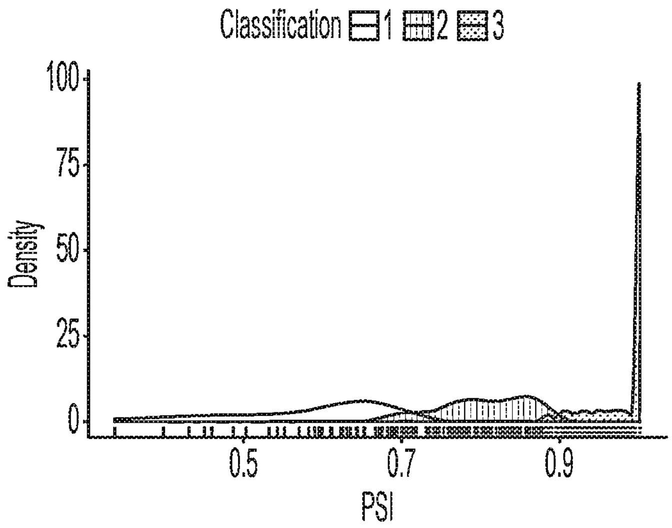
FIG. 26A: GMM analysis of mixed normal and breast cancer samples for the splicing event 7106 (RHOH gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 26B:
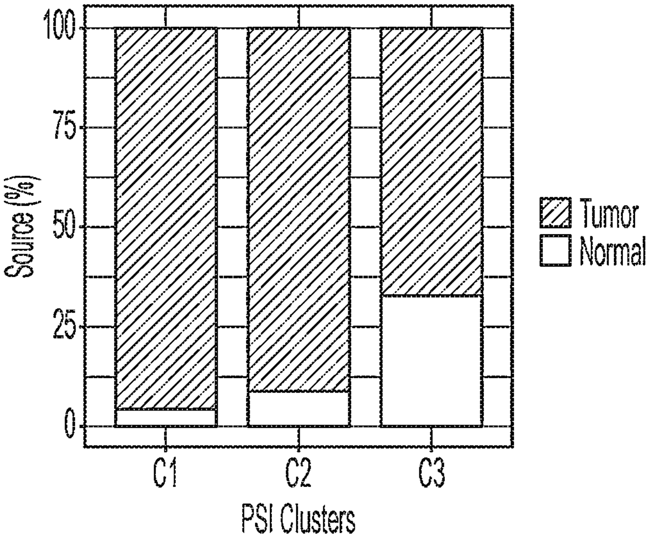
FIG. 26B: Frequency (%) of tumor and normal samples across the 3 clusters identified for the splicing event 7106 (RHOH gene). Clusters 1-3 are composed mostly of breast cancer samples.
Figure 26C:
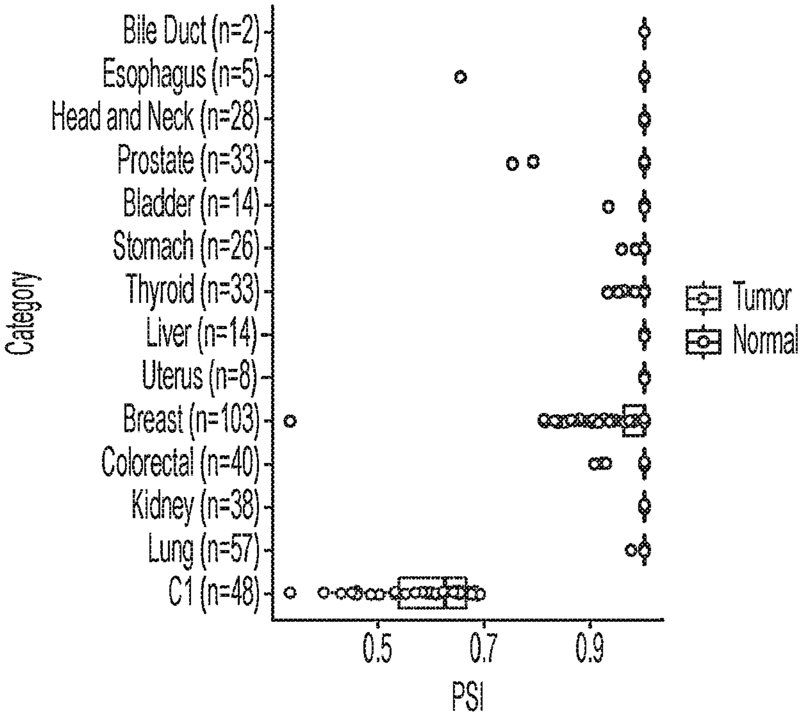
FIG. 26C: Exon splicing levels (PSI) for tumor specific cluster C1 and normal tissues in TCGA. This analysis indicates that the target exon is expressed in 48 breast cancer patients in cluster C1, while very low or absent in normal tissues.
Figure 26D:
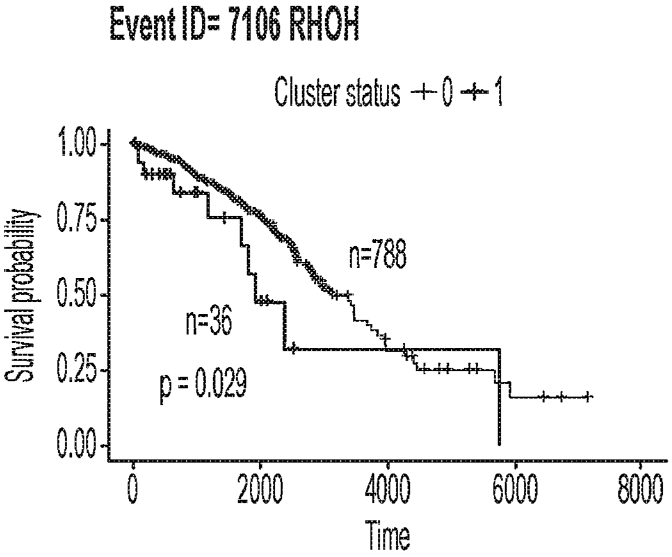
FIG. 26D: Survival analysis of breast cancer patients in cluster C1 versus the remaining breast cancer patients in TCGA. This analysis indicates that patients in C1 (expressing the target exon) have a worse overall survival (shorter survival time, days).
Figure 27A:
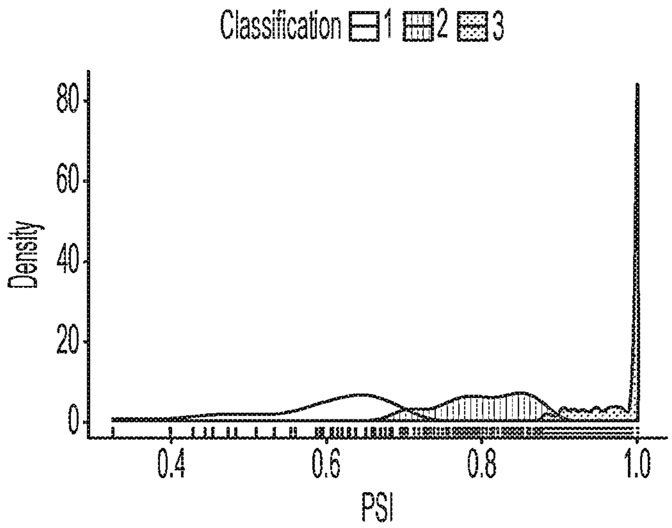
FIG. 27A: GMM analysis of mixed normal and breast cancer samples for the splicing event 7108 (RHOH gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 27B:
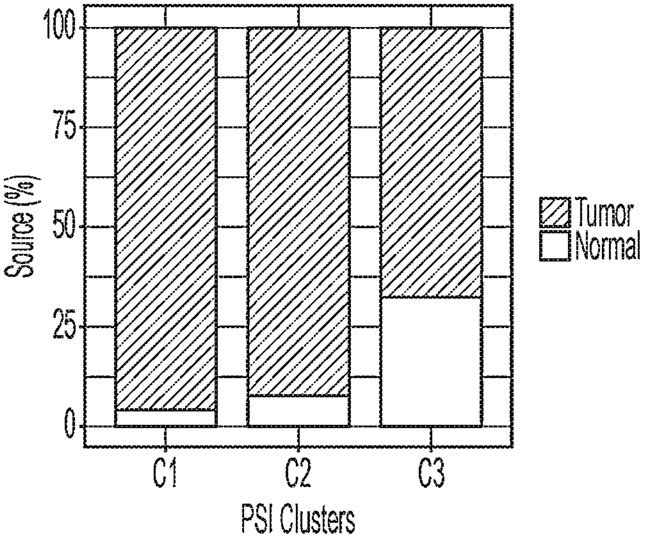
FIG. 27B: Frequency (%) of tumor and normal samples across the 3 clusters identified for the splicing event 7108 (RHOH gene). Clusters 1-3 are composed mostly of breast cancer samples.
Figure 27C:
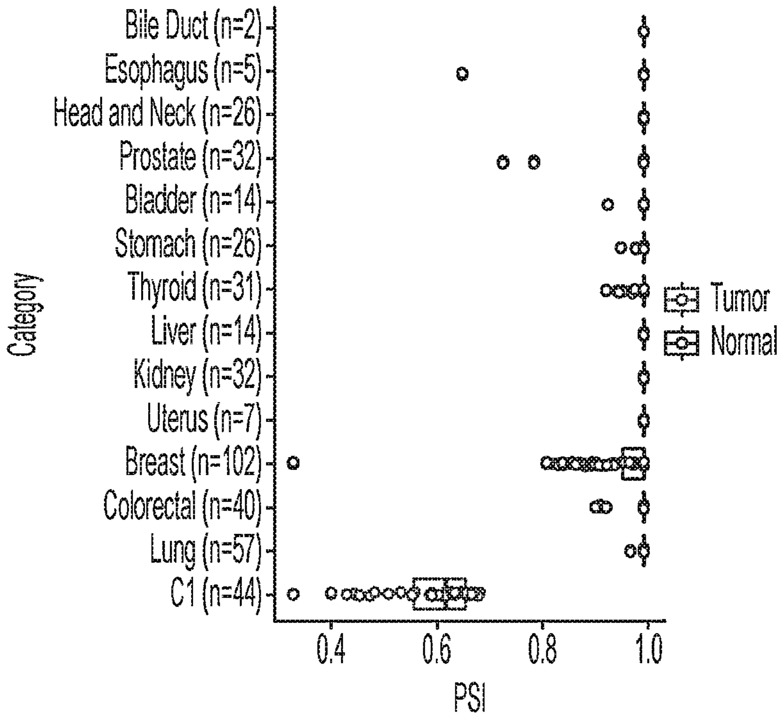
FIG. 27C: Exon splicing levels (PSI) for tumor specific cluster C1 and normal tissues in TCGA. This analysis indicates that the target exon is expressed in 44 breast cancer patients in cluster C1, while very low or absent in normal tissues.
Figure 27D:
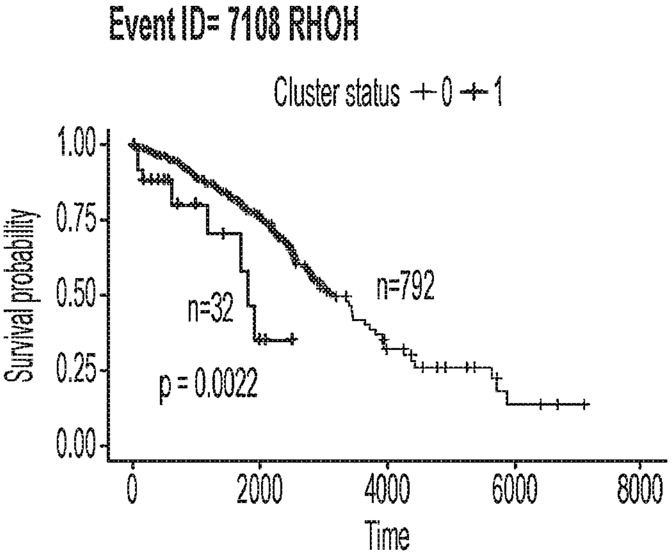
FIG. 27D: Survival analysis of breast cancer patients in cluster C1 versus the remaining breast cancer patients in TCGA. This analysis indicates that patients in C1 (expressing the target exon) have a worse overall survival (shorter survival time, days).
Figure 28A:
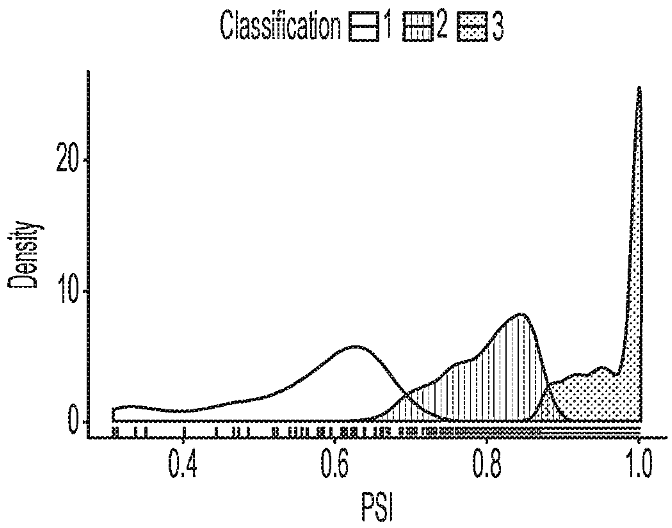
FIG. 28A: GMM analysis of mixed normal and breast cancer samples for the splicing event 9442 (QPRT gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 28B:
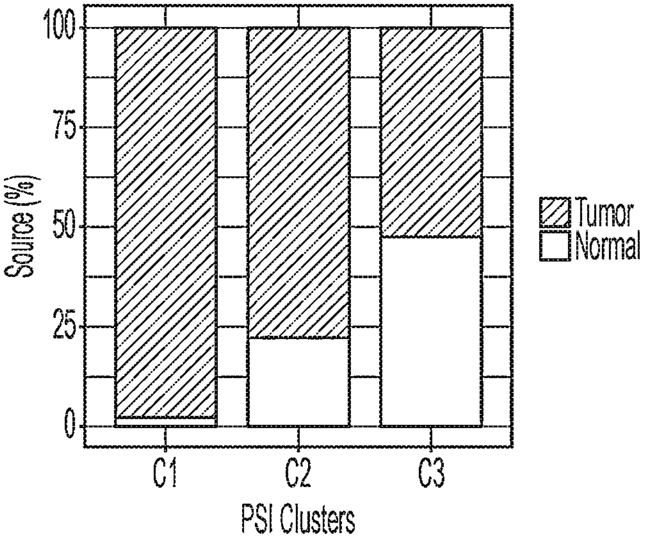
FIG. 28B: Frequency (%) of tumor and normal samples across the 3 clusters identified for the splicing event 9442 (QPRT gene). Clusters 1-2 are composed mostly of breast cancer samples.
Figure 28C:
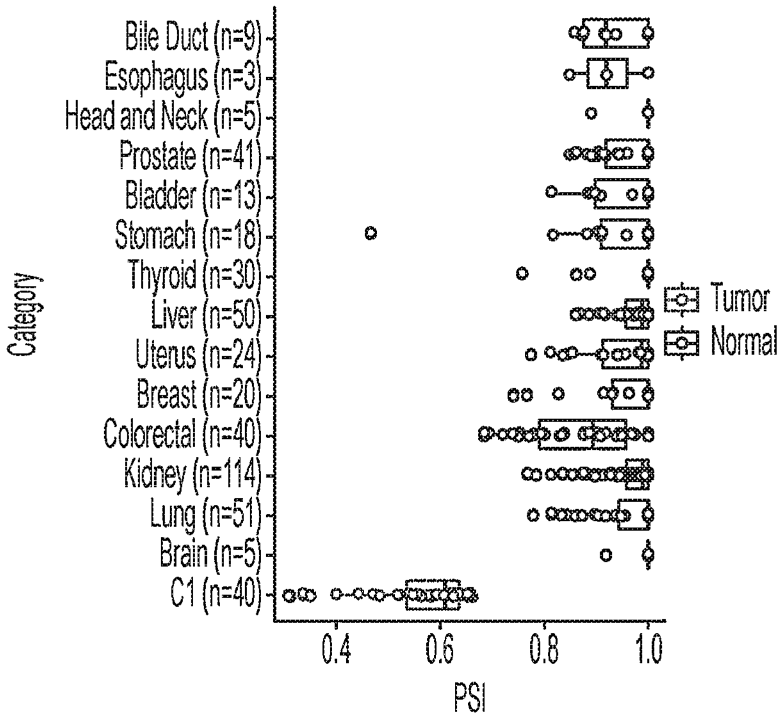
FIG. 28C: Exon splicing levels (PSI) for tumor specific cluster C1 and normal tissues in TCGA. This analysis indicates that the target exon is expressed in 40 breast cancer patients in cluster C1, while very low or absent in normal tissues.
Figure 28D:
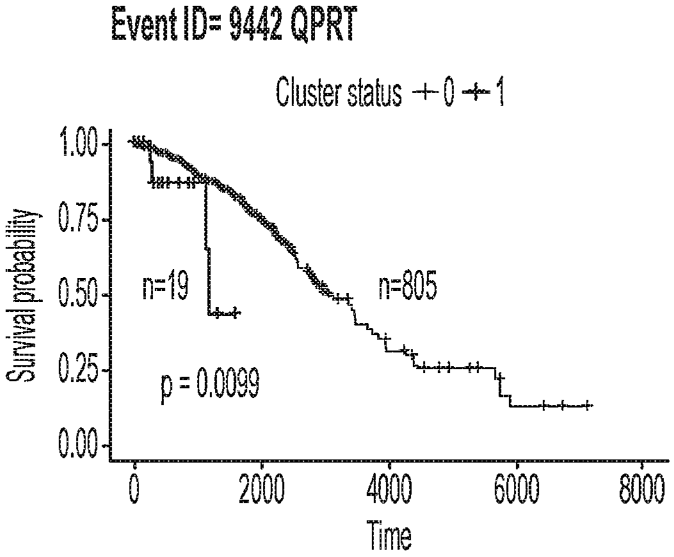
FIG. 28D: Survival analysis of breast cancer patients in cluster C1 versus the remaining breast cancer patients in TCGA. This analysis indicates that patients in C1 (expressing the target exon) have a worse overall survival (shorter survival time, days).
Figure 29A:
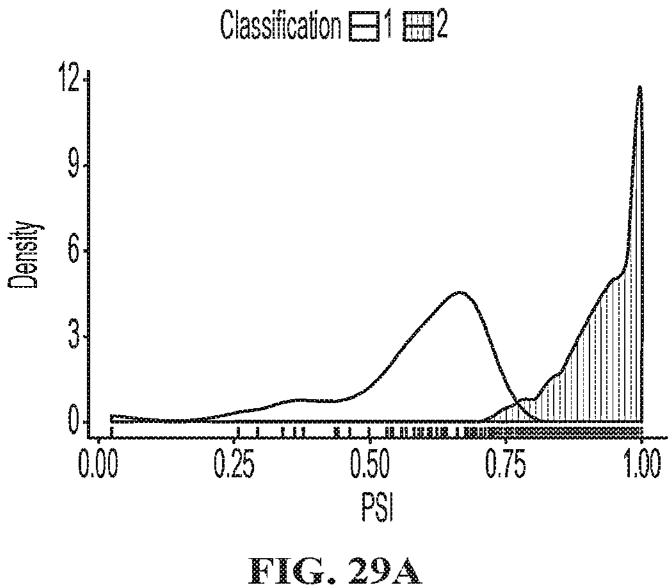
FIG. 29A: GMM analysis of mixed normal and breast cancer samples for the splicing event 10439 (IL17RB gene). The GMM analysis showed 2 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 29B:
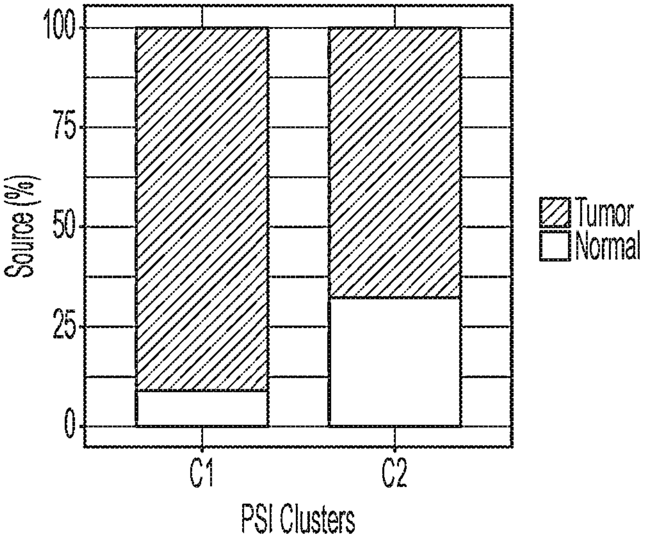
FIG. 29B: Frequency (%) of tumor and normal samples across the 2 clusters identified for the splicing event 10439 (IL17RB gene). Clusters 1-2 are composed mostly of breast cancer samples.
Figure 29C:
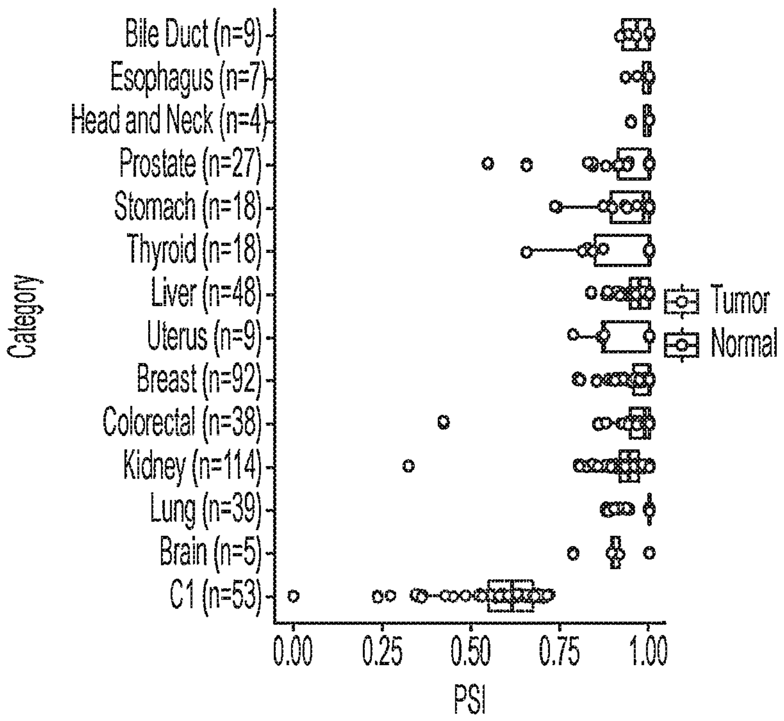
FIG. 29C: Exon splicing levels (PSI) for tumor specific cluster C1 and normal tissues in TCGA. This analysis indicates that the target exon is expressed in 53 breast cancer patients in cluster C1, while very low or absent in normal tissues.
Figure 29D:
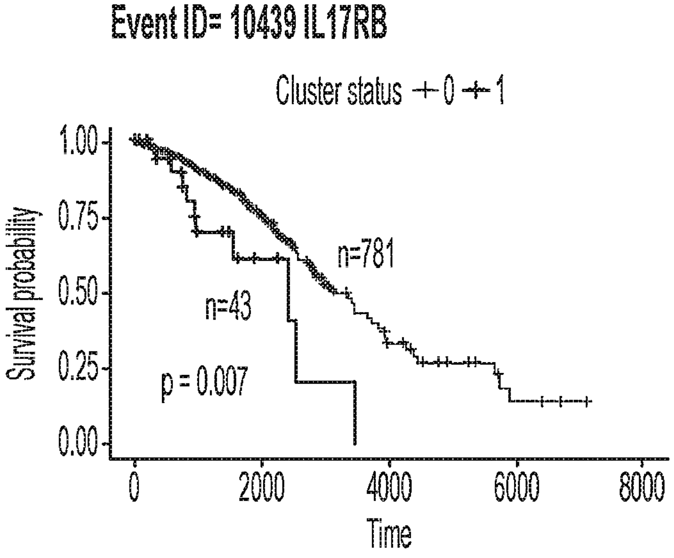
FIG. 29D: Survival analysis of breast cancer patients in cluster C1 versus the remaining breast cancer patients in TCGA. This analysis indicates that patients in C1 (expressing the target exon) have a worse overall survival (shorter survival time, days).
Figure 30A:
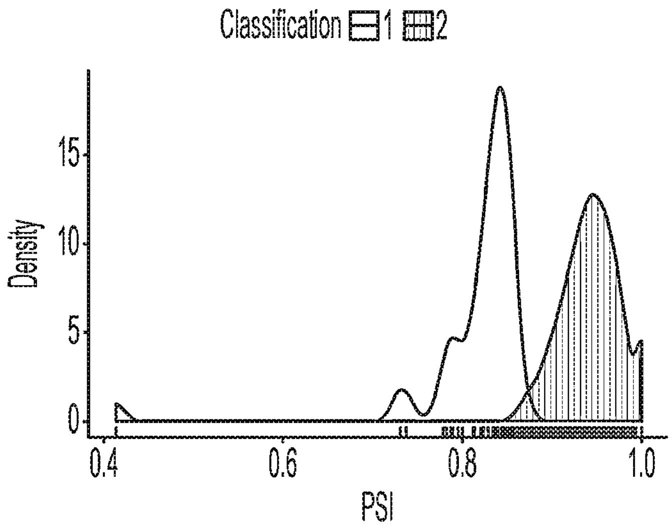
FIG. 30A: GMM analysis of mixed normal and breast cancer samples for the splicing event 11685 (STAU1 gene). The GMM analysis showed 2 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 30B:
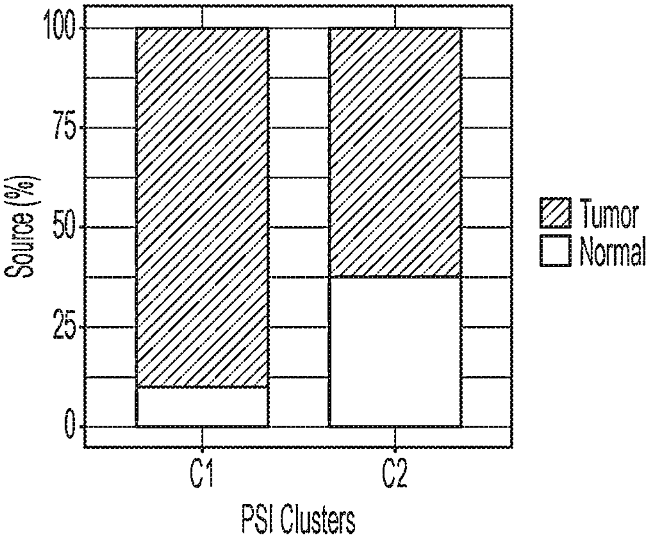
FIG. 30B: Frequency (%) of tumor and normal samples across the 2 clusters identified for the splicing event 11685 (STAU1 gene). Clusters 1-2 are composed mostly of breast cancer samples.
Figure 30C:
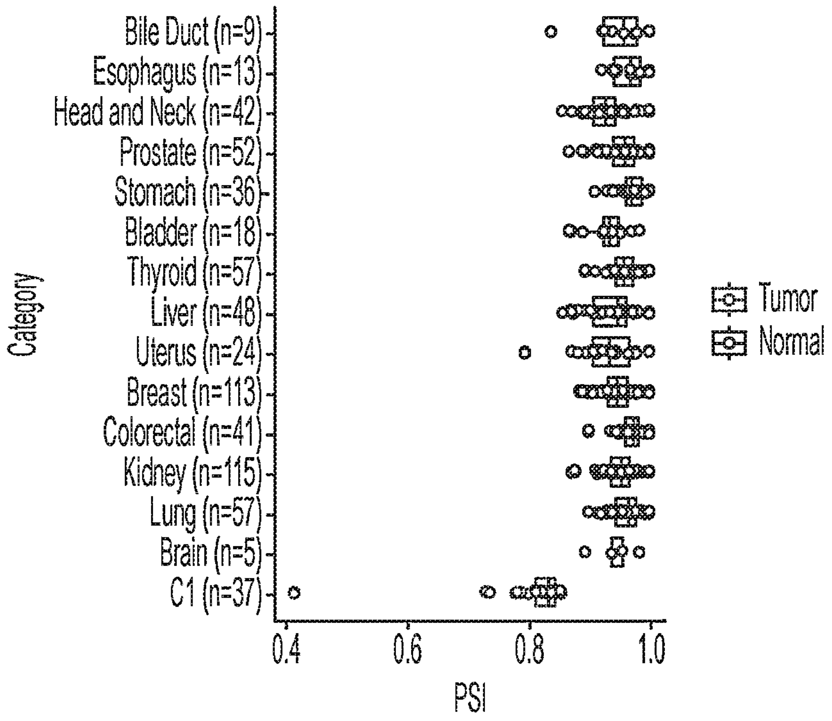
FIG. 30C: Exon splicing levels (PSI) for tumor specific cluster C1 and normal tissues in TCGA. This analysis indicates that the target exon is expressed in 37 breast cancer patients in cluster C1, while very low or absent in normal tissues.
Figure 30D:
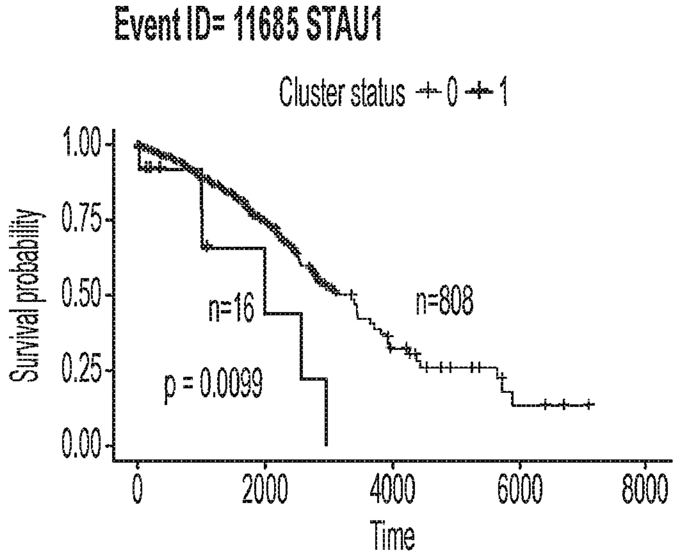
FIG. 30D: Survival analysis of breast cancer patients in cluster C1 versus the remaining breast cancer patients in TCGA. This analysis indicates that patients in C1 (expressing the target exon) have a worse overall survival (shorter survival time, days).
Figure 31A:
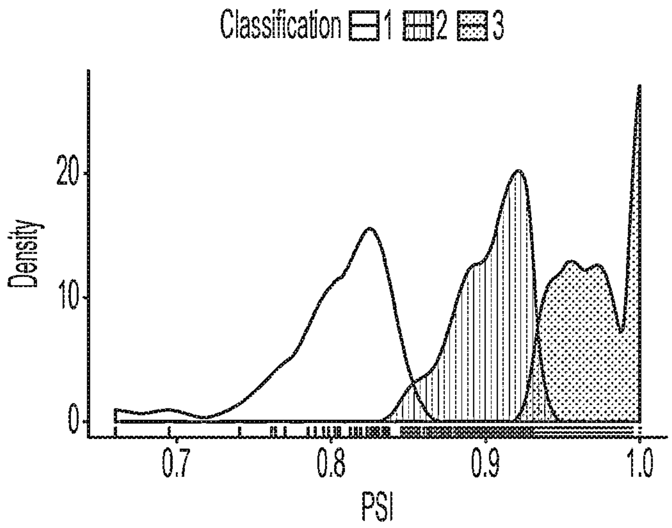
FIG. 31A: GMM analysis of mixed normal and breast cancer samples for the splicing event 13451 (LYRM1 gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 31B:
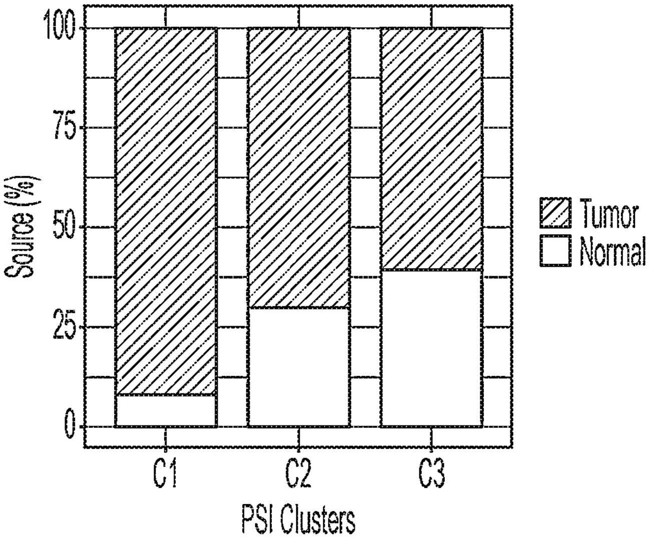
FIG. 31B: Frequency (%) of tumor and normal samples across the 3 clusters identified for the splicing event 13451 (LYRM1 gene). Clusters 1-3 are composed mostly of breast cancer samples.
Figure 31C:
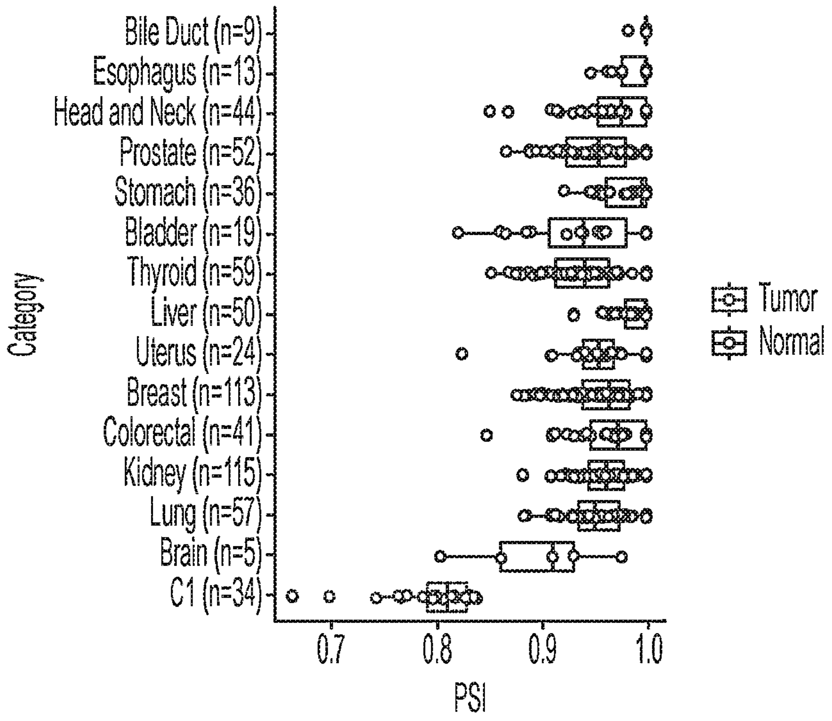
FIG. 31C: Exon splicing levels (PSI) for tumor specific cluster C1 and normal tissues in TCGA. This analysis indicates that the target exon is expressed in 34 breast cancer patients in cluster C1, while very low or absent in normal tissues.
Figure 31D:
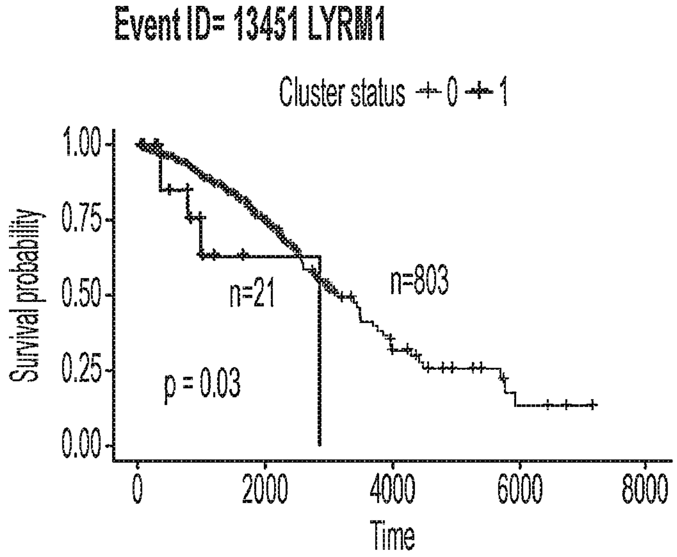
FIG. 31D: Survival analysis of breast cancer patients in cluster C1 versus the remaining breast cancer patients in TCGA. This analysis indicates that patients in C1 (expressing the target exon) have a worse overall survival (shorter survival time, days).
Figure 32A:
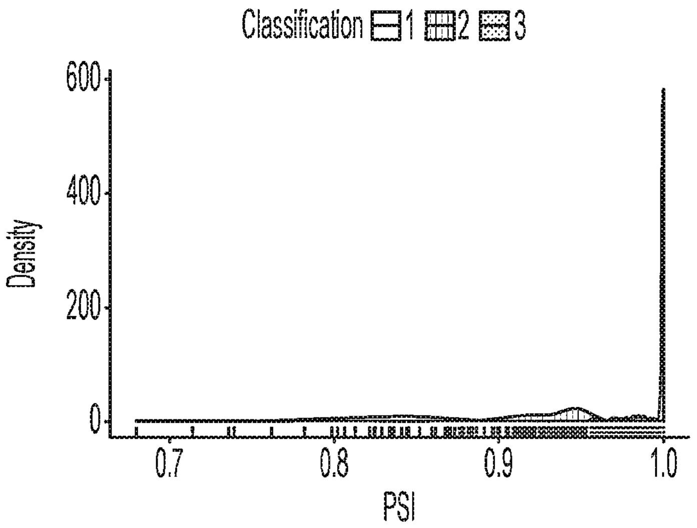
FIG. 32A: GMM analysis of mixed normal and breast cancer samples for the splicing event 14574 (PPARG gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 32B:
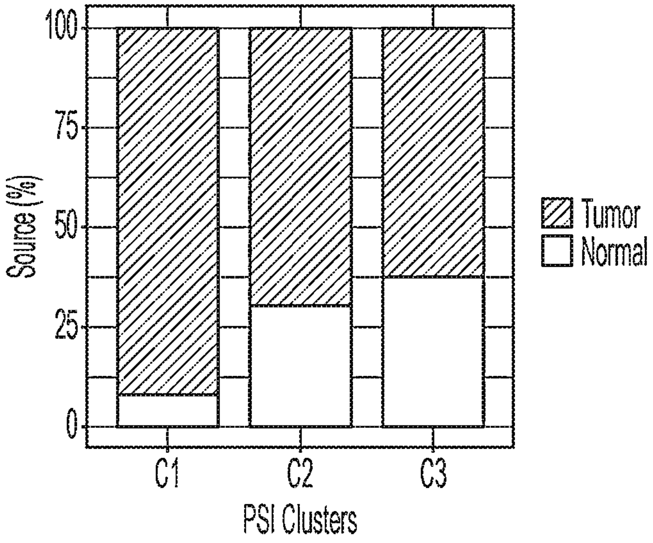
FIG. 32B: Frequency (%) of tumor and normal samples across the 3 clusters identified for the splicing event 14574 (PPARG gene). Clusters 1-3 are composed mostly of breast cancer samples.
Figure 32C:
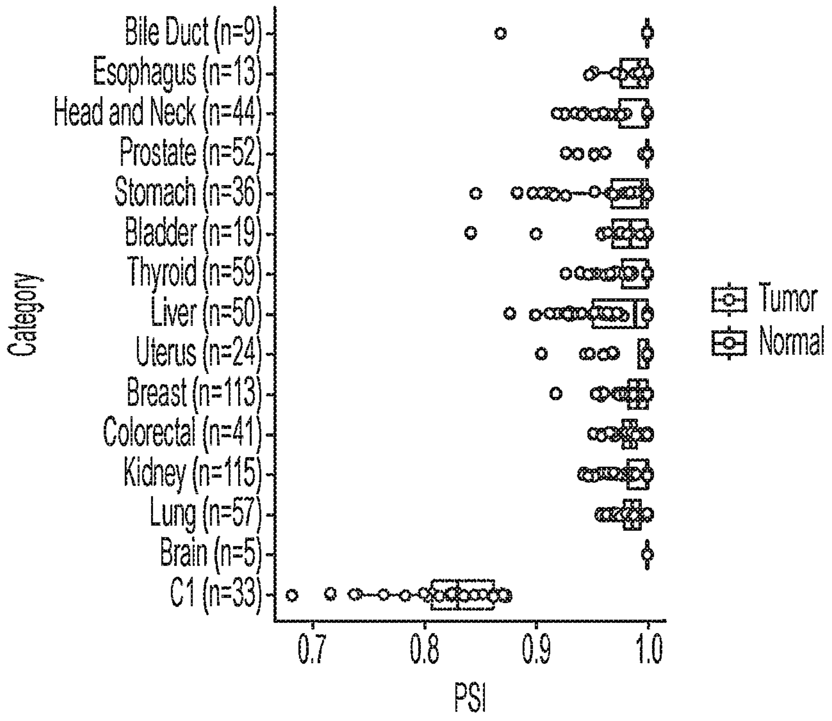
FIG. 32C: Exon splicing levels (PSI) for tumor specific cluster C1 and normal tissues in TCGA. This analysis indicates that the target exon is expressed in 33 breast cancer patients in cluster C1, while very low or absent in normal tissues.
Figure 32D:
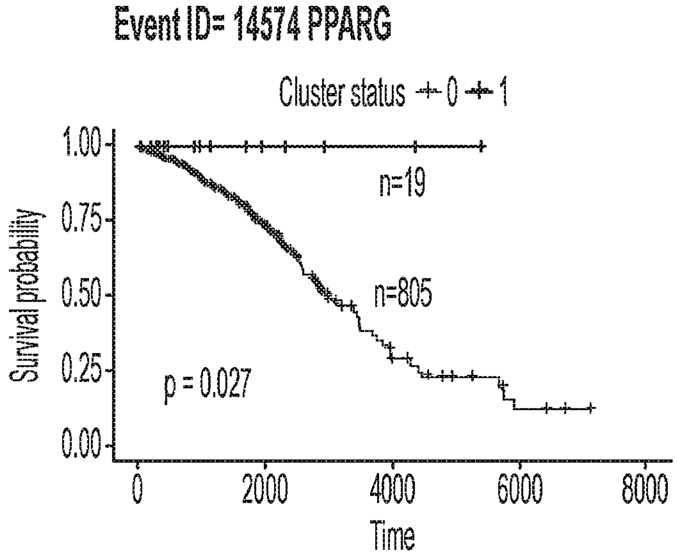
FIG. 32D: Survival analysis of breast cancer patients in cluster C1 versus the remaining breast cancer patients in TCGA. This analysis indicates that patients in C1 (expressing the target exon) have a better overall survival (longer survival time, days).
Figure 33A:
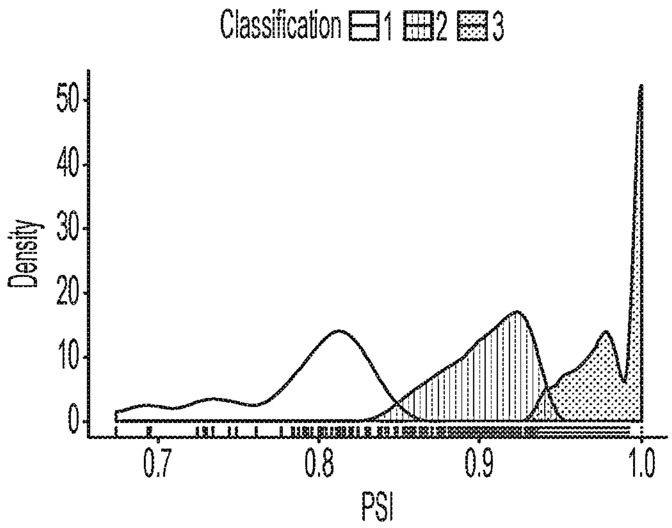
FIG. 33A: GMM analysis of mixed normal and breast cancer samples for the splicing event 16269 (BORCS8-MEF2B gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 33B:
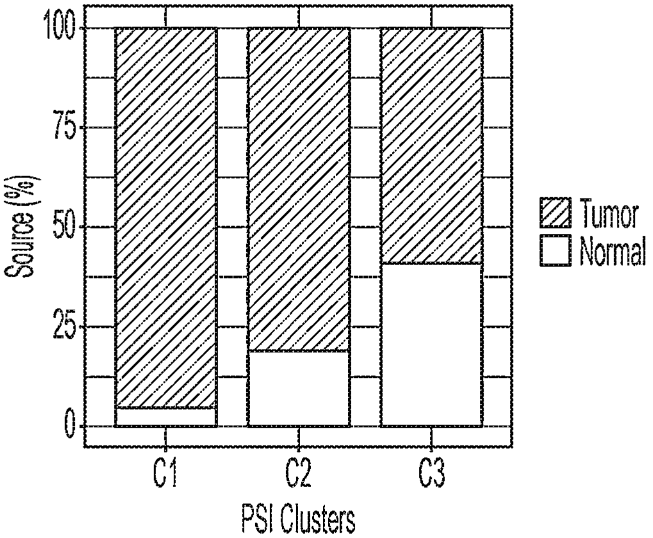
FIG. 33B: Frequency (%) of tumor and normal samples across the 3 clusters identified for the splicing event 16269 (BORCS8-MEF2B gene). Clusters 1-3 are composed mostly of breast cancer samples.
Figure 33C:
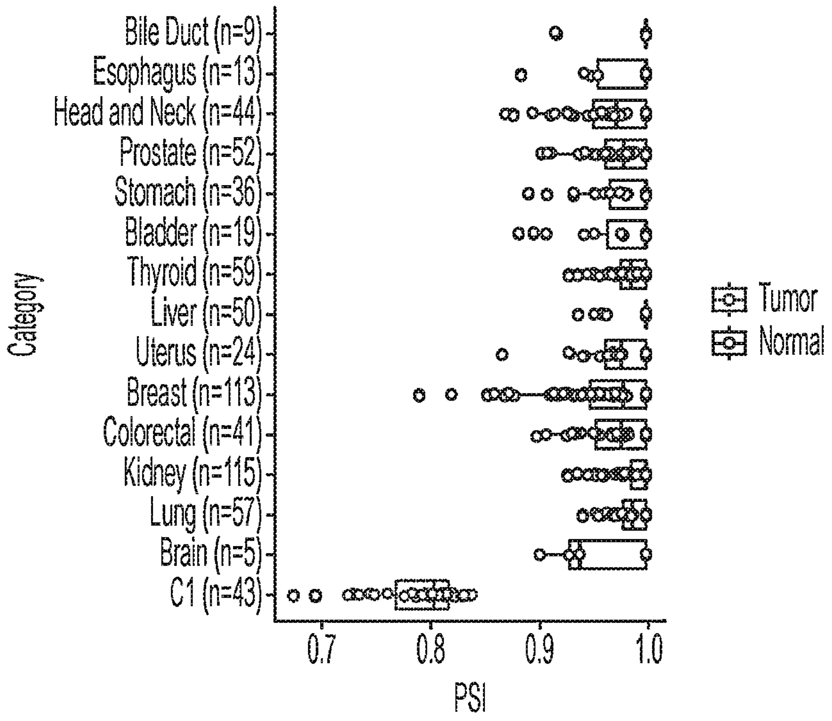
FIG. 33C: Exon splicing levels (PSI) for tumor specific cluster C1 and normal tissues in TCGA. This analysis indicates that the target exon is expressed in 43 breast cancer patients in cluster C1, while very low or absent in normal tissues.
Figure 33D:
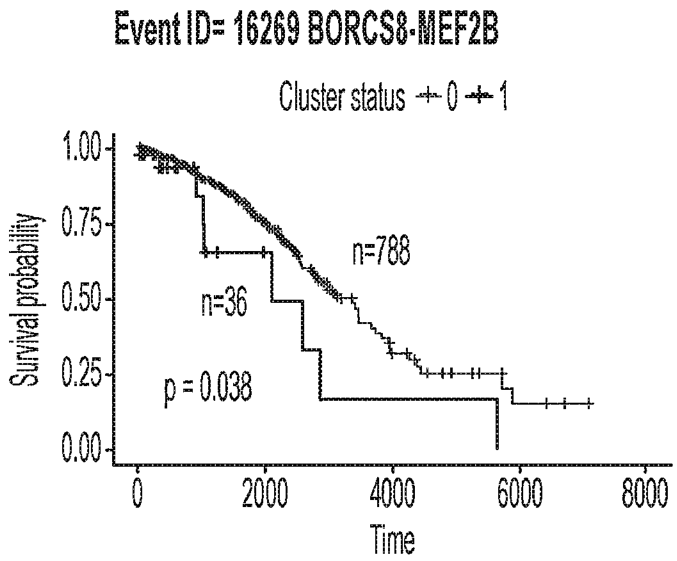
FIG. 33D: Survival analysis of breast cancer patients in cluster C1 versus the remaining breast cancer patients in TCGA. This analysis indicates that patients in C1 (expressing the target exon) have a worse overall survival (shorter survival time, days).
Figure 34A:
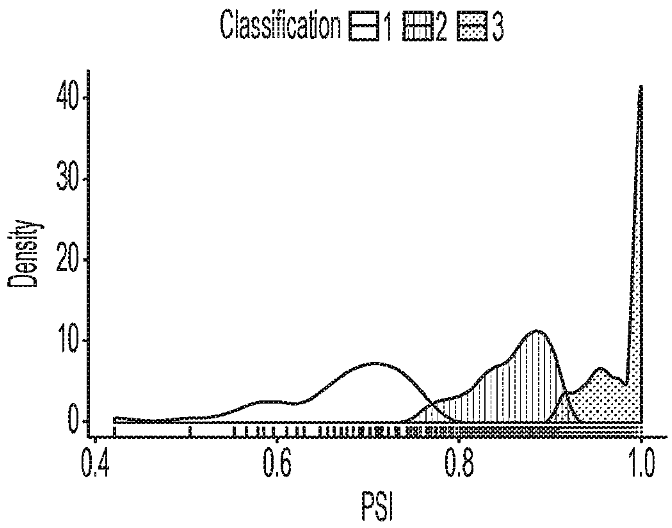
FIG. 34A: GMM analysis of mixed normal and breast cancer samples for the splicing event 16833 (ENOSF1 gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 34B:
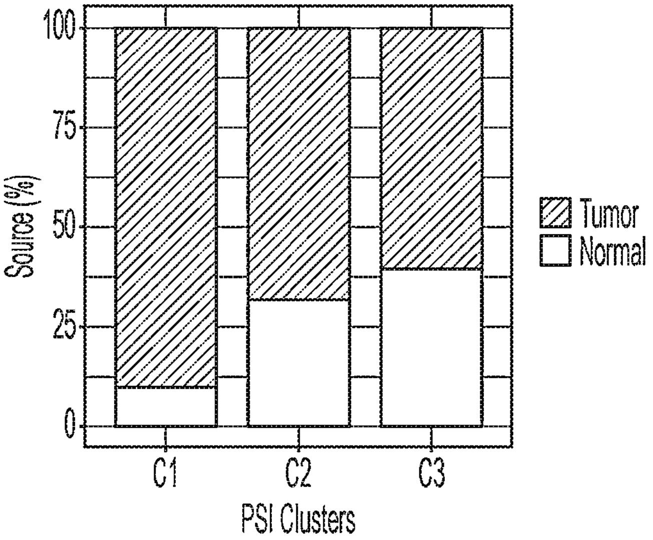
FIG. 34B: Frequency (%) of tumor and normal samples across the 3 clusters identified for the splicing event 16833 (ENOSF1 gene). Clusters 1-3 are composed mostly of breast cancer samples.
Figure 34C:
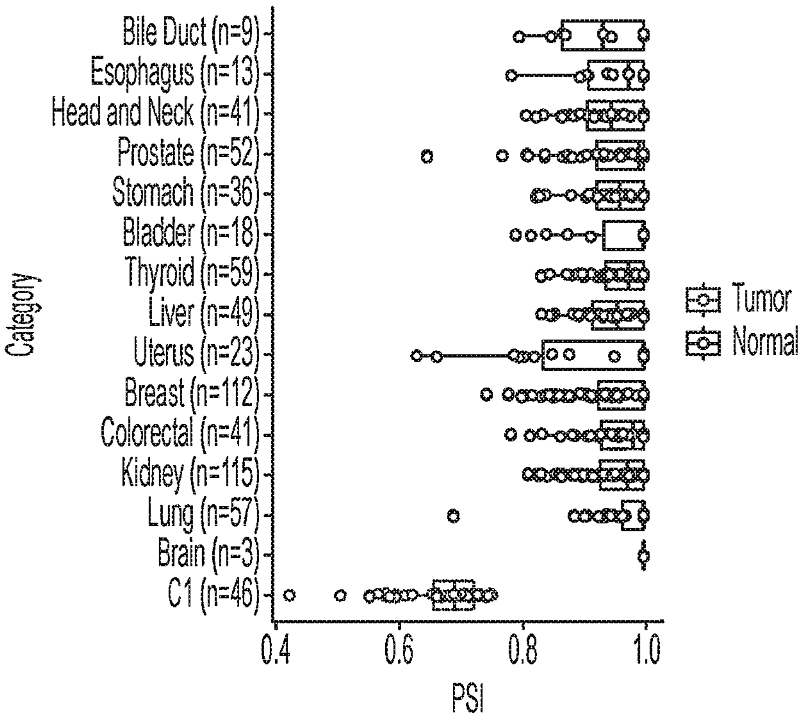
FIG. 34C: Exon splicing levels (PSI) for tumor specific cluster C1 and normal tissues in TCGA. This analysis indicates that the target exon is expressed in 46 breast cancer patients in cluster C1, while very low or absent in normal tissues.
Figure 34D:
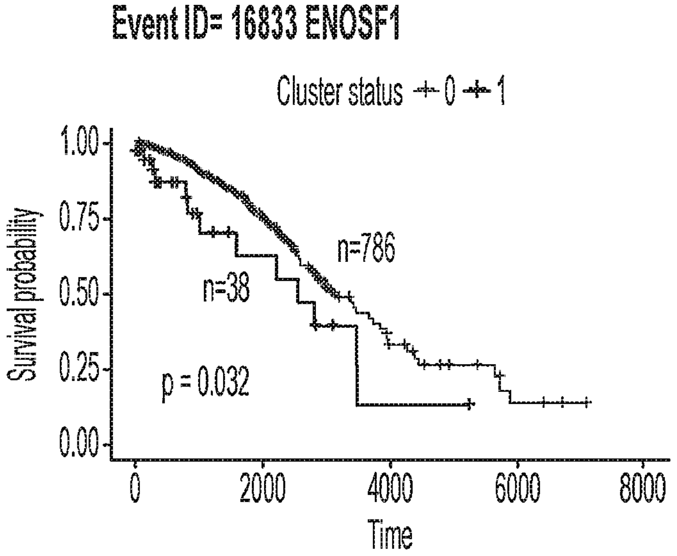
FIG. 34D: Survival analysis of breast cancer patients in cluster C1 versus the remaining breast cancer patients in TCGA. This analysis indicates that patients in C1 (expressing the target exon) have a worse overall survival (shorter survival time, days).
Figure 35A:
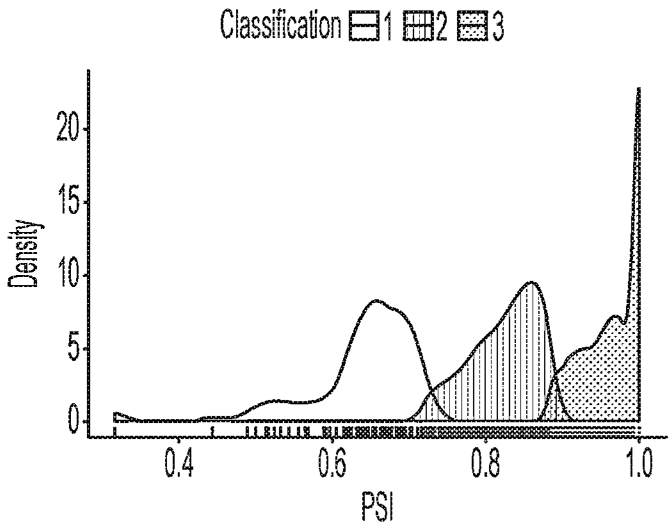
FIG. 35A: GMM analysis of mixed normal and breast cancer samples for the splicing event 16929 (DHRS4-AS1 gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 35B:
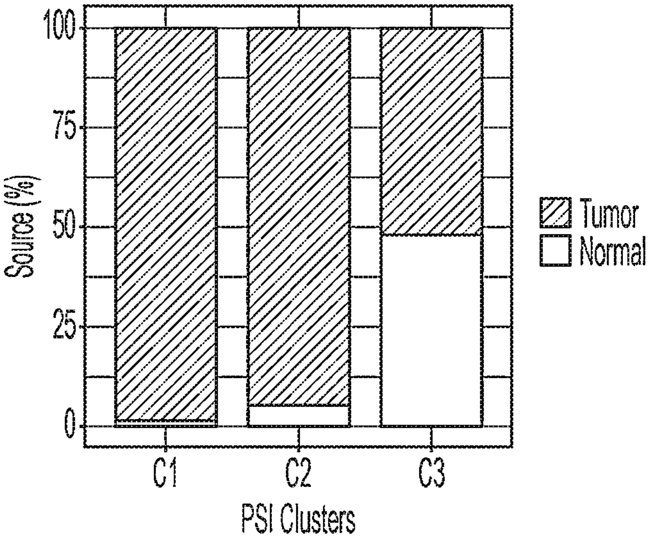
FIG. 35B: Frequency (%) of tumor and normal samples across the 3 clusters identified for the splicing event 16929 (DHRS4-AS1 gene). Clusters 1-2 are composed mostly of breast cancer samples.
Figure 35C:
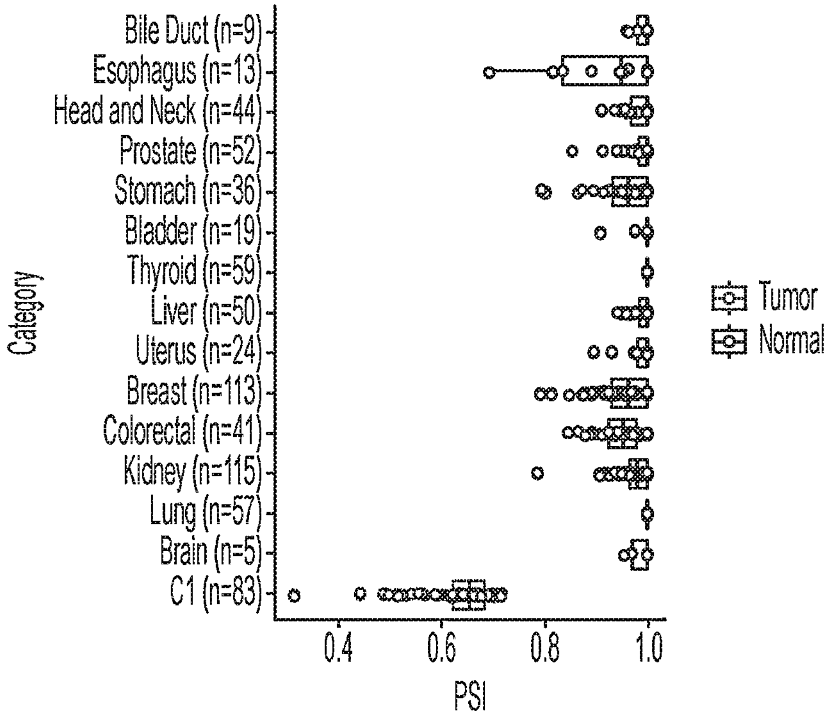
FIG. 35C: Exon splicing levels (PSI) for tumor specific cluster C1 and normal tissues in TCGA. This analysis indicates that the target exon is expressed in 83 breast cancer patients in cluster C1, while very low or absent in normal tissues.
Figure 35D:
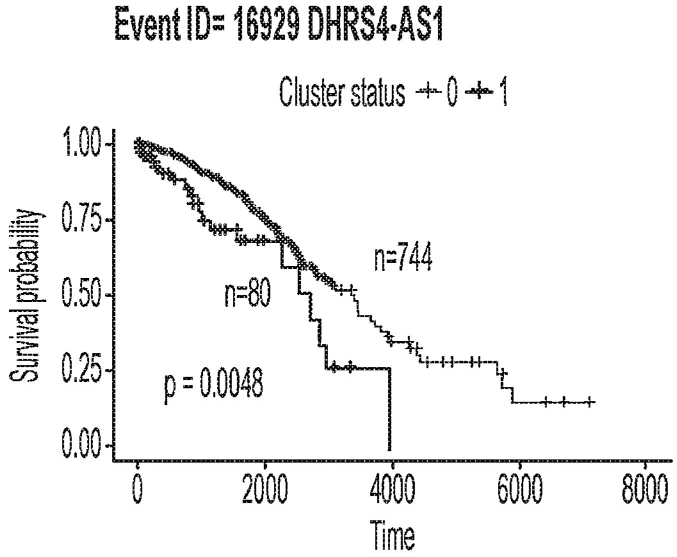
FIG. 35D: Survival analysis of breast cancer patients in cluster C1 versus the remaining breast cancer patients in TCGA. This analysis indicates that patients in C1 (expressing the target exon) have a worse overall survival (shorter survival time, days).
Figure 36A:
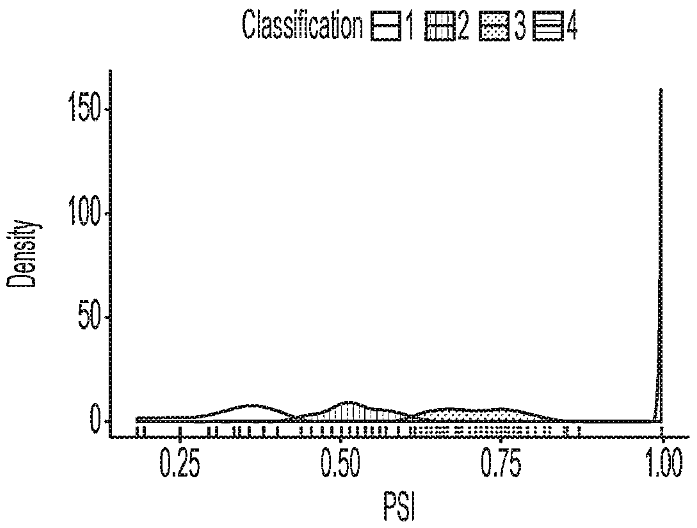
FIG. 36A: GMM analysis of mixed normal and breast cancer samples for the splicing event 16943 (NDUFV2 gene). The GMM analysis showed 4 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 36B:
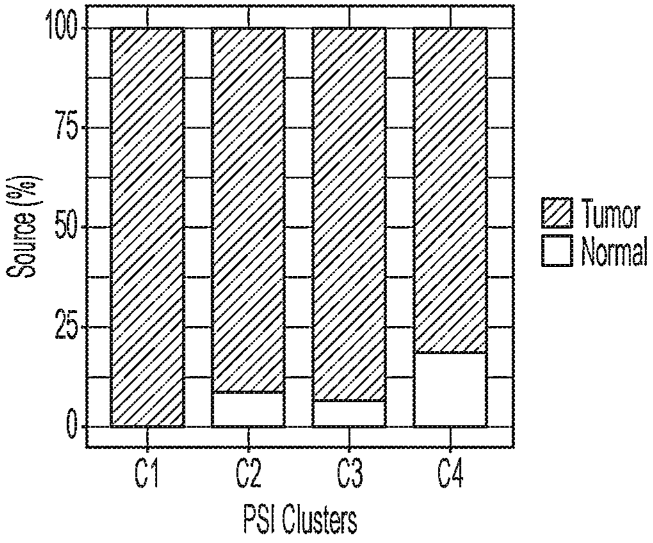
FIG. 36B: Frequency (%) of tumor and normal samples across the 4 clusters identified for the splicing event 16943 (NDUFV2 gene). Clusters 1-4 are composed mostly of breast cancer samples.
Figure 36C:
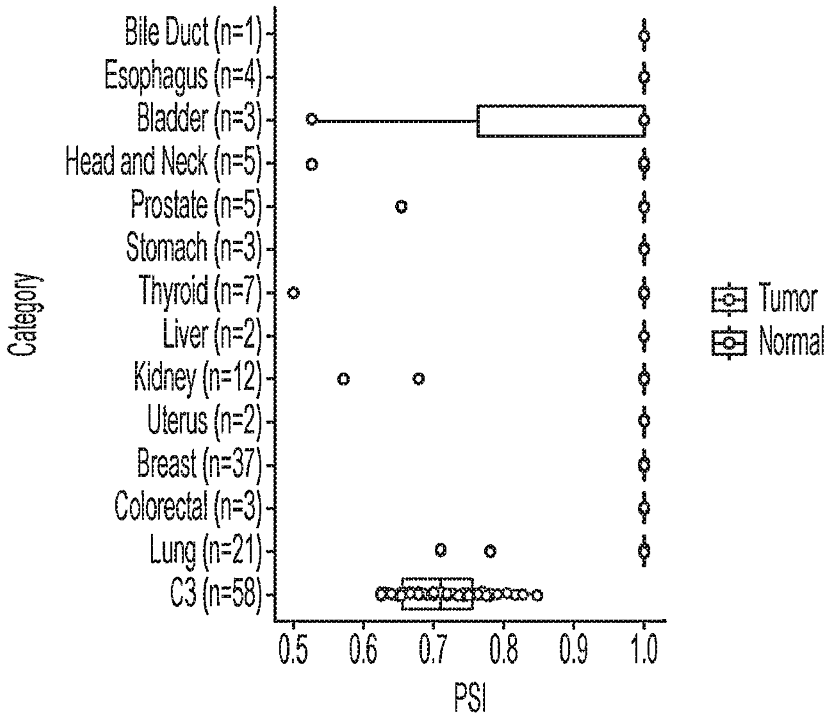
FIG. 36C: Exon splicing levels (PSI) for tumor specific cluster C3 and normal tissues in TCGA. This analysis indicates that the target exon is expressed in 58 breast cancer patients in cluster C3, while very low or absent in normal tissues except bladder.
Figure 36D:
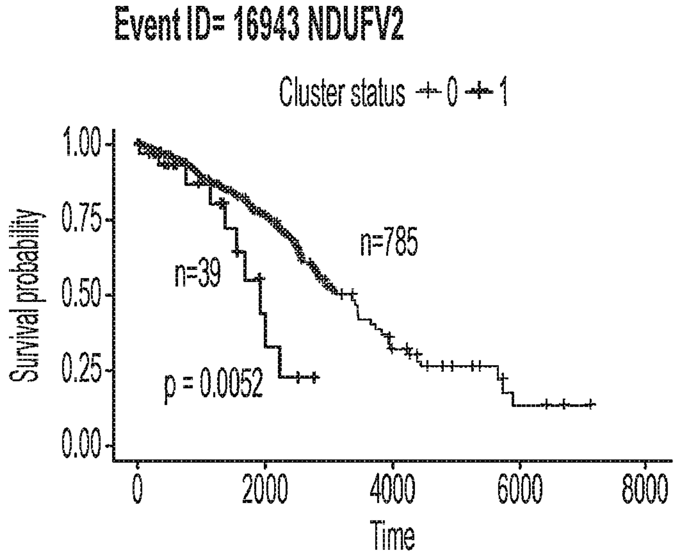
FIG. 36D: Survival analysis of breast cancer patients in cluster C3 versus the remaining breast cancer patients in TCGA. This analysis indicates that patients in C3 (expressing the target exon) have a worse overall survival (shorter survival time, days).
Figure 37A:
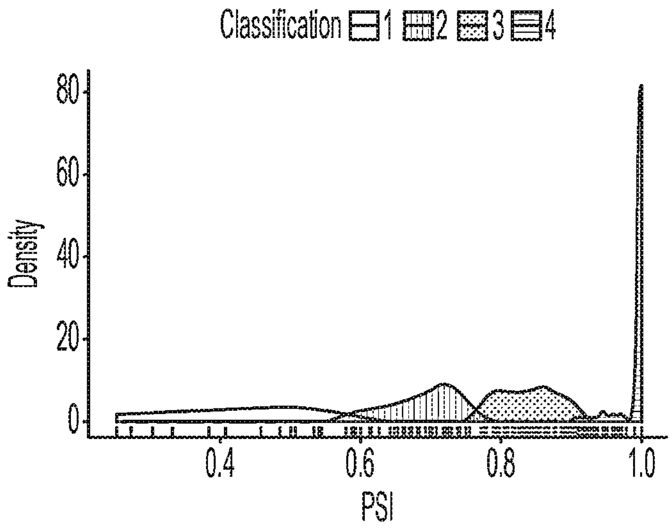
FIG. 37A: GMM analysis of mixed normal and breast cancer samples for the splicing event 18745 (FER1L4 gene). The GMM analysis showed 4 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 37B:
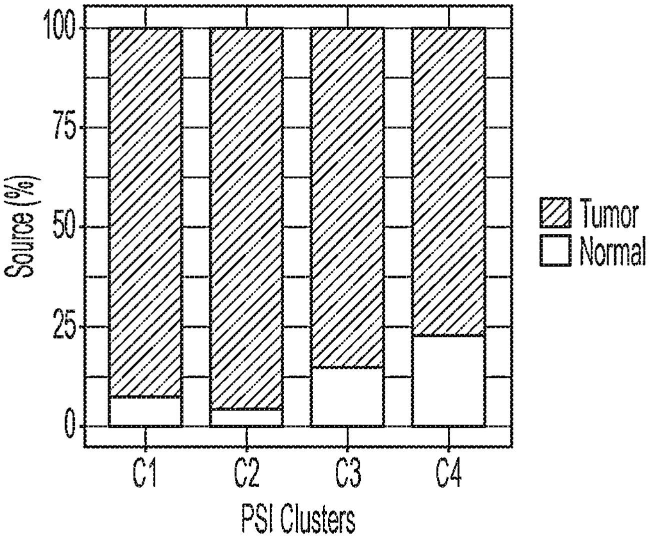
FIG. 37B: Frequency (%) of tumor and normal samples across the 4 clusters identified for the splicing event 18745 (FER1L4 gene). Clusters 1-4 are composed mostly of breast cancer samples.
Figure 37C:
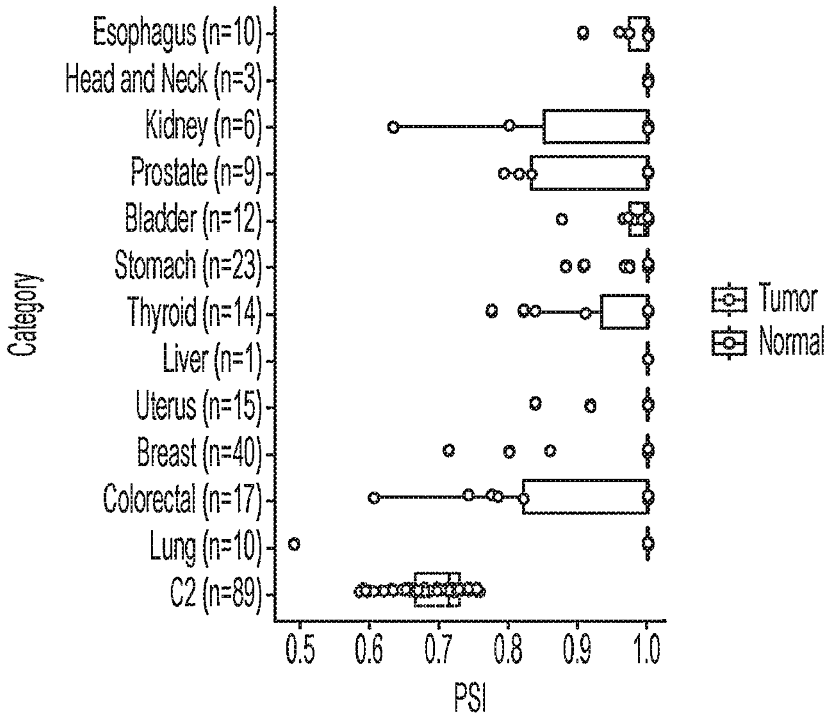
FIG. 37C: Exon splicing levels (PSI) for tumor specific cluster C2 and normal tissues in TCGA. This analysis indicates that the target exon is expressed in 89 breast cancer patients in cluster C2, while very low or absent in normal tissues.
Figure 37D:
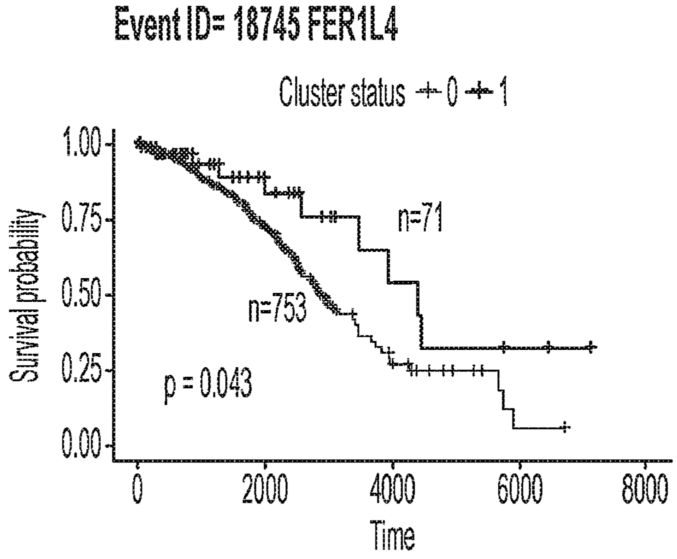
FIG. 37D: Survival analysis of breast cancer patients in cluster C2 versus the remaining breast cancer patients in TCGA. This analysis indicates that patients in C2 (expressing the target exon) have a better overall survival (longer survival time, days).
Figure 38A:
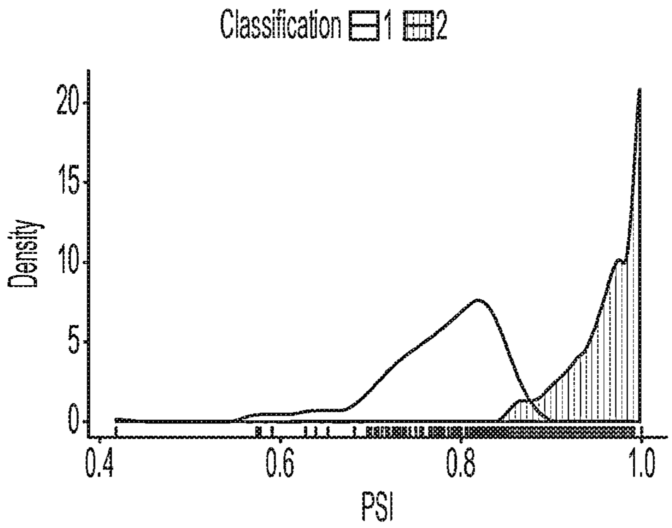
FIG. 38A: GMM analysis of mixed normal and breast cancer samples for the splicing event 19824 (PHF14 gene). The GMM analysis showed 2 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 38B:
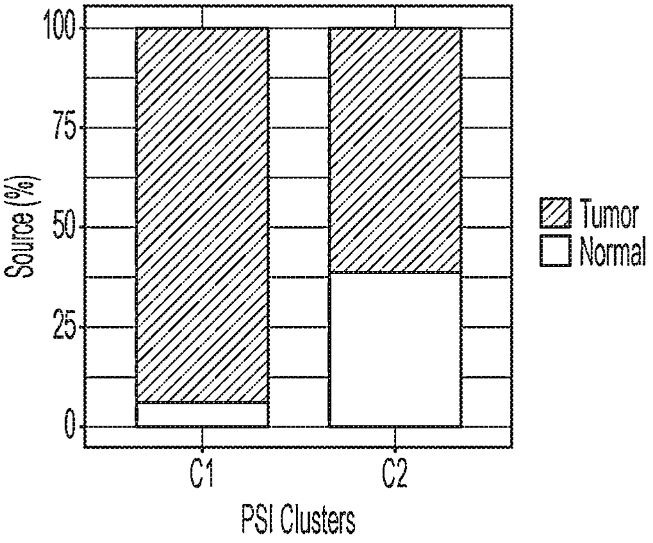
FIG. 38B: Frequency (%) of tumor and normal samples across the 2 clusters identified for the splicing event 19824 (PHF14 gene). Clusters 1-2 are composed mostly of breast cancer samples.
Figure 38C:
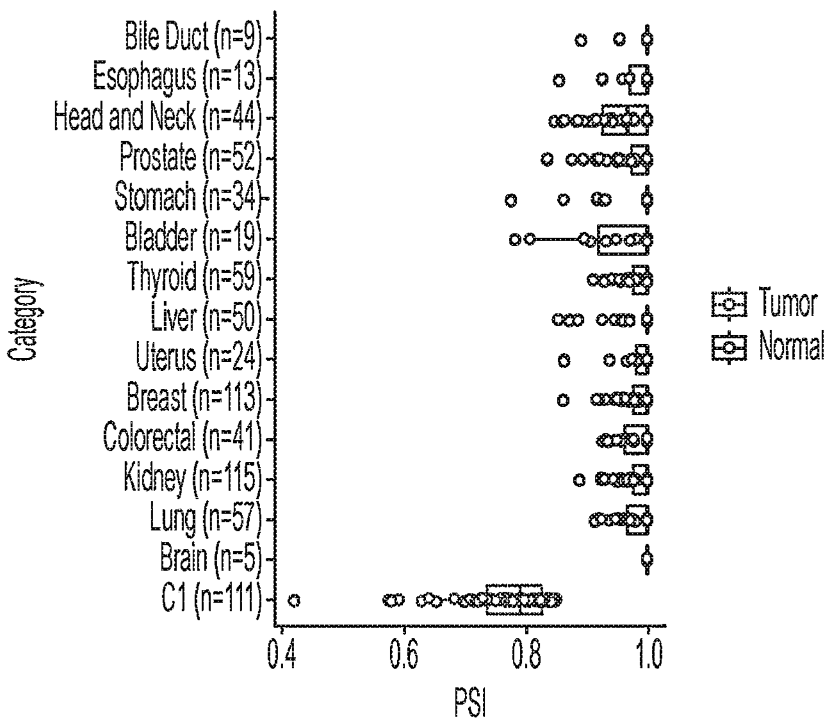
FIG. 38C: Exon splicing levels (PSI) for tumor specific cluster C1 and normal tissues in TCGA. This analysis indicates that the target exon is expressed in 111 breast cancer patients in cluster C1, while very low or absent in normal tissues.
Figure 38D:
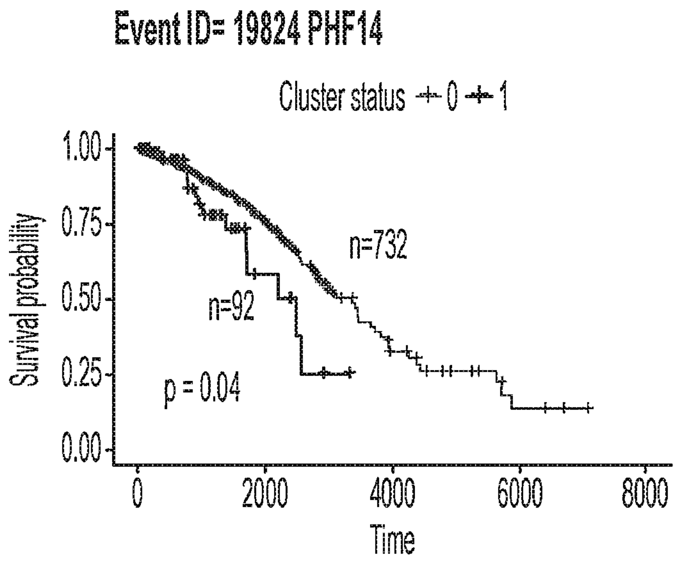
FIG. 38D: Survival analysis of breast cancer patients in cluster C1 versus the remaining breast cancer patients in TCGA. This analysis indicates that patients in C1 (expressing the target exon) have a worse overall survival (shorter survival time, days).
Figure 39A:
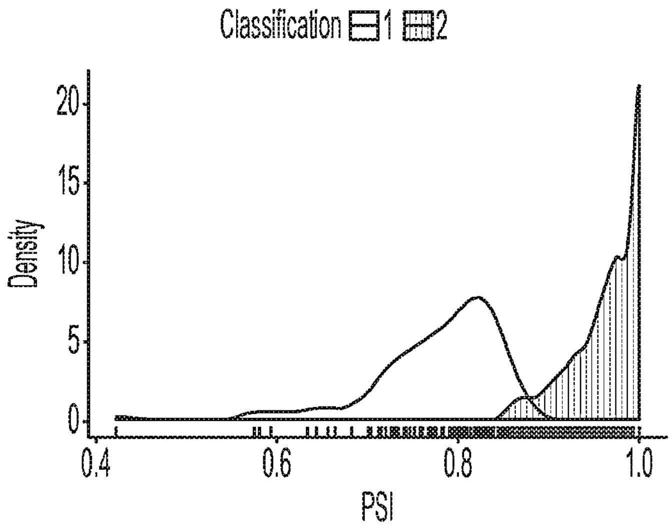
FIG. 39A: GMM analysis of mixed normal and breast cancer samples for the splicing event 19828 (PHF14 gene). The GMM analysis showed 2 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 39B:
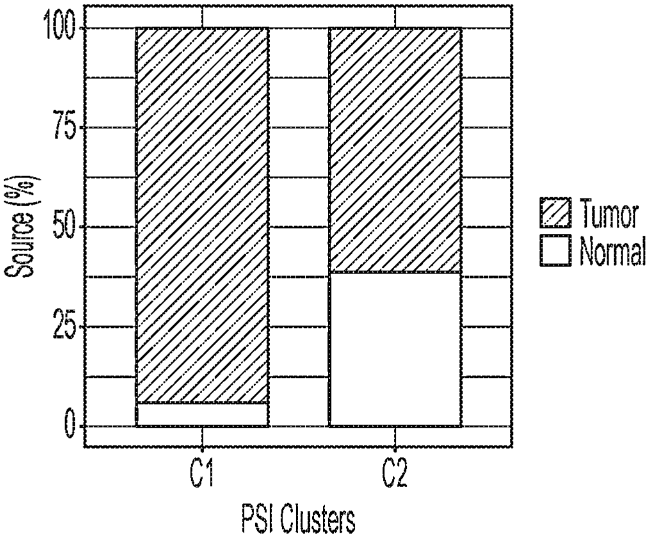
FIG. 39B: Frequency (%) of tumor and normal samples across the 2 clusters identified for the splicing event 19828 (PHF14 gene). Clusters 1-2 are composed mostly of breast cancer samples.
Figure 39C:
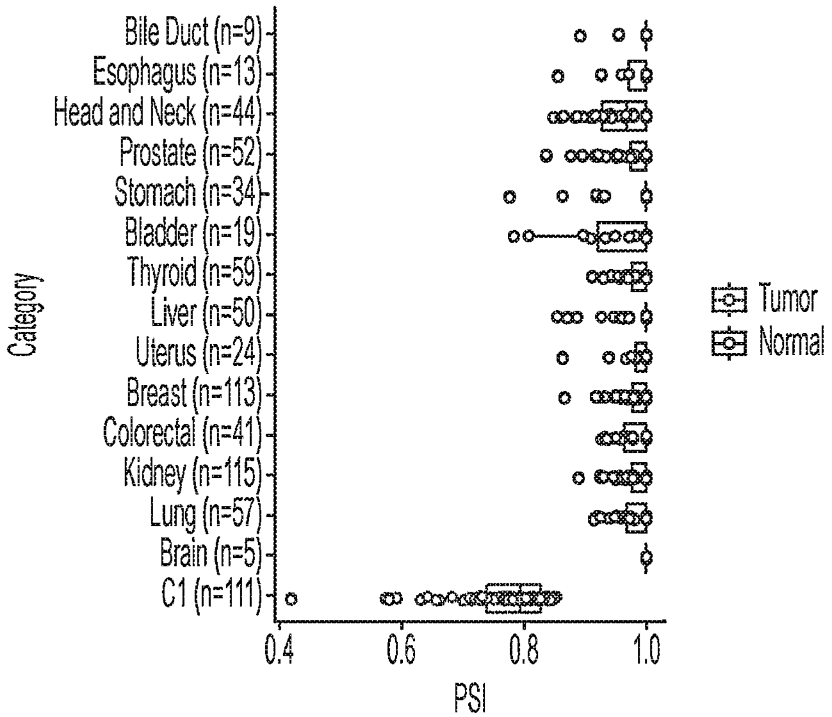
FIG. 39C: Exon splicing levels (PSI) for tumor specific cluster C1 and normal tissues in TCGA. This analysis indicates that the target exon is expressed in 111 breast cancer patients in cluster C1, while very low or absent in normal tissues.
Figure 39D:
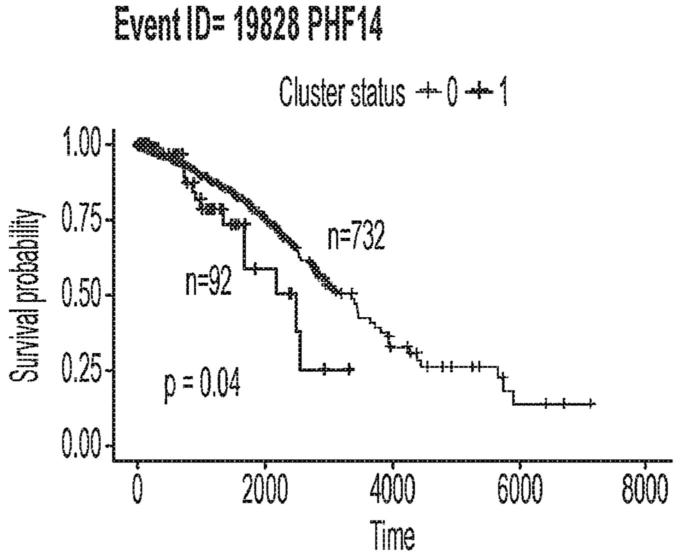
FIG. 39D: Survival analysis of breast cancer patients in cluster C1 versus the remaining breast cancer patients in TCGA. This analysis indicates that patients in C1 (expressing the target exon) have a worse overall survival (shorter survival time, days).
Figure 40A:
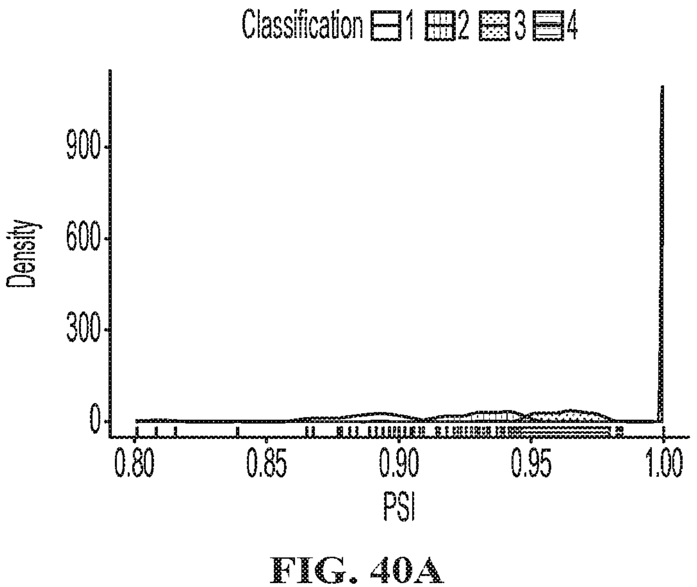
FIG. 40A: GMM analysis of mixed normal and breast cancer samples for the splicing event 21024 (BCL2L13 gene). The GMM analysis showed 4 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 40B:
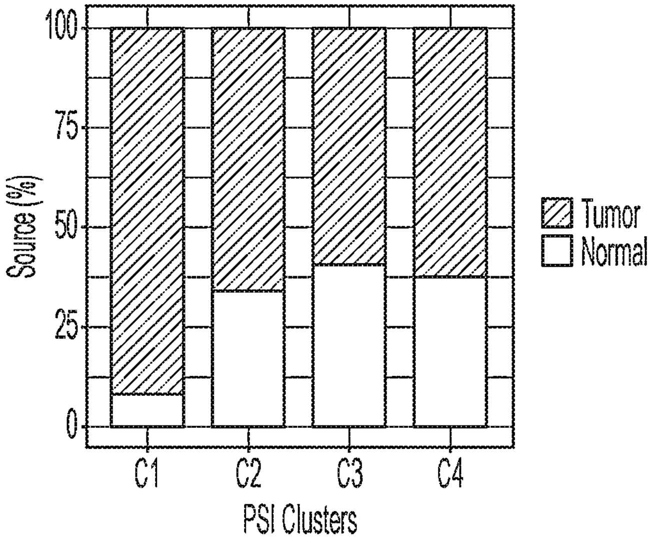
FIG. 40B: Frequency (%) of tumor and normal samples across the 4 clusters identified for the splicing event 21024 (BCL2L13 gene). Clusters 1-4 are composed mostly of breast cancer samples.
Figure 40C:
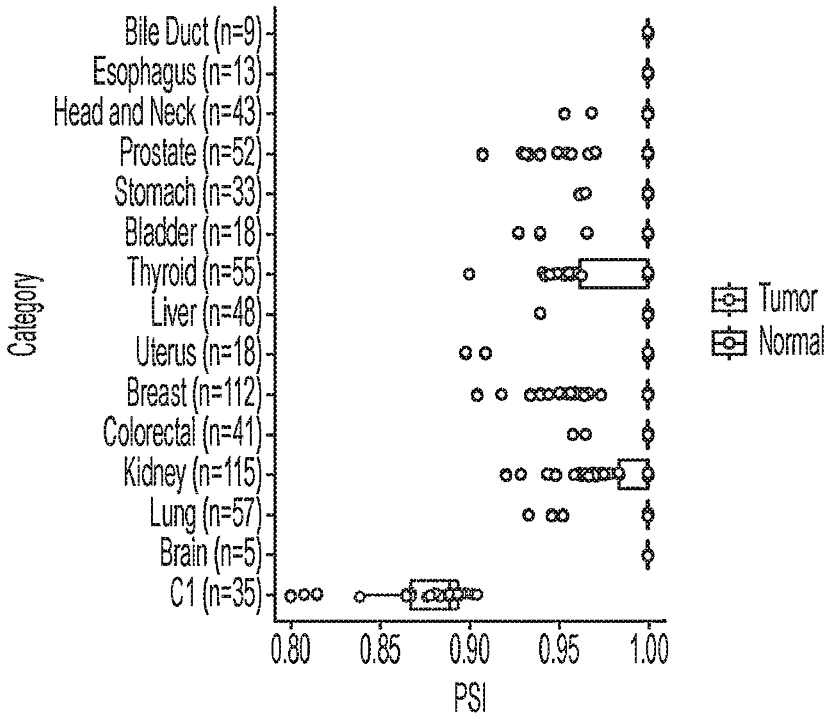
FIG. 40C: Exon splicing levels (PSI) for tumor specific cluster C1 and normal tissues in TCGA. This analysis indicates that the target exon is expressed in 35 breast cancer patients in cluster C1, while very low or absent in normal tissues.
Figure 40D:
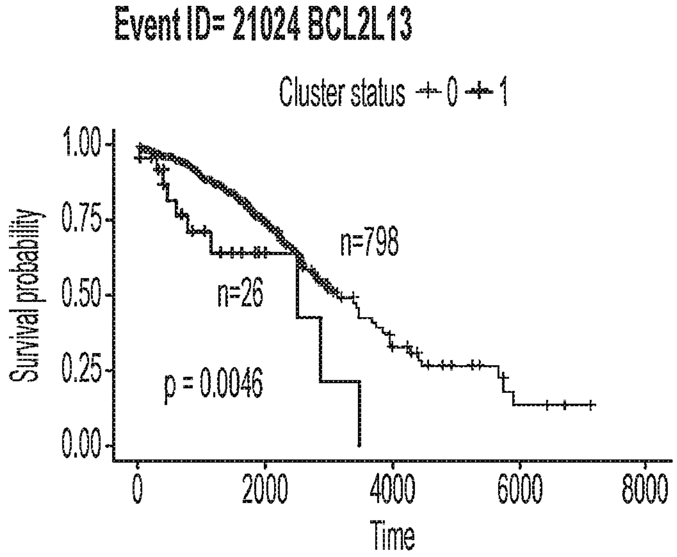
FIG. 40D: Survival analysis of breast cancer patients in cluster C1 versus the remaining breast cancer patients in TCGA. This analysis indicates that patients in C1 (expressing the target exon) have a worse overall survival (shorter survival time, days).
Figure 41A:
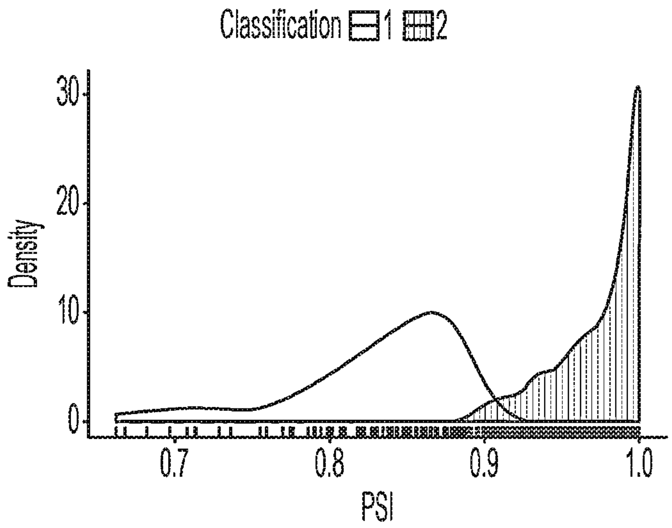
FIG. 41A: GMM analysis of mixed normal and breast cancer samples for the splicing event 22227 (SELENBP1 gene). The GMM analysis showed 2 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 41B:
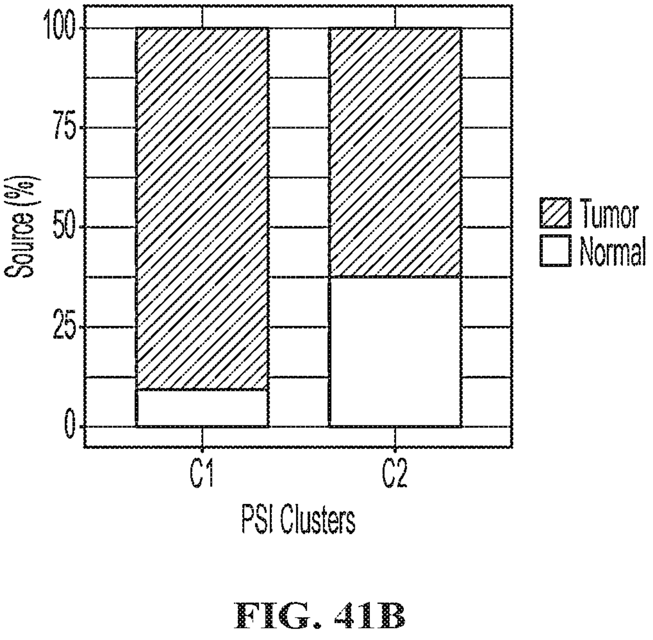
FIG. 41B: Frequency (%) of tumor and normal samples across the 2 clusters identified for the splicing event 22227 (SELENBP1 gene). Clusters 1-2 are composed mostly of breast cancer samples.
Figure 41C:
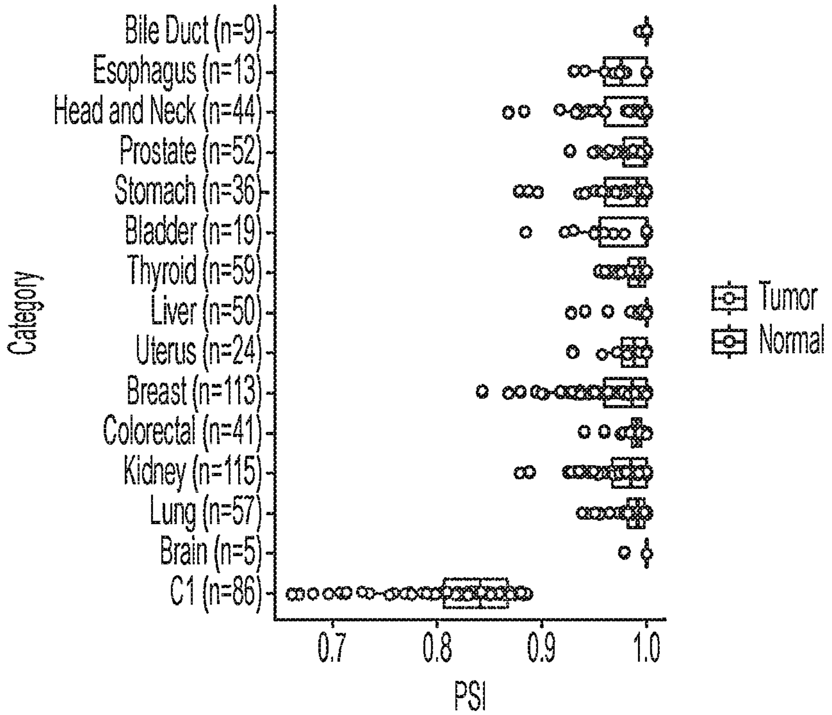
FIG. 41C: Exon splicing levels (PSI) for tumor specific cluster C1 and normal tissues in TCGA. This analysis indicates that the target exon is expressed in 86 breast cancer patients in cluster C1, while very low or absent in normal tissues.
Figure 41D:
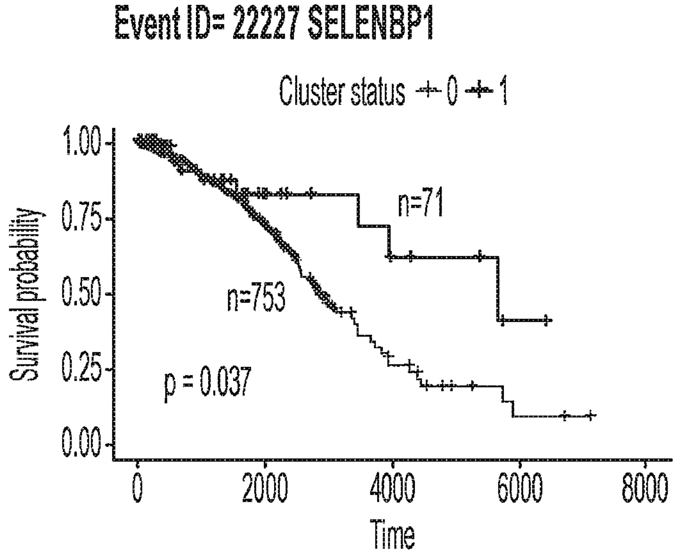
FIG. 41D: Survival analysis of breast cancer patients in cluster C1 versus the remaining breast cancer patients in TCGA. This analysis indicates that patients in C1 (expressing the target exon) have a better overall survival (longer survival time, days).
Figure 42A:
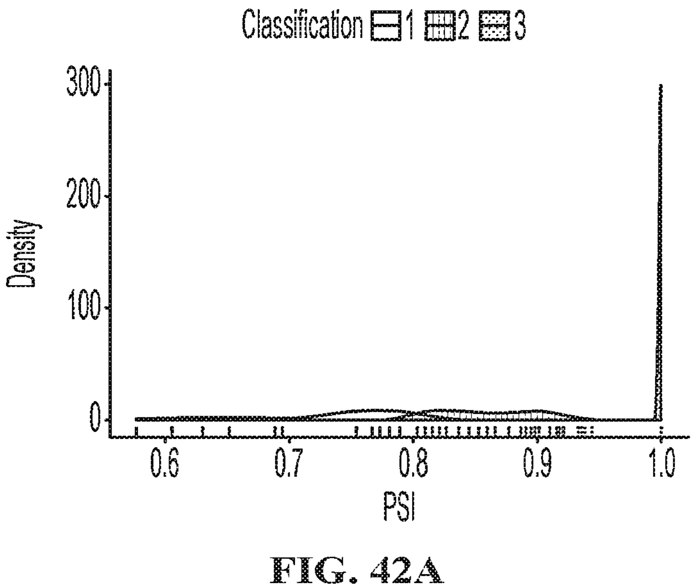
FIG. 42A: GMM analysis of mixed normal and breast cancer samples for the splicing event 24742 (LINC00630 gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 42B:
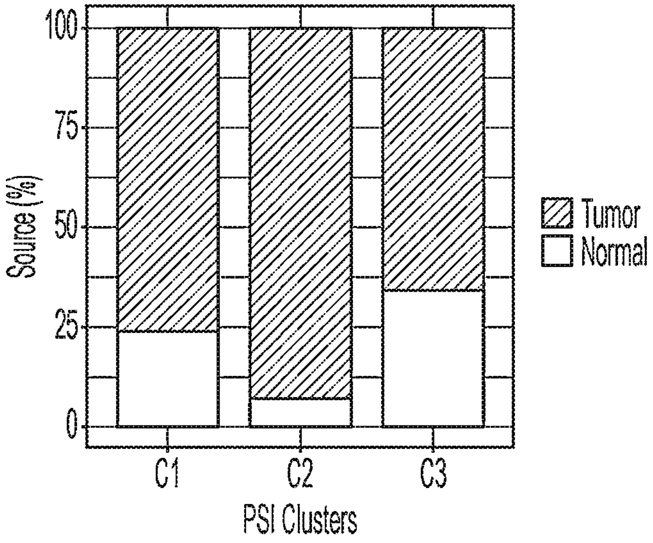
FIG. 42B: Frequency (%) of tumor and normal samples across the 3 clusters identified for the splicing event 24742 (LINC00630 gene). Clusters 1-3 are composed mostly of breast cancer samples.
Figure 42C:
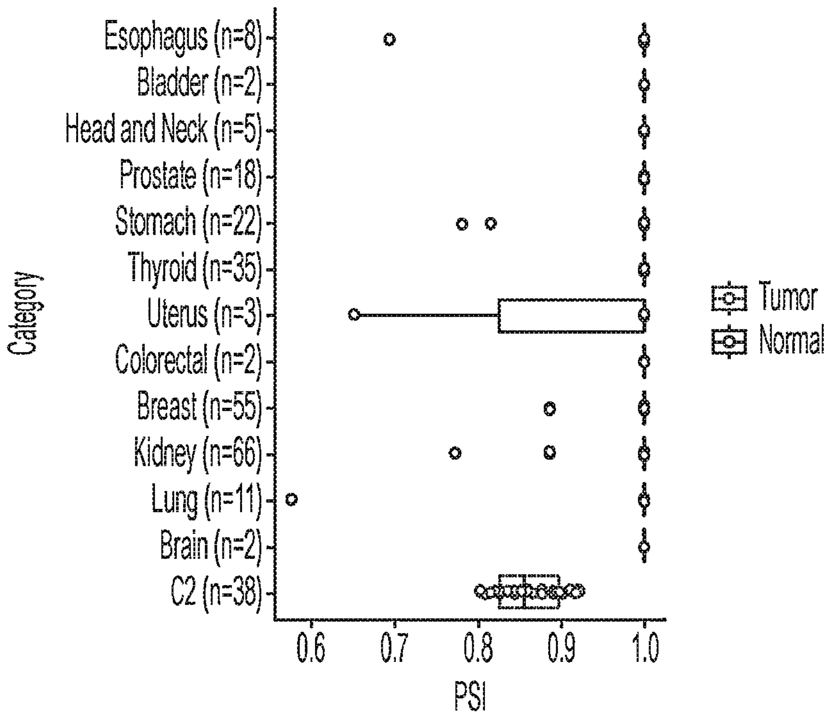
FIG. 42C: Exon splicing levels (PSI) for tumor specific cluster C2 and normal tissues in TCGA. This analysis indicates that the target exon is expressed in 38 breast cancer patients in cluster C2, while very low or absent in normal tissues except uterus.
Figure 42D:
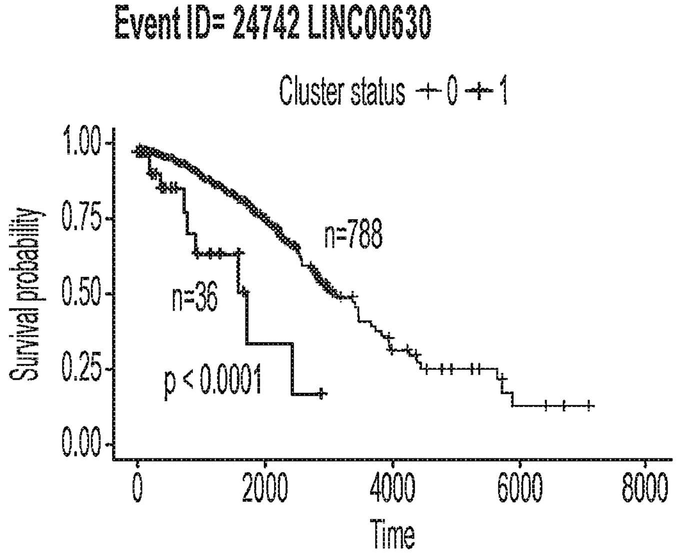
FIG. 42D: Survival analysis of breast cancer patients in cluster C2 versus the remaining breast cancer patients in TCGA. This analysis indicates that patients in C2 (expressing the target exon) have a worse overall survival (shorter survival time, days).
Figure 43A:
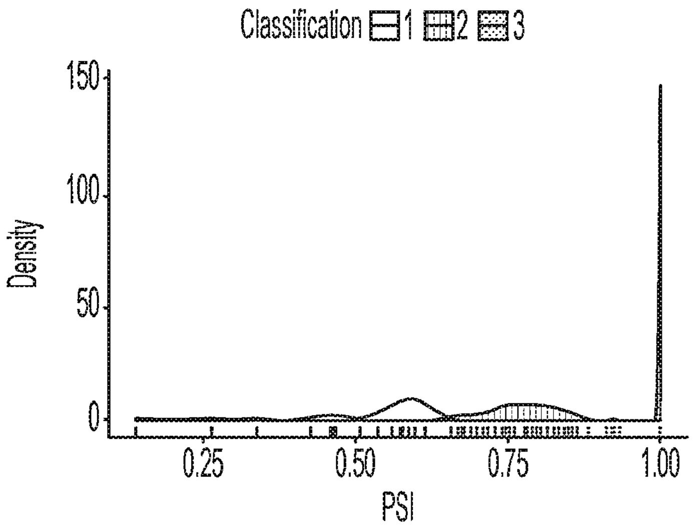
FIG. 43A: GMM analysis of mixed normal and breast cancer samples for the splicing event 27194 (CTBP2 gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 43B:
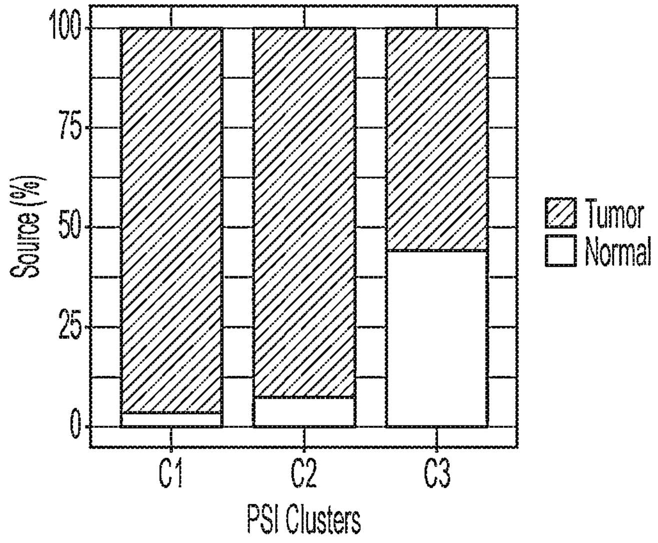
FIG. 43B: Frequency (%) of tumor and normal samples across the 3 clusters identified for the splicing event 27194 (CTBP2 gene). Clusters 1-3 are composed mostly of breast cancer samples.
Figure 43C:
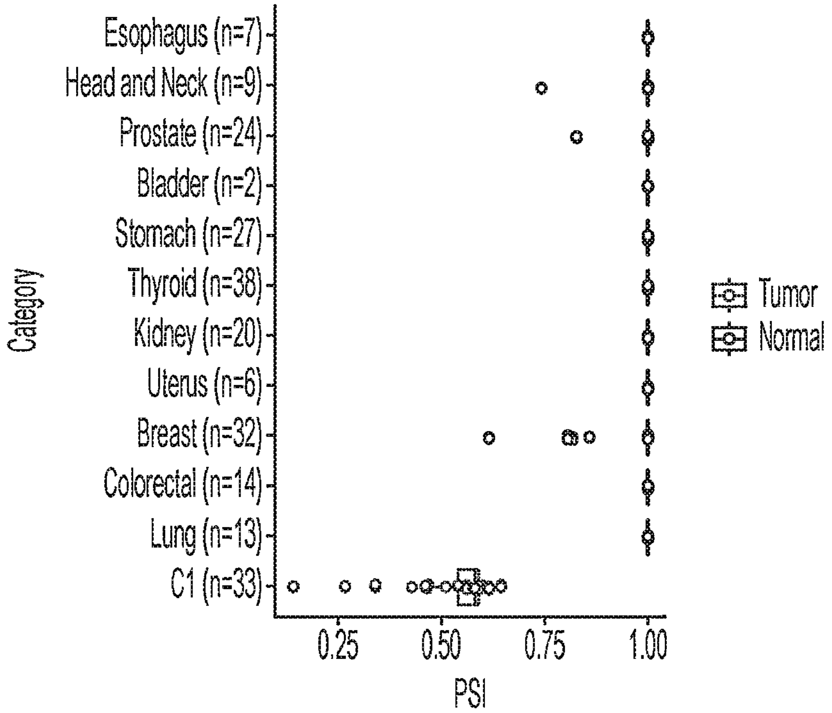
FIG. 43C: Exon splicing levels (PSI) for tumor specific cluster C1 and normal tissues in TCGA. This analysis indicates that the target exon is expressed in 33 breast cancer patients in cluster C1, while very low or absent in normal tissues.
Figure 43D:
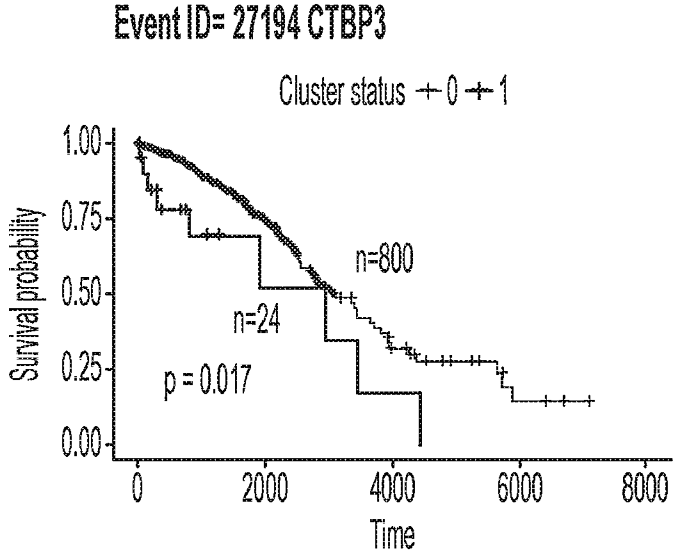
FIG. 43D: Survival analysis of breast cancer patients in cluster C1 versus the remaining breast cancer patients in TCGA. This analysis indicates that patients in C1 (expressing the target exon) have a worse overall survival (shorter survival time, days).
Figure 44A:
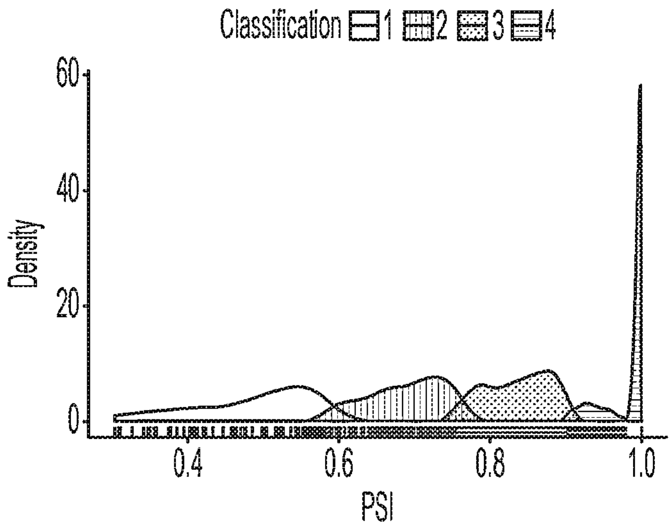
FIG. 44A: GMM analysis of mixed normal and breast cancer samples for the splicing event 30244 (SLC52A2 gene). The GMM analysis showed 4 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 44B:
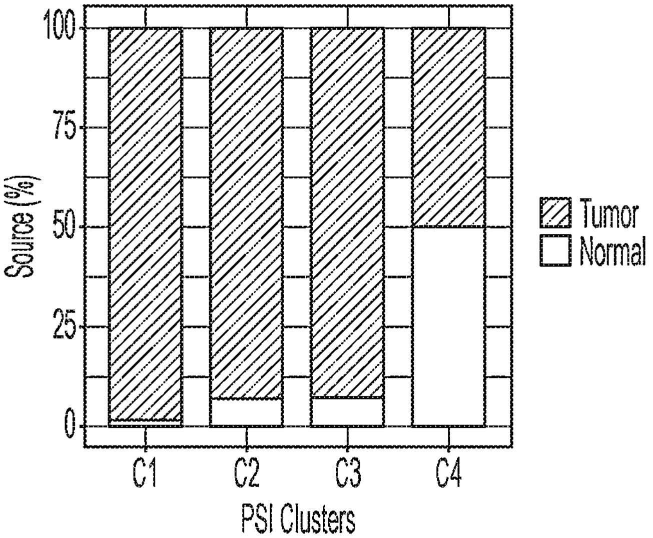
FIG. 44B: Frequency (%) of tumor and normal samples across the 4 clusters identified for the splicing event 30244 (SLC52A2 gene). Clusters 1-3 are composed mostly of breast cancer samples.
Figure 44C:
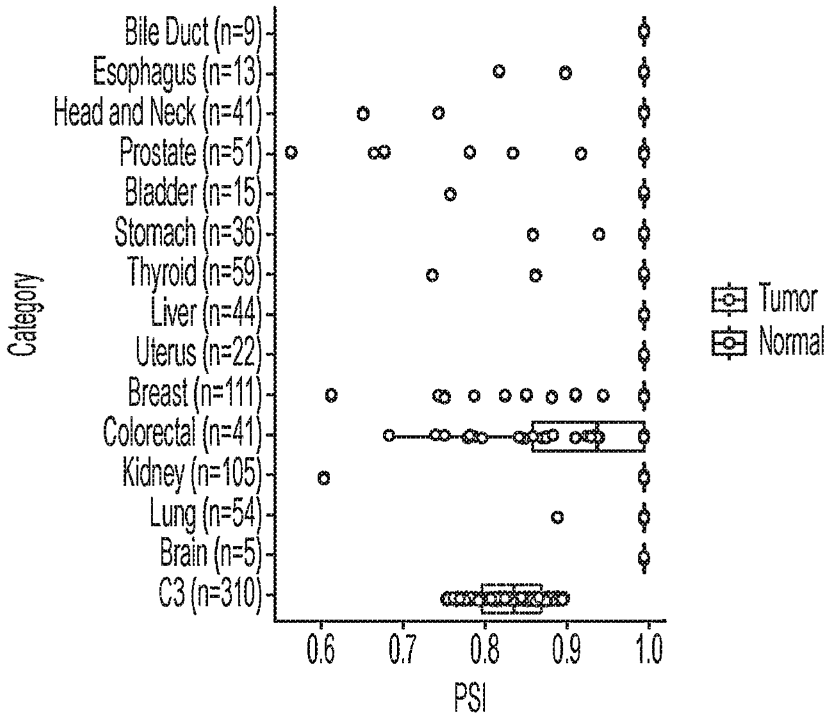
FIG. 44C: Exon splicing levels (PSI) for tumor specific cluster C3 and normal tissues in TCGA. This analysis indicates that the target exon is expressed in 310 breast cancer patients in cluster C3, while very low or absent in normal tissues.
Figure 44D:
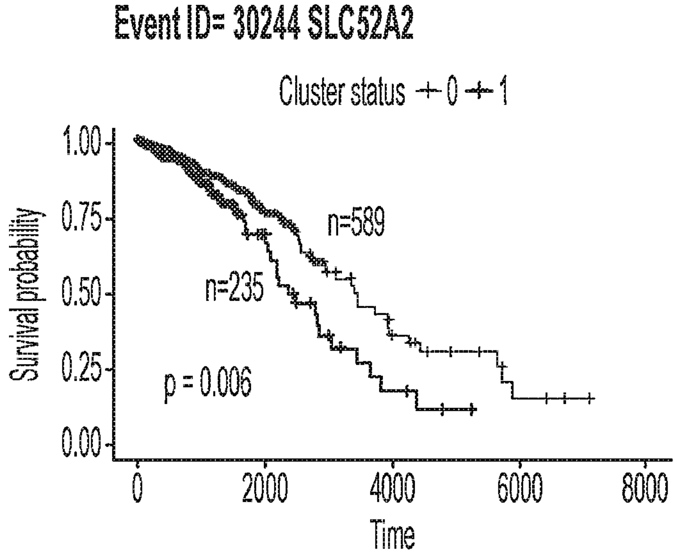
FIG. 44D: Survival analysis of breast cancer patients in cluster C3 versus the remaining breast cancer patients in TCGA. This analysis indicates that patients in C3 (expressing the target exon) have a worse overall survival (shorter survival time, days).
Figure 45A:
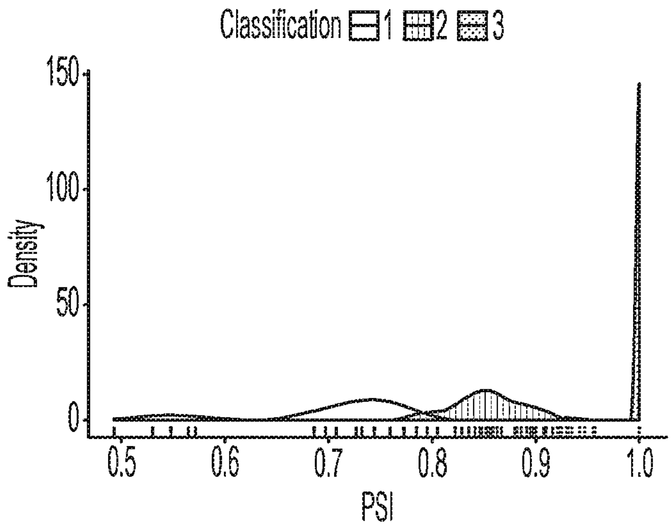
FIG. 45A: GMM analysis of mixed normal and breast cancer samples for the splicing event 33377 (SLC38A1 gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 45B:
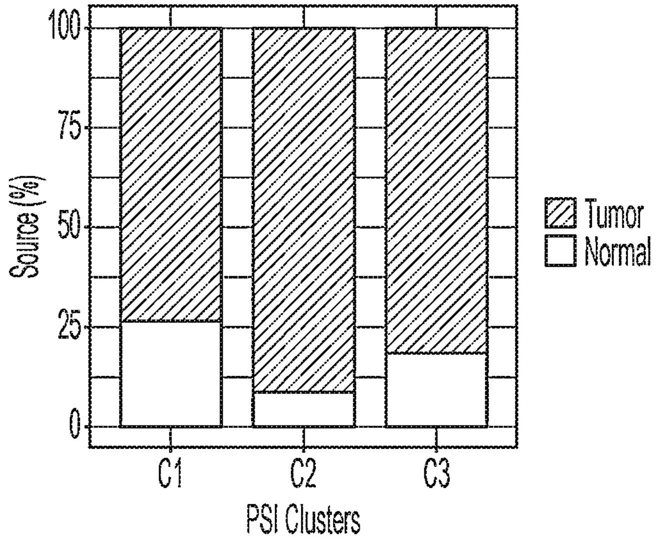
FIG. 45B: Frequency (%) of tumor and normal samples across the 3 clusters identified for the splicing event 33377 (SLC38A1 gene). Clusters 1-3 are composed mostly of breast cancer samples.
Figure 45C:
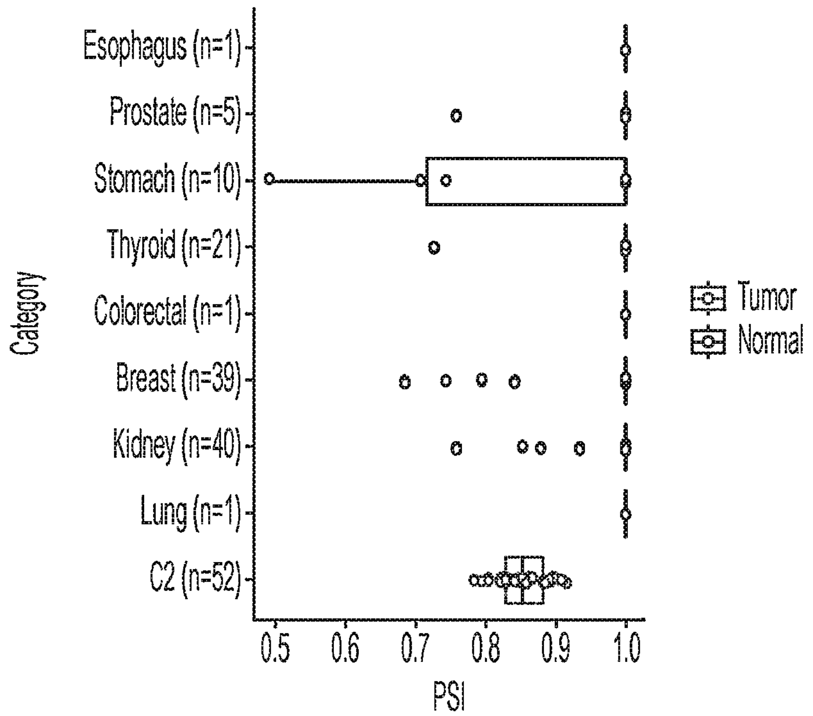
FIG. 45C: Exon splicing levels (PSI) for tumor specific cluster C2 and normal tissues in TCGA. This analysis indicates that the target exon is expressed in 52 breast cancer patients in cluster C2, while very low or absent in normal tissues except stomach.
Figure 45D:
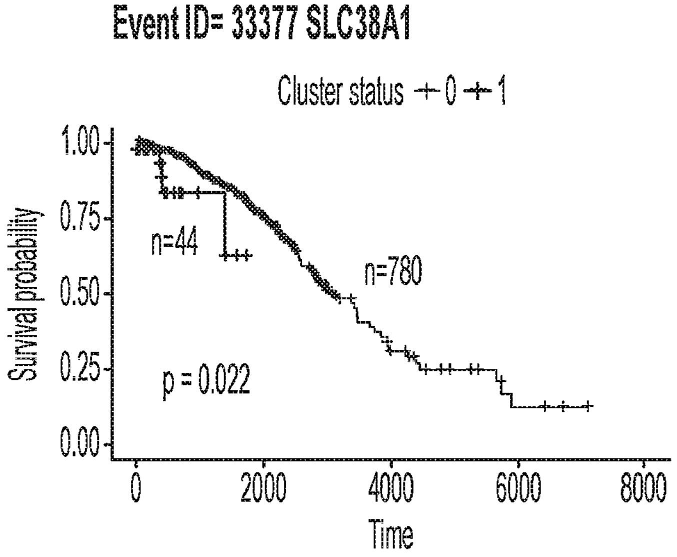
FIG. 45D: Survival analysis of breast cancer patients in cluster C2 versus the remaining breast cancer patients in TCGA. This analysis indicates that patients in C2 (expressing the target exon) have a worse overall survival (shorter survival time, days).
Figure 46A:
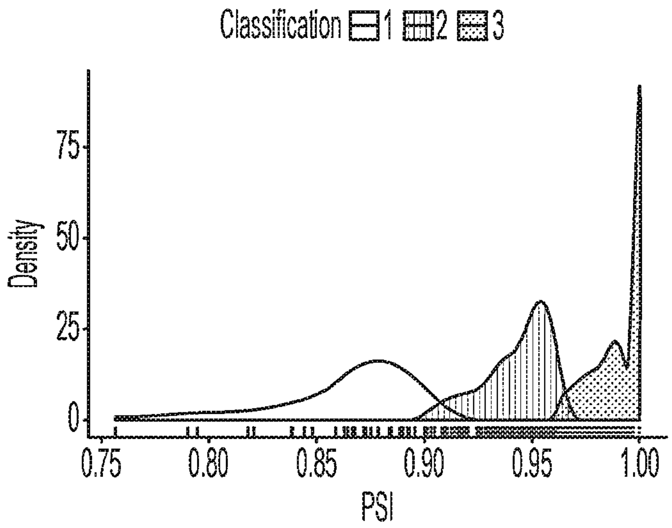
FIG. 46A: GMM analysis of mixed normal and breast cancer samples for the splicing event 40521 (FAM65A gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 46B:
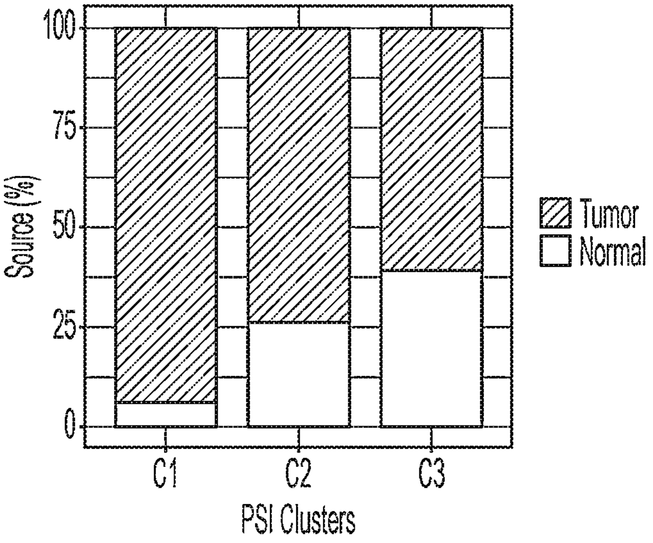
FIG. 46B: Frequency (%) of tumor and normal samples across the 3 clusters identified for the splicing event 40521 (FAM65A gene). Clusters 1-3 are composed mostly of breast cancer samples.
Figure 46C:
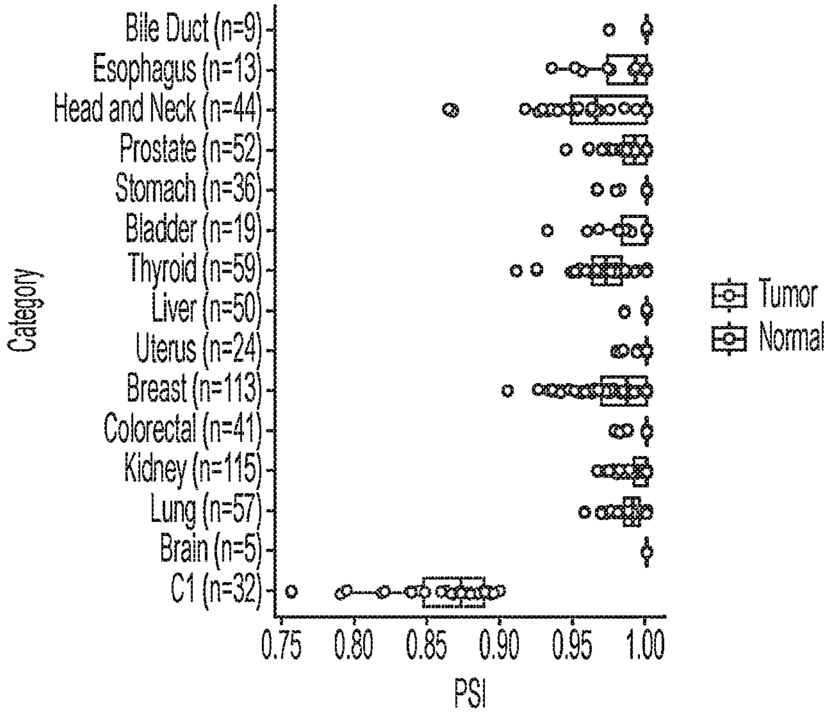
FIG. 46C: Exon splicing levels (PSI) for tumor specific cluster C1 and normal tissues in TCGA. This analysis indicates that the target exon is expressed in 32 breast cancer patients in cluster C1, while very low or absent in normal tissues.
Figure 46D:
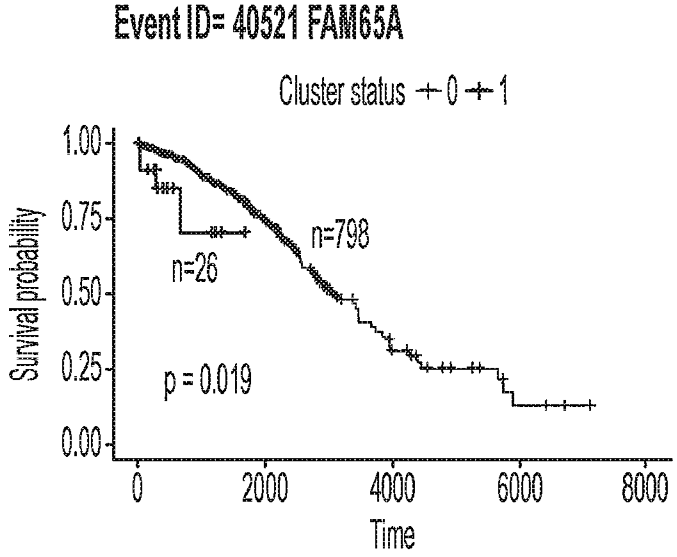
FIG. 46D: Survival analysis of breast cancer patients in cluster C1 versus the remaining breast cancer patients in TCGA. This analysis indicates that patients in C1 (expressing the target exon) have a worse overall survival (shorter survival time, days).
Figure 47A:
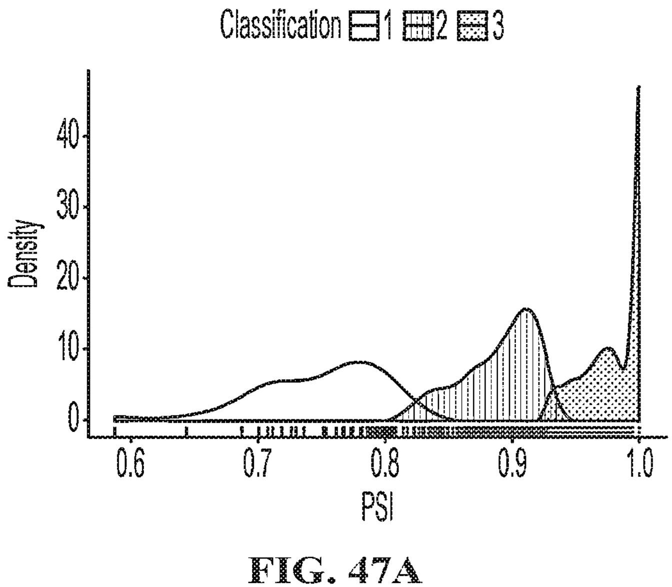
FIG. 47A: GMM analysis of mixed normal and breast cancer samples for the splicing event 41168 (USP25 gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 47B:
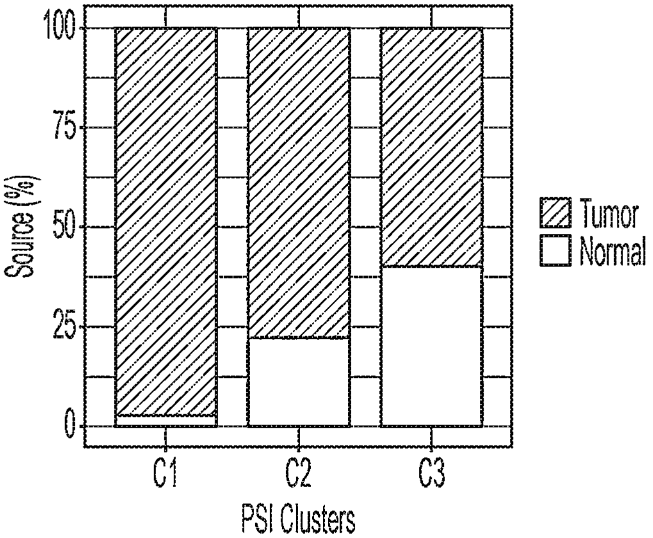
FIG. 47B: Frequency (%) of tumor and normal samples across the 3 clusters identified for the splicing event 41168 (USP25 gene). Clusters 1-3 are composed mostly of breast cancer samples.
Figure 47C:
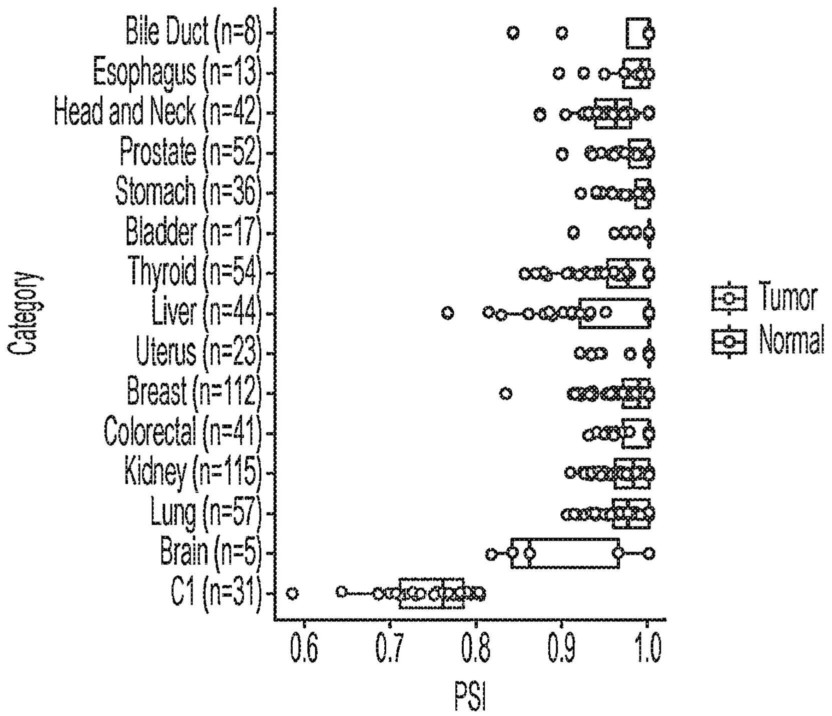
FIG. 47C: Exon splicing levels (PSI) for tumor specific cluster C1 and normal tissues in TCGA. This analysis indicates that the target exon is expressed in 31 breast cancer patients in cluster C1, while very low or absent in normal tissues.
Figure 47D:
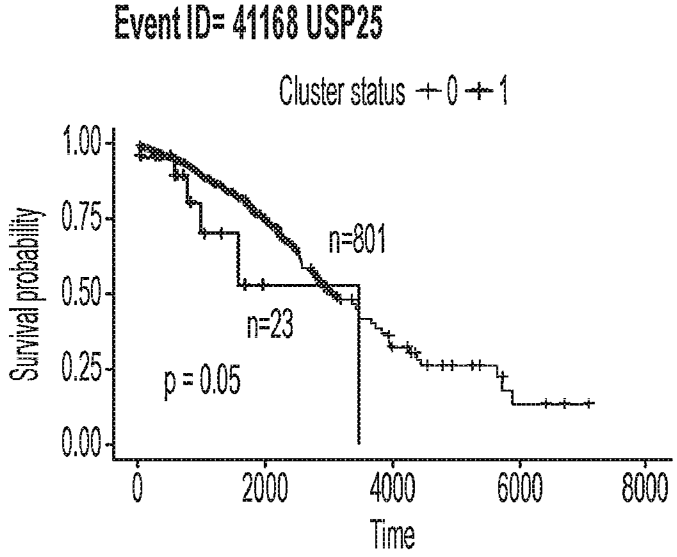
FIG. 47D: Survival analysis of breast cancer patients in cluster C1 versus the remaining breast cancer patients in TCGA. This analysis indicates that patients in C1 (expressing the target exon) have a worse overall survival (shorter survival time, days).
Figure 48A:
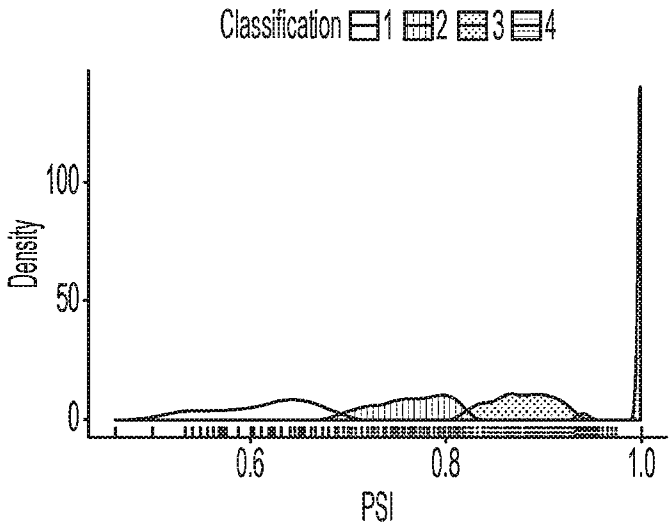
FIG. 48A: GMM analysis of mixed normal and breast cancer samples for the splicing event 45885 (HMOX2 gene). The GMM analysis showed 4 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 48B:
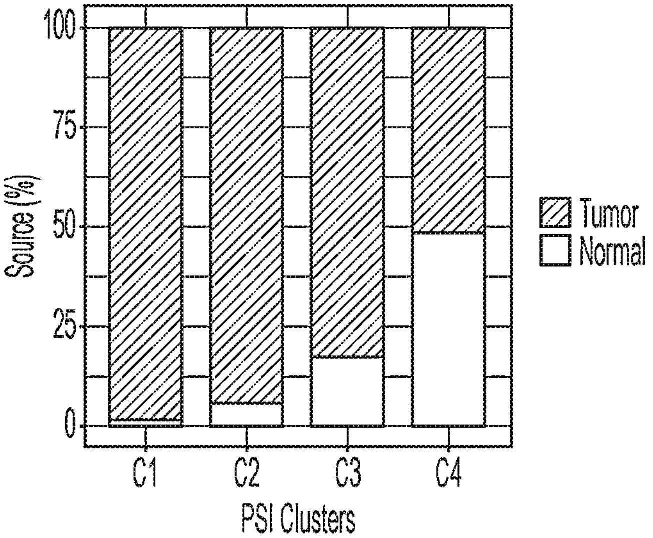
FIG. 48B: Frequency (%) of tumor and normal samples across the 4 clusters identified for the splicing event 45885 (HMOX2 gene). Clusters 1-3 are composed mostly of breast cancer samples.
Figure 48C:
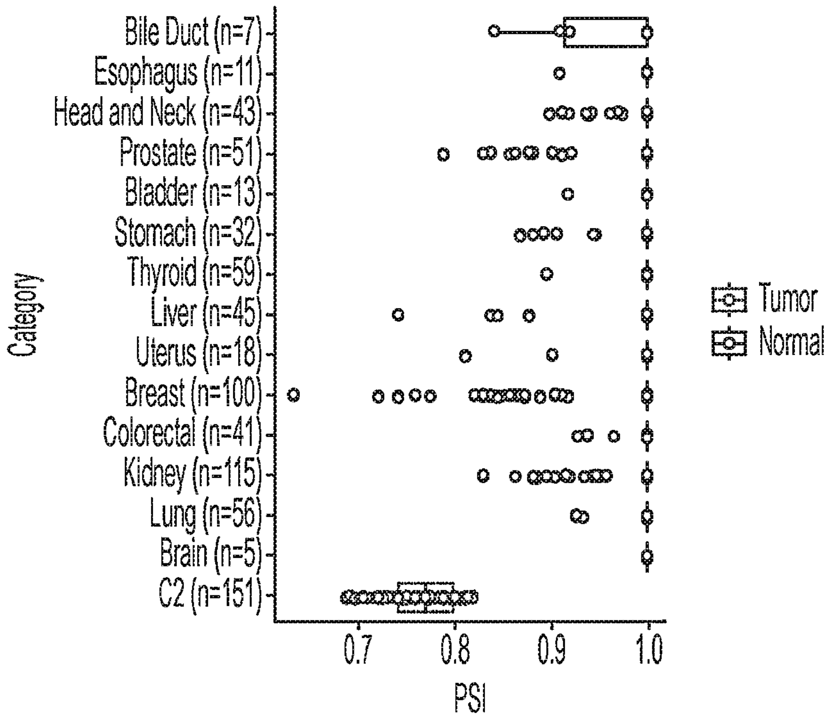
FIG. 48C: Exon splicing levels (PSI) for tumor specific cluster C2 and normal tissues in TCGA. This analysis indicates that the target exon is expressed in 151 breast cancer patients in cluster C2, while very low or absent in normal tissues.
Figure 48D:
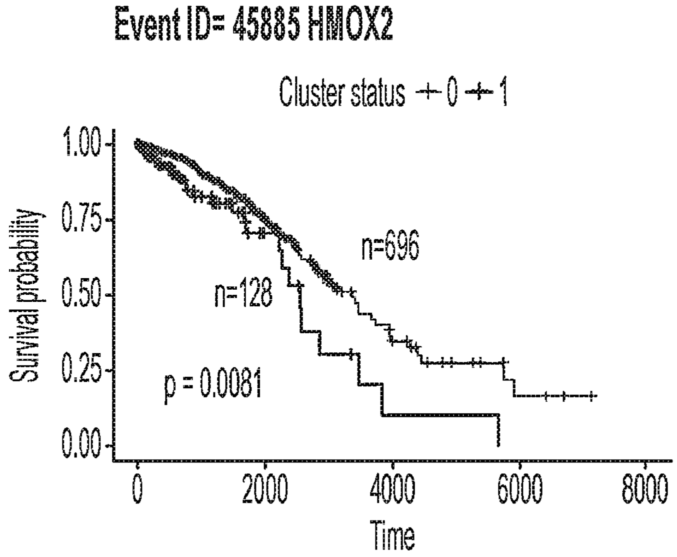
FIG. 48D: Survival analysis of breast cancer patients in cluster C2 versus the remaining breast cancer patients in TCGA. This analysis indicates that patients in C2 (expressing the target exon) have a worse overall survival (shorter survival time, days).
Figure 49A:
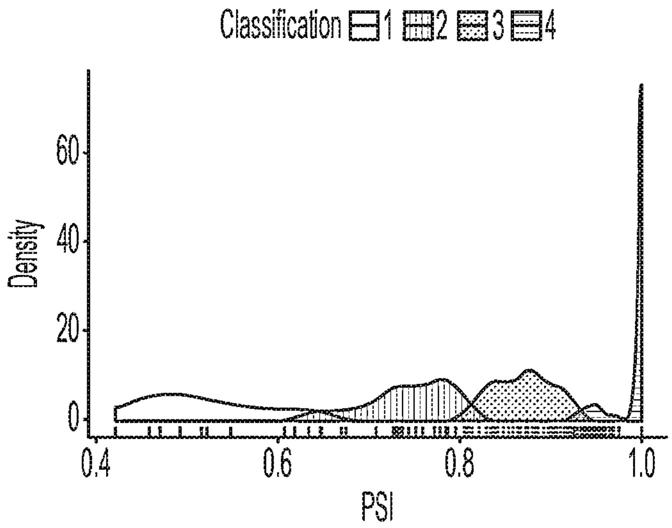
FIG. 49A: GMM analysis of mixed normal and breast cancer samples for the splicing event 50148 (MKRN2OS gene). The GMM analysis showed 4 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 49B:
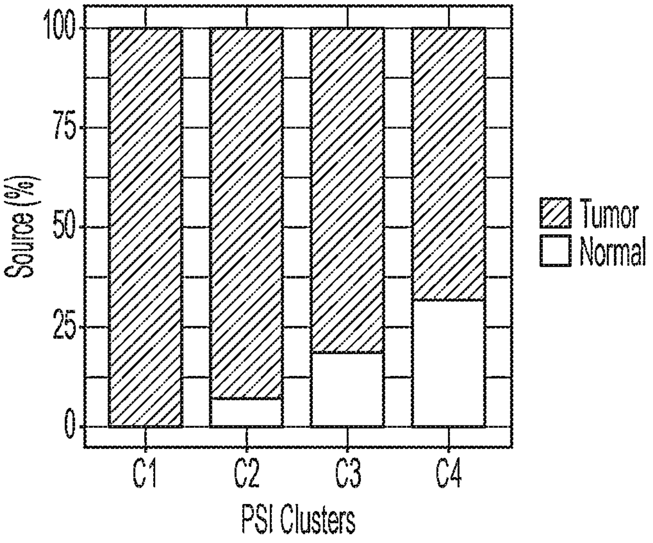
FIG. 49B: Frequency (%) of tumor and normal samples across the 4 clusters identified for the splicing event 50148 (MKRN2OS gene). Clusters 1-4 are composed mostly of breast cancer samples.
Figure 49C:
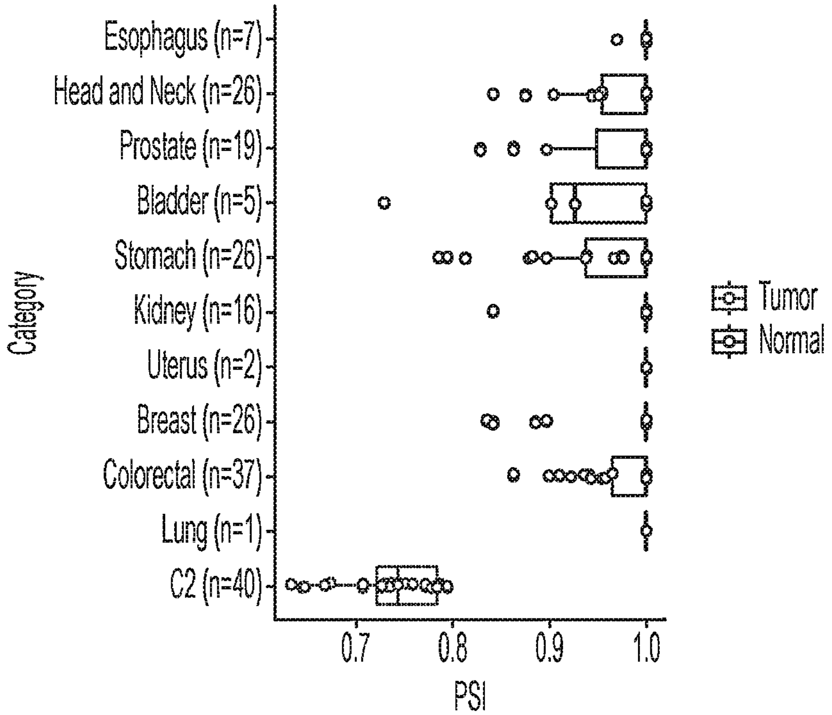
FIG. 49C: Exon splicing levels (PSI) for tumor specific cluster C2 and normal tissues in TCGA. This analysis indicates that the target exon is expressed in 40 breast cancer patients in cluster C2, while very low or absent in normal tissues.
Figure 49D:
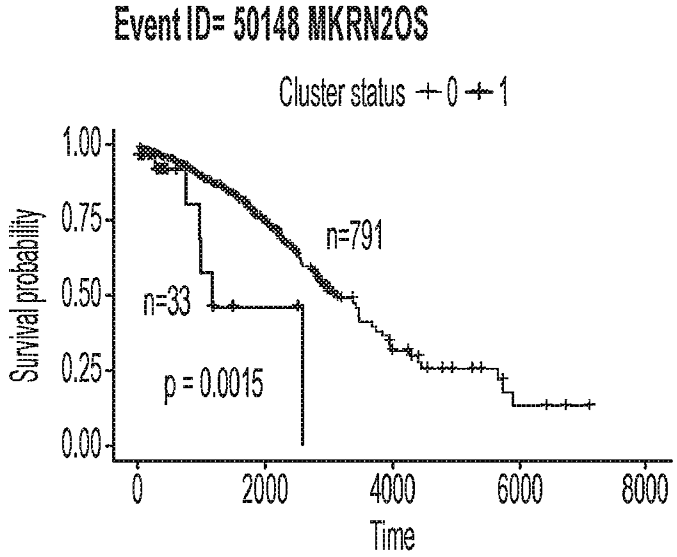
FIG. 49D: Survival analysis of breast cancer patients in cluster C2 versus the remaining breast cancer patients in TCGA. This analysis indicates that patients in C2 (expressing the target exon) have a worse overall survival (shorter survival time, days).
Figure 50A:
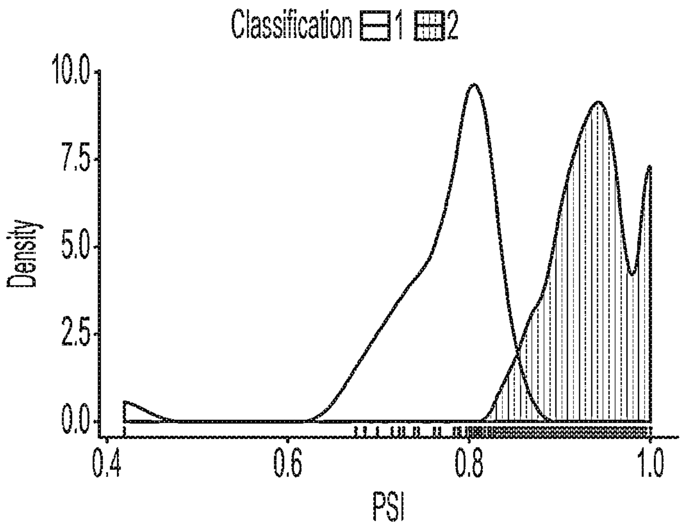
FIG. 50A: GMM analysis of mixed normal and breast cancer samples for the splicing event 52249 (ATP8A2P1 gene). The GMM analysis showed 2 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 50B:
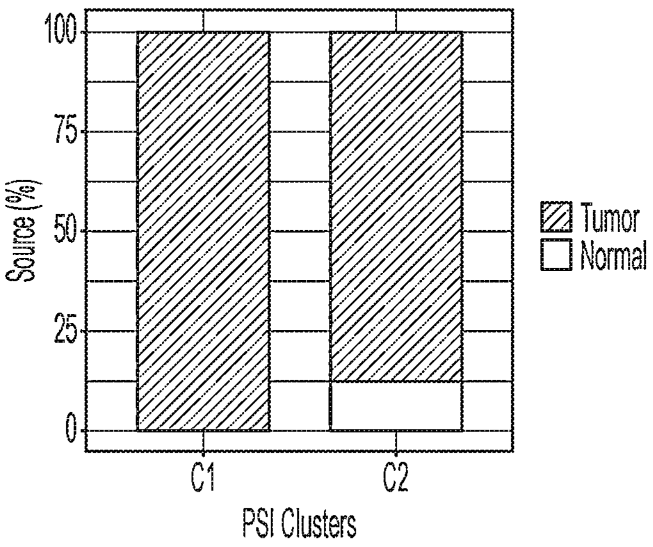
FIG. 50B: Frequency (%) of tumor and normal samples across the 2 clusters identified for the splicing event 52249 (ATP8A2P1 gene). Clusters 1-2 are composed mostly of breast cancer samples.
Figure 50C:
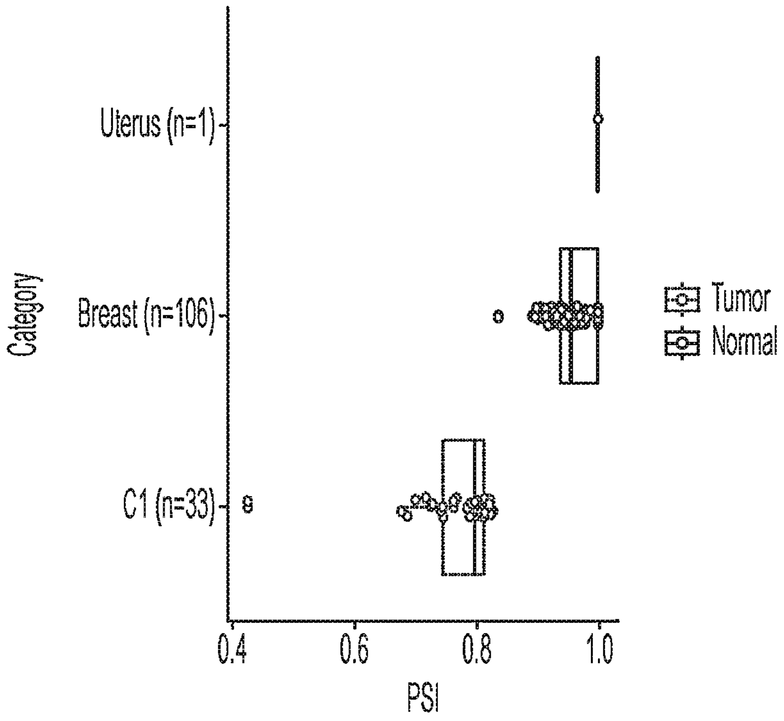
FIG. 50C: Exon splicing levels (PSI) for tumor specific cluster C1 and normal tissues in TCGA. This analysis indicates that the target exon is expressed in 33 breast cancer patients in cluster C1, while very low or absent in normal tissues.
Figure 50D:
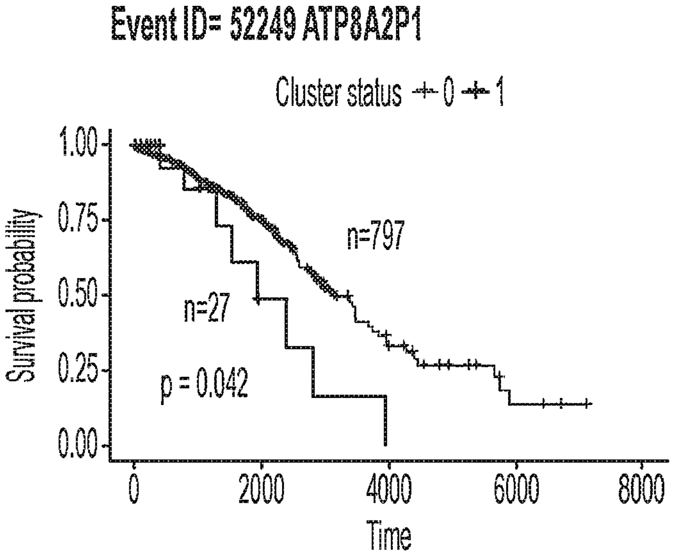
FIG. 50D: Survival analysis of breast cancer patients in cluster C1 versus the remaining breast cancer patients in TCGA. This analysis indicates that patients in C1 (expressing the target exon) have a worse overall survival (shorter survival time, days).
Figure 51A:
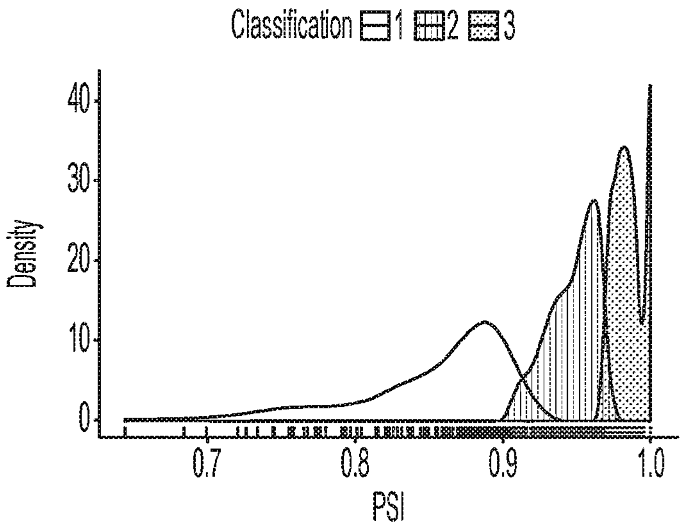
FIG. 51A: GMM analysis of mixed normal and breast cancer samples for the splicing event 53188 (HIBCH gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 51B:
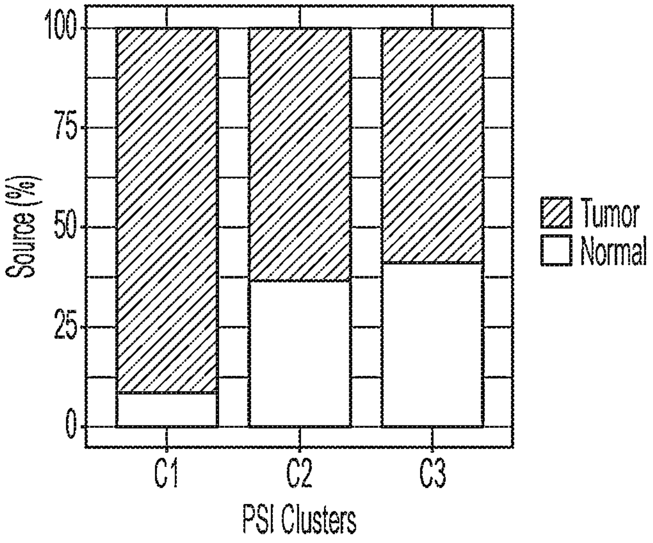
FIG. 51B: Frequency (%) of tumor and normal samples across the 3 clusters identified for the splicing event 53188 (HIBCH gene). Clusters 1-3 are composed mostly of breast cancer samples.
Figure 51C:
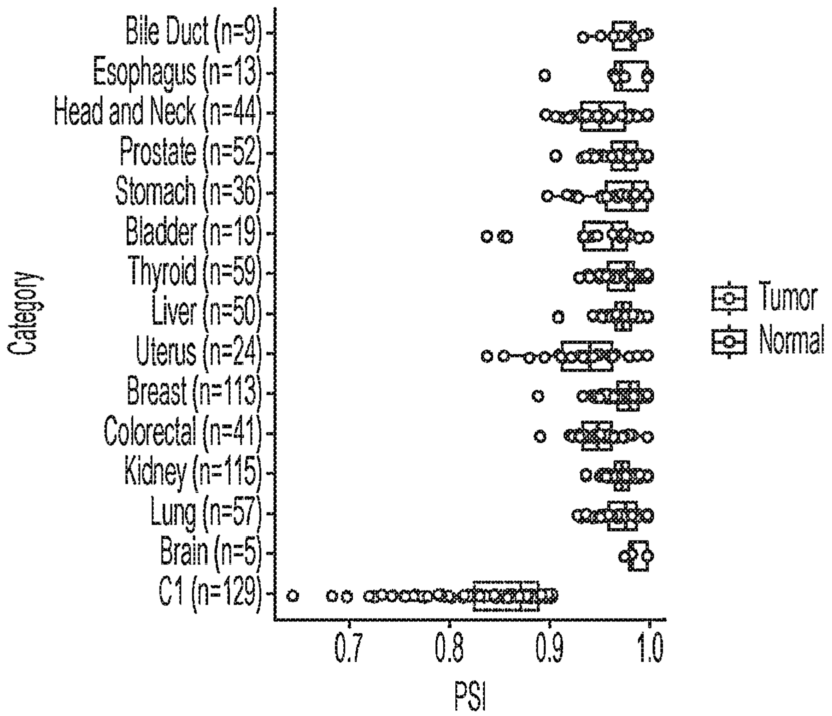
FIG. 51C: Exon splicing levels (PSI) for tumor specific cluster C1 and normal tissues in TCGA. This analysis indicates that the target exon is expressed in 129 breast cancer patients in cluster C1, while very low or absent in normal tissues.
Figure 51D:
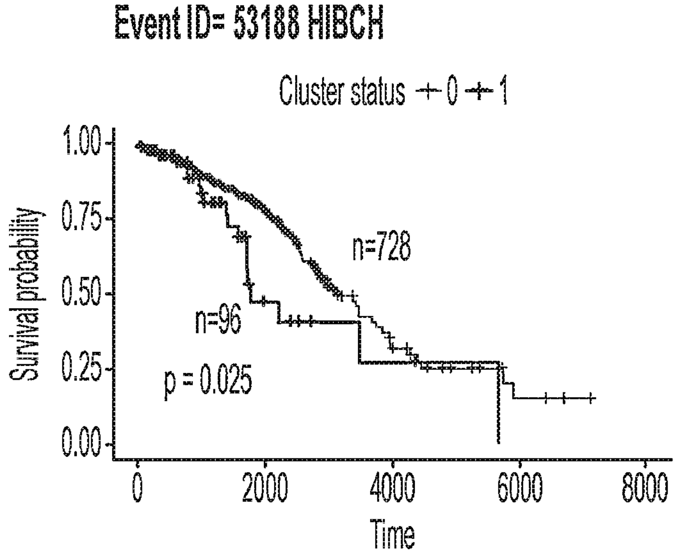
FIG. 51D: Survival analysis of breast cancer patients in cluster C1 versus the remaining breast cancer patients in TCGA. This analysis indicates that patients in C1 (expressing the target exon) have a worse overall survival (shorter survival time, days).
Figure 52A:
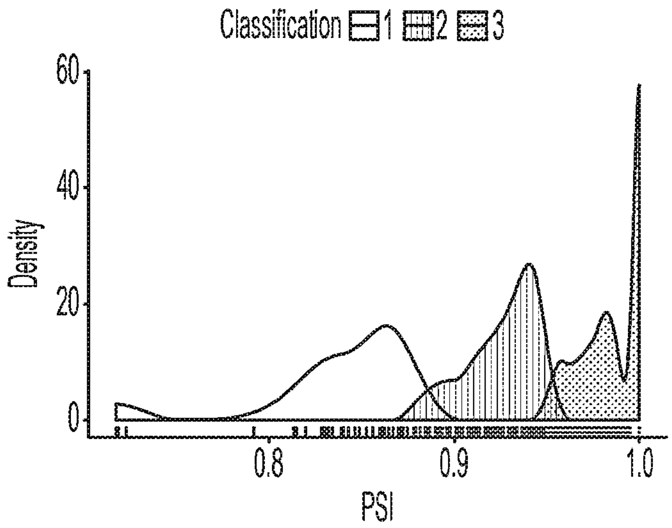
FIG. 52A: GMM analysis of mixed normal and breast cancer samples for the splicing event 58853 (SLC35C2 gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 52B:
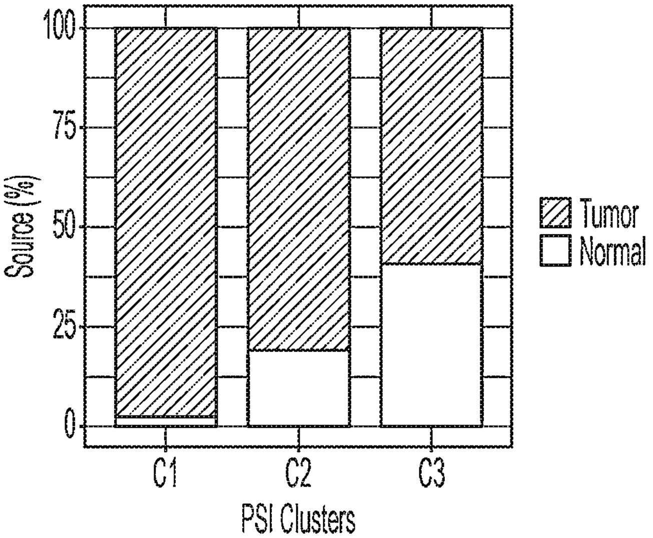
FIG. 52B: Frequency (%) of tumor and normal samples across the 3 clusters identified for the splicing event 58853 (SLC35C2 gene). Clusters 1-3 are composed mostly of breast cancer samples.
Figure 52C:
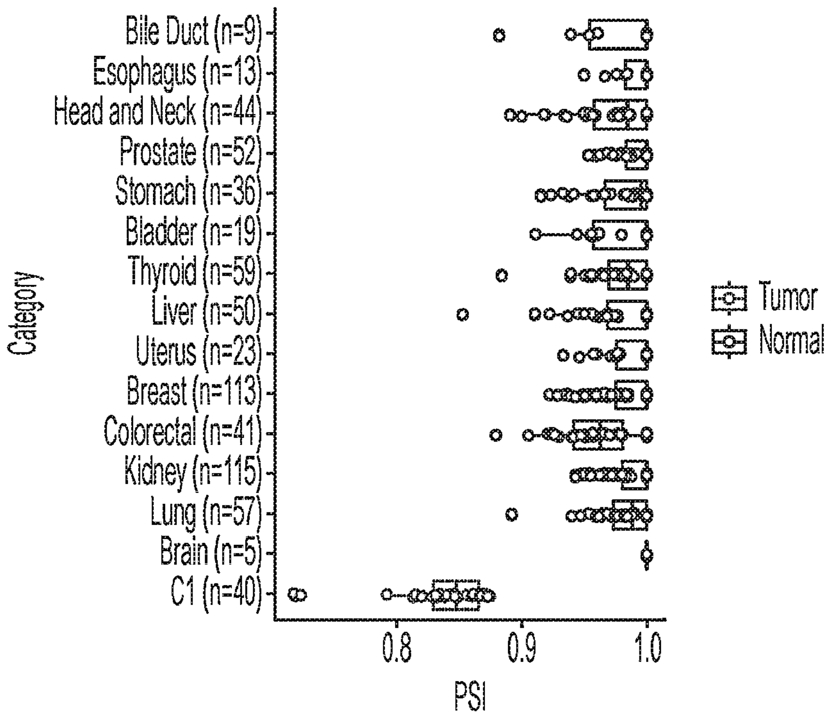
FIG. 52C: Exon splicing levels (PSI) for tumor specific cluster C1 and normal tissues in TCGA. This analysis indicates that the target exon is expressed in 40 breast cancer patients in cluster C1, while very low or absent in normal tissues.
Figure 52D:
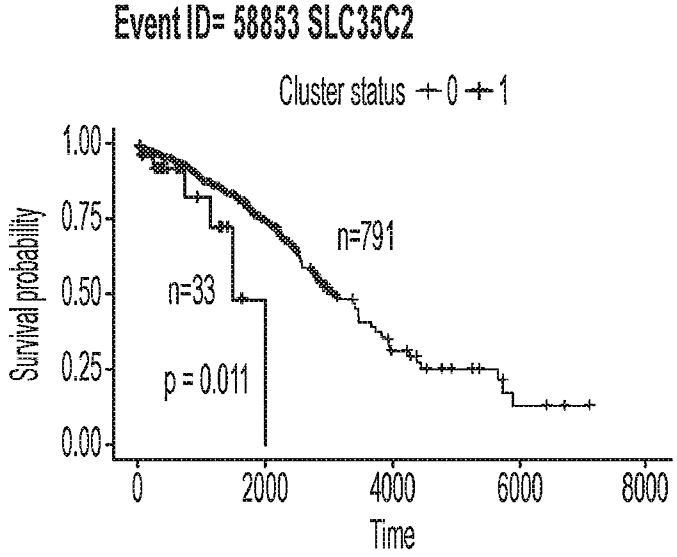
FIG. 52D: Survival analysis of breast cancer patients in cluster C1 versus the remaining breast cancer patients in TCGA. This analysis indicates that patients in C1 (expressing the target exon) have a worse overall survival (shorter survival time, days).
Figure 53A:
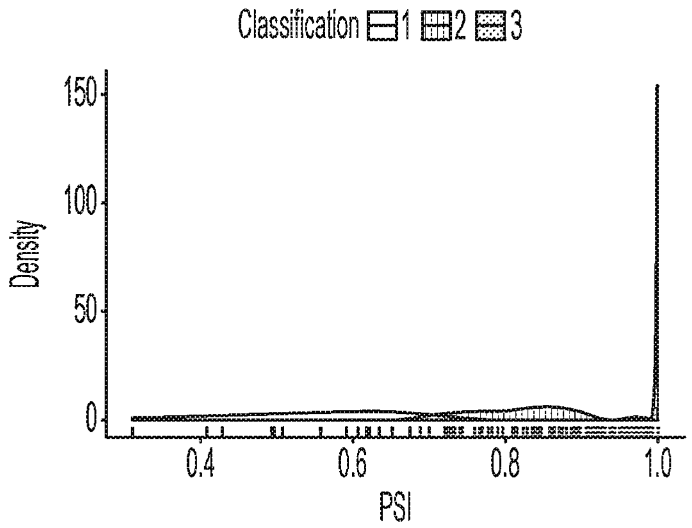
FIG. 53A: GMM analysis of mixed normal and breast cancer samples for the splicing event 59314 (TRIM5 gene). The GMM analysis showed 3 distinct clusters (subpopulations). The x-axis indicates the exon percent spliced in (PSI, ψ) level within samples, and y-axis denotes the number of samples in a normalized density scale. Shading indicates the cluster assignment of each sample.
Figure 53B:
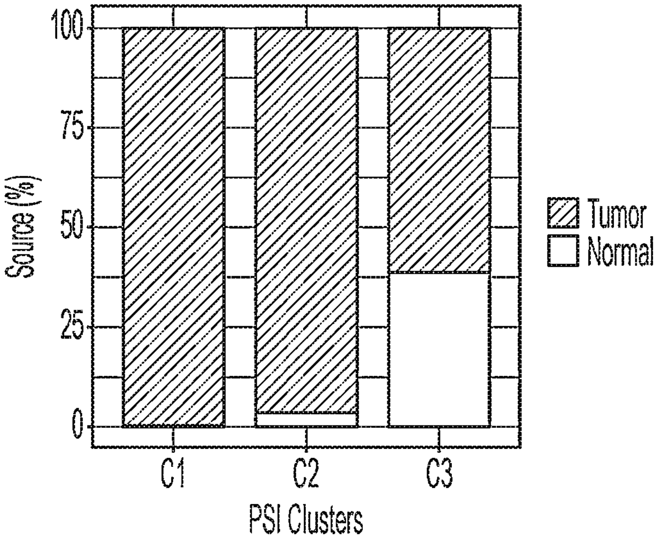
FIG. 53B: Frequency (%) of tumor and normal samples across the 3 clusters identified for the splicing event 59314 (TRIM5 gene). Clusters 1-3 are composed mostly of breast cancer samples.
Figure 53C:
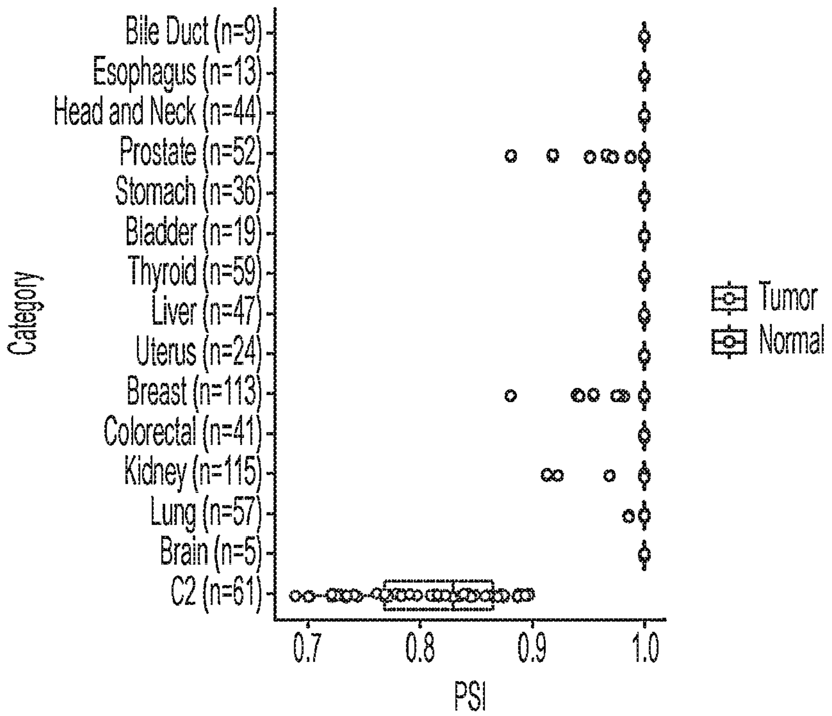
FIG. 53C: Exon splicing levels (PSI) for tumor specific cluster C2 and normal tissues in TCGA. This analysis indicates that the target exon is expressed in 61 breast cancer patients in cluster C2, while very low or absent in normal tissues.
Figure 53D:
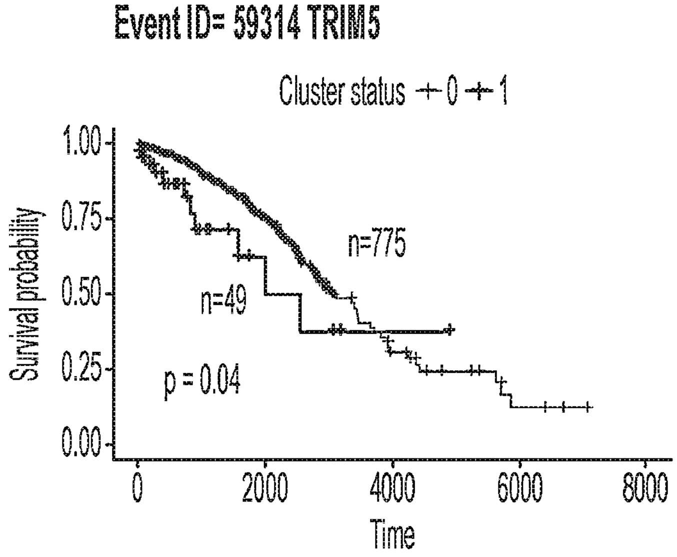
FIG. 53D: Survival analysis of breast cancer patients in cluster C1 versus the remaining breast cancer patients in TCGA. This analysis indicates that patients in C1 (expressing the target exon) have a worse overall survival (shorter survival time, days).

The cluster C1 contains 37 breast cancer patients out of 824 analyzed, which means that the exon exclusion event was detected in ~4% of TCGA breast cancer patients. Moreover, survival analysis of breast cancer patients in cluster C1 versus the remaining breast cancer patients in TCGA indicates that patients in C1 (the targeting exon is spliced out) have a worse overall survival (FIG. 23D). Therefore, the exon exclusion event 1506 (CENPK) is (i) specific to breast cancer, (ii) is detected in a subpopulation of breast cancer patients, and (iii) is associated to unfavorable overall survival.

TABLE 6

| Exon Inclusion Event Sequences | | | |
|---|---|---|---|
| Splicing Event ID | Gene Name | cDNA Sequence | SEQ ID NO: |
| 1446 | CCDC115 | GCCTGCAGCTGGCCGCAGACATAGCCAGCCTCC<br>AGAACCGCATTGACTGGGGTCGAAGCCAGCTCC<br>GGGGACTCCAAGAGAAACTCAAGCAGCTGGAGC<br>CTGGGGCTGCCTGACATGCGCGCAAAGAGGCAG<br>GGCAGCGAGCACAGCTGTTCTCCGACATGGCTA<br>CGTGATCTCAGGCCTTCTTCCTTCACAATTAGCT<br>CTTGCCCCTACCCCACGCCAGCTAATGCCCCTTC<br>TGTGTCCCTGCTCTGCATGTTTCCATTTTCCTTAG<br>GTGTGAAGTTTGAAGAGGCAAACAGTAATTTTG<br>AAAGCCACTACTTTGAAACCATTCTAAGGCCTG<br>AGTTCCCATAGGACACACTCACATAGGCAGGTA<br>CACGTTAGTCAACAATTGGAACTGCCTCTTGGAT<br>CACTCAGCTGTGCTTTCATGGCTGGATGATGGAA<br>CACTGTGCGAAGAGAGATGGGGGCCAGGAAGTA<br>GCGCTTCATGCTTAGTACATCCTCCAAATTGTCT<br>TTGCTGGAGGAGAAAACCGTACTCAGCCAAAAG<br>ATCAGGACAATATGACTTGAGTCCACAAGGACA<br>CAAACACCTGAGTAGCTGGGCAGCCCTTGGCAG<br>GGTCTAAGCCAGGAAGTAAAAATGATCTGGCCT<br>AGATATTTAAGGGAACTCTAGGAAGAGGCCTAG<br>GTTTTTAAAATCCTGTCTCTTTGTCTTACCATAAG<br>AGGCTGAGCCTCTCTTCATTTTTTTGAAGGGCCA<br>CTTGTGTTTTCTGTTCTGGGAACTTCATTCATTTT<br>TCTACTGGGTTGTTGATCTTTGCAGTAATTTCTA<br>GGAGCTGTTTATGTTTGGAGGTAATTGGTCCTTT<br>GTCCATATATATGAGATGTAAGTCTTATTTTCCA<br>GTTTATCTTTTTGCTTATTTTTTTTGACTTTTTATT<br>GTAAAATAAAACATCAAACTGCACAGAACAGTT<br>GAATAGCTTAATGAATAACTACAGTAAAAGCTA<br>TGGTAACC**CCCTGCTGCTGAACAGGAGGCCGA**<br>**AGACGAGAGCTGCCCGGAGGACTGGGCAGCA**<br>**GCTGTTCCAGCAGAGACATCAGCAAAAGCCA**<br>**TCTAGAGGTGGATCCAGAGTGTGGACTAACA**<br>**GAGAAAAGAAGTGGAGGGAGAGCAG**GTCTGC<br>GGAGGCGCAAGGGCCCCACTAAGACCCCAGAAC<br>CGGAGTCCTCTGAGGCCCCTCAGGACCCCCTGA<br>ACTGGTTTGGAATCCTAGTTCCTCACAGTCTACG<br>TCAGGCTCAAGCAAGCTTCCGGGATG | 1<br>The underlined exon inclusion sequence is SEQ ID NO: 21. |
| 13343 | ENAH | TGAACAGAGTATCTGTCAGGCAAGAGCTGCTGT<br>GATGGTTTATGATGATGCCAATAAGAAGTGGGT<br>GCCAGCTGGTGGCTCAACTGGATTCAGCAGAGT<br>TCATATCTATCACCATACAGGCAACAACACATTC<br>AGAGTGGTGGGCAGGAAGATTCAGGACCATCAG<br>**ACAGAGTCTCGCTCTGTTGCCCAGGCTAGAG**<br>**TGCAATGGCGTAATCTCAGCTCACTGCAACCT**<br>**CCGCCTCCCGTGTTCAAGCGATTCTCCTGCCT**<br>**CAGCCTCCTGAGTAGCTGGGATCACAG**ACAG<br>AGTCTGACTGTTGCCCAGGCTGGAGTGCAATGG<br>CACCAACATGGCTCACTGCAACCTTGACCTCCTG<br>GGCTCAAGTGATCCTCCCGGCCTCCGTCTCCCGA<br>ATAGCGGTCTTACTCATTTTCTACGTGTGTGTTG<br>AGTGCACCATTTGAGA | 2<br>The underlined exon inclusion sequence is SEQ ID NO: 22. |
| 15088 | POLI | GAGTTCATGATCAAGTGTTGCCCCACACCAAATG<br>CTTCATCCAGAGTCATAGTACATGTGGATCTGGA<br>TTGCTTTTATGCACAAGTAGAAATGATCTCAAAT<br>CCAGAGCTAAAAGACAAACCTTTAG**GAAAGATT**<br>**CCTCTTTTAGTGTAAGCATAAAGAACATTTTT**<br>**GGTTCACTTGCTGCTACCCTCTTGTGCCCACT**<br>**TTGGCTTAATAAATCCCAATCCAGCCTAGCTG**<br>**ATTTACTGAAGAACAAAGGGATGACTAGTTTT**<br>**TGCTACGCCAAG**GGGTTCAACAGAAATATTTGG<br>TGGTTACCTGCAACTATGAAGCTAGGAAACTTG<br>GAGTTAAGAAACTTATGAATGTCAGAGATGCAA<br>AAGAAAAGTGTCCACAGTTGGTATTAGTTAATG<br>GAGAAGACCTGACCCGCTACAGAGAAATGTCTT<br>ATAAGGTTACAG | 3<br>The underlined exon inclusion sequence is SEQ ID NO: 23. |
| 16864 | PLXNB1 | GAGGAAGAGCAAGCAGGCCCTGAGGGACTATA<br>AGAAGGTTCAGATCCAGCTGGAGAATCTGGAGA<br>GCAGTGTGCGGGACCGCTGCAAGAAGGAATTCA<br>CAG**GCCAAGTGGTCTCTGTTCAACAACTCAGC**<br>**TTTGCCACTGTGGCACAAAGGCAGCCAGGGA**<br>**CGACATGGAAACACATGAAA**GTGCAGATGGGG | 4<br>The underlined exon inclusion sequence is SEQ ID NO: 24. |

TABLE 6-continued

Exon Inclusion Event Sequences

| Splicing Event ID | Gene Name | cDNA Sequence | SEQ ID NO: |
|---|---|---|---|
| | | AACTTGCGCTTCTCCCTGGGTCACGTGCAGTATG<br>ACGGCGAGAGCCCTGGGGCTTTTCCTGTGGCAG<br>CCCAGGTGGGCTTGGGGGTGGGCACCTCTCTTCT<br>GGCTCTGGGTGTCATCATCATTGTCCTCATGTAC<br>AG | |
| 21181 | SH3GLB1 | AAAGAAAGGAAACTATTGCAAAATAAGAGACTG<br>GATTTGGATGCTGCAAAAACGAGACTAAAAAAG<br>GCAAAAGCTGCAGAAACTAGAAATTCA**CAACTA**<br>**AACTCAGCTCGCCTTGAAGGAGATAACATTAT**<br>**GGTAAATTTCTCTTACATGCTCAACTTCCTGC**<br>**ATGTAAAATGGCTGAAG**TCTGAACAGGAATTA<br>AGAATAACTCAAAGTGAATTTGATCGTCAAGCA<br>GAGATTACCAGACTTCTGCTAGAGGGAATCAGC<br>AGTACACAT | 5<br>The underlined exon inclusion sequence is SEQ ID NO: 25. |
| 34793 | TCF25 | ACCCCGCGCGAAGAGTGCGCAGGCGCGCCGACA<br>GCCGAGTTTTCTGCGCTTCCTTCTCCCTCTCTCCA<br>GACGTCGTGGTCGTTCGGTCCTATGTCGCGCCGG<br>GCCCTCCGGAGGCTGAGGGGGGAACAGCGCGGC<br>CAGGAGCCCCTCGGGCCCGGCGCCTTGCATTTCG<br>ATCTCCGTGATGACGATGACGCGGAAGAAGAAG<br>GGCCCAAGCGGGAGCTTGGTGTCCGGCGTCCCG<br>GGGGCGCAGGGAAGGAGGGCGTCCGAGTCAAC<br>AACCGCTTCGAGCTG**GAAAAATGGACATTTTCC**<br>**TCTCCCCCTAAAAAAAGATAAAACTCCTTCCT**<br>**GGTTATTAACTGAAATGCTGATCGAGCTTTAT**<br>**CCTAAAGAAGATCAGTCGTGGACAAGAACCT**<br>**TGTGAAATGTTCCCCATTTGAGACCCTAAAAC**<br>**TAATGAAAATCACAGCTTTTGG**ATAAACATTG<br>ACGATCTTGAGGATGACCCTGTGGTGAACGGGG<br>AGAGGTCTGGCTGTGCGCTCACAGACGCTGTGG<br>CACCAGGGAACAAAGGAAGGGGTCAGCGTGGA<br>AACACAGAGAGCAAGACGGATGGAGATGACAC<br>CGAGACAGTGCCCTCAGAGCAG | 6<br>The underlined exon inclusion sequence is SEQ ID NO: 26. |
| 42420 | PRR5-ARHGAP8 | GTATTTGAAGTACACACTGGACCAATACGTTGA<br>GAACGATTATACCATCGTCTATTTCCACTACGGG<br>CTGAACAGCCGGAACAAGCCTTCCCTGGGCTGG<br>CTCCAGAGCGCATACAAGGAGTTCGATAGGAA**A**<br>**GACGGGGATCTCACTATGTGGCCCAGGCTGG**<br>**TCTCGAACTCCAAGCTCAAGCGATCCTCCCAC**<br>**CTCAGCCTCCCAAAGTACTGGGATTACAGGC**<br>**AGGAGCCACCATGCCAAGCCAACACTCTTGTT**<br>**CTTAAAGGGCCAGACAGTCAGCATTTTAGCTT**<br>**TGCAGGCCTGTTGCTCTATTGCAACAACTCTG**<br>**CTGGACTGTGTTCCAGTAAAACATTATGGACG**<br>**CTGAAATGTGAATTTCATGTCATTTTCACGTG**<br>**TCATGAAATATTCTTCTGTTTTTTTTTTTCAAC**<br>**CACTTAAAAACATAAAAAGCCATTTTTAGCTT**<br>**GCAGCCTGTACCAAAGCAGGAAGCAGGCTAG**<br>**GTTCATCCTGCCTGCCCATTCTCCCACCCCTG**<br>**GTCCAGTGAATTACTGGCAAAGAAACAACTG**<br>**CATGACCGTTTCTTCACTAAAGCCTCTTCTTG**<br>**CTTTCACAGCCCTTTACAGTCTGCAAGGGGCA**<br>**TTCTGATGCCTCTTGTTGGTGAGATGGCAGCC**<br>**TCATTTTACAGATGAGGACATAGGCCCCAGG**<br>**GAGCAAGTGACTTACCCGTGGTCACTCAGCTT**<br>**GTGTGTGGTAGGGCAGGATCCCACCCCAGGC**<br>**CCCCGCCTCCCTCTCCCACCCAACGCTACTCA**<br>**CCGCTTGGCCATGGCCTGGAGCCGGCAGACT**<br>**TTTCCTGAGGGACGTCCGGCCTAATAATCAAC**<br>**TTGGCAATATATCTGGCTCGTAGACTGCGGC**<br>**GATGGGCGTTGATGTGGATATCCTAGATTCCT**<br>**CTGGGTTTTCCTTCTTCAAAGTCCTTTCAAAC**<br>**CTGTAACAGAAATCTGCTTCACAGATATCTGA**<br>**GTCAGTGGGACAGTGGAAGGCAGTGCCTGAA**<br>**TGTCCCAGAAGTCCTCCCTCCAGTTGCCTTTT**<br>**GGGTCCTGCTGTCATTATCAATAGGACCTTCG**<br>**GAGGGACTTCTTGGTTCCCCATCCTATGTCTT**<br>**AGGGAAAGAATTGTTGCTGTATTTTGCAGTCA**<br>**TTTACTGGGCACCTGTATAAGCTGGAGATGG**<br>**CCTAGCCCCAGCGCATGTCCTCCTCCAGGAA**<br>**GGCTTCCTGGGTTGTCCTGGGAGAATCAATA**<br>**GCCCCTTCCCTGCAGCCTCACTGTGCCTAAGC** | 7<br>The underlined exon inclusion sequence is SEQ ID NO: 27. |

TABLE 6-continued

Exon Inclusion Event Sequences

| Splicing Event ID | Gene Name | cDNA Sequence | SEQ ID NO: |
|---|---|---|---|
| | | **AGACACCAATCCTAGCTAGCACTTAGGGGTTT**<br>**GTGAACAGGTCTGCCTCCTGCACTAGGCTGT**<br>**GATCCCGGACCTGTCTCTGCATCCCTTGCAGG**<br>**TGGGAAAGGATCTGCATATGGCAGCCTTTTTT**<br>**TTTTTTTTTTTTTTTTGAGACAGAGTCTCATT**<br>**CTATTGCCTGGGCTGGAGCACAGTGGCGAGA**<br>**TCTCGGCTCACCACAACCTCCACCTCCCAGGT**<br>**TCAAGTGATTCTCCTGCCTCAGCCTCCTGAGT**<br>**ACCTGGGACTACAGGCGTGAGCCACCATGCC**<br>**CGGCTAATTTTTGTATTTTTAGTAGAGACGGG**<br>**GTTTCACTATGTTGGCCAGGCTGGTCTTGAAC**<br>**TCCTGACCTCGTGATCCGCCTGCCTTGGCCTC**<br>**CCAAAGTGCCGGGATTACAGGCGTGAGCCAC**<br>**TGTGCCCAGCCGGCAGGCTTTTATTAAGCGTT**<br>**AGATGGGAGGATAGAGGAGTGAAGTGGTACT**<br>**GGCAGGAAGTACCAAGGTTCCAGCTGGCGTA**<br>**ATCAGGAAGGCTGCATGGAGGAAGCAGCCTT**<br>**TGAGCTGCCTGTGGAGTGGTGGGCAGGGTGT**<br>**TGTGAAGTGGCAATCACTGGATTTTGCTTCTG**<br>**GTACGAGGTGTGGCCAGATGCAAGAAAGAGC**<br>**AGGGTGGACTTTGGTGCAATTGGTGGGGGTC**<br>**TGGTCTGTAGGGTTCCCGTGGGGAGCCGTGG**<br>**AGGGAGGCAGCAAAGGAGGGAGGGGCACAG**<br>**AGGATGCTGGACTGTGTTTAAGAGGCAGCAG**<br>**GGAGCCATGGCAGGTGCTTGAGGAGAAGCGA**<br>**GTGATGTGTTTAAAGCAGCCCTTTCAGGAGG**<br>**CTCAGGCTCACAGCAGGATGTGCACAGTAGC**<br>**CCTGTCTTGAGCTAAAGCAGATGAAGGTTTTG**<br>**CCCTCTGCACTTCCCCACGTGAGAAACGAAG**<br>**ATGCACCCGCAGATTCCTTGAGGCAGCTCCC**<br>**CCACTTCTCAGTTGCCAGAAATCAGCCCAGAG**<br>**AAACAAACCCGTAATCAGCCCAGGGTGCTTTC**<br>**CCTTCCCTTTCTCGAGGGGGCTGCTGGTTCGC**<br>**ACATAAGGAGTGGGTCACTCCCGCTTGGGAG**<br>**AAAGCAGCAGAATTCCTTCACAGCCAGGTAA**<br>**GATGTGCCAGTGGTCGATGGATGAAATCTAG**<br>**CCGGGGAGTTGGAATCTGTGTTGCCAGCAGT**<br>**GACCTGTGAGCAGTGACAAAGCCAAAG**GTAC<br>AAGAAGAACTTGAAGGCCCTCTACGTGGTGCAC<br>CCCACCAGCTTCATCAAGGTCCTGTGGAACATCT<br>TGAAGCCCCTCATCAG | |
| 4322 | WDR45B | AATTGTGGTGGTTTTGGACTCCATGATTAAGGTG<br>TTCACATTCACACACAATCCCCATCAGTTGCACG<br>TCTTCGAAACCTGCTATAACCCCAAAG**ATGGAG**<br>**TGTTTGATGATGTCTCTCTGAACCTCAGAGAC**<br>**GTCTCTTAGGCTGACCTTCACCCAGGCGAGA**<br>**AGCACTCCCTCAGCAGAGCCAGCCCACGTGC**<br>**ACTCGCCGAGCTCCAGGCCTGGCGCTGGCTA**<br>**CCTGCCTCCAGAGCTTTTTCTTCAGGAACACT**<br>**CCTTTTCTGTGTG**TAATGATCTGGGATGACCTG<br>AAGAAGAAGACTGTTATTGAAATAGAATTTTCT<br>ACAGAAGTCAAGGCAGTCAAGCTGCGGCGAGAT<br>AG | 8<br>The underlined exon inclusion sequence is SEQ ID NO: 28. |
| 44438 | VPS29 | TTGGTGTTGGTATTAGGAGATCTGCACATCCCAC<br>ACCGGTGCAACAGTTTGCCAGCTAAATTCAAAA<br>AACTCCTGGTGCCAGGAAAAATTCAGCACATTC<br>TCTGCACAGGAAACCTTTGCACCAAAGAGAGTT<br>ATGACTATCTCAAGACTCTGGCTGGTGATGTTCA<br>TATTGTGAGAGGAGACTTCGATGAGG**CTGGGCA**<br>**CAGAGTAAGTTTCTTCACTTAGCTCCTACTAA**<br>**CAGTGGTGGTTGGGTGGCTGTTTACTGACTG**<br>**GATTTCTTACCCTTTTAAGGTCTGTTGAAAGG**<br>**AAGTAACCGAATTCCCATGCTTTGATTGGGTT**<br>**GGCTCTTTATTTTAATTTAATAAGACTGCCAT**<br>**TTCCAGGATCTTTTGCTTTCTTAAAGGACTCT**<br>**ATCATCTATGTCTATCCCGATTTGTCAAAGTG**<br>**TGGAATTTGGGCGGGAACATGTTTCAAAGTAT**<br>**GACACGTGTTATGTAACACTATTTCCCCATAA**<br>**CTTTGTCATCAGCAGGAAACCAGAGGATTCTG**<br>**TCCTAGTAAGGATCCCTACTAATTTGAAATGA**<br>**TTGTGTGGTCATTCATACAGTTATATCTTTAG**<br>**ACTGCTAATAGTCTTGAGTCTTGGAGATAATC**<br>**CACAGTACTTTATAGAATTAGGTCATCAATCA** | 9<br>The underlined exon inclusion sequence is SEQ ID NO: 29. |

TABLE 6-continued

Exon Inclusion Event Sequences

| Splicing Event ID | Gene Name | cDNA Sequence | SEQ ID NO: |
|---|---|---|---|
| | | **TTATAAAGTACCATGTCTTACTAATGTTCTTT**<br>**CTGGTACATTCAGATTGAACAGCTCATTCATT**<br>**ATTAGTACCAAACATTTCAACCTGTTGTAGAC**<br>**ATATACCCTTTTATGAGTTTGGGGTGGTGGTT**<br>**GTTGTTGTTGTTCTTCTTCTTCTTTTAAATATA**<br>**GAAATCTATTATTTTTACCTTTTTCTCAAAGCA**<br>**AGATTCCCATACTAACTATGTACTTCAATCCA**<br>**TATCAGAAGGAATCCCCCTCTAAAATGAAGAT**<br>**TGTTCTATATCCAG**GAGCCTGAGGAAGAGGGC<br>GGCGACGGTGGTGGTGACTGAGCGGAGCCCGGT<br>GACAGGATG | |
| 48175 | E4F1 | ATCTTCCTGCGGCGCGTTGCGACATGGAGGGCG<br>CGATGGCAGTGCGGGTGACGGCCGCTCATACGG<br>CAGAAGCCCAGGCCGAAGCCGGGCGGGAAGCG<br>GGCGAGGGTGCAGTTGCGGCGGTGGCGGCGGCC<br>TTGGCCCCCAGCGGCTTCCTCGGCCTCCCGGCGC<br>CCTTCAGCGAGGAAG**CTTGGAGAAGGGCAGTG**<br>**CCCTCATGGCGAGGAGTCCCTTTAGAGGTTG**<br>**CTGGGCCTGCTTGTGGCCTTGTCTGGTGTGA**<br>**AATGGGCTGG**ATGAGGACGATGTGCACAGATG<br>CGGCCGCTGCCAGGCAGAGTTCACCGCCTTGGA<br>GGATTTTGTTCAGCACAAGATTCAGAAGGCCTG<br>CCAGCGGGCCCCTCCGGAGGCCCTGCCTGCCAC<br>CCCTGCCACCACAGCGTTGCTGGGCCAGGAG | 10<br>The underlined exon inclusion sequence is SEQ ID NO: 30. |
| 49765 | TEN1-CDK3 | GGGGCGATGTCCGCGTCGTGGCTGGGGCCGGTC<br>GCGGGGCAGACTAATCCCCTGCTCCTGGCCAGG<br>GGAGGCTCCCGAGCGGATCCTCGGGAAAGGGGC<br>TCCGAAGGTCAAGAAACTGCCCTGCTGGGCGTC<br>CGGGGAGTGGGAAAATAAAGCACTTTTTGTATC<br>CCGCCCCTCCCCCGTCACGTGACCACGCGAGGC<br>GGAAAGAAGAAATCCGAGGACCGGCGACGCCT<br>AGAACAG**GGTCTTACTCTATTGCCGAGGCTAC**<br>**AGTATAGTGGTGTGATCATAGCTCACTGCAGC**<br>**TTCAACCTCCTGTGGTGGTGATCCTCCTGCCT**<br>**CAGCCTCCTAAGTTGCTGGGACTACAG**GAGCC<br>CATGATGCTGCCCAAACCTGGGACCTATTACCTC<br>CCCTGGGAGGTTAGTGCAGGCCAAGTTCCTGAT<br>GGGAGCACGCTGAGAACATTTGGCAG | 11<br>The underlined exon inclusion sequence is SEQ ID NO: 31. |
| 5134 | PLEKHA6 | GCAACTCGCACAGCCCGCAAAGCCGTCGCCTTT<br>GGCAAGCGCTCACACTCCATGAAGCGGAACCCC<br>AATGCACCTGTCACCAAGGCGGGCTGGCTCTTC<br>AAACAG**TTGCTGAGTGCTTGTTATGGCTGGAT**<br>**ACCTTGCTGGCTCTGGTGATAAAGAGATGAA**<br>**AAAGACAAAAGTTCCTCCCTGCAAAGAGCTCA**<br>**TGGTGCAATGGAAGAGATAGAAAGCTGCATT**<br>**GTGACAG**ATCGACCTTGGACATGTCCAATAAAA<br>CAGGTGGGAAACGCCCGGCTACCACCAACAGTG<br>ACATACCCAACCACAACATGGTGTCCGAGGTCC<br>CTCCAGAGCGGCCCAGCGTCCGG | 12<br>The underlined exon inclusion sequence is SEQ ID NO: 32. |
| 56552 | GNAZ | GGCAAAGCTCAGAGGAAAAAGAAGCAGCCCGG<br>CGGTCCCGGAGAATTGACCGCCACCTGCGCTCA<br>GAGAGCCAGCGGCAACGCCGCGAAATCAAGCTG<br>CTCCTGCTGGGCACCAGCAACTCAGGCAAGAGC<br>ACCATCGTCAAACAGATGAAGATCATCCACAGC<br>GGCGGCTTCAACCTGGAGGCCTGCAAGGAGTAC<br>AAGCCCCTCATCATCTACAATGCCATCGACTCGC<br>TGACCCGCATCATCCGGGCCCTGGCCGCCCTCAG<br>GATCGACTTCCACAACCCCGACCGCGCCTACGA<br>CGCTGTGCAGCTCTTTGCGCTGACGGGCCCCGCT<br>GAGAGCAAGGGCGAGATCACACCCGAGCTGCTG<br>GGTGTCATGCGACGGCTCTGGGCCGACCCAGGG<br>GCACAGGCCTGCTTCAGCCGCTCCAGCGAGTAC<br>CACCTGGAGGACAACGCGGCCTACTACCTGAAC<br>GACCTGGAGCGCATCGCCGCAGCTGACTATATC<br>CCCACTGTCGAGGACATCCTGCGCTCCCGGGAC<br>ATGACCACGGGCATTGTGGAGAACAAGTTCACC<br>TTCAAGGAGCTCACCTTCAAGATGGTGGACGTG<br>GGGGGGCAGAGGTCAGAGCGCAAAAAGTGGAT<br>CCACTGCTTCGAGGGCGTCACAGCCATCATCTTC<br>TGTGTGGAGCTCAGCGGCTACGACCTGAAACTC<br>TACGAGGATAACCAGACA**GGAAGTGGTGAACT** | 13<br>The underlined exon inclusion sequence is SEQ ID NO: 33. |

TABLE 6-continued

| Exon Inclusion Event Sequences | | | |
|---|---|---|---|
| Splicing Event ID | Gene Name | cDNA Sequence | SEQ ID NO: |
| | | **GGGGAGTCAGACAAGAGCATCATGCTTCTTA**<br>**AAAGCCCAGACCCCTGGCTATAACACATCGA**<br>**AGATTCTCAGAAGAGAATTGAGGAGCGGACA**<br>**GGCGCCACACTCCGTTGTGGTCACTGCCTCTT**<br>**CCTGGCCCACCACACTCCTGTCCTCTGCATGT**<br>**ACTGAGAGCTCTGTCCAGGATGCCAGGGTCC**<br>**TGCCTCGGCAGAGAGGCGGTGCCAGATGCCC**<br>**CACAGCAGCTGGTGGGAGTGCCCACAGCTGG**<br>**AGGGCAGGGGAGGAGCCTGGCCTCTGGCTGG**<br>**TGTTTCCTTCCCAGCTCTCAAGAACTGGAGAC**<br>**TTTGGTTACAGAAGTGAAGGCTGCTCCCTCAC**<br>**AGACTTCCTAGTGTCCGATGGTACCACATGGA**<br>**AGGATCAGAGTTTTGAAGGACTGGGCCAGAA**<br>**CCCAGATAGGGCACAAGGCTGCCAGCGCCTG**<br>**CATTGAGGGAGCTATGATGTGACGGGGGCTC**<br>**CTGCAGAAGATGGCCTTCCTTGTACAG**AGTCG<br>GATGGCAGAGAGCTTGCGCCTCTTTGACTCCATC<br>TGCAACAACAACTGGTTCATCAACACCTCACTCA<br>TCCTCTTCCTGAACAAGAAGGACCTGCTGGCAG<br>AGAAGATCCGCCGCATCCCGCTCACCATCTGCTT<br>TCCCGAGTACAAGGGCCAGAACACGTACGAGGA<br>GGCCGCTGTCTACATCCAGCGGCAGTTTGAAGA<br>CCTGAACCGCAACAAGGAGACCAAGGAGATCTA<br>CTCCCACTTCACCTGCGCCACCGACACCAGTAAC<br>ATCCAGTTTGTCTTCGACGCGGTGACAGACGTCA<br>TCATACAGAACAATCTCAAGTACATTGGCCTTTG<br>CTGAGGAGCTGGGCCCGGGGCCCGCCTGCCTAT<br>GGTGAAACCCACGGGGTGTCATGCCCCAACGCG<br>TGCTAGAGAGGCCCAATCCAGGGGCAGAAAACA<br>GGGGGCCTAAAGAATGTCCCCCACCCCTTGGCC<br>TCTGCCTCCTTGGCCCCACATTTCTGCAAACATA<br>AATATTTACGGATAGATTGCTAGGTAGATAGAC<br>ACACACACATGCACACACACACATCTGGAGATG<br>GCAAAATCCTCTAAAATGTCGAGGTCTCTTGAA<br>GACTTGAGAAGCTGTCACAAGGTCACTACAAGC<br>CCAACCTGCCCCTTCACTTTGCCTTCCTGAGTTG<br>GCCCCACTCCACTTGGGGGTCTGCATTGGATTGT<br>TAGGGATAGGCAGCAGGGCTGAGGCAAGGTAG<br>GCCAACTGCACCCCTGTCGCCTGGAGGAGGGCC<br>AGCTCGCTGCCCGAGCTCTGGCCTAGGGACCTTG<br>CCGCTGACCAAGAGGGAGGACCAGTGCAGGGTC<br>TGTGCACCTTCCCTGCTGGCCTGCACACAGCTGC<br>TCAGCACCACTTTCATTCTGGACCTGGGACCTTA<br>GGAGCCGGGTGACAGCACTAACCAGACCTCCAG<br>CCACTCACAGCTCTTTTTAAAAAACAGCTTCAAA<br>ATATGCAGCAAAAACCAATACAACAAAACGAGT<br>GGCACGATTTATTTCAAACTAGGCCAGCTGGGA<br>TTCCAGCTTTTCTTCTACTAGTCTGATGTTTTATA<br>AATCAAAACCTGGTTTTCCTTCTCTGACATTTTTT<br>TTTTGTTTTGTTTTTTGGTTTTTTTTTTTTTTTGGC<br>CAAATCTCGTGGTGTTTCGCAGAAAAAAATCCA<br>GAAAATTTCAAATGCAGTTGAGTATTCTTTTTTA<br>AATGCAGATTTTCAAAACATATTTTTTTTCAGGT<br>GGTCTTTTTTGTGTCTGGCTTGCTGAGTGTAAAA<br>GTTGTTATCTGGACGATCTGTCTCTCTGCTCCAA<br>AGAAATTTTGGAGTGAGTGGCAGTCCTGCGCCA<br>GCCTCGCGGGACACGTGTTGTACATAAGCCTCTG<br>CAGTGTCCTCTTGTTAATGGTGGGGTTTTCTGCT<br>TTGTTTTTATTTAAGAAAATAAACACGACATATT<br>TAAAGAAGGTTCTTTCACCTGGGAGCAAATGAA<br>CAATAGCTAAGTGTCTTGGTATTTAAAGAGTAA<br>ATTATTTGTGGCTTTGCTGAGTGAAGGAAGGGG<br>AGCAAGGGGTGGTGCCCCTGGTCCCAGCATGCC<br>CCGCGCCTGAGACTGGCTGGAAATGCTCTGACT<br>CCTGTGAAGGCACAGCCAGCGTTGTGGCCTGAG<br>GGAGGCCCTGCTGGGACCCTGATCTGGGCCTTCC<br>TGTCCCAGGGCCTATGGGCAACTGCGTTGAAAG<br>GACGTTCGCCAAGGGCCGTGTGTAAATACGAAC<br>TGCGCCATGGAGAGGAGAGGCACTGCCGGAGCC<br>CTTGCCAGATCTCCCTCCCTCTCTCCGTGCAGTA<br>GCTGTGTGTCCGAGGTCAGTGTGCGGAATCACA<br>GCCAAGGACGTGAAGAGATGTACGGGGGAAAG<br>AGAAGCTGGGGATTGGATGAAAGTCAAAGGTTG<br>TCTACTTTAAGAAAATAAAATACCCTG | |

TABLE 6-continued

| Exon Inclusion Event Sequences | | | |
|---|---|---|---|
| Splicing Event ID | Gene Name | cDNA Sequence | SEQ ID NO: |
| 5696 | TTC3 | CCGTCGGCTGACGTGGAGGGCCGGAGGTGGCGG<br>CGGCGGCGGCGGCGGCTGCTGCTGCTGCTGCCC<br>GCGTCCGAGGCTCGCGGGCGGCGGGCCCGG**TAT**<br>**TTGATAAATTCAAAATATATGTAAAACATATG**<br>**CAAGCTGTATAGCAGAACAATAAAATGAACAC**<br>**CTATGAATTCACCACTCAATCCAATAATCAAA**<br>**ATGACCAGTATTGAATGTGCTTACTTCCAGAG**<br>AAATGCACTCGGTGATGGAAAGAGAGCCACTAT<br>TCTGAAGAACACTTGGCCAAAG | 14<br>The underlined exon inclusion sequence is SEQ ID NO: 34. |
| 57139 | RNF8 | GGCGAGCGGAGCCTGCTTTCGCAGCGATCGCGA<br>GCGTGTGGCGATTGCTTCTGTCTGTTATTTAGAT<br>ATGGAAGCTGAGGGGATGCACAGAGGCAGCCA<br>GAACCTAGGTCAGGGTCTCGCTCGGTGCTGACC<br>GCCCCCGGGGTCGAGTAGGCGATGGGGGAGCCC<br>GGCTTCTTCGTCACAGGAGACCGCGCCGGTGGC<br>CGGAGCTGGTGCCTGCGGCGGGTGGGGATGAGC<br>GCCGGGTGGCTGCTGCTGGAAGATGGGTGCGAG<br>**GGTTGTTATGAACTAGACTGGTCCAACAGGA**<br>**AAGTATGATAGATGTGAACTGGGGCTTCTTTT**<br>**CAACCTTTTCCGGAAGCTCTCAAGCTGTTCTT**<br>**GTGGATAAGACAGAGAATATGTACTCCAATG**<br>**CAAAGACTTTTGGTTGAATTATAACTGGCTGA**<br>**AG**GTGACTGTAGGACGAGGATTTGGTGTCACAT<br>ACCAACTGGTATCAAAAATCTGCCCCCTGATGAT<br>TTCTCGAAACCACTGTGTTTTGAAGCAGAATCCT<br>GAGGGCCAATGGACAATTATGGACAACAAG | 15<br>The underlined exon inclusion sequence is SEQ ID NO: 35. |
| 57874 | ZDHHC13 | CCAGCAGGAAGTGGGAGAAGAGGCGACCCAAG<br>GCGGGCTGGCGGGCTGGCGGCAGTCGCTACTTG<br>CCTAGTAGCCTCAGCCGCTGTGGGCTCCTGGGG<br>AGATGGAGGGGCCGGGGCTGGGCTCGCAG**CCTT**<br>**GACTTGAGCCCTGGAAATAAGCATCAGTGCA**<br>**GACGAGTGCTCTATGAGAAGCTATCTAGTTAA**<br>**AGCTCAAGGAGCCACAAAGGGATTTCCTGGC**<br>**AGCACAGTCACCAGAAACACTGAGGGAGAAC**<br>**TCTCTGAACAGAGGAATTGTGACCCCAAGAC**<br>**AGTAGTTTTTAGACGTGACACCAAAAGCACAA**<br>**TCCATAAAAGAACAAATTGATAAATTGGACTT**<br>**TTTTAAAATTTAAAACTTCTGCTCTATGAAAC**<br>**AGACTTTTAAGAGATGGGAAG**TGCAGGAATCA<br>CAGCCATGGCCCCCACCCTCCAGGATTTGGTCGA<br>TATGGCATCTGTGCACATGAAAACAAAGAACTT<br>GCCAATGCAAGAGAAGCTCTTCCTCTTATAGAG<br>GACTCTAGTAACTGTGACATTGTCAAAGCTACTC<br>A | 16<br>The underlined exon inclusion sequence is SEQ ID NO: 36. |
| 60615 | SH3GLB2 | ATTTCCCGGCACCTTCGTGGGCACCACAGAGCCC<br>GCCTCCCCACCCCTGAGCAGCACCTCACCCACCA<br>CTGCTGCGGCCACTATGCCTGTGGTGCCCTCTGT<br>GGCCAGCCTGGCCCCTCCGGGGGAGGCCTCGCT<br>CTGCCTGGAAGAGGTGGCCCCCCCTGCCAGTGG<br>GACCCGCAAAGCTCGGGTGCTCTATGACTACGA<br>GGCAGCCGACAGCAGTGAGCTGGCCCTGCTGGC<br>TGATGAG**CTCCCAGGGTGCCAT**GTGAACCACC<br>TGCGCTGCCTCCACGAGTTCGTCAAGTCTCAGAC<br>AACCTACTACGCACAGTGCTACCGCCACATGCT<br>GGACTTGCAGAAGCAGCTGGGCAG | 17<br>The underlined exon inclusion sequence is SEQ ID NO: 37. |
| 62560 | ITFG1 | GAATTTATCATGGCATCCAGCATTGACCACTACA<br>AGTAAAATGCGAATTCCACATTCTCATGCATTTA<br>TTGATCTGACTGAAGATTTTACAGCAG**CCATAC**<br>**CACCCTGAACGCGCCCCATCTCTTCTGATCTC**<br>**GGAAGCTAACCAAGGTCAGACCTGGTTAGTG**<br>**CTTGGATGGGAGATCACCTATTACTTTTTCT**T<br>TTCAATGGTGATCTAATTCCTGATATTTTTGGTA<br>TCACAAATGAATCCAACCAGCCACAGATACTAT<br>TAGGAGG | 18<br>The underlined exon inclusion sequence is SEQ ID NO: 38. |
| 6785 | SPATS2 | CTGCTGGCTACCAATATTCTACTTTCTGTCTCTAT<br>GAATGTGACTACCCTGGTTACCTCATAT**TTATTT**<br>**GCAGTGACTTAAAATTTGGAGGCAAATTTTCC**<br>**TTAAGAGGATATCAAGTTCCAGTATCTTCAGA**<br>**TGTTGATAAGCCGTTAG**AATCTCCCTGGAAAA<br>GGAGACATGAATGTCTGCAATGATACTTCCTGA | 19<br>The underlined exon inclusion sequence is SEQ ID NO: 39. |

TABLE 6-continued

Exon Inclusion Event Sequences

| Splicing Event ID | Gene Name | cDNA Sequence | SEQ ID NO: |
|---|---|---|---|
| | | CAAGAAGTTGATACAAGAAAAGGAAAGGAGAT<br>TAACAGCTAGTGAGCAGAATTTCGAACAGCAGG<br>ATTTCGTATTTTTTGCTTCCAACTGCACACTTCCG<br>TTGCCCACTTTTAAATCAGAGATACCTACACTCA<br>AAACCCAGACAAGGCAAAAGGATACTTTTCTTG<br>TATATTTTTTGAGATCGAAGAAACGACAATGTCC<br>AGGAAACAGAACCAGAAGG | |
| 8742 | DHRS11 | GATCGGACCCAAGCAGGTCGGCGGCGGCGGCAG<br>GAGAGCGGCCGGGCGTCAGCTCCTCGACCCCCG<br>TGTCGGGCTAGTCCAGCGAGGCGGACGGGCGGC<br>GTGGGCCCATGGCCAGGCCCGGCATGGAGCGGT<br>GGCGCGACCGGCTGGCGCTGGTGACGGGGGCCT<br>CGGGGGGCATCGGCGCGGCCGTGGCCCGGGCCC<br>TGGTCCAGCAGGGACTGAAGGTGGTGGGCTGCG<br>CCCGCACTGTGGGCAACATCGA**GGAATTTTGAG**<br>**TCTAGAGGAGGAAGCGGGAAGATGTACACCA**<br>**GGGGAGGGGAAAGCTGCAGTCTTCCTTGCCC**<br>**ACAGTCTGCTTTGATTGATTCAGTCATTGATG**<br>**TTAAAGCAGAATTTGGGTTCTAGCTTCCTACA**<br>**GAGAAAACTCCTGTTTCCTGAAGTGATCAAAT**<br>GAGCTGGCTGCTGAATGTAAGAGTGCAGGCTAC<br>CCCGGGACTTTGATCCCCTACAGATGTGACCTAT<br>CAAATGAAGAGGACATCCTCTCCATGTTCTCAGC<br>TATCCGTTCTCAGCACAGCGGTGTAGACATCTGC<br>ATCAACAATGCTGGCTTGGCCCGGCCTGACACC<br>CTGCTCTCAGGCAGCACCAGTGGTTGGAAGGAC<br>ATGTTCAAT | 20<br>The underlined exon inclusion sequence is SEQ ID NO: 40. |

TABLE 7

Exon Exclusion Event Sequences

| Splicing Event Id | Gene Name | cDNA Sequence | SEQ ID NO: |
|---|---|---|---|
| 1506 | CENPK | AATCTTTAATGAACTGAAAACTAAAATGCTTAA<br>TATAAAAGAATATAAGGAGAAACTCTTGAGTAC<br>CTTGGGCGAGTTTCTAGAAGACCATTTTCCTCTG<br>CCTGATAGAAGTGTTAAAAAGAAAAAG**GGAAC**<br>**AACGGTGGTTGGATGAACAGCAACAGATAAT**<br>**GGAATCTCTTAATGTACTACACAGTGAATTG**<br>**AAAAATAAGGTTGAAACATTTTCTGAATCAA**<br>**G**TTCCAAAAGCTGAGACAAGATCTTGAAATGGT<br>ACTGTCCACTAAGGAGTCAAAGAATGAAAAGTT<br>AAAGGAAGACTTAGAAAG | 41<br>The underlined exon exclusion sequence is SEQ ID NO: 73.<br>The sequence without the underlined exon exclusion sequence is SEQ ID NO: 105. |
| 2098 | METTL5 | AACTTCGATATGACCTGCCAGCATCATACAAGTT<br>TCACAAAAAGAAATCAGTAAGTCTCTTGATTTTG<br>GCTGGTCTACATTCGGTATTGAAAAGCTTTCTGG<br>GCCGGATGTGGTGGTTCATGCCTGTAATCCCAGC<br>TACTCGGGAGGCTGAGGCAAGAGAATCGCTTGA<br>ACTCAGGAGGCAGAGGTTGCAGTGAGCTGAGAT<br>TGCCCCACTGAACTCCAGCCTGCGCGATAAGAG<br>TGAGACTCAGTCTCGAAAAAGAAAAAAAAAAGGA<br>AAGCTTTGTGACAAGTAATTATTTCTAGTGTTAC<br>CAACTTTCCTGTGTAAATATACAAAGCCAGCCTA<br>GGAGACACCATAAATGGCCTGTGGGAAAGGCCC<br>ATCGTCAATAGCTAATATTCTAGTTCTTTCCTAA<br>ATGCTTTGGGTACAAAAAGAAAAAAAAAAATCAA<br>AAACTGTTTTTGCTCTTTTCATATAGTATATATTT<br>TATTAGTTAGTTTGTACTAATACATTCTCATATTA<br>CAAAGGCAATTTAATGGAAGAATCTTCCTTTTGA<br>TATTTGAATCATCTGAAATAACACAAACAGAAC<br>AATACATTCAAAGAAATCTCATTTGCATAACAA<br>AAAGACAAGTTAAACAACAAAAAAATTTTTCCT<br>TTCTCACAGGTGGACATTGAAGTGGACCTAATTC<br>GGTTTTCCTTTTAAAAGCCCCGCAAACAAAAGTC<br>GTTTAAAACCTATTTAAAATGAATAAAAAAATTGG | 42<br>The underlined exon exclusion sequence is SEQ ID NO: 74.<br>The sequence without the underlined exon exclusion sequence is SEQ ID NO: 106. |

TABLE 7-continued

| Exon Exclusion Event Sequences | | | |
|---|---|---|---|
| Splicing Event Id | Gene Name | cDNA Sequence | SEQ ID NO: |
| | | TT**CATGTTCAAAAGAAAGCTGCAGAATGGAAA**<br>**ATCAAGATAGATATTATAGCAG**GGACAGATAT<br>GGCTTTTCTAAAGACTGCTTTGGAAATGGCAAGA<br>ACAGCAGTATATTCCTTACACAAATCCTCAACTA<br>GAGAA | |
| 2242 | PLA2R1 | ATTCCAAGTCACAATACCACTGAAGTTCAGAAA<br>CACATTCCTCTCTGTGCCTTACTCTCAAGTAATC<br>CTAATTTTCATTTCACTGGAAAATGGTATTTTGA<br>AGACTGTGGAAAGGAAGGCTATGGGTTTGTTTGT<br>GAAAAAATGCAAG**CTTTCATTACTATGAATCTT**<br>**TTTGGCCAGACCACCAGTGTGTGGATAGGTTT**<br>**ACAAAATGATGATTATGAAACATGGCTAAATG**<br>**GAAAGCCTGTGGTATATTCTAACTGGTCTCCA**<br>**TTTGATATAATAAAT**TGCCTTCTGCTGAATATCC<br>CCAAAGACCCAAGCAGTTGGAAGAACTGGACGC<br>ATGCTCAACATTTCTGTGCTGAAGAAGGGGGA<br>CCCTGGTCGCCATTGAAAGTGAGGTGGAGCAAG | 43<br>The underlined exon exclusion sequence is SEQ ID NO: 75.<br>The sequence without the underlined exon exclusion sequence is SEQ ID NO: 107. |
| 7106 | RHOH | AGAGAGAGAGAGAGAGAGAGGAGAGGAGGGGC<br>GGGGTGGGGGAGGAGGGGAGTGGGGAGAGAGA<br>AAGAGAGAAACACCAAAAAGACATTTTCAAGGA<br>AGGAAGAAAATTAGATGGCAACCCCCTGTCCCC<br>TCCCCCTAAGAAAATCCTCTCTGAGATTAAACTG<br>TGTGAAGATTAGAGGCGTGTAGGTCAGGAGCAG<br>GAGGAAGCCCAACGCTGGACTGTACCAGATCAT<br>CTAAAACTGGCAATTCCAGGCACAGAAAACCAG<br>TTCTTCAGAAGCAGAAGGGTGGTCAGCCAGGGG<br>GTGAAAGGGACAGGGGTCTCGCAGCCAG**CCCAA**<br>**CTGTTGTATTTTCAGTTCTTCCAGTGTGAATC**<br>**AGTTAATATTCTCGGGAACGAGGGAGAGGTT**<br>**GATCCTATGAGGAAATCAACCACAGTGAAAA**<br>**GGCTTGGGCCGCTTTTGTTTTCACCTGCTTTT**<br>**GTTGAACAAATTTGATTTCCGGAGTCAGTCAT**<br>**TTTACTGTCAAGACATTTCTTCGGCATTCTGC**<br>**AACAG**TTTCCAACATGGCTAGATCCATCAGAAA<br>CTGAAGCCGTGGAGAACGCTCTCGGGGCCTTTG<br>CCACTTCTTGGAGTAGAAGCCGACAGAGAGCTG<br>TTTGGAAACTTCTCCTTCACACACCAG | 44<br>The underlined exon exclusion sequence is SEQ ID NO: 76.<br>The sequence without the underlined exon exclusion sequence is SEQ ID NO: 108. |
| 7108 | RHOH | GAGAGAGAAAGAGAGAAACACCAAAAAGACAT<br>TTTCAAGGAAGGAAGAAAATTAGATGGCAACCC<br>CCTGTCCCCTCCCCCTAAGAAAATCCTCTCTGAG<br>ATTAAACTGTGTGAAGATTAGAGGCGTGTAGGT<br>CAGGAGCAGGAGGAAGCCCAACGCTGGACTGTA<br>CCAGATCATCTAAAACTGGCAATTCCAGGCACA<br>GAAAACCAGTTCTTCAGAAGCAGAAGGGTGGTC<br>AGCCAGGGGGTGAAAGGGACAGGGGTCTCGCAG<br>CCAG**TTCTTCCAGTGTGAATCAGTTAATATTC**<br>**TCGGGAACGAGGGAGAGGTTGATCCTATGAG**<br>**GAAATCAACCACAGTGAAAAGGCTTGGGCCG**<br>**CTTTTGTTTTCACCTGCTTTTGTTGAACAAATT**<br>**TGATTTCCGGAGTCAGTCATTTTACTGTCAAG**<br>**ACATTTCTTCGGCATTCTGCAACAG**TTTCCAAC<br>ATGGCTAGATCCATCAGAAACTGAAGCCGTGGA<br>GAACGCTCTCGGGGCCTTTGCCACTTCTTGGAGT<br>AGAAGCCGACAGAGAGCTGTTTGGAAACTTCTC<br>CTTCACACACCAG | 45<br>The underlined exon exclusion sequence is SEQ ID NO: 77.<br>The sequence without the underlined exon exclusion sequence is SEQ ID NO: 109. |
| 9442 | QPRT | GCCTGGCGCTGCTGCTGCCGCCCGTCACCCTGGC<br>AGCCCTGGTGGACAGCTGGCTCCGAGAGGACTG<br>CCCAGGGCTCAACTACGCAGCCTTGGTCAGCGG<br>GGCAGGCCCCTCGCAGGCGGCGCTGTGGGCCAA<br>ATCCCCTGGGGTACTGGCAGGGCAGCCTTTCTTC<br>GATGCCATATTTACCCAACTCAACTGCCAAGTCT<br>CCTGGTTCCTCCCCGAGGGATCGAAGCTGGTGCC<br>GGTGGCCAGAGTGGCCGAGGTCCGGGGCCCTGC<br>CCACTGCCTGCTGCTGGGGGAACGGGTGGCCCT<br>CAACACGCTGGCCCGCTGCAGTGGCATTGCCAG<br>TGCTGCCGCCGCTGCAGTGGAGGCCGCCAGGGG<br>GGCCGGCTGGACTGGGCACGTGGCAGGCACGAG<br>GAAGACCACGCCAGGCTTCCGGCTGGTGGAGAA<br>**TGTGGTGGCCGCCGGTGGCGTGGAGAAG**GCG<br>GTGCGGGCGGCCAGACAGGCGGCTGACTTCACT | 46<br>The underlined exon exclusion sequence is SEQ ID NO: 78.<br>The sequence without the underlined exon exclusion sequence is SEQ ID NO: 110. |

TABLE 7-continued

Exon Exclusion Event Sequences

| Splicing Event Id | Gene Name | cDNA Sequence | SEQ ID NO: |
|---|---|---|---|
| | | CTGAAGGTGGAAGTGGAATGCAGCAGCCTGCAG<br>GAGGCCGTGCAGGCAGCTGAGGCTGGTGCCGAC<br>CTTGTCCTGCTGGACAACTTCAAGCCAGAG | |
| 10439 | IL17RB | TGGACATTTTCCTACATCGGCTTCCCTGTAGAGC<br>TGAACACAGTCTATTTCATTGGGGCCCATAATAT<br>TCCTAATGCAAATATGAATGAAGATGGCCCTTCC<br>ATGTCTGTGAATTTCACCTCACCAG**GCTGCCTA**<br>**GACCACATAATGAAATATAAAAAAAAGTGTGT**<br>**CAAGGCCGG**AAGCCTGTGGGATCCGAACATCAC<br>TGCTTGTAAGAAGAATGAGGAGACAGTAGAAGT<br>GAACTTCACAACCACTCCCCTGGGAAACAGATA<br>CATGGCTCTTATCCAACACAGCACTATCATCGGG<br>TTTTCTCAGGTGTTTGAG | 47<br>The underlined exon exclusion sequence is SEQ ID NO: 79.<br>The sequence without the underlined exon exclusion sequence is SEQ ID NO: 111. |
| 11685 | STAU1 | AAAGCATAACCCCTACTGTAGAACTAAATGCAC<br>TGTGCATGAAACTTGGAAAAAAACCAATGTATA<br>AGCCTGTTGACCCTTACTCTCGGATGCAGTCCAC<br>CTATAACTACAACATGAGAGGAGGTGCTTATCC<br>CCCGAG**AGTTTATTAACCACTTAACCTCTCAG**<br>**AACTGAACAAAGACAACATTGTTCCTGGAACG**<br>**CCCTCTTTTTAAAAAAG**GGGCTGCGGGCGCCTG<br>AGCGGCTCTTCAGCGTTTGCGCCGGCGGCTGCCG<br>CGTCTCTCTCGGCTCCCGCTTCCTTTGACCGCCTC<br>CCCCCCCCGGCCCGGCGGCGCCCGCCTCCTCCAC<br>GGCCACTCCGCCTCTTCCCTCCCTTCGTCCCTTCT<br>TCCTCTCCCTTTTTTCCTTCTTCCTTCCCCTCCTCG<br>CCGCCACCGCCCAGGACCGCCGGCCGGGGGACG<br>AGCTCGGAGCAGCAGCCAG | 48<br>The underlined exon exclusion sequence is SEQ ID NO: 80.<br>The sequence without the underlined exon exclusion sequence is SEQ ID NO: 112. |
| 13451 | LYRM1 | AGAGTACCCAGAGAAGGAGAAGCCAGCAAAGG<br>AGACGACACAGACAAGACCTCAGAGATCAAAGG<br>AAGAGGCCCCTTAATATCCTGGAATAATGGGAC<br>CCATCCCCGTAATCAGTGAATCTCATCCACCCGC<br>TTGCCAGCTTCTACCCGCAGCAAGTAGAAGCTA<br>AGTCCTGGCTCAAATCTCTTCCCTCCCTCCCTCTC<br>CCAGCTGTCAGTGCTTTTGGACTTGTGCTCAG**AT**<br>**GACAACGGCAACACGACAAGAAGTCCTTGGC**<br>**CTCTACCGCAGCATTTTCAGGCTTGCGAGGAA**<br>**ATGGCAGGCGACATCAGGGCAGATGGAAGAC**<br>**ACCATCAAAGAAAAACAGTACATACTAAATGA**<br>**AGCCAGAACGCTGTTCCGGAAAAACAAAAAT**C<br>TCACGGACACAGACCTAATTAAACAGTGTATAG<br>ATGAATGCACAGCCAGGATTGAAATTGGACTGC<br>ATTACAAGATTCCTTACCCAAGGCCA | 49<br>The underlined exon exclusion sequence is SEQ ID NO: 81.<br>The sequence without the underlined exon exclusion sequence is SEQ ID NO: 113. |
| 14574 | PPARG | CCATCAGGTTTGGGCGGATGCCACAGGCCGAGA<br>AGGAGAAGCTGTTGGCGGAGATCTCCAGTGATA<br>TCGACCAGCTGAATCCAGAGTCCGCTGACCTCCG<br>GGCCCTGGCAAAACATTTGTATGACTCATACATA<br>AAGTCCTTCCCGCTGACCAAAGCAAAGGCGAGG<br>GCGATCTTGACAGGAAAGACAACAGACAAATCA<br>**CCATTCGTTATCTATGACATGAATTCCTTAAT**<br>**GATGGGAGAAGATAAAATCAAGTTCAAACAC**<br>**ATCACCCCCCTGCAGGAGCAGAGCAAAGAGG**<br>**TGGCCATCCGCATCTTTCAGGGCTGCCAGTTT**<br>**CGCTCCGTGGAGGCTGTGCAGGAGATCACAG**<br>**AGTATGCCAAAAGCATTCCTGGTTTTGTAAAT**<br>**CTTGACTTGAACGACCAAGTAACTCTCCTCAA**<br>**ATATGGAGTCCACGAGATCATTTACACAATGC**<br>**TGGCCTCCTTGATGAATAAAGATGGGGTTCTC**<br>**ATATCCGAGGGCCAAGGCTTCATGACAAGGG**<br>**AGTTTCTAAAGAGCCTGCGAAAGCCTTTTGGT**<br>**GACTTTATGGAGCCCAAGTTTGAGTTTGCTGT**<br>**GAAGTTCAATGCACTGGAATTAGATGACAGC**<br>**GACTTGGCAATATTTATTGCTGTCATTATTCT**<br>**CAGTGGAG**ACCGCCCAGGTTTGCTGAATGTGAA<br>GCCCATTGAAGACATTCAAGACAACCTGCTACA<br>AGCCCTGGAGCTCCAGCTGAAGCTGAACCACCC<br>TGAGTCCTCACAGCTGTTTGCCAAGCTGCTCCAG<br>AAAATGACAGACCTCAGACAGATTGTCACGGAA<br>CACGTGCAGCTACTGCAGGTGATCAAGAAGACG | 50<br>The underlined exon exclusion sequence is SEQ ID NO: 82.<br>The sequence without the underlined exon exclusion sequence is SEQ ID NO: 114. |

TABLE 7-continued

Exon Exclusion Event Sequences

| Splicing Event Id | Gene Name | cDNA Sequence | SEQ ID NO: |
|---|---|---|---|
| | | GAGACAGACATGAGTCTTCACCCGCTCCTGCAG<br>GAGATCTACAAGGACTTGTACTAGCAGAGAGTC<br>CTGAGCCACTGCCAACATTTCCCTTCTTCCAGTT<br>GCACTATTCTGAGGGAAAATCTGACACCTAAGA<br>AATTTACTGTGAAAAAGCATTTTAAAAAGAAAA<br>GGTTTTAGAATATGATCTATTTTATGCATATTGTT<br>TATAAAGACACATTTACAATTTACTTTTAATATT<br>AAAAATTACCATATTATGAAATTGCTGATAGTAT<br>TTGAAGACTGAGTCTTGTGTGTTTCCCACCCTAG<br>CCCCCAGGCTTTCTTTTTTACCCCTTTTCCTTCTC<br>CCCTCCCTCCCTCCATCCCTCTCACTCTTCCTCCC<br>TCCCTTCCCTCCTTTCCTTCTTCCTTTATTTTTCTT<br>TTCTTTCTTAGACATTTTAAAATATGTGAGTGGA<br>ACTGCTGATACACTTTCATTCTCAGTAAATTAAT<br>TTTTTACTCAAT | |
| 16269 | BORCS8-<br>MEF2B | ACAAAGATCATTCCACTCAGCCTGGGACGATGG<br>GGAGGAAAAAAATCCAGATCTCCCGCATCCTGG<br>ACCAAAGGAATCGGCAG**CCCGGAGGAACCACC**<br>**CCCGCCCTCCTCAGCCTGATCCTGGAAGAGA**<br>**CTCGGGGCCCCCCAGCCTCCGCCAACCCAG**C<br>GCCGTGAAGAACCTGGTGGACAGCAGCGTCTAC<br>TTCCGCAGCGTGGAGGGTCTGCTCAAACAGGCC<br>ATCAGCATCCGGGACCATATGAATGCCAGTGCC<br>CAGGGCCACAG | 51<br>The underlined exon exclusion sequence is SEQ ID NO: 83.<br>The sequence without the underlined exon exclusion sequence is SEQ ID NO: 115. |
| 16833 | ENOSF1 | AGAAGCAAATGCTGGCACAAGGATACCCTGCTT<br>ACACGACATCGTGCGCCTGGCTGGGGTACTCAG<br>ATGACACGTTGAAGCAG**GATCCCAGGATGCTG**<br>**GTATCCTGCATAGATTTCAGGTACATCACTGA**<br>**TGTCCTGACTGAGGAGGATGCCCTAG**CCTGTC<br>TGGAAGTTACTTGTGGACATG | 52<br>The underlined exon exclusion sequence is SEQ ID NO: 84.<br>The sequence without the underlined exon exclusion sequence is SEQ ID NO: 116. |
| 16929 | DHRS4-<br>AS1 | GTGCCACTTCGGATAAACCCTTTGGACTCCTAAC<br>TCCAATCAGGTGTCTGCTTTGTTGAGGACTCACA<br>GACACAGTCTCCTTTCTTCAAGATCTTTACAATG<br>CAAGACCTCACTAACACACAGGGATGGTCTCCC<br>AGAGGGTCTGTGCTGTTCCTTCACTCAGAACATC<br>AAGATGCACTGAAGTAAGGATCCTCTATTCTACA<br>GTTCCTGCTAGCTGAGCTATTCCATGGGGGCTTC<br>AGCAGGAAATTCCAAGGTTGGCTTTGACAAGCT<br>AAGGCCGGCTGGTGGAGCACATCGAGTTCTGGA<br>GGTTCATGTGTGTTTTCATGAAGATCTGTCTGCC<br>CGTAGCAGATAAAGAGTTGTTGCCCCACTCCTCC<br>TGGGGTCTTCTATTTTCCTGGGAGGAATTTCTGG<br>ATTAACTGAACACACACACACACACACACACACCC<br>TTTTGAAGCATCAACAGTAATTCTGAGTTCTTAG<br>GGACAATGCAGATTAAATCCACAATAAGAAAGA<br>CAACTATGGCCAGGTGTGGTGGCTCACGCCTGTA<br>ATCCCAGAACTTTGGGAGGCTGAGGCGGATGGA<br>TCACCTGAGGTCAGGAGTTAGAGACCAACCTGA<br>CCAACATGGAGAAACCCCGTTTCTACTAAAAAT<br>GCAAAATTAGCCGGGCATGGTGGCAGGCGCCTG<br>TAATCCCAAATACTCGGGAGGCTGAGGCAGGAG<br>AATCACTTAAACCCGGGAGGCAGAGGTTGCAGT<br>GAGCCAAGATCGCGCCATTGCACTCCAGC**GGCC**<br>**AGACTTTGGCAGCGTGTAAGGTCTGAGGACA**<br>**GGGGCACCGGAGGCCGAGGATGAGAGGCCA**<br>**GTGCCTGTTTCCAGGCAGCCAGGGCCTCAGA**<br>**AACTCCGGCCGGAGCACTCACCCGTCGGTGG**<br>**AGGCCGTTACCAGGGCCACCTTATTTGCGAG**<br>**CGGGTCCCGGCGGGTCATCCCGGAGCTGGCC**<br>**ATCCGCACCGAATTCCAAGCCCGGGCACAGA**<br>**GGCCTAGCAGCCCCGCCTTGTGCATGGATCA** | 53<br>The underlined exon exclusion sequence is SEQ ID NO: 85.<br>The sequence without the underlined exon exclusion sequence is SEQ ID NO: 117. |

TABLE 7-continued

Exon Exclusion Event Sequences

| Splicing Event Id | Gene Name | cDNA Sequence | SEQ ID NO: |
|---|---|---|---|
| | | **GACCAGCAA**ACATGGGCCCCGTCCTGGGCCAAA<br>CGCCGGGCGATGGCGAAGCCGATCCTGTGAGCA<br>GAAAGAGACAAAGACTGCTAAGGCCTGTGCAGG<br>GGAAGAGGTCGACAGTATGAGCTCTGAAGTTAA<br>GACTGCCCGGGTTTGAATTCTGGCTCTTTCTCTA<br>TATAACCCCTACGTGTGCCTACTATGTGTAAAAC<br>AGGCTTAATGGCATGGCCATTTTTGGCATTCCTT<br>TACTTGTTTTTATTATGACCTGGACCACAGCCTC<br>AGTTCCCAAGAACTGACATCACTTTCTACAGTTC<br>CCACCATGGGTGACAGGCTTCATCCCCTCTTGGG<br>ACTGAGAG | |
| 16943 | NDUFV2 | CGCAGAATCTAGGCCTGCTCTGGCCAGATCAGTT<br>TCGAAGACCGTCGCTCCGAAGGAGGCACCTCTC<br>GTTTCAAGCCTAGTGACCTCGATGCTTTTAGGTT<br>GCAGCATACTGGAGAGCTCTGGCTTGCTTCGTGA<br>AGGCTTAGGGAGAACTTCATTAGGGCTGGAAAA<br>GGGTGGCCAATGTTTGATTTACTGCAGTTGTGCT<br>TTGCATATCGGAAATGCTGGCTAAATAAACGGT<br>ATCAAACTAACTCTGAAAGAACGGCGCCGCAAA<br>TAACAGCACCCAATTAAAGAACCACAGGATTTT<br>AGAGATTAAATGATCTTTTTGAGATCCAAGTACA<br>TCTCATG**GAAAAATACCTAGGTTAGAATTACT**<br>**AAATTAAAAAAATGGACACTTGGGGCCAGGCG**<br>**CAGTGGCTTACGCCTGTAATTCCACCACTTTG**<br>**GGGAGCTGAGGCGGGCAGATCACTTGACATC**<br>**GAGAGTTCAAGACCAGCCTGACCAACATGGA**<br>**GAAACCCCGTCTCTACTAAAAATACAAAAAAT**<br>**TATCCAGACGTAGTGGCACATGCCTGTAATCT**<br>**CAGCTACTTGGGAGGCTGAGGTAGGAGAATC**<br>**GCTTGAACCCGGGAGGCAGAGGTTGTGGTGA**<br>**GCCGAGATCATGCCATTGAACTCCAGCCTGG**<br>**GCAACAAGAGCGAAACTCCGTCTCCAAAAAA**<br>**AAAAAAAGACACTTATTTAGGCTTTCCATATA**<br>**TCATG**GGAAGACATGTAAGGAATTTGCATAAGA<br>CAGTTATGCAAAATGGAGCTGGAGGAGCTTTATT<br>TGTG | 54<br>The underlined exon exclusion sequence is SEQ ID NO: 86.<br>The sequence without the underlined exon exclusion sequence is SEQ ID NO: 118. |
| 18745 | FER1L4 | GATCCCTGGAGTTGCAGCTACCAGACATGGTGC<br>GTGGGGCCCGGGGCCCCGAGCTCTGCTCTGTGC<br>AGCTGGCCCGCAATGGGGCCGGGCCGAGGTGCA<br>ATCTGTTTCGCTGCTGCCGCCGCCTGAGGGGCTG<br>GTGGCCGGTAGTGAAGCTGAAGGAGGCAGAGGA<br>CGTGGAGCGGGAGGCGCAGGAGGCTCAGGCTGG<br>CAAGAAGAAGCGAAAGCAGAGGAGGAGGAAGG<br>GCCGGCCAGAAGACCTGGAGTTCACAGACATGG<br>GTGGCAATGTGTACATCCTCACG**CTGGGTGAAG**<br>**GGGTTGGAGCATGACAAGCAGGAGACAGACG**<br>**TTCACTTCAACTCCCTGACTGGGGAGGGGAA**<br>**CTTCAATTGGCGCTTTGTGTTCCGCTTTGACT**<br>**ACCTGCCCACGGAGCGGGAGGTGAGCGTCCG**<br>**GCGCAGGTCTGGACCCTTTGCCCTGGAGGAG**<br>**GCGGAGTTCCGGCAGCCTGCAGTGCTGGTCC**<br>**TGCAG**CTATGAGCTCAGAGTTGTCATCTGGAAC<br>ACGGAGGATGTGGTTCTGGACGACGAGAATCCA<br>CTCACCGGAGAGATGTCGAGTGACATCTATGTG<br>AAGAG | 55<br>The underlined exon exclusion sequence is SEQ ID NO: 87.<br>The sequence without the underlined exon exclusion sequence is SEQ ID NO: 119. |
| 19824 | PHF14 | GCAGTGCTCGGAATGTGACCAGGCAGGGAGCAG<br>TGACATGGAAGCAGATATGGCCATGGAAACCCT<br>ACCAGATGGAACCAAACGATCAAGGAGGCAGAT<br>TAAGGAACCAGTGAAATTTGTTCCACAGGATGT<br>GCCACCAGAACCCAAGAAGATTCCGATAAGAAA<br>CACG**AGAACCAGAGGACGAAAACGAAGCTTC**<br>**GTTCCTGAGGAAGAAAAACATGAGGTTGGAA**<br>**TAAG**GAAAGAGTTCCTAGAGAGAGAAGACAAA<br>GACAGTCTGTGTTGCAAAAGAAGCCCAAGGCTG<br>AAGATTTAAGAACTGAATGTGCAACTTGCAAGG<br>GAACTGGAGACAATGAAAATCTTGTCAGGTAAG<br>TTGGATGCTAAAACCTTGTCTTTAGGGGATGAAA<br>GTTCTATATTTATTTTCTCATCACAGAAAAAATG<br>AAAAAACAATTGCAGGATAAGACCTTTCTTAAA<br>ATATTATATAGTGGAAACAGTACTTTAGAAACA<br>GATTTCATCCACTTCTTAACCTCTCACACATGGT<br>TATACTCTGGATTTAAATGTAAATAAGAGTGATA | 56<br>The underlined exon exclusion sequence is SEQ ID NO: 88.<br>The sequence without the underlined exon exclusion sequence is SEQ ID NO: 120. |

TABLE 7-continued

Exon Exclusion Event Sequences

| Splicing Event Id | Gene Name | cDNA Sequence | SEQ ID NO: |
|---|---|---|---|
| | | ATCTGCCTGTTTAACACAGGGAATTATTTTTCTCT<br>TGACAAGAGAAATTGACAGTGCTCTCTATTTAGA<br>GGCCATGAAAGTAATTTGATCTAAACACTGTGTA<br>CTAAGATTATTATGTTTTATGTCAGAAAACAATA<br>AAGTTACTAAGCTCTGTTAGCATATTCTAAATGT<br>TTGAAATTTAGAAGCAATGGTGAGAAGACAGAC<br>TTTTTATTGACAAGAACTTAATTAGCACTTTCTTA<br>TTGCTTATCAAAACAAATGTGTTAAATGCTTCTC<br>CCTTACGAAATAAAGAAAGGTGAAAAGATGGCC<br>TAGGTTGATTTTATTTTTTGTTTTGTCTTTGTTTCT<br>TTGTTTCGTTTTGGTACTTTATTTTTTTTAATCA<br>GACATAATGCTAATCAGAAATCTTAGCTGATGCT<br>GCACATTGGCTTTTCCCAACGGTCCAGAGGCTGC<br>TAATTTTAGCGGAAATGAAGACATTGATCAAAG<br>CTCTGGTGAGATGGGGGAGTGAGTGTGTGAACA<br>AAAAGAGAGCTAATTTAAAAGAGGCATCAGACT<br>TTCAAAGGACAGTGTCACAAAAGTTCTTACAGTT<br>CTTACAGGGACTTTGTAAGGGAATCCATTCTTAT<br>TTCTTTAAAAAATTGTCTTCTGGTAAAGCCCTGT<br>TAAATTAACTGAGGACACAGAAATTAAACATTT<br>CAAAAAGAATAAACATATTGATAAAACAAATAT<br>ATTAGTGTTGTTGTATGTTTTTAAATACTTACTTC<br>CAAATGATTTAATCTATTTTGGTCATTAAAATAT<br>GTCTTAATTTCTCAAAGAAAGGCATGAAGTCTTA<br>AATTTTATGAGTTTTTTATGCTATCAATGAGAAA<br>GATAAAGTAAAAATTACAGTAGAAAAAGACAAA<br>GTCCTTCAACAAAGTTAAGAAAGTTTATAATAAT<br>TGGCTAATTTTTTTGAGGTAGTTCATGTAGAGTG<br>TGTTGGGAGCTATCCTGAAGGTTAAGTTTATTAA<br>AATTTAGGGTAAAGTAGTAAGTAGTTCCAAGTTC<br>AGGAGATACACCTGAATAATTCTGACCACAGTA<br>TAAATTTTGCAATATGTCGAAAATGAAATCCCAA<br>GCATAAGCGTAACATAATGGAGTAAAT | |
| 19828 | PHF14 | GCAGTGCTCGGAATGTGACCAGGCAGGGAGCAG<br>TGACATGGAAGCAGATATGGCCATGGAAACCCT<br>ACCAGATGGAACCAAACGATCAAGGAGGCAGAT<br>TAAGGAACCAGTGAAATTTGTTCCACAGGATGT<br>GCCACCAGAACCCAAGAAGATTCCGATAAGAAA<br>CACG**AGAACCAGAGGACGAAAACGAAGCTTC<br>GTTCCTGAGGAAGAAAAACATGAGGTTGGAA<br>TAA**GAAAGAGTTCCTAGAGAGAGAAGACAAAG<br>ACAGTCTGTGTTGCAAAAGAAGCCCAAGGCTGA<br>AGATTTAAGAACTGAATGTGCAACTTGCAAGGG<br>AACTGGAGACAATGAAAATCTTGTCAG | 57<br>The underlined exon exclusion sequence is SEQ ID NO: 89.<br>The sequence without the underlined exon exclusion sequence is SEQ ID NO: 121. |
| 21024 | BCL2L13 | GGGTTCAACTAGATATAGCTTCACAATCTCTGGA<br>TCAAGAAATTTTATTAAAAGTTAAAACTGAAATT<br>GAAGAAGAGCTAAAATCTCTGGACAAAGAAATT<br>TCTGAAG**GCCAGTGACATATCAGGCATTTCGG<br>GAATGTACACTGGAGACCACAGTTCATGCCA<br>GCGGCTGGAATAAG**GGCACTGTGTTTAGTCTTG<br>AGTCAGAGGAGGAGGAATACCCTGGAATCACTG<br>CAGAAGATAGCAATGACATTTACATCCTGCCCA<br>GCGACAACTCTGGACAAGTCAGTCCCCCAGAGT<br>CTCCAACTGTGACCACTTCCTGGCAGTCTGAGAG<br>CTTACCTGTGTCACTGTCAGCTAGCCAGAGTTGG<br>CACACAGAAAGCCTGCCAGTGTCACTAGGCCCT<br>GAGTCCTGGCAGCAGATTGCAATGGATCCTGAA<br>GAAGTGAAAAGCTTAGACAGCAACGGAGCTGGA<br>GAGAAGAGTGAGAACAACTCCTCTAATTCTGAC<br>ATTGTGCACGTGGAGAAAGAAGAGGTGCCCGAG<br>GGCATGGAAGAGGCTGCTGTGGCTTCTGTGGTCT<br>TGCCAGCGCGGGAGCTGCAAGAGGCACTTCCTG<br>AAGCCCCAGCTCCCTTGCTTCCACATATCACTGC<br>CACCTCCCTGCTGGGGACAAGGGAACCTGACAC<br>AGAAGTGATCACAGTTGAGAAATCCAGCCCTGC<br>TACATCTCTGTTTGTAGAACTTGATGAAGAAGAG<br>GTGAAAGCAGCAACAACTGAACCTACTGAAGTG<br>GAGGAGGTGGTCCCCGCACTGGAACCCACAGAA<br>ACGCTGCTGAGTGAGAAGGAGATAAACGCAAGG<br>GAAGAGAGCCTTGTGGAAGAGCTGTCCCCTGCC<br>AGCGAGAAGAAGCCCGTGCCGCCGTCTGAGGGC | 58<br>The underlined exon exclusion sequence is SEQ ID NO: 90.<br>The sequence without the underlined exon exclusion sequence is SEQ ID NO: 122. |

TABLE 7-continued

Exon Exclusion Event Sequences

| Splicing Event Id | Gene Name | cDNA Sequence | SEQ ID NO: |
|---|---|---|---|
| | | AAGTCTAGACTGTCCCCCGCCGGTGAGATGAAG<br>CCCATGCCGCTGTCTGAGGGCAAGTCTATACTGC<br>TGTTTGGAGGGGCTGCTGCTGTTGCCATCCTGGC<br>AGTGGCCATCGGGGTAGCCCTGGCTCTGAGAAA<br>GAAATAGGAGGCTTTTCAGAAGAGAAAGACAGA<br>AGGATGTAAGGTTGGAGTTGTATTGGCTGGAATT<br>TGAACCTCCAGCAGCTGTCTGGACATTTGTGGAA<br>CACTCTGGGATAATTGGGGACTTCTGCTCAACAT<br>GGCAGTGGCATGTTAGGCATGTTAGGGCTTGAG<br>GTGGGGCATTCACATTCATCTGACTGTAAATCCC<br>AAGGGCCTCCGCTCATGCTAAATTGAGAATCTTA<br>GGGGTAAAGCACCCCCTCCAGGACCGGGTTTCT<br>CAGCCTTGGCACTAGTGCTGTTCTGACCATTCTC<br>TGTGTTGGGGCTGTCCTGTGTGTGGTGGGCTCCA<br>CCCACTAGATGCCAGTGGCACCCCCTCCCAGAG<br>ATGACAAACGAAAATGTCTCTAGACATTGCCAA<br>ATGTCCCGTGTGAACATCCCCTATTGAGACCCAC<br>TGCTTTAGCGAGAGAGGGTTTACTTAGGAAGAA<br>TTGGGATAGAAATTCCCAGCTGAGAGAACTTAG<br>CTGTGGGCTCCTCAGCTACTGACTTCTTAGCTCT<br>TAATCCCCTTAGAATTTCATCTTTCTCGATGAGC<br>AGGCTCTGCACCCACTCTTTTTTTGCCCCCCGCC<br>CTCATCCTGGAGTGTGAGGGTGCTCGCCCGTACT<br>CTCAGCTGCCTCTCAGGGACTGCACTGTTCCTCT<br>TCACCCCCAGGTTCCTGCTAAGATCCCACGGGCG<br>AGGGCTTGCTCTGGACTCAGTCTGTCAAGTCCCC<br>GAAGCTTCCTGCAGCTCCACCTTGTAAAAATGCT<br>GCCTTTGGGAATCTTCGAAATATGTACACAGAG<br>AAAATCACATGAAGGAGACCTGGGGTCCCCACT<br>TGTGAGTGCAACTGCAAGTAACTCTGGCTAGAG<br>AGACACATGTGTCTTGTGTCAAGGCAGGAGGAT<br>AACCTGGATGACCTTCTGAGGTCTCTTCAGCCCT<br>TTTCGCTAGTGGTCACCCACCACCATGGTTACTT<br>GCCAGCAACATCTCTATTGCTGGATGGTCCCTGT<br>CTATAACCTTGGGCTAGTATATTTTTTCCAATAT<br>GGGACCTTAGTCTTACTACTGATGAGTTCTATGG<br>GTCTCTTGCTAGGGGGTAAGGATTTTTATTCTTG<br>GGCTTATAGAGCCAGTTAGATCATAATTCTTATG<br>AAATAGAGAGTGTCCTAAATATCACTGAAATAA<br>AAAGTAGGAAAAAGAAGCTTGAATTTTAAGACT<br>GAGGCTGCTCTGCAGATTCTAGTTTGGCTTTCAG<br>AGTTCAAGAGTGGTGGCATCTTCACCTGAATTCT<br>TCAATGCCAGGGTAATAAACCAAAATAGTCCTA<br>ATCAGTATATGCTAGTTGAGCATCGGCATAATTT<br>TCTTTCCTCTGGCTGATCCCAGCCCTAAAGGAAG<br>GGTAGACCCGTGTCTTTCCAGCCCTAAAGGAAG<br>GGTAGACCCGTGTCTTTCCAGCCCTAAAGGAAG<br>GGCAGACCCGTGTCTTTCCATGCCCGAGGGCCAC<br>GACGTCACTATGCAGGGCACACGTGGCTTGGTTT<br>AAAAAGGTCATCTTAGATTTATCTTAGTAAATGT<br>AATAAATTATTTTTTAGATCTTGAAATTTATAAT<br>AAAAATACTTTACCTACCCTGATC | |
| 22227 | SELENBP1 | GTCATTGAGCCCAAGGACATCCATGCCAAGTGC<br>GAACTGGCCTTTCTCCACACCAGCCACTGCCTGG<br>CCAGCGGGGAAGTGATGATCAGCTCCCTGGGAG<br>ACGTCAAGGGCAATGGCAAAG**GTCATCCACCG**<br>**GCTGCCCATGCCCAACCTGAAGGACGAGCTG**<br>**CATCACTCAGGATGGAACACCTGCAGCAGCT**<br>**GCTTCGGTGATAGCACCAAGTCGCGCACCAA**<br>**GCTGGTGCTGCCCAGTCTCATCTCCTCTCGCA**<br>**TCTATGTGGTGGACGTGGGCTCTGAGCCCCG**<br>**GGCCCCAAAGCTGCACAAG**CTACGAAATGTGG<br>GAATTGTGGACCCGGCTACTCCACCCCTCTGGAG<br>GCCATGAAAG | 59<br>The underlined exon exclusion sequence is SEQ ID NO: 91.<br>The sequence without the underlined exon exclusion sequence is SEQ ID NO: 123. |

TABLE 7-continued

Exon Exclusion Event Sequences

| Splicing Event Id | Gene Name | cDNA Sequence | SEQ ID NO: |
|---|---|---|---|
| 24742 | LINC00630 | GTTGATTCCATACCCTGGCTATTGTGAATAATGCTGCAGTGAACATGGGAGTACATACATCTGTTTGAG**GAACTCAGAGTGGTTTTCCAGATGGGAATCACATTGCTCTCTGTCCCTGAGATCTTGCTGGAGACAGGGCTACTCAGTCCCTCTTTGCCAG**GTAATCTGTTCCAGAAGAAACATGTGTCGTTCTGACTGAGCCCCTGCCTGTCTGTCACCTTAAGAGCCAGTCAATTCATATGGTCCCCATATCAAAGTCTCCTGTGCCCAGAGAGAGGATTTCATTTCAACCATCACCATCACCACCATCATCATCATCACCAAGAGATGTTGTTGA | 60 The underlined exon exclusion sequence is SEQ ID NO: 92. The sequence without the underlined exon exclusion sequence is SEQ ID NO: 124. |
| 27194 | CTBP2 | GGTTCATAGTGGCGTCATGCACGCAGACTCCTGCAAGTTCCCCTAAGTTCTTAGAGGACTGCTTTGCCTTTTGATCTGAGAGTTGCAAAGTTCCATAAAGAATGGCCCTTGTGGATAAGCACAAAGTCAAGAGACAGCGATTGGACAGAATTTGTGAAG**ATGGAGAAAACAAAGGATTCAGATTGAAGGACTGCTCAGACACCCTCCGAAGAGGTGGCCCTGCCTGCGCTCCTCCTGGCTGCAGAGTACCCCACCAGCGC**GAGATCCAGGGTTGCCAGAAGACGAGACAACCGTGATTGCATGTGCGGAGGTTCCTCGATGGAAGCGCAGCCCGGCGCGCCCCTCAGCTGGCCTGGCCAGGCCCTATGAAGGTCACGCGAAAACCCTGCTGCGGGCTTCTTAGCGACCGCATTACGTGGACTAGCGGGCAAGAAAAGCCTGGTCGGCGCTGCCCTCACAG | 61 The underlined exon exclusion sequence is SEQ ID NO: 93. The sequence without the underlined exon exclusion sequence is SEQ ID NO: 125. |
| 30244 | SLC52A2 | AGGCGTCTGGCCAGGTGGCGCTCCGGGCAG**GCCTACTTGGGTGTCCCCGCCTCTGATACCTCCCTGCTGGAGGAAACAGCAGGAAAAGAGAACCAGGCAGGCAGGCAGACATCCCCACGGAGCAGCGTTGGGCCCCCAAGGTGCCTGACCCACTTCCTAGAGTACTGAACAGTCCCAGAGTGTCACAGCTGATGTGCAGGACAGCCTGGAGCTCTCACCTTCAACACGGGGTGTACCTGAGACTTCCAGTGGATGAGGGTCAGCCTCTGGAGCTGTGAAAACCTGGGCCGACAGCGGAGGCAGAGCTGCACTAATGTTCCCACACGAGTCCTTCCCACCCAACACCTTGGTGCAGGGAGACGGAAGGAGCCTGGAGCCAGGG**CTAGAAGAAGTCTTCACTTCCCAGGAGAGCCAAAGCGTGTCTGGCCCTAGGTGGGAAAAGAACTGGCTGTGACCTTTGCCCTGACCTGGAAGGGCCCAGCCTTGGGCTGAATGGCAGCACCCACGCCCGCCCGTCCGGTGCTGACCCACCTGCTGGTGGCTCTCTTCGGCATGGGCTCCTGGGCTGCGGTCAATGGGATCTGGGTGGAGCTACCTGTGGTGGTCAAAGAGCTTCCAGAGG | 62 The underlined exon exclusion sequence is SEQ ID NO: 94. The sequence without the underlined exon exclusion sequence is SEQ ID NO: 126. |
| 33377 | SLC38A1 | CTCTTTCTCTTCCTCCAGTTTCCAGTCCAGCCCTGTTGGCTCTCAGAATGCATCATCCTTCTCCCTGCAGCGCTCTCACTGAACATGCTCAAGCGCAAGGAACTTATAATCTTGTGTTCTCTGGATTCTGGATTTAGTAATCTGTATTAGTCTGTTCTCACACTGCTAATAAAGAAATACCTGAGGTTGCTTCCAAGATAGCCAAATAGGAACAGCTCTGGTCTGCAGCTCCCAGCAAGATCGATGTAGAAGATGGGTGATTTCTGCATTTCCAACTGAGGTACCTGGTTCATCTCACTGGGACTGGTTGGACAGTGGGTGCAGCCCATGGAAGGTGAGCTGAAGCAAGGTGGGGCGTCACCTCACCCAGGAAGCACAAGGGGTCAGGGGATTTACCTTTCCCAGCCAAGGGAAGCCATGACAGACTGTAACTGGAGAAACGGTACACTCCTGACCAAATACTGCACTTTTCCCACAGTCTTAGCAACTGGCAGACCAGGTAATACCCTCCCGTGCCTGGCTCAGTGGGTTCCATGCCAACGGAGCCTTGCTCACTGCTAGCGCAACAGTCTAAGATCGACCTGCGACGCTGCAGCTTGATGCAGGGAGAGGCATCCAACATTGCTGAGGCTTGAGTAGCTCACAGTGTAAGCAAAGAGGCCCGGAAGCACAAGTTGGGCAGAGCTCATCGCTGCTCAGCAGGGCCTACTGCCTCTATAGATTCCACCTCTGGAGGCAGGGCATGGCAGAAAAAAACGCAGCAGACAGCTTTTGCAGACTTAAACGTCCCTGTCTGATGGCTCTA | 63 The underlined exon exclusion sequence is SEQ ID NO: 95. The sequence without the underlined exon exclusion sequence is SEQ ID NO: 127. |

TABLE 7-continued

| Exon Exclusion Event Sequences | | | |
|---|---|---|---|
| Splicing Event Id | Gene Name | cDNA Sequence | SEQ ID NO: |
| | | AAGAGAGCAATGGTTCTCTCAGCATGGCATTCG<br>AGCTCCAAGAACAGACAGACTGCCTCCCCAAGC<br>AGGTCCCTGACCCCCATGTAGCTGGACTGGGAA<br>ACACCTCCCCATCAGGGGCTGAGAGATACCTCA<br>AACACGTGGGTGCCCCTCTGGGACGAAGCTTCC<br>AGAGGAAGGATCAGGCAGCAATATTTGCTATTC<br>TGCAGCCTTTGCTGGTGATACCCAGGCAAACAG<br>ATTCTGGAGTGGACCTCCAGCAAACTCCAACAA<br>ACCTGCAGCTGAGGGGTCTGACTGTGGGAAGGA<br>AAACTAACAAAGAGAAAGCAATAGCATCAACAT<br>CAACAAAAAGGACATCCACACCAAATCCCCATC<br>TATAGGTCACCAACATCAAAGACCAAAGGTAGA<br>TAAAACCACAAAGATGGGGAGAGAAACCAGAG<br>CAGAAAAGCTGAAAATTCCAAAAAACAAGCACC<br>TCTTCTCCTCCAAAGGATCGCAGCTCCTTGCCAG<br>CAAGGGAACAAAACTAGACGGAGAATGAGTTTG<br>ACAAGTTGACAGAAGTAGGCTTCAGAAGGTTGG<br>TAATAACAAACTTCTCTGAGCTAAAGGAGCATCT<br>TCTAACCCATCGCAAAGAGGCTAAAAACTGTGG<br>AAAAAAAAAAGGTTAGATGAATGGCTAACTAGA<br>ATAACCAGTGTAGAGAAGACCTCAAATGACCTG<br>ATGAAGCTGAAACCCACAGCACAAGAACTTCGA<br>GACTCATGCACAAGCTTCAATAGCCGATTCGATC<br>AAGTGGAAGAAAGGATATCAGTGATTGAAGATC<br>AAATTAATGAAATAAAGTGAGAAGAAT**GTCTG**<br>**GTGAAGTTCAAGGGCATCTTGAACGTGGTGC**<br>**ACTTGGAGACAGTGAGGGAAGCAGGGGTGAA**<br>**GTGGCTGCTACCTGAGTCCCTTCTGGAGCTCC**<br>**ATTTTGCTTGGTCTTGGAGAAGGCTTCTCAGC**<br>**TGCCCTCCCAGCTAGT**GAGTTACATCTGCTAAC<br>ATGCTTATTTTCATTCTTCCTTCATCTCTTTATTTA<br>AAAATCACAGACCAGGATGGAGATAAAGGAACT<br>CAAAGAATTTGG | |
| 40521 | FAM65A | AAACTGGGCACATTTGGGCCCCTGCGCTGCCAG<br>GAGGCATGGGCCCTGGAGCGGCTGCTGCGGGAA<br>GCCCGAGTACTGGAGGCAGTATGCGAGTTCAGC<br>AGGCGGTGGGAGATCCCGGCCAGCTCTGCCCAG<br>GAAG**TGGTGCAGTTCTCGGCCTCTCGGCCTG**<br>**GCTTCCTGACCTTCTGGGACCAGTGCACAGA**<br>**GAGACTCAGCTGCTTCCTCTGCCCGGTGGAG**<br>**CGGGTGCTTCTCACCTTCTGCAACCAGTATGG**<br>**TGCCCGCCTCTCCCTGCGCCAGCCAGGCTTG**<br>**GCTGAGGCTG**TGTGTGTGAAGTTCCTGGAGGAT<br>GCCCTGGGGCAGAAGCTGCCCAGAAGGCCCCAG<br>CCAGGGCCTGGAGAGCAGCTCACAGTCTTCCAG<br>TTCTGGAGTTTTGTGGAAACCTTGGACAGCCCCA<br>CCATGGAGGCCTACGTGACTGAGACCGCTGAGG<br>AGG | 64<br>The underlined exon exclusion sequence is SEQ ID NO: 96.<br>The sequence without the underlined exon exclusion sequence is SEQ ID NO: 128. |
| 41168 | USP25 | TAATGGAAACTTGGAATTAGCAGTGGCTTTCCTT<br>ACTGCGAAGAATGCTAAGACCCCTCAGCAGGAG<br>GAGACAACTTACTACCAAACAGCACTTCCTGGC<br>AATGATAGATACATCAGTGTGGGAAGCCAAGCA<br>GATACAA**ATGTGATTGATCTCACTGGAGATGA**<br>**TAAAGATGATCTTCAGAGAGCAATTGCCTTGA**<br>**GTTTGGCCGAATCAAACAGGGCATTCAGGGA**<br>**GACTGGAATAACTGATGAGGAACAAGCCATT**<br>**AGCAG**AGTTCTTGAAGCCAGCATAGCAGAGAAT<br>AAAGCATGTTTGAAGAGGACACCTACAGAAGTT<br>TGGAGGGATTCTCGAAACCCTTATGATAGAAAA<br>AGACAGGACAAAGCTCCCGTTGGGCTAAAGAAT<br>GTTGGCAATACTTGTTGGTTTAGTGCTGTTATTC<br>AG | 65<br>The underlined exon exclusion sequence is SEQ ID NO: 97.<br>The sequence without the underlined exon exclusion sequence is SEQ ID NO: 129. |

TABLE 7-continued

Exon Exclusion Event Sequences

| Splicing Event Id | Gene Name | cDNA Sequence | SEQ ID NO: |
|---|---|---|---|
| 45885 | HMOX2 | AACCGGATGCTACGGGTGATGACTGGGAGGAGG<br>AGAAAAATTACCTCTTTATCTTGCATGAACATCT<br>TAATTTTCAG**AGTCTTGCTGCGACACCCAGGC<br>TGGAGTGCAATGGCGCTATCTCGGCTCACTG<br>CAACCTCCGCTTCCCGGATTCAAGCGATTCTC<br>CTGCCTCAGCCTCCCGAGTAGGTGGGACTAC<br>AG**GACCAGAGGAGCGAGAGCAGCAAGAACCAC<br>ACCCAGCAGCAATGTCAGCGGAAGTGGAAACCT<br>CAGAGGGGGTAGACGAGTCAGAAAAAAAGAAC<br>TCTGGGGCCCTAGAAAAGGAGAACCAAATGAG | 66<br>The underlined exon exclusion sequence is SEQ ID NO: 98.<br>The sequence without the underlined exon exclusion sequence is SEQ ID NO: 130. |
| 50148 | MKRN2OS | GGGTTGTGTATAATTACAGTGCACATGGTGTCCA<br>GCGAGACGGAGAAGGGTGGGAAGAGAGCATAA<br>GCATCCCATTACTGCAGCCCAACATGTATGGAAT<br>GATGGAGCAATGGGACAAGTACCTGGAAGACTT<br>CTCCACCTCGGGGGCCTGGCTGCCTCACAG**AGA<br>GTATGATGGAAGGTCTGATCTTCATGTTGGAA<br>TAACTAACACAAATG**GTATAATGAGGAAAAGG<br>AAGTCTCCGGAAACCTCCCCTAGCATTCCAGGA<br>GGCGAAAGCTATGCACTGCGCAGAGGCTGGGAA<br>GGCTTTAATTAAATTCAACCACTGTGAGAAATAC<br>ATCTACAGCTTCAGTGTGCCCCAGTGCTGCCCTC<br>TCTGCCAGCAGGACCTGGGCTCGAGGAAGCTGG<br>AGGACGCACCTGTTAGCATCGCTAATCCATTTAC<br>TAATGGACATCAAGAAAAATGTTCATTCCTCCTC<br>AGACCAACTCAGGGGACATTTCTTAG | 67<br>The underlined exon exclusion sequence is SEQ ID NO: 99.<br>The sequence without the underlined exon exclusion sequence is SEQ ID NO: 131. |
| 52249 | ATP8A2P1 | GTAAACAAATTGCTCCTGTGGAGATGATTGGCAT<br>CACATGGTGTTTTGAGCTGATACACCCAACACTT<br>GAGCTCACTGCAACAGTACCAG**ATTTTCACCGC<br>TATGCCTCCTTTCACTCTGGGAGTCTTCCAGA<br>GGTCTTGCACTCGGGAGAGCATGCTCAGGTT<br>TCCCCAGCTCTACAAAATCACCCAGAATGCCA<br>AAGACTTCAACACAAGGGTAAATAAGGTTGAT<br>CTCAGAATTGTCACCTCAAAAAGGCCCTGCCT<br>TCCACTGTTCAGTTCTGGTCATCTGCCTATGA<br>GATATCTGAAGCTTGAAAGAGAACACTTGAAA<br>ATCACTGAGACCGTGACTCCCATCCCAGCACA<br>CACAGCAAGCCAA**ATACTGTGTTGACCAGTGGT<br>CATGCCACTGCCTGTTGATTTGTTGAAAATATTG<br>TTTACACG | 68<br>The underlined exon exclusion sequence is SEQ ID NO: 100.<br>The sequence without the underlined exon exclusion sequence is SEQ ID NO: 132. |
| 53188 | HIBCH | TTTTAATTGATAAAGACCAGAGTCCAAAATGGA<br>AACCAGCTGATCTAAAAGAAGTTACTGAGGAAG<br>ATTTGAATAATCACTTTAAGTCTTTGGGAAGCAG<br>TGATTTGAAATTTTGAGGTGACAGGCTTTTAAGG<br>TATATTTTGTAGCATGGGTTGGCAATCTACAGCA<br>TGTGGGCCAAATCCAGCCTGCTGCCTGTTTTTAT<br>ATACCCTGTAAGCTAAGAATGGTTTCCGCATTTT<br>TAAATGGTTGGGAAAAGAAATCAAAGACTAATA<br>ATTCATGACGTGAAAATTATCAGAATTCACAAAT<br>AAAGCTTTATTGGAACTAGCTATACTCATCTGTT<br>TATATATTATCTGTGGCTGCTTTGAAATGAGTAG<br>TTGCAATAGAGATGGTAAAGCCTACAAAGCCTA<br>ATTATTTACTGTCTGGTTTTTGTCAGAAAAAAGT<br>TTGTCAATCCTTGTTTTAGAAGATGGAAAAATGT<br>GAAGATCTTTGGAGATTCTCTTGAGTGGTATATC<br>TAATTGAAATGGGATCTTCGTTTGGCTTGTATGT<br>TGATGAAATCAACTTAGGTATACAATATAAAAA<br>ATAAAGACCCTGAAAATTGTTTTGG**AGAGGTCA<br>TGACTTTCATGAAGGCGTTAGAGCTG**GGTAATT<br>AATAAAATGTCTCCAACATCTCTAAAGATCACAC<br>TAAGGCAACTCATGGAGGGGTCTTCAAAGACCT<br>TGCAAGAAGTACTAACTATGGAGTATCGGCTAA<br>GTCAAGCTTGTATG | 69<br>The underlined exon exclusion sequence is SEQ ID NO: 101.<br>The sequence without the underlined exon exclusion sequence is SEQ ID NO: 133. |

TABLE 7-continued

Exon Exclusion Event Sequences

| Splicing Event Id | Gene Name | cDNA Sequence | SEQ ID NO: |
|---|---|---|---|
| 58853 | SLC35C2 | CGCGCGGCACTGGTCCTGGTGGTCCTCCTCATCG<br>CCGGGGGTCTCTTCATGTTCACCTACAAGTCCAC<br>ACAGTTCAACGTGGAGGGCTTCGCCTTGGTGCTG<br>GGGGCCTCGTTCATCGGTGGCATTCGCTGGACCC<br>TCACCCAGATGCTCCTGCAGAAGGCTGAACTCG<br>**GACCAAATCCTCAGCTGTCCTCTTCATCTTGA**<br>**TCTTCTCTCTGATCTTCAAGCTGGAGGAGCTG**<br>CTCTGGCGACGGCGCTTGACGTGGGCTTGTCCAA<br>CTGGAGCTTCCTGTATGTCACCGTCTCGCT | 70<br>The underlined exon exclusion sequence is SEQ ID NO: 102.<br>The sequence without the underlined exon exclusion sequence is SEQ ID NO: 134. |
| 59314 | TRIM5 | GGATCTGTGAACAAGAGGAACCTCAGCAGCCAG<br>GACAGGCAGGAGCAGTGGAATAGCTACTATGGC<br>TTCTGGAATCCTGGTTAATGTAAAGGAGGAGGT<br>GACCTGCCCCATCTGCCTGGAACTCCTGACACAA<br>CCCCTGAGCCTGGACTGCGGCCACAGCTTCTGCC<br>AAGCATGCCTCACTGCAAACCACAAGAAGTCCA<br>TGCTAGACAAAGGAGAGAGTAGCTGCCCTGTGT<br>GCCGGATCAGTTACCAGCCTGAGAACATACGGC<br>CTAATCGGCATGTAGCCAACATAGTGGAGAAGC<br>TCAGGGAGGTCAAGTTGAGCCCAGAGGGGCAGA<br>AAGTTGATCATTGTGCACGCCATGGAGAGAAAC<br>TTCTACTCTTCTGTCAGGAGGACGGGAAGGTCAT<br>TTGCTGGCTTTGTGAGCGGTCTCAGGAGCACCGT<br>GGTCACCACACGTTCCTCACAGAGGAGGTTGCC<br>CGGGAGTACCAA**GATCCAGGCAATCTTTCCAG**<br>**ACACATCTACTTCCCAGTAATATTTCCCCGAA**<br>**GAGAAATATTGGCAGCCGAAGACACCAAAAG**<br>**CAGAAAAATCACATGGATTTGAATTCTTAAAT**<br>**GTGCAG**CAGGTCTAAGGCCCGCCTGTTCTGTGC<br>CGTGACCTGTGCTACCGAAGTCATCTGTTGCTGT<br>AGGGAGGCCAGGGACTCAGCCGATGCCTCAATG<br>GCCAACTGCAG | 71<br>The underlined exon exclusion sequence is SEQ ID NO: 103.<br>The sequence without the underlined exon exclusion sequence is SEQ ID NO: 135. |
| 60239 | HSD17B6 | TCCTCGCCTCCATCACCTCCACCGTAGTTGAGCC<br>AGCGATAGTACTGAGAGTAGGGAAAGAGCCTCC<br>GGTAATAAAGTTTAAGCAGCTCGGGCAGCTCGG<br>TGGGGTCAAACGTCTCCATTGAGCGCGGAACTC<br>GCCACG**TAACAGATCTGATTCTGCAGCTGATC**<br>**AAGGATGACACTGGTGAGAACCCTATGAGGG**<br>**AGTGAAGCAGCCTGGACTCTTACCACAAGAG**<br>**GGAGGTGTTATAAGAGCAATGCAGAGGTTGG**<br>**AGTGGGCAGCAGTTGGGGCAGGAGGAAGCCG**<br>**ACTGCTGCCTGGTCTGCAAAGAAGTCCTTTCA**<br>**AGTCTCTAGGACTGGACTCTTCCTAAGCAAGT**<br>**CCG**AGAAGGAAGCACCCTCACTATGTGGCTCTA<br>CCTGGCGGCCTTCGTGGGCCTGTACTACCTTCTG<br>CACTGGTACCGGGAGAGGCAGGTGGTGAGCCAC<br>CTCCAAGACAAGTATGTCTTTATCACGGGCTGTG<br>ACTCGGGCTTTGGGAACCTGCTGGCCAGACAGC<br>TGGATGCACGAGGCTTGAGAGTGCTGGCTGCGT<br>GTCTGACGGAGAAGGGGGCCGAGCAGCTGAGGG<br>GCCAGACGTCTGACAGGCTGGAGACGGTGACCC<br>TGGATGTTACCAAGATGGAGAGCATCGCTGCAG<br>CTACTCAGTGGGTGAAGGAGCATGTGGGGGACA<br>GAG | 72<br>The underlined exon exclusion sequence is SEQ ID NO: 104.<br>The sequence without the underlined exon exclusion sequence is SEQ ID NO: 136. |

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A method comprising assaying nucleic acids of a sample subject obtained from a breast cancer for the presence or absence of a target exon comprising the nucleotide sequence of SEQ ID NO: 27 and a target exon comprising the nucleotide sequence of SEQ ID NO: 104, wherein the assaying comprises combining the sample with a first probe that binds to a 5' region of the nucleotide sequence of SEQ ID NO: 27 and a second probe that binds to a 3' region of the nucleotide sequence of SEQ ID NO: 27 such that the first probe and the second probe flank the nucleotide sequence of SEQ ID NO: 27.

2. The method of claim 1, further comprising assaying the nucleic acids of the sample for the presence or absence of a target exon comprising the nucleotide sequence selected from any one of SEQ ID NOS: 21, 23, 30, 31, 32, 35, 36, 39, 85, 87-89, 91, 94, 98, or 101-103.

3. The method of claim 1, wherein the sample is a breast tissue sample.

4. The method of claim 1, wherein the subject is a female subject.

5. The method of claim 1, wherein the nucleic acids comprise messenger ribonucleic acid (mRNA).

6. The method of claim 1, wherein the nucleic acids comprise complementary deoxyribonucleic acid (cDNA) synthesized from mRNA obtained from the sample.

* * * * *

UNITED STATES PATENT AND TRADEMARK OFFICE

CERTIFICATE OF CORRECTION

PATENT NO. : 11,674,187 B2
APPLICATION NO. : 17/253974
DATED : June 13, 2023
INVENTOR(S) : Jacques Banchereau et al.

It is certified that error appears in the above-identified patent and that said Letters Patent is hereby corrected as shown below:

In the Claims

In Claim 1, Column 165, beginning at Line 29 the text:
"sample subject obtained from a breast cancer for the pres-"

Should read:
--sample obtained from a human breast cancer subject for the pres- --

Signed and Sealed this
Twenty-sixth Day of December, 2023

Katherine Kelly Vidal

Katherine Kelly Vidal
*Director of the United States Patent and Trademark Office*

SEQUENCE LISTING

```
<160> NUMBER OF SEQ ID NOS: 136

<210> SEQ ID NO 1
<211> LENGTH: 1257
<212> TYPE: DNA
<213> ORGANISM: Artificial Sequence
<220> FEATURE:
<223> OTHER INFORMATION: Synthetic polynucleotide

<400> SEQUENCE: 1

gcctgcagct ggccgcagac atagccagcc tccagaaccg cattgactgg ggtcgaagcc     60

agctccgggg actccaagag aaactcaagc agctggagcc tggggctgcc tgacatgcgc    120

gcaaagaggc agggcagcga gcacagctgt tctccgacat ggctacgtga tctcaggcct    180

tcttccttca caattagctc ttgcccctac cccacgccag ctaatgcccc ttctgtgtcc    240

ctgctctgca tgtttccatt ttccttaggt gtgaagtttg aagaggcaaa cagtaatttt    300

gaaagccact actttgaaac cattctaagg cctgagttcc cataggacac actcacatag    360

gcaggtacac gttagtcaac aattggaact gcctcttgga tcactcagct gtgctttcat    420

ggctggatga tggaacactg tgcgaagaga gatgggggcc aggaagtagc gcttcatgct    480

tagtacatcc tccaaattgt ctttgctgga ggagaaaacc gtactcagcc aaaagatcag    540

gacaatatga cttgagtcca caaggacaca aacacctgag tagctgggca gcccttggca    600

gggtctaagc caggaagtaa aaatgatctg gcctagatat ttaagggaac tctaggaaga    660

ggcctaggtt tttaaaatcc tgtctctttg tcttaccata agaggctgag cctctcttca    720

ttttttgaa gggccacttg tgttttctgt tctgggaact tcattcattt ttctactggg    780

ttgttgatct ttgcagtaat ttctaggagc tgtttatgtt tggaggtaat tggtcctttg    840

tccatatata tgagatgtaa gtcttatttt ccagtttatc tttttgctta ttttttttga    900

ctttttattg taaaataaaa catcaaactg cacagaacag ttgaatagct taatgaataa    960

ctacagtaaa agctatggta accccctgct gctgaacagg aggccgaaga cgagagctgc   1020

ccggaggact gggcagcagc tgttccagca gagacatcag caaaagccat ctagaggtgg   1080

atccagagtg tggactaaca gagaaaagaa gtggagggag agcaggtctg cggaggcgca   1140

agggccccac taagacccca gaaccggagt cctctgaggc ccctcaggac cccctgaact   1200

ggtttggaat cctagttcct cacagtctac gtcaggctca agcaagcttc cgggatg      1257


<210> SEQ ID NO 2
<211> LENGTH: 443
<212> TYPE: DNA
<213> ORGANISM: Artificial Sequence
<220> FEATURE:
<223> OTHER INFORMATION: Synthetic polynucleotide
```

<400> SEQUENCE: 2

```
tgaacagagt atctgtcagg caagagctgc tgtgatggtt tatgatgatg ccaataagaa     60
gtgggtgcca gctggtggct caactggatt cagcagagtt catatctatc accatacagg    120
caacaacaca ttcagagtgg tgggcaggaa gattcaggac catcagacag agtctcgctc    180
tgttgcccag gctagagtgc aatggcgtaa tctcagctca ctgcaacctc cgcctcccgt    240
gttcaagcga ttctcctgcc tcagcctcct gagtagctgg gatcacagac agagtctgac    300
tgttgcccag gctggagtgc aatggcacca acatggctca ctgcaacctt gacctcctgg    360
gctcaagtga tcctcccggc ctccgtctcc cgaatagcgg tcttactcat tttctacgtg    420
tgtgttgagt gcaccatttg aga                                            443
```

<210> SEQ ID NO 3
<211> LENGTH: 439
<212> TYPE: DNA
<213> ORGANISM: Artificial Sequence
<220> FEATURE:
<223> OTHER INFORMATION: Synthetic polynucleotide

<400> SEQUENCE: 3

```
gagttcatga tcaagtgttg cccacaccaa atgcttcatc cagagtcata gtacatgtgg     60
atctggattg cttttatgca caagtagaaa tgatctcaaa tccagagcta aaagacaaac    120
ctttaggaaa gattcctctt ttagtgtaag cataaagaac atttttggtt cacttgctgc    180
taccctcttg tgcccacttt ggcttaataa atcccaatcc agcctagctg atttactgaa    240
gaacaaaggg atgactagtt tttgctacgc caaggggttc aacagaaata tttggtggtt    300
acctgcaact atgaagctag gaaacttgga gttaagaaac ttatgaatgt cagagatgca    360
aaagaaaagt gtccacagtt ggtattagtt aatggagaag acctgacccg ctacagagaa    420
atgtcttata aggttacag                                                 439
```

<210> SEQ ID NO 4
<211> LENGTH: 330
<212> TYPE: DNA
<213> ORGANISM: Artificial Sequence
<220> FEATURE:
<223> OTHER INFORMATION: Synthetic polynucleotide

<400> SEQUENCE: 4

```
gaggaagagc aagcaggccc tgagggacta taagaaggtt cagatccagc tggagaatct     60
ggagagcagt gtgcgggacc gctgcaagaa ggaattcaca ggccaagtgg tctctgttca    120
acaactcagc tttgccactg tggcacaaag gcagccaggg acgacatgga aacacatgaa    180
agtgcagatg gggaacttgc gcttctccct gggtcacgtg cagtatgacg gcgagagccc    240
tggggctttt cctgtggcag cccaggtggg cttgggggtg ggcacctctc ttctggctct    300
gggtgtcatc atcattgtcc tcatgtacag                                     330
```

<210> SEQ ID NO 5
<211> LENGTH: 270
<212> TYPE: DNA
<213> ORGANISM: Artificial Sequence
<220> FEATURE:
<223> OTHER INFORMATION: Synthetic polynucleotide

<400> SEQUENCE: 5

```
aaagaaagga aactattgca aaataagaga ctggatttgg atgctgcaaa aacgagacta     60
```

aaaaaggcaa aagctgcaga aactagaaat tcacaactaa actcagctcg ccttgaagga 120
gataacatta tggtaaattt ctcttacatg ctcaacttcc tgcatgtaaa atggctgaag 180
tctgaacagg aattaagaat aactcaaagt gaatttgatc gtcaagcaga gattaccaga 240
cttctgctag agggaatcag cagtacacat 270

<210> SEQ ID NO 6
<211> LENGTH: 611
<212> TYPE: DNA
<213> ORGANISM: Artificial Sequence
<220> FEATURE:
<223> OTHER INFORMATION: Synthetic polynucleotide

<400> SEQUENCE: 6
accccgcgcg aagagtgcgc aggcgcgccg acagccgagt tttctgcgct tccttctccc 60
tctctccaga cgtcgtggtc gttcggtcct atgtcgcgcc gggccctccg gaggctgagg 120
ggggaacagc gcggccagga gcccctcggg cccggcgcct tgcatttcga tctccgtgat 180
gacgatgacg cggaagaaga agggcccaag cgggagcttg gtgtccggcg tcccgggggc 240
gcagggaagg agggcgtccg agtcaacaac cgcttcgagc tggaaaaatg gacattttcc 300
tctcccccta aaaaaagata aaactccttc ctggttatta actgaaatgc tgatcgagct 360
ttatcctaaa gaagatcagt cgtggacaag aaccttgtga aatgttcccc atttgagacc 420
ctaaaactaa tgaaaatcac agcttttgga taaacattga cgatcttgag gatgaccctg 480
tggtgaacgg ggagaggtct ggctgtgcgc tcacagacgc tgtggcacca gggaacaaag 540
gaaggggtca gcgtggaaac acagagagca agacggatgg agatgacacc gagacagtgc 600
cctcagagca g 611

<210> SEQ ID NO 7
<211> LENGTH: 2518
<212> TYPE: DNA
<213> ORGANISM: Artificial Sequence
<220> FEATURE:
<223> OTHER INFORMATION: Synthetic polynucleotide

<400> SEQUENCE: 7
gtatttgaag tacacactgg accaatacgt tgagaacgat tataccatcg tctatttcca 60
ctacgggctg aacagccgga acaagccttc cctgggctgg ctccagagcg catacaagga 120
gttcgatagg aaagacgggg atctcactat gtggcccagg ctggtctcga actccaagct 180
caagcgatcc tcccacctca gcctcccaaa gtactgggat tacaggcagg agccaccatg 240
ccaagccaac actcttgttc ttaaagggcc agacagtcag cattttagct ttgcaggcct 300
gttgctctat tgcaacaact ctgctggact gtgttccagt aaaacattat ggacgctgaa 360
atgtgaattt catgtcattt tcacgtgtca tgaaatattc ttctgttttt ttttttcaac 420
cacttaaaaa cataaaaagc catttttagc ttgcagcctg taccaaagca ggaagcaggc 480
taggttcatc ctgcctgccc attctcccac ccctggtcca gtgaattact ggcaaagaaa 540
caactgcatg accgtttctt cactaaagcc tcttcttgct ttcacagccc tttacagtct 600
gcaaggggca ttctgatgcc tcttgttggt gagatggcag cctcatttta cagatgagga 660
cataggcccc agggagcaag tgacttaccc gtggtcactc agcttgtgtg tggtagggca 720
ggatcccacc ccaggccccc gcctccctct cccacccaac gctactcacc gcttggccat 780
ggcctggagc cggcagactt ttcctgaggg acgtccggcc taataatcaa cttggcaata 840
tatctggctc gtagactgcg gcgatgggcg ttgatgtgga tatcctagat tcctctgggt 900

-continued

```
tttccttctt caaagtcctt tcaaacctgt aacagaaatc tgcttcacag atatctgagt    960
cagtgggaca gtggaaggca gtgcctgaat gtcccagaag tcctccctcc agttgccttt   1020
tgggtcctgc tgtcattatc aataggacct tcggagggac ttcttggttc cccatcctat   1080
gtcttaggga aagaattgtt gctgtatttt gcagtcattt actgggcacc tgtataagct   1140
ggagatggcc tagccccagc gcatgtcctc ctccaggaag gcttcctggg ttgtcctggg   1200
agaatcaata gccccttccc tgcagcctca ctgtgcctaa gcagacacca atcctagcta   1260
gcacttaggg gtttgtgaac aggtctgcct cctgcactag gctgtgatcc cggacctgtc   1320
tctgcatccc ttgcaggtgg gaaaggatct gcatatggca gccttttttt ttttttttt   1380
tttttgaga cagagtctca ttctattgcc tgggctggag cacagtggcg agatctcggc   1440
tcaccacaac ctccacctcc caggttcaag tgattctcct gcctcagcct cctgagtacc   1500
tgggactaca ggcgtgagcc accatgcccg gctaattttt gtatttttag tagagacggg   1560
gtttcactat gttggccagg ctggtcttga actcctgacc tcgtgatccg cctgccttgg   1620
cctcccaaag tgccgggatt acaggcgtga gccactgtgc ccagccggca ggcttttatt   1680
aagcgttaga tgggaggata gaggagtgaa gtggtactgg caggaagtac caaggttcca   1740
gctggcgtaa tcaggaaggc tgcatggagg aagcagcctt tgagctgcct gtggagtggt   1800
gggcagggtg ttgtgaagtg gcaatcactg gattttgctt ctggtacgag gtgtggccag   1860
atgcaagaaa gagcagggtg gactttggtg caattggtgg gggtctggtc tgtagggttc   1920
ccgtggggag ccgtggaggg aggcagcaaa ggagggaggg gcacagagga tgctggactg   1980
tgtttaagag gcagcaggga gccatggcag gtgcttgagg agaagcgagt gatgtgttta   2040
aagcagccct ttcaggaggc tcaggctcac agcaggatgt gcacagtagc cctgtcttga   2100
gctaaagcag atgaaggttt tgccctctgc acttccccac gtgagaaacg aagatgcacc   2160
cgcagattcc ttgaggcagc tcccccactt ctcagttgcc agaaatcagc ccagagaaac   2220
aaacccgtaa tcagcccagg gtgctttccc ttccctttct cgagggggct gctggttcgc   2280
acataaggag tgggtcactc ccgcttggga gaaagcagca gaattccttc acagccaggt   2340
aagatgtgcc agtggtcgat ggatgaaatc tagccgggga gttggaatct gtgttgccag   2400
cagtgacctg tgagcagtga caaagccaaa ggtacaagaa gaacttgaag gccctctacg   2460
tggtgcaccc caccagcttc atcaaggtcc tgtggaacat cttgaagccc ctcatcag     2518
```

<210> SEQ ID NO 8
<211> LENGTH: 359
<212> TYPE: DNA
<213> ORGANISM: Artificial Sequence
<220> FEATURE:
<223> OTHER INFORMATION: Synthetic polynucleotide

<400> SEQUENCE: 8

```
aattgtggtg gttttggact ccatgattaa ggtgttcaca ttcacacaca atccccatca     60
gttgcacgtc ttcgaaacct gctataaccc caaagatgga gtgtttgatg atgtctctct    120
gaacctcaga gacgtctctt aggctgacct tcacccaggc gagaagcact ccctcagcag    180
agccagccca cgtgcactcg ccgagctcca ggcctggcgc tggctacctg cctccagagc    240
tttttcttca ggaacactcc ttttctgtgt gtaatgatct gggatgacct gaagaagaag    300
actgttattg aaatagaatt ttctacagaa gtcaaggcag tcaagctgcg gcgagatag     359
```

<210> SEQ ID NO 9

<211> LENGTH: 979
<212> TYPE: DNA
<213> ORGANISM: Artificial Sequence
<220> FEATURE:
<223> OTHER INFORMATION: Synthetic polynucleotide

<400> SEQUENCE: 9
ttggtgttgg tattaggaga tctgcacatc ccacaccggt gcaacagttt gccagctaaa 60
ttcaaaaaac tcctggtgcc aggaaaaatt cagcacattc tctgcacagg aaacctttgc 120
accaaagaga gttatgacta tctcaagact ctggctggtg atgttcatat tgtgagagga 180
gacttcgatg aggctgggca cagagtaagt ttcttcactt agctcctact aacagtggtg 240
gttgggtggc tgtttactga ctggatttct taccctttta aggtctgttg aaaggaagta 300
accgaattcc catgctttga ttgggttggc tctttatttt aatttaataa gactgccatt 360
tccaggatct tttgctttct taaaggactc tatcatctat gtctatcccg atttgtcaaa 420
gtgtggaatt tgggcgggaa catgtttcaa agtatgacac gtgttatgta acactatttc 480
cccataactt tgtcatcagc aggaaaccag aggattctgt cctagtaagg atccctacta 540
atttgaaatg attgtgtggt cattcataca gttatatctt tagactgcta atagtcttga 600
gtcttggaga taatccacag tactttatag aattaggtca tcaatcatta taaagtacca 660
tgtcttacta atgttctttc tggtacattc agattgaaca gctcattcat tattagtacc 720
aaacatttca acctgttgta gacatatacc cttttatgag tttggggtgg tggttgttgt 780
tgttgttctt cttcttcttt taaatataga aatctattat ttttaccttt ttctcaaagc 840
aagattccca tactaactat gtacttcaat ccatatcaga aggaatcccc ctctaaaatg 900
aagattgttc tatatccagg agcctgagga agagggcggc gacggtggtg gtgactgagc 960
ggagcccggt gacaggatg 979

<210> SEQ ID NO 10
<211> LENGTH: 421
<212> TYPE: DNA
<213> ORGANISM: Artificial Sequence
<220> FEATURE:
<223> OTHER INFORMATION: Synthetic polynucleotide

<400> SEQUENCE: 10
atcttcctgc ggcgcgttgc gacatggagg gcgcgatggc agtgcgggtg acggccgctc 60
atacggcaga agcccaggcc gaagccgggc gggaagcggg cgagggtgca gttgcggcgg 120
tggcggcggc cttggccccc agcggcttcc tcggcctccc ggcgcccttc agcgaggaag 180
cttggagaag ggcagtgccc tcatggcgag gagtcccttt agaggttgct gggcctgctt 240
gtggccttgt ctggtgtgaa atgggctgga tgaggacgat gtgcacagat gcggccgctg 300
ccaggcagag ttcaccgcct tggaggattt tgttcagcac aagattcaga aggcctgcca 360
gcgggcccct ccggaggccc tgcctgccac ccctgccacc acagcgttgc tgggccagga 420
g 421

<210> SEQ ID NO 11
<211> LENGTH: 451
<212> TYPE: DNA
<213> ORGANISM: Artificial Sequence
<220> FEATURE:
<223> OTHER INFORMATION: Synthetic polynucleotide

<400> SEQUENCE: 11
ggggcgatgt ccgcgtcgtg gctggggccg gtcgcggggc agactaatcc cctgctcctg 60

```
gccaggggag gctcccgagc ggatcctcgg gaaaggggct ccgaaggtca agaaactgcc    120

ctgctgggcg tccggggagt gggaaaataa agcacttttt gtatcccgcc cctcccccgt    180

cacgtgacca cgcgaggcgg aaagaagaaa tccgaggacc ggcgacgcct agaacagggt    240

cttactctat tgccgaggct acagtatagt ggtgtgatca tagctcactg cagcttcaac    300

ctcctgtggt ggtgatcctc ctgcctcagc ctcctaagtt gctgggacta caggagccca    360

tgatgctgcc caaacctggg acctattacc tcccctggga ggttagtgca ggccaagttc    420

ctgatgggag cacgctgaga acatttggca g                                   451
```

<210> SEQ ID NO 12
<211> LENGTH: 347
<212> TYPE: DNA
<213> ORGANISM: Artificial Sequence
<220> FEATURE:
<223> OTHER INFORMATION: Synthetic polynucleotide

<400> SEQUENCE: 12

```
gcaactcgca cagcccgcaa agccgtcgcc tttggcaagc gctcacactc catgaagcgg     60

aaccccaatg cacctgtcac caaggcgggc tggctcttca aacagttgct gagtgcttgt    120

tatggctgga taccttgctg gctctggtga taaagagatg aaaaagacaa aagttcctcc    180

ctgcaaagag ctcatggtgc aatggaagag atagaaagct gcattgtgac agatcgacct    240

tggacatgtc caataaaaca ggtgggaaac gcccggctac caccaacagt gacataccca    300

accacaacat ggtgtccgag gtccctccag agcggcccag cgtccgg                  347
```

<210> SEQ ID NO 13
<211> LENGTH: 3164
<212> TYPE: DNA
<213> ORGANISM: Artificial Sequence
<220> FEATURE:
<223> OTHER INFORMATION: Synthetic polynucleotide

<400> SEQUENCE: 13

```
ggcaaagctc agaggaaaaa gaagcagccc ggcggtcccg gagaattgac cgccacctgc     60

gctcagagag ccagcggcaa cgccgcgaaa tcaagctgct cctgctgggc accagcaact    120

caggcaagag caccatcgtc aaacagatga agatcatcca cagcggcggc ttcaacctgg    180

aggcctgcaa ggagtacaag cccctcatca tctacaatgc catcgactcg ctgacccgca    240

tcatccgggc cctggccgcc ctcaggatcg acttccacaa ccccgaccgc gcctacgacg    300

ctgtgcagct ctttgcgctg acgggccccg ctgagagcaa gggcgagatc acacccgagc    360

tgctgggtgt catgcgacgg ctctgggccg acccaggggc acaggcctgc ttcagccgct    420

ccagcgagta ccacctggag gacaacgcgg cctactacct gaacgacctg gagcgcatcg    480

ccgcagctga ctatatcccc actgtcgagg acatcctgcg ctcccgggac atgaccacgg    540

gcattgtgga gaacaagttc accttcaagg agctcacctt caagatggtg gacgtggggg    600

ggcagaggtc agagcgcaaa aagtggatcc actgcttcga gggcgtcaca gccatcatct    660

tctgtgtgga gctcagcggc tacgacctga aactctacga ggataaccag acaggaagtg    720

gtgaactggg gagtcagaca agagcatcat gcttcttaaa agcccagacc cctggctata    780

acacatcgaa gattctcaga agagaattga ggagcggaca ggcgccacac tccgttgtgg    840

tcactgcctc ttcctggccc accacactcc tgtcctctgc atgtactgag agctctgtcc    900

aggatgccag ggtcctgcct cggcagagag gcggtgccag atgccccaca gcagctggtg    960
```

-continued

```
ggagtgccca cagctggagg gcaggggagg agcctggcct ctggctggtg tttccttccc   1020
agctctcaag aactggagac tttggttaca gaagtgaagg ctgctccctc acagacttcc   1080
tagtgtccga tggtaccaca tggaaggatc agagttttga aggactgggc cagaacccag   1140
atagggcaca aggctgccag cgcctgcatt gagggagcta tgatgtgacg gggctcctg    1200
cagaagatgg ccttccttgt acagagtcgg atggcagaga gcttgcgcct ctttgactcc   1260
atctgcaaca acaactggtt catcaacacc tcactcatcc tcttcctgaa caagaaggac   1320
ctgctggcag agaagatccg ccgcatcccg ctcaccatct gctttcccga gtacaagggc   1380
cagaacacgt acgaggaggc cgctgtctac atccagcggc agtttgaaga cctgaaccgc   1440
aacaaggaga ccaaggagat ctactcccac ttcacctgcg ccaccgacac cagtaacatc   1500
cagtttgtct tcgacgcggt gacagacgtc atcatacaga acaatctcaa gtacattggc   1560
ctttgctgag gagctgggcc cggggcccgc ctgcctatgg tgaaacccac ggggtgtcat   1620
gccccaacgc gtgctagaga ggcccaatcc aggggcagaa aacagggggc ctaaagaatg   1680
tcccccaccc cttggcctct gcctccttgg ccccacattt ctgcaaacat aaatatttac   1740
ggatagattg ctaggtagat agacacacac acatgcacac acacacatct ggagatggca   1800
aaatcctcta aaatgtcgag gtctcttgaa gacttgagaa gctgtcacaa ggtcactaca   1860
agcccaacct gccccttcac tttgccttcc tgagttggcc ccactccact tgggggtctg   1920
cattggattg ttagggatag gcagcagggc tgaggcaagg taggccaact gcacccctgt   1980
cgcctggagg agggccagct cgctgcccga gctctggcct agggaccttg ccgctgacca   2040
agagggagga ccagtgcagg gtctgtgcac cttccctgct ggcctgcaca cagctgctca   2100
gcaccacttt cattctggac ctgggacctt aggagccggg tgacagcact aaccagacct   2160
ccagccactc acagctcttt ttaaaaaaca gcttcaaaat atgcagcaaa aaccaataca   2220
acaaaacgag tggcacgatt tatttcaaac taggccagct gggattccag cttttcttct   2280
actagtctga tgttttataa atcaaaacct ggttttcctt ctctgacatt tttttttgt    2340
tttgtttttt ggtttttttt tttttttggc caaatctcgt ggtgtttcgc agaaaaaaat   2400
ccagaaaatt tcaaatgcag ttgagtattc tttttaaat gcagattttc aaaacatatt    2460
tttttcagg tggtcttttt tgtgtctggc ttgctgagtg taaaagttgt tatctggacg    2520
atctgtctct ctgctccaaa gaaattttgg agtgagtggc agtcctgcgc cagcctcgcg   2580
ggacacgtgt tgtacataag cctctgcagt gtcctcttgt taatggtggg gttttctgct   2640
ttgtttttat ttaagaaaat aaacacgaca tatttaaaga aggttctttc acctgggagc   2700
aaatgaacaa tagctaagtg tcttggtatt taaagagtaa attatttgtg gctttgctga   2760
gtgaaggaag gggagcaagg ggtggtgccc ctggtcccag catgccccgc gcctgagact   2820
ggctggaaat gctctgactc ctgtgaaggc acagccagcg ttgtggcctg agggaggccc   2880
tgctgggacc ctgatctggg ccttcctgtc ccagggccta tgggcaactg cgttgaaagg   2940
acgttcgcca agggccgtgt gtaaatacga actgcgccat ggagaggaga ggcactgccg   3000
gagcccttgc cagatctccc tccctctctc cgtgcagtag ctgtgtgtcc gaggtcagtg   3060
tgcggaatca cagccaagga cgtgaagaga tgtacggggg aaagagaagc tggggattgg   3120
atgaaagtca aaggttgtct actttaagaa aataaaatac cctg                    3164
```

<210> SEQ ID NO 14
<211> LENGTH: 282
<212> TYPE: DNA
<213> ORGANISM: Artificial Sequence
<220> FEATURE:
<223> OTHER INFORMATION: Synthetic polynucleotide

<400> SEQUENCE: 14
ccgtcggctg acgtggaggg ccggaggtgg cggcggcggc ggcggcggct gctgctgctg 60
ctgcccgcgt ccgaggctcg cgggcggcgg gcccggtatt tgataaattc aaaatatatg 120
taaaacatat gcaagctgta tagcagaaca ataaaatgaa cacctatgaa ttcaccactc 180
aatccaataa tcaaaatgac cagtattgaa tgtgcttact tccagagaaa tgcactcggt 240
gatggaaaga gagccactat tctgaagaac acttggccaa ag 282

<210> SEQ ID NO 15
<211> LENGTH: 553
<212> TYPE: DNA
<213> ORGANISM: Artificial Sequence
<220> FEATURE:
<223> OTHER INFORMATION: Synthetic polynucleotide

<400> SEQUENCE: 15
ggcgagcgga gcctgctttc gcagcgatcg cgagcgtgtg gcgattgctt ctgtctgtta 60
tttagatatg gaagctgagg ggatgcacag aggcagccag aacctaggtc agggtctcgc 120
tcggtgctga ccgcccccgg ggtcgagtag gcgatggggg agcccggctt cttcgtcaca 180
ggagaccgcg ccggtggccg gagctggtgc ctgcggcggg tggggatgag cgccgggtgg 240
ctgctgctgg aagatgggtg cgagggttgt tatgaactag actggtccaa caggaaagta 300
tgatagatgt gaactggggc ttcttttcaa ccttttccgg aagctctcaa gctgttcttg 360
tggataagac agagaatatg tactccaatg caaagacttt tggttgaatt ataactggct 420
gaaggtgact gtaggacgag gatttggtgt cacataccaa ctggtatcaa aaatctgccc 480
cctgatgatt tctcgaaacc actgtgtttt gaagcagaat cctgagggcc aatggacaat 540
tatggacaac aag 553

<210> SEQ ID NO 16
<211> LENGTH: 550
<212> TYPE: DNA
<213> ORGANISM: Artificial Sequence
<220> FEATURE:
<223> OTHER INFORMATION: Synthetic polynucleotide

<400> SEQUENCE: 16
ccagcaggaa gtgggagaag aggcgaccca aggcgggctg gcgggctggc ggcagtcgct 60
acttgcctag tagcctcagc cgctgtgggc tcctggggag atggaggggc cggggctggg 120
ctcgcagcct tgacttgagc cctggaaata agcatcagtg cagacgagtg ctctatgaga 180
agctatctag ttaaagctca aggagccaca aagggatttc ctggcagcac agtcaccaga 240
aacactgagg gagaactctc tgaacagagg aattgtgacc ccaagacagt agtttttaga 300
cgtgacacca aaagcacaat ccataaaaga acaaattgat aaattggact tttttaaaat 360
ttaaaacttc tgctctatga aacagacttt taagagatgg gaagtgcagg aatcacagcc 420
atggccccca ccctccagga tttggtcgat atggcatctg tgcacatgaa aacaaagaac 480
ttgccaatgc aagagaagct cttcctctta tagaggactc tagtaactgt gacattgtca 540
aagctactca 550

<210> SEQ ID NO 17
<211> LENGTH: 357
<212> TYPE: DNA

<213> ORGANISM: Artificial Sequence
<220> FEATURE:
<223> OTHER INFORMATION: Synthetic polynucleotide

<400> SEQUENCE: 17
atttcccggc accttcgtgg gcaccacaga gcccgcctcc ccacccctga gcagcacctc 60
acccaccact gctgcggcca ctatgcctgt ggtgccctct gtggccagcc tggcccctcc 120
gggggaggcc tcgctctgcc tggaagaggt ggcccccccct gccagtggga cccgcaaagc 180
tcgggtgctc tatgactacg aggcagccga cagcagtgag ctggccctgc tggctgatga 240
gctcccaggg tgccatgtga accacctgcg ctgcctccac gagttcgtca agtctcagac 300
aacctactac gcacagtgct accgccacat gctggacttg cagaagcagc tgggcag 357

<210> SEQ ID NO 18
<211> LENGTH: 270
<212> TYPE: DNA
<213> ORGANISM: Artificial Sequence
<220> FEATURE:
<223> OTHER INFORMATION: Synthetic polynucleotide

<400> SEQUENCE: 18
gaatttatca tggcatccag cattgaccac tacaagtaaa atgcgaattc cacattctca 60
tgcatttatt gatctgactg aagattttac agcagccata ccaccctgaa cgcgccccat 120
ctcttctgat ctcggaagct aaccaaggtc agacctggtt agtgcttgga tgggagatca 180
cctattactt tttcttttca atggtgatct aattcctgat atttttggta tcacaaatga 240
atccaaccag ccacagatac tattaggagg 270

<210> SEQ ID NO 19
<211> LENGTH: 418
<212> TYPE: DNA
<213> ORGANISM: Artificial Sequence
<220> FEATURE:
<223> OTHER INFORMATION: Synthetic polynucleotide

<400> SEQUENCE: 19
ctgctggcta ccaatattct actttctgtc tctatgaatg tgactaccct ggttacctca 60
tatttatttg cagtgactta aaatttggag gcaaattttc cttaagagga tatcaagttc 120
cagtatcttc agatgttgat aagccgttag aatctccctg gaaaaggaga catgaatgtc 180
tgcaatgata cttcctgaca agaagttgat acaagaaaag gaaaggagat taacagctag 240
tgagcagaat ttcgaacagc aggatttcgt attttttgct tccaactgca cacttccgtt 300
gcccactttt aaatcagaga tacctacact caaaacccag acaaggcaaa aggatacttt 360
tcttgtatat tttttgagat cgaagaaacg acaatgtcca ggaaacagaa ccagaagg 418

<210> SEQ ID NO 20
<211> LENGTH: 632
<212> TYPE: DNA
<213> ORGANISM: Artificial Sequence
<220> FEATURE:
<223> OTHER INFORMATION: Synthetic polynucleotide

<400> SEQUENCE: 20
gatcggaccc aagcaggtcg gcggcggcgg caggagagcg gccgggcgtc agctcctcga 60
cccccgtgtc gggctagtcc agcgaggcgg acgggcggcg tgggcccatg gccaggcccg 120
gcatggagcg gtggcgcgac cggctggcgc tggtgacggg ggcctcgggg ggcatcggcg 180
cggccgtggc ccgggccctg gtccagcagg gactgaaggt ggtgggctgc gcccgcactg 240
tgggcaacat cgaggaattt tgagtctaga ggaggaagcg ggaagatgta caccagggga 300
ggggaaagct gcagtcttcc ttgcccacag tctgctttga ttgattcagt cattgatgtt 360
aaagcagaat ttgggttcta gcttcctaca gagaaaactc ctgtttcctg aagtgatcaa 420
atgagctggc tgctgaatgt aagagtgcag gctaccccgg gactttgatc ccctacagat 480
gtgacctatc aaatgaagag gacatcctct ccatgttctc agctatccgt tctcagcaca 540
gcggtgtaga catctgcatc aacaatgctg gcttggcccg gcctgacacc ctgctctcag 600
gcagcaccag tggttggaag gacatgttca at 632

<210> SEQ ID NO 21
<211> LENGTH: 142
<212> TYPE: DNA
<213> ORGANISM: Artificial Sequence
<220> FEATURE:
<223> OTHER INFORMATION: Synthetic polynucleotide

<400> SEQUENCE: 21
ccctgctgct gaacaggagg ccgaagacga gagctgcccg gaggactggg cagcagctgt 60
tccagcagag acatcagcaa aagccatcta gaggtggatc cagagtgtgg actaacagag 120
aaaagaagtg gagggagagc ag 142

<210> SEQ ID NO 22
<211> LENGTH: 122
<212> TYPE: DNA
<213> ORGANISM: Artificial Sequence
<220> FEATURE:
<223> OTHER INFORMATION: Synthetic polynucleotide

<400> SEQUENCE: 22
acagagtctc gctctgttgc ccaggctaga gtgcaatggc gtaatctcag ctcactgcaa 60
cctccgcctc ccgtgttcaa gcgattctcc tgcctcagcc tcctgagtag ctgggatcac 120
ag 122

<210> SEQ ID NO 23
<211> LENGTH: 148
<212> TYPE: DNA
<213> ORGANISM: Artificial Sequence
<220> FEATURE:
<223> OTHER INFORMATION: Synthetic polynucleotide

<400> SEQUENCE: 23
gaaagattcc tcttttagtg taagcataaa gaacattttt ggttcacttg ctgctaccct 60
cttgtgccca ctttggctta ataaatccca atccagccta gctgatttac tgaagaacaa 120
agggatgact agtttttgct acgccaag 148

<210> SEQ ID NO 24
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 24
gccaagtggt ctctgttcaa caactcagct ttgccactgt ggcacaaagg cagccaggga 60
cgacatggaa acacatgaaa 80

<210> SEQ ID NO 25

<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 25
caactaaact cagctcgcct tgaaggagat aacattatgg taaatttctc ttacatgctc 60
aacttcctgc atgtaaaatg gctgaag 87

<210> SEQ ID NO 26
<211> LENGTH: 167
<212> TYPE: DNA
<213> ORGANISM: Artificial Sequence
<220> FEATURE:
<223> OTHER INFORMATION: Synthetic polynucleotide

<400> SEQUENCE: 26
gaaaaatgga cattttcctc tccccctaaa aaaagataaa actccttcct ggttattaac 60
tgaaatgctg atcgagcttt atcctaaaga agatcagtcg tggacaagaa ccttgtgaaa 120
tgttccccat ttgagaccct aaaactaatg aaaatcacag cttttgg 167

<210> SEQ ID NO 27
<211> LENGTH: 2299
<212> TYPE: DNA
<213> ORGANISM: Artificial Sequence
<220> FEATURE:
<223> OTHER INFORMATION: Synthetic polynucleotide

<400> SEQUENCE: 27
agacggggat ctcactatgt ggcccaggct ggtctcgaac tccaagctca agcgatcctc 60
ccacctcagc ctcccaaagt actgggatta caggcaggag ccaccatgcc aagccaacac 120
tcttgttctt aaagggccag acagtcagca ttttagcttt gcaggcctgt tgctctattg 180
caacaactct gctggactgt gttccagtaa aacattatgg acgctgaaat gtgaatttca 240
tgtcattttc acgtgtcatg aaatattctt ctgttttttt ttttcaacca cttaaaaaca 300
taaaaagcca tttttagctt gcagcctgta ccaaagcagg aagcaggcta ggttcatcct 360
gcctgcccat tctcccaccc ctggtccagt gaattactgg caaagaaaca actgcatgac 420
cgtttcttca ctaaagcctc ttcttgcttt cacagccctt tacagtctgc aaggggcatt 480
ctgatgcctc ttgttggtga gatggcagcc tcattttaca gatgaggaca taggccccag 540
ggagcaagtg acttacccgt ggtcactcag cttgtgtgtg gtagggcagg atcccacccc 600
aggcccccgc ctccctctcc cacccaacgc tactcaccgc ttggccatgg cctggagccg 660
gcagactttt cctgagggac gtccggccta ataatcaact tggcaatata tctggctcgt 720
agactgcggc gatgggcgtt gatgtggata tcctagattc ctctgggttt tccttcttca 780
aagtcctttc aaacctgtaa cagaaatctg cttcacagat atctgagtca gtgggacagt 840
ggaaggcagt gcctgaatgt cccagaagtc ctccctccag ttgccttttg ggtcctgctg 900
tcattatcaa taggaccttc ggagggactt cttggttccc catcctatgt cttagggaaa 960
gaattgttgc tgtattttgc agtcatttac tgggcacctg tataagctgg agatggccta 1020
gccccagcgc atgtcctcct ccaggaaggc ttcctgggtt gtcctgggag aatcaatagc 1080
cccttccctg cagcctcact gtgcctaagc agacaccaat cctagctagc acttaggggt 1140
ttgtgaacag gtctgcctcc tgcactaggc tgtgatcccg gacctgtctc tgcatccctt 1200
gcaggtggga aaggatctgc atatggcagc cttttttttt tttttttttt ttttgagaca 1260

```
gagtctcatt ctattgcctg ggctggagca cagtggcgag atctcggctc accacaacct   1320
ccacctccca ggttcaagtg attctcctgc ctcagcctcc tgagtacctg ggactacagg   1380
cgtgagccac catgcccggc taatttttgt atttttagta gagacggggt ttcactatgt   1440
tggccaggct ggtcttgaac tcctgacctc gtgatccgcc tgccttggcc tcccaaagtg   1500
ccgggattac aggcgtgagc cactgtgccc agccggcagg cttttattaa gcgttagatg   1560
ggaggataga ggagtgaagt ggtactggca ggaagtacca aggttccagc tggcgtaatc   1620
aggaaggctg catggaggaa gcagcctttg agctgcctgt ggagtggtgg gcagggtgtt   1680
gtgaagtggc aatcactgga ttttgcttct ggtacgaggt gtggccagat gcaagaaaga   1740
gcagggtgga ctttggtgca attggtgggg gtctggtctg tagggttccc gtggggagcc   1800
gtggagggag gcagcaaagg agggaggggc acagaggatg ctggactgtg tttaagaggc   1860
agcagggagc catggcaggt gcttgaggag aagcgagtga tgtgtttaaa gcagcccttt   1920
caggaggctc aggctcacag caggatgtgc acagtagccc tgtcttgagc taaagcagat   1980
gaaggttttg ccctctgcac ttccccacgt gagaaacgaa gatgcacccg cagattcctt   2040
gaggcagctc ccccacttct cagttgccag aaatcagccc agagaaacaa acccgtaatc   2100
agcccagggt gctttccctt ccctttctcg agggggctgc tggttcgcac ataaggagtg   2160
ggtcactccc gcttgggaga aagcagcaga attccttcac agccaggtaa gatgtgccag   2220
tggtcgatgg atgaaatcta gccggggagt tggaatctgt gttgccagca gtgacctgtg   2280
agcagtgaca aagccaaag                                                2299
```

<210> SEQ ID NO 28
<211> LENGTH: 176
<212> TYPE: DNA
<213> ORGANISM: Artificial Sequence
<220> FEATURE:
<223> OTHER INFORMATION: Synthetic polynucleotide

<400> SEQUENCE: 28

```
atggagtgtt tgatgatgtc tctctgaacc tcagagacgt ctcttaggct gaccttcacc     60
caggcgagaa gcactccctc agcagagcca gcccacgtgc actcgccgag ctccaggcct    120
ggcgctggct acctgcctcc agagcttttt cttcaggaac actccttttc tgtgtg        176
```

<210> SEQ ID NO 29
<211> LENGTH: 727
<212> TYPE: DNA
<213> ORGANISM: Artificial Sequence
<220> FEATURE:
<223> OTHER INFORMATION: Synthetic polynucleotide

<400> SEQUENCE: 29

```
gctgggcaca gagtaagttt cttcacttag ctcctactaa cagtggtggt tgggtggctg     60
tttactgact ggatttctta cccttttaag gtctgttgaa aggaagtaac cgaattccca    120
tgctttgatt gggttggctc tttattttaa tttaataaga ctgccatttc caggatcttt    180
tgctttctta aaggactcta tcatctatgt ctatcccgat ttgtcaaagt gtggaatttg    240
ggcgggaaca tgtttcaaag tatgacacgt gttatgtaac actatttccc cataactttg    300
tcatcagcag gaaaccagag gattctgtcc tagtaaggat ccctactaat ttgaaatgat    360
tgtgtggtca ttcatacagt tatatcttta gactgctaat agtcttgagt cttggagata    420
atccacagta ctttatagaa ttaggtcatc aatcattata aagtaccatg tcttactaat    480
```

-continued

```
gttctttctg gtacattcag attgaacagc tcattcatta ttagtaccaa acatttcaac    540

ctgttgtaga catataccct tttatgagtt tggggtggtg gttgttgttg ttgttcttct    600

tcttctttta aatatagaaa tctattattt ttaccttttt ctcaaagcaa gattcccata    660

ctaactatgt acttcaatcc atatcagaag gaatccccct ctaaaatgaa gattgttcta    720

tatccag                                                              727
```

<210> SEQ ID NO 30
<211> LENGTH: 89
<212> TYPE: DNA
<213> ORGANISM: Artificial Sequence
<220> FEATURE:
<223> OTHER INFORMATION: Synthetic polynucleotide

<400> SEQUENCE: 30

```
cttggagaag ggcagtgccc tcatggcgag gagtcccttt agaggttgct gggcctgctt     60

gtggccttgt ctggtgtgaa atgggctgg                                       89
```

<210> SEQ ID NO 31
<211> LENGTH: 116
<212> TYPE: DNA
<213> ORGANISM: Artificial Sequence
<220> FEATURE:
<223> OTHER INFORMATION: Synthetic polynucleotide

<400> SEQUENCE: 31

```
ggtcttactc tattgccgag gctacagtat agtggtgtga tcatagctca ctgcagcttc     60

aacctcctgt ggtggtgatc ctcctgcctc agcctcctaa gttgctggga ctacag        116
```

<210> SEQ ID NO 32
<211> LENGTH: 127
<212> TYPE: DNA
<213> ORGANISM: Artificial Sequence
<220> FEATURE:
<223> OTHER INFORMATION: Synthetic polynucleotide

<400> SEQUENCE: 32

```
ttgctgagtg cttgttatgg ctggatacct tgctggctct ggtgataaag agatgaaaaa     60

gacaaaagtt cctccctgca aagagctcat ggtgcaatgg aagagataga aagctgcatt    120

gtgacag                                                              127
```

<210> SEQ ID NO 33
<211> LENGTH: 511
<212> TYPE: DNA
<213> ORGANISM: Artificial Sequence
<220> FEATURE:
<223> OTHER INFORMATION: Synthetic polynucleotide

<400> SEQUENCE: 33

```
ggaagtggtg aactggggag tcagacaaga gcatcatgct tcttaaaagc ccagacccct     60

ggctataaca catcgaagat tctcagaaga gaattgagga gcggacaggc gccacactcc    120

gttgtggtca ctgcctcttc ctggcccacc acactcctgt cctctgcatg tactgagagc    180

tctgtccagg atgccagggt cctgcctcgg cagagaggcg gtgccagatg ccccacagca    240

gctggtggga gtgcccacag ctggagggca ggggaggagc ctggcctctg gctggtgttt    300

ccttcccagc tctcaagaac tggagacttt ggttacagaa gtgaaggctg ctccctcaca    360

gacttcctag tgtccgatgg taccacatgg aaggatcaga gttttgaagg actgggccag    420

aacccagata gggcacaagg ctgccagcgc ctgcattgag ggagctatga tgtgacgggg    480
```

gctcctgcag aagatggcct tccttgtaca g 511

<210> SEQ ID NO 34
<211> LENGTH: 131
<212> TYPE: DNA
<213> ORGANISM: Artificial Sequence
<220> FEATURE:
<223> OTHER INFORMATION: Synthetic polynucleotide

<400> SEQUENCE: 34
tatttgataa attcaaaata tatgtaaaac atatgcaagc tgtatagcag aacaataaaa 60
tgaacaccta tgaattcacc actcaatcca ataatcaaaa tgaccagtat tgaatgtgct 120
tacttccaga g 131

<210> SEQ ID NO 35
<211> LENGTH: 160
<212> TYPE: DNA
<213> ORGANISM: Artificial Sequence
<220> FEATURE:
<223> OTHER INFORMATION: Synthetic polynucleotide

<400> SEQUENCE: 35
ggttgttatg aactagactg gtccaacagg aaagtatgat agatgtgaac tggggcttct 60
tttcaacctt ttccggaagc tctcaagctg ttcttgtgga taagacagag aatatgtact 120
ccaatgcaaa gacttttggt tgaattataa ctggctgaag 160

<210> SEQ ID NO 36
<211> LENGTH: 277
<212> TYPE: DNA
<213> ORGANISM: Artificial Sequence
<220> FEATURE:
<223> OTHER INFORMATION: Synthetic polynucleotide

<400> SEQUENCE: 36
ccttgacttg agccctggaa ataagcatca gtgcagacga gtgctctatg agaagctatc 60
tagttaaagc tcaaggagcc acaaagggat ttcctggcag cacagtcacc agaaacactg 120
agggagaact ctctgaacag aggaattgtg accccaagac agtagttttt agacgtgaca 180
ccaaaagcac aatccataaa agaacaaatt gataaattgg acttttttaa aatttaaaac 240
ttctgctcta tgaaacagac ttttaagaga tgggaag 277

<210> SEQ ID NO 37
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 37
ctcccagggt gccat 15

<210> SEQ ID NO 38
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 38
ccataccacc ctgaacgcgc cccatctctt ctgatctcgg aagctaacca aggtcagacc 60
tggttagtgc ttggatggga gatcacctat tactttttct 100

<210> SEQ ID NO 39
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 39
ttatttgcag tgacttaaaa tttggaggca aattttcctt aagaggatat caagttccag 60
tatcttcaga tgttgataag ccgttag 87

<210> SEQ ID NO 40
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 40
gaattttgag tctagaggag gaagcgggaa gatgtacacc aggggagggg aaagctgcag 60
tcttccttgc ccacagtctg ctttgattga ttcagtcatt gatgttaaag cagaatttgg 120
gttctagctt cctacagaga aaactcctgt ttcctgaagt gatcaaat 168

<210> SEQ ID NO 41
<211> LENGTH: 309
<212> TYPE: DNA
<213> ORGANISM: Artificial Sequence
<220> FEATURE:
<223> OTHER INFORMATION: Synthetic polynucleotide

<400> SEQUENCE: 41
aatctttaat gaactgaaaa ctaaaatgct taatataaaa gaatataagg agaaactctt 60
gagtaccttg ggcgagtttc tagaagacca ttttcctctg cctgatagaa gtgttaaaaa 120
gaaaaaggga acaacggtgg ttggatgaac agcaacagat aatggaatct cttaatgtac 180
tacacagtga attgaaaaat aaggttgaaa cattttctga atcaagttcc aaaagctgag 240
acaagatctt gaaatggtac tgtccactaa ggagtcaaag aatgaaaagt taaaggaaga 300
cttagaaag 309

<210> SEQ ID NO 42
<211> LENGTH: 878
<212> TYPE: DNA
<213> ORGANISM: Artificial Sequence
<220> FEATURE:
<223> OTHER INFORMATION: Synthetic polynucleotide

<400> SEQUENCE: 42
aacttcgata tgacctgcca gcatcataca agtttcacaa aaagaaatca gtaagtctct 60
tgattttggc tggtctacat tcggtattga aaagctttct gggccggatg tggtggttca 120
tgcctgtaat cccagctact cgggaggctg aggcaagaga atcgcttgaa ctcaggaggc 180
agaggttgca gtgagctgag attgccccac tgaactccag cctgcgcgat aagagtgaga 240
ctcagtctcg aaaaagaaaa aaaaaggaaa gctttgtgac aagtaattat ttctagtgtt 300
accaactttc ctgtgtaaat atacaaagcc agcctaggag acaccataaa tggcctgtgg 360
gaaaggccca tcgtcaatag ctaatattct agttctttcc taaatgcttt gggtacaaaa 420
agaaaaaaaa aatcaaaaac tgtttttgct cttttcatat agtatatatt ttattagtta 480
gtttgtacta atacattctc atattacaaa ggcaatttaa tggaagaatc ttccttttga 540
tatttgaatc atctgaaata acacaaacag aacaatacat tcaaagaaat ctcatttgca 600
taacaaaaag acaagttaaa caacaaaaaa atttttcctt tctcacaggt ggacattgaa 660
gtggacctaa ttcggttttc cttttaaaag ccccgcaaac aaaagtcgtt taaaacctat 720
ttaaaatgaa taaaaaattg gttcatgttc aaaagaaagc tgcagaatgg aaaatcaaga 780
tagatattat agcagggaca gatatggctt ttctaaagac tgctttggaa atggcaagaa 840
cagcagtata ttccttacac aaatcctcaa ctagagaa 878

<210> SEQ ID NO 43
<211> LENGTH: 397
<212> TYPE: DNA
<213> ORGANISM: Artificial Sequence
<220> FEATURE:
<223> OTHER INFORMATION: Synthetic polynucleotide

<400> SEQUENCE: 43
attccaagtc acaataccac tgaagttcag aaacacattc ctctctgtgc cttactctca 60
agtaatccta attttcattt cactggaaaa tggtattttg aagactgtgg aaaggaaggc 120
tatgggtttg tttgtgaaaa aatgcaagct ttcattacta tgaatctttt tggccagacc 180
accagtgtgt ggataggttt acaaaatgat gattatgaaa catggctaaa tggaaagcct 240
gtggtatatt ctaactggtc tccatttgat ataataaatt gccttctgct gaatatcccc 300
aaagacccaa gcagttggaa gaactggacg catgctcaac atttctgtgc tgaagaaggg 360
gggaccctgg tcgccattga aagtgaggtg gagcaag 397

<210> SEQ ID NO 44
<211> LENGTH: 645
<212> TYPE: DNA
<213> ORGANISM: Artificial Sequence
<220> FEATURE:
<223> OTHER INFORMATION: Synthetic polynucleotide

<400> SEQUENCE: 44
agagagagag agagagagag gagaggaggg gcggggtggg ggaggagggg agtggggaga 60
gagaaagaga gaaacaccaa aaagacattt tcaaggaagg aagaaaatta gatggcaacc 120
ccctgtcccc tccccctaag aaaatcctct ctgagattaa actgtgtgaa gattagaggc 180
gtgtaggtca ggagcaggag gaagcccaac gctggactgt accagatcat ctaaaactgg 240
caattccagg cacagaaaac cagttcttca gaagcagaag ggtggtcagc caggggggtga 300 aagggacagg ggtctcgcag ccagcccaac tgttgtattt tcagttcttc cagtgtgaat 360
cagttaatat tctcgggaac gagggagagg ttgatcctat gaggaaatca accacagtga 420
aaaggcttgg gccgcttttg ttttcacctg cttttgttga acaaatttga tttccggagt 480
cagtcatttt actgtcaaga catttcttcg gcattctgca acagtttcca acatggctag 540
atccatcaga aactgaagcc gtggagaacg ctctcggggc ctttgccact tcttggagta 600
gaagccgaca gagagctgtt tggaaacttc tccttcacac accag 645

<210> SEQ ID NO 45
<211> LENGTH: 569
<212> TYPE: DNA
<213> ORGANISM: Artificial Sequence
<220> FEATURE:
<223> OTHER INFORMATION: Synthetic polynucleotide

<400> SEQUENCE: 45
gagagagaaa gagagaaaca ccaaaaagac attttcaagg aaggaagaaa attagatggc 60
aaccccctgt cccctccccc taagaaaatc ctctctgaga ttaaactgtg tgaagattag 120
aggcgtgtag gtcaggagca ggaggaagcc caacgctgga ctgtaccaga tcatctaaaa 180
ctggcaattc caggcacaga aaaccagttc ttcagaagca gaagggtggt cagccagggg 240
gtgaaaggga caggggtctc gcagccagtt cttccagtgt gaatcagtta atattctcgg 300
gaacgaggga gaggttgatc ctatgaggaa atcaaccaca gtgaaaaggc ttgggccgct 360
tttgttttca cctgcttttg ttgaacaaat ttgatttccg gagtcagtca ttttactgtc 420
aagacatttc ttcggcattc tgcaacagtt tccaacatgg ctagatccat cagaaactga 480
agccgtggag aacgctctcg gggcctttgc cacttcttgg agtagaagcc gacagagagc 540
tgtttggaaa cttctccttc acacaccag 569

<210> SEQ ID NO 46
<211> LENGTH: 593
<212> TYPE: DNA
<213> ORGANISM: Artificial Sequence
<220> FEATURE:
<223> OTHER INFORMATION: Synthetic polynucleotide

<400> SEQUENCE: 46
gcctggcgct gctgctgccg cccgtcaccc tggcagccct ggtggacagc tggctccgag 60
aggactgccc agggctcaac tacgcagcct tggtcagcgg ggcaggcccc tcgcaggcgg 120
cgctgtgggc caaatcccct ggggtactgg cagggcagcc tttcttcgat gccatattta 180
cccaactcaa ctgccaagtc tcctggttcc tccccgaggg atcgaagctg gtgccggtgg 240
ccagagtggc cgaggtccgg ggccctgccc actgcctgct gctgggggaa cgggtggccc 300
tcaacacgct ggcccgctgc agtggcattg ccagtgctgc cgccgctgca gtggaggccg 360
ccaggggggc cggctggact gggcacgtgg caggcacgag gaagaccacg ccaggcttcc 420
ggctggtgga gaatgtggtg gccgccggtg gcgtggagaa ggcggtgcgg gcggccagac 480
aggcggctga cttcactctg aaggtggaag tggaatgcag cagcctgcag gaggccgtgc 540
aggcagctga ggctggtgcc gaccttgtcc tgctggacaa cttcaagcca gag 593

<210> SEQ ID NO 47
<211> LENGTH: 318
<212> TYPE: DNA
<213> ORGANISM: Artificial Sequence
<220> FEATURE:
<223> OTHER INFORMATION: Synthetic polynucleotide

<400> SEQUENCE: 47
tggacatttt cctacatcgg cttccctgta gagctgaaca cagtctattt cattggggcc 60
cataatattc ctaatgcaaa tatgaatgaa gatggccctt ccatgtctgt gaatttcacc 120
tcaccaggct gcctagacca cataatgaaa tataaaaaaa agtgtgtcaa ggccggaagc 180
ctgtgggatc cgaacatcac tgcttgtaag aagaatgagg agacagtaga agtgaacttc 240
acaaccactc ccctgggaaa cagatacatg gctcttatcc aacacagcac tatcatcggg 300
ttttctcagg tgtttgag 318

<210> SEQ ID NO 48
<211> LENGTH: 456
<212> TYPE: DNA
<213> ORGANISM: Artificial Sequence
<220> FEATURE:
<223> OTHER INFORMATION: Synthetic polynucleotide

<400> SEQUENCE: 48

```
aaagcataac ccctactgta gaactaaatg cactgtgcat gaaacttgga aaaaaaccaa     60

tgtataagcc tgttgaccct tactctcgga tgcagtccac ctataactac aacatgagag    120

gaggtgctta tcccccgaga gtttattaac cacttaacct ctcagaactg aacaaagaca    180

acattgttcc tggaacgccc tctttttaaa aaaggggctg cgggcgcctg agcggctctt    240

cagcgtttgc gccggcggct gccgcgtctc tctcggctcc cgcttccttt gaccgcctcc    300

ccccccggc ccggcggcgc ccgcctcctc cacggccact ccgcctcttc cctcccttcg    360

tcccttcttc ctctcccttt tttccttctt ccttcccctc ctcgccgcca ccgcccagga    420

ccgccggccg ggggacgagc tcggagcagc agccag                             456
```

<210> SEQ ID NO 49
<211> LENGTH: 484
<212> TYPE: DNA
<213> ORGANISM: Artificial Sequence
<220> FEATURE:
<223> OTHER INFORMATION: Synthetic polynucleotide

<400> SEQUENCE: 49

```
agagtaccca gagaaggaga agccagcaaa ggagacgaca cagacaagac ctcagagatc     60

aaaggaagag gccccttaat atcctggaat aatgggaccc atccccgtaa tcagtgaatc    120

tcatccaccc gcttgccagc ttctacccgc agcaagtaga agctaagtcc tggctcaaat    180

ctcttccctc cctccctctc ccagctgtca gtgcttttgg acttgtgctc agatgacaac    240

ggcaacacga caagaagtcc ttggcctcta ccgcagcatt ttcaggcttg cgaggaaatg    300

gcaggcgaca tcagggcaga tggaagacac catcaaagaa aaacagtaca tactaaatga    360

agccagaacg ctgttccgga aaaacaaaaa tctcacggac acagacctaa ttaaacagtg    420

tatagatgaa tgcacagcca ggattgaaat tggactgcat tacaagattc cttacccaag    480

gcca                                                                484
```

<210> SEQ ID NO 50
<211> LENGTH: 1331
<212> TYPE: DNA
<213> ORGANISM: Artificial Sequence
<220> FEATURE:
<223> OTHER INFORMATION: Synthetic polynucleotide

<400> SEQUENCE: 50

```
ccatcaggtt tgggcggatg ccacaggccg agaaggagaa gctgttggcg gagatctcca     60

gtgatatcga ccagctgaat ccagagtccg ctgacctccg ggccctggca aaacatttgt    120

atgactcata cataaagtcc ttcccgctga ccaaagcaaa ggcgagggcg atcttgacag    180

gaaagacaac agacaaatca ccattcgtta tctatgacat gaattcctta atgatgggag    240

aagataaaat caagttcaaa cacatcaccc ccctgcagga gcagagcaaa gaggtggcca    300

tccgcatctt tcagggctgc cagtttcgct ccgtggaggc tgtgcaggag atcacagagt    360

atgccaaaag cattcctggt tttgtaaatc ttgacttgaa cgaccaagta actctcctca    420

aatatggagt ccacgagatc atttacacaa tgctggcctc cttgatgaat aaagatgggg    480

ttctcatatc cgagggccaa ggcttcatga caagggagtt tctaaagagc ctgcgaaagc    540

cttttggtga ctttatggag cccaagtttg agtttgctgt gaagttcaat gcactggaat    600
```

-continued

```
tagatgacag cgacttggca atatttattg ctgtcattat tctcagtgga gaccgcccag    660

gtttgctgaa tgtgaagccc attgaagaca ttcaagacaa cctgctacaa gccctggagc    720

tccagctgaa gctgaaccac cctgagtcct cacagctgtt tgccaagctg ctccagaaaa    780

tgacagacct cagacagatt gtcacggaac acgtgcagct actgcaggtg atcaagaaga    840

cggagacaga catgagtctt cacccgctcc tgcaggagat ctacaaggac ttgtactagc    900

agagagtcct gagccactgc caacatttcc cttcttccag ttgcactatt ctgagggaaa    960

atctgacacc taagaaattt actgtgaaaa agcattttaa aaagaaaagg ttttagaata   1020

tgatctattt tatgcatatt gtttataaag acacatttac aatttacttt taatattaaa   1080

aattaccata ttatgaaatt gctgatagta tttgaagact gagtcttgtg tgtttcccac   1140

cctagccccc aggctttctt ttttacccct tttccttctc ccctccctcc ctccatccct   1200

ctcactcttc ctccctccct tccctccttt ccttcttcct ttatttttct tttctttctt   1260

agacatttta aaatatgtga gtggaactgc tgatacactt tcattctcag taaattaatt   1320

ttttactcaa t                                                        1331
```

<210> SEQ ID NO 51
<211> LENGTH: 270
<212> TYPE: DNA
<213> ORGANISM: Artificial Sequence
<220> FEATURE:
<223> OTHER INFORMATION: Synthetic polynucleotide

<400> SEQUENCE: 51

```
acaaagatca ttccactcag cctgggacga tggggaggaa aaaaatccag atctcccgca     60

tcctggacca aaggaatcgg cagcccggag gaaccacccc cgccctcctc agcctgatcc    120

tggaagagac tcggggcccc ccagcctccg ccaacccagc gccgtgaaga acctggtgga    180

cagcagcgtc tacttccgca gcgtggaggg tctgctcaaa caggccatca gcatccggga    240

ccatatgaat gccagtgccc agggccacag                                     270
```

<210> SEQ ID NO 52
<211> LENGTH: 183
<212> TYPE: DNA
<213> ORGANISM: Artificial Sequence
<220> FEATURE:
<223> OTHER INFORMATION: Synthetic polynucleotide

<400> SEQUENCE: 52

```
agaagcaaat gctggcacaa ggataccctg cttacacgac atcgtgcgcc tggctggggt     60

actcagatga cacgttgaag caggatccca ggatgctggt atcctgcata gatttcaggt    120

acatcactga tgtcctgact gaggaggatg ccctagcctg tctggaagtt acttgtggac    180

atg                                                                  183
```

<210> SEQ ID NO 53
<211> LENGTH: 1361
<212> TYPE: DNA
<213> ORGANISM: Artificial Sequence
<220> FEATURE:
<223> OTHER INFORMATION: Synthetic polynucleotide

<400> SEQUENCE: 53

```
gtgccacttc ggataaaccc tttggactcc taactccaat caggtgtctg ctttgttgag     60

gactcacaga cacagtctcc tttcttcaag atctttacaa tgcaagacct cactaacaca    120

cagggatggt ctcccagagg gtctgtgctg ttccttcact cagaacatca agatgcactg    180
```

```
aagtaaggat cctctattct acagttcctg ctagctgagc tattccatgg gggcttcagc    240

aggaaattcc aaggttggct ttgacaagct aaggccggct ggtggagcac atcgagttct    300

ggaggttcat gtgtgttttc atgaagatct gtctgcccgt agcagataaa gagttgttgc    360

cccactcctc ctggggtctt ctattttcct gggaggaatt tctggattaa ctgaacacac    420

acacacacac acacaccctt ttgaagcatc aacagtaatt ctgagttctt agggacaatg    480

cagattaaat ccacaataag aaagacaact atggccaggt gtggtggctc acgcctgtaa    540

tcccagaact ttgggaggct gaggcggatg gatcacctga ggtcaggagt tagagaccaa    600

cctgaccaac atggagaaac cccgtttcta ctaaaaatgc aaaattagcc gggcatggtg    660

gcaggcgcct gtaatcccaa atactcggga ggctgaggca ggagaatcac ttaaacccgg    720

gaggcagagg ttgcagtgag ccaagatcgc gccattgcac tccagcggcc agactttggc    780

agcgtgtaag gtctgaggac aggggcaccg gaggccgagg atgagaggcc agtgcctgtt    840

tccaggcagc cagggcctca gaaactccgg ccggagcact cacccgtcgg tggaggccgt    900

taccagggcc accttatttg cgagcgggtc ccggcgggtc atcccggagc tggccatccg    960

caccgaattc caagcccggg cacagaggcc tagcagcccc gccttgtgca tggatcagac   1020

cagcaaacat gggccccgtc ctgggccaaa cgccgggcga tggcgaagcc gatcctgtga   1080

gcagaaagag acaaagactg ctaaggcctg tgcaggggaa gaggtcgaca gtatgagctc   1140

tgaagttaag actgcccggg tttgaattct ggctctttct ctatataacc cctacgtgtg   1200

cctactatgt gtaaaacagg cttaatggca tggccatttt tggcattcct ttacttgttt   1260

ttattatgac ctggaccaca gcctcagttc ccaagaactg acatcacttt ctacagttcc   1320

caccatgggt gacaggcttc atcccctctt gggactgaga g                       1361
```

<210> SEQ ID NO 54
<211> LENGTH: 783
<212> TYPE: DNA
<213> ORGANISM: Artificial Sequence
<220> FEATURE:
<223> OTHER INFORMATION: Synthetic polynucleotide

<400> SEQUENCE: 54

```
cgcagaatct aggcctgctc tggccagatc agtttcgaag accgtcgctc cgaaggaggc     60

acctctcgtt tcaagcctag tgacctcgat gcttttaggt tgcagcatac tggagagctc    120

tggcttgctt cgtgaaggct tagggagaac ttcattaggg ctggaaaagg gtggccaatg    180

tttgatttac tgcagttgtg ctttgcatat cggaaatgct ggctaaataa acggtatcaa    240

actaactctg aaagaacggc gccgcaaata acagcaccca attaaagaac cacaggattt    300

tagagattaa atgatctttt tgagatccaa gtacatctca tggaaaaata cctaggttag    360

aattactaaa ttaaaaaatg gacacttggg gccaggcgca gtggcttacg cctgtaattc    420

caccactttg gggagctgag gcgggcagat cacttgacat cgagagttca agaccagcct    480

gaccaacatg gagaaacccc gtctctacta aaaatacaaa aaattatcca gacgtagtgg    540

cacatgcctg taatctcagc tacttgggag gctgaggtag gagaatcgct tgaacccggg    600

aggcagaggt tgtggtgagc cgagatcatg ccattgaact ccagcctggg caacaagagc    660

gaaactccgt ctccaaaaaa aaaaaaagac acttatttag gctttccata tatcatggga    720

agacatgtaa ggaatttgca taagacagtt atgcaaaatg gagctggagg agctttattt    780

gtg                                                                  783
```

<210> SEQ ID NO 55
<211> LENGTH: 588
<212> TYPE: DNA
<213> ORGANISM: Artificial Sequence
<220> FEATURE:
<223> OTHER INFORMATION: Synthetic polynucleotide

<400> SEQUENCE: 55
gatccctgga gttgcagcta ccagacatgg tgcgtggggc ccggggcccc gagctctgct 60
ctgtgcagct ggcccgcaat ggggccgggc cgaggtgcaa tctgtttcgc tgctgccgcc 120
gcctgagggg ctggtggccg gtagtgaagc tgaaggaggc agaggacgtg gagcgggagg 180
cgcaggaggc tcaggctggc aagaagaagc gaaagcagag gaggaggaag ggccggccag 240
aagacctgga gttcacagac atgggtggca atgtgtacat cctcacgctg ggtgaagggg 300
ttggagcatg acaagcagga gacagacgtt cacttcaact ccctgactgg ggaggggaac 360
ttcaattggc gctttgtgtt ccgctttgac tacctgccca cggagcggga ggtgagcgtc 420
cggcgcaggt ctggaccctt tgccctggag gaggcggagt tccggcagcc tgcagtgctg 480
gtcctgcagc tatgagctca gagttgtcat ctggaacacg gaggatgtgg ttctggacga 540
cgagaatcca ctcaccggag agatgtcgag tgacatctat gtgaagag 588

<210> SEQ ID NO 56
<211> LENGTH: 1672
<212> TYPE: DNA
<213> ORGANISM: Artificial Sequence
<220> FEATURE:
<223> OTHER INFORMATION: Synthetic polynucleotide

<400> SEQUENCE: 56
gcagtgctcg gaatgtgacc aggcagggag cagtgacatg gaagcagata tggccatgga 60
aaccctacca gatggaacca aacgatcaag gaggcagatt aaggaaccag tgaaatttgt 120
tccacaggat gtgccaccag aacccaagaa gattccgata agaaacacga gaaccagagg 180
acgaaaacga agcttcgttc ctgaggaaga aaaacatgag gttggaataa ggaaagagtt 240
cctagagaga gaagacaaag acagtctgtg ttgcaaaaga agcccaaggc tgaagattta 300
agaactgaat gtgcaacttg caagggaact ggagacaatg aaaatcttgt caggtaagtt 360
ggatgctaaa accttgtctt taggggatga aagttctata tttattttct catcacagaa 420
aaaatgaaaa aacaattgca ggataagacc tttcttaaaa tattatatag tggaaacagt 480
actttagaaa cagatttcat ccacttctta acctctcaca catggttata ctctggattt 540
aaatgtaaat aagagtgata atctgcctgt ttaacacagg gaattatttt tctcttgaca 600
agagaaattg acagtgctct ctatttagag gccatgaaag taatttgatc taaacactgt 660
gtactaagat tattatgttt tatgtcagaa aacaataaag ttactaagct ctgttagcat 720
attctaaatg tttgaaattt agaagcaatg gtgagaagac agacttttta ttgacaagaa 780
cttaattagc actttcttat tgcttatcaa aacaaatgtg ttaaatgctt ctcccttacg 840
aaataaagaa aggtgaaaag atggcctagg ttgattttat tttttgtttt gtctttgttt 900
ctttgtttcg ttttggtact ttattttttt ttaatcagac ataatgctaa tcagaaatct 960
tagctgatgc tgcacattgg cttttcccaa cggtccagag gctgctaatt ttagcggaaa 1020
tgaagacatt gatcaaagct ctggtgagat gggggagtga gtgtgtgaac aaaaagagag 1080
ctaatttaaa agaggcatca gactttcaaa ggacagtgtc acaaaagttc ttacagttct 1140
tacagggact ttgtaaggga atccattctt atttctttaa aaaattgtct tctggtaaag 1200

-continued

```
ccctgttaaa ttaactgagg acacagaaat taaacatttc aaaaagaata aacatattga   1260

taaaacaaat atattagtgt tgttgtatgt ttttaaatac ttacttccaa atgatttaat   1320

ctattttggt cattaaaata tgtcttaatt tctcaaagaa aggcatgaag tcttaaattt   1380

tatgagtttt ttatgctatc aatgagaaag ataaagtaaa aattacagta gaaaaagaca   1440

aagtccttca acaaagttaa gaaagtttat aataattggc taattttttt gaggtagttc   1500

atgtagagtg tgttgggagc tatcctgaag gttaagttta ttaaaattta gggtaaagta   1560

gtaagtagtt ccaagttcag gagatacacc tgaataattc tgaccacagt ataaattttg   1620

caatatgtcg aaaatgaaat cccaagcata agcgtaacat aatggagtaa at           1672
```

```
<210> SEQ ID NO 57
<211> LENGTH: 352
<212> TYPE: DNA
<213> ORGANISM: Artificial Sequence
<220> FEATURE:
<223> OTHER INFORMATION: Synthetic polynucleotide

<400> SEQUENCE: 57

gcagtgctcg gaatgtgacc aggcagggag cagtgacatg gaagcagata tggccatgga     60

aaccctacca gatggaacca aacgatcaag gaggcagatt aaggaaccag tgaaatttgt    120

tccacaggat gtgccaccag aacccaagaa gattccgata agaaacacga gaaccagagg    180

acgaaaacga agcttcgttc ctgaggaaga aaaacatgag gttggaataa gaaagagttc    240

ctagagagag aagacaaaga cagtctgtgt tgcaaaagaa gcccaaggct gaagatttaa    300

gaactgaatg tgcaacttgc aagggaactg gagacaatga aaatcttgtc ag            352
```

```
<210> SEQ ID NO 58
<211> LENGTH: 2635
<212> TYPE: DNA
<213> ORGANISM: Artificial Sequence
<220> FEATURE:
<223> OTHER INFORMATION: Synthetic polynucleotide

<400> SEQUENCE: 58

gggttcaact agatatagct tcacaatctc tggatcaaga aattttatta aaagttaaaa     60

ctgaaattga agaagagcta aaatctctgg acaaagaaat ttctgaaggc cagtgacata    120

tcaggcattt cgggaatgta cactggagac cacagttcat gccagcggct ggaataaggg    180

cactgtgttt agtcttgagt cagaggagga ggaataccct ggaatcactg cagaagatag    240

caatgacatt tacatcctgc ccagcgacaa ctctggacaa gtcagtcccc cagagtctcc    300

aactgtgacc acttcctggc agtctgagag cttacctgtg tcactgtcag ctagccagag    360

ttggcacaca gaaagcctgc cagtgtcact aggccctgag tcctggcagc agattgcaat    420

ggatcctgaa gaagtgaaaa gcttagacag caacggagct ggagagaaga gtgagaacaa    480

ctcctctaat tctgacattg tgcacgtgga gaaagaagag gtgcccgagg gcatggaaga    540

ggctgctgtg gcttctgtgg tcttgccagc gcgggagctg caagaggcac ttcctgaagc    600

cccagctccc ttgcttccac atatcactgc cacctccctg ctggggacaa gggaacctga    660

cacagaagtg atcacagttg agaaatccag ccctgctaca tctctgtttg tagaacttga    720

tgaagaagag gtgaaagcag caacaactga acctactgaa gtggaggagg tggtccccgc    780

actggaaccc acagaaacgc tgctgagtga gaaggagata aacgcaaggg aagagagcct    840

tgtggaagag ctgtcccctg ccagcgagaa gaagcccgtg ccgccgtctg agggcaagtc    900
```

tagactgtcc cccgccggtg agatgaagcc catgccgctg tctgagggca agtctatact 960
gctgtttgga ggggctgctg ctgttgccat cctggcagtg gccatcgggg tagccctggc 1020
tctgagaaag aaataggagg cttttcagaa gagaaagaca gaaggatgta aggttggagt 1080
tgtattggct ggaatttgaa cctccagcag ctgtctggac atttgtggaa cactctggga 1140
taattgggga cttctgctca acatggcagt ggcatgttag gcatgttagg gcttgaggtg 1200
gggcattcac attcatctga ctgtaaatcc caagggcctc cgctcatgct aaattgagaa 1260
tcttaggggt aaagcacccc ctccaggacc gggtttctca gccttggcac tagtgctgtt 1320
ctgaccattc tctgtgttgg ggctgtcctg tgtgtggtgg gctccaccca ctagatgcca 1380
gtggcacccc ctcccagaga tgacaaacga aaatgtctct agacattgcc aaatgtcccg 1440
tgtgaacatc ccctattgag acccactgct ttagcgagag agggtttact taggaagaat 1500
tgggatagaa attcccagct gagagaactt agctgtgggc tcctcagcta ctgacttctt 1560
agctcttaat ccccttagaa tttcatcttt ctcgatgagc aggctctgca cccactcttt 1620
ttttgccccc cgccctcatc ctggagtgtg agggtgctcg cccgtactct cagctgcctc 1680
tcagggactg cactgttcct cttcaccccc aggttcctgc taagatccca cgggcgaggg 1740
cttgctctgg actcagtctg tcaagtcccc gaagcttcct gcagctccac cttgtaaaaa 1800
tgctgccttt gggaatcttc gaaatatgta cacagagaaa atcacatgaa ggagacctgg 1860
ggtccccact tgtgagtgca actgcaagta actctggcta gagagacaca tgtgtcttgt 1920
gtcaaggcag gaggataacc tggatgacct tctgaggtct cttcagccct tttcgctagt 1980
ggtcacccac caccatggtt acttgccagc aacatctcta ttgctggatg gtccctgtct 2040
ataaccttgg gctagtatat tttttccaat atgggacctt agtcttacta ctgatgagtt 2100
ctatgggtct cttgctaggg ggtaaggatt tttattcttg ggcttataga gccagttaga 2160
tcataattct tatgaaatag agagtgtcct aaatatcact gaaataaaaa gtaggaaaaa 2220
gaagcttgaa ttttaagact gaggctgctc tgcagattct agtttggctt tcagagttca 2280
agagtggtgg catcttcacc tgaattcttc aatgccaggg taataaacca aaatagtcct 2340
aatcagtata tgctagttga gcatcggcat aattttcttt cctctggctg atcccagccc 2400
taaaggaagg gtagacccgt gtctttccag ccctaaagga agggtagacc cgtgtctttc 2460
cagccctaaa ggaagggcag acccgtgtct ttccatgccc gagggccacg acgtcactat 2520
gcagggcaca cgtggcttgg tttaaaaagg tcatcttaga tttatcttag taaatgtaat 2580
aaattatttt ttagatcttg aaatttataa taaaaatact ttacctaccc tgatc 2635

<210> SEQ ID NO 59
<211> LENGTH: 364
<212> TYPE: DNA
<213> ORGANISM: Artificial Sequence
<220> FEATURE:
<223> OTHER INFORMATION: Synthetic polynucleotide

<400> SEQUENCE: 59
gtcattgagc ccaaggacat ccatgccaag tgcgaactgg cctttctcca caccagccac 60
tgcctggcca gcggggaagt gatgatcagc tccctgggag acgtcaaggg caatggcaaa 120
ggtcatccac cggctgccca tgcccaacct gaaggacgag ctgcatcact caggatggaa 180
cacctgcagc agctgcttcg gtgatagcac caagtcgcgc accaagctgg tgctgcccag 240
tctcatctcc tctcgcatct atgtggtgga cgtgggctct gagccccggg ccccaaagct 300
gcacaagcta cgaaatgtgg gaattgtgga cccggctact ccacccctct ggaggccatg 360
aaag 364

<210> SEQ ID NO 60
<211> LENGTH: 337
<212> TYPE: DNA
<213> ORGANISM: Artificial Sequence
<220> FEATURE:
<223> OTHER INFORMATION: Synthetic polynucleotide

<400> SEQUENCE: 60
gttgattcca taccctggct attgtgaata atgctgcagt gaacatggga gtacatacat 60
ctgtttgagg aactcagagt ggttttccag atgggaatca cattgctctc tgtccctgag 120
atcttgctgg agacagggct actcagtccc tctttgccag gtaatctgtt ccagaagaaa 180
catgtgtcgt tctgactgag cccctgcctg tctgtcacct taagagccag tcaattcata 240
tggtccccat atcaaagtct cctgtgccca gagagaggat ttcatttcaa ccatcaccat 300
caccaccatc atcatcatca ccaagagatg ttgttga 337

<210> SEQ ID NO 61
<211> LENGTH: 460
<212> TYPE: DNA
<213> ORGANISM: Artificial Sequence
<220> FEATURE:
<223> OTHER INFORMATION: Synthetic polynucleotide

<400> SEQUENCE: 61
ggttcatagt ggcgtcatgc acgcagactc ctgcaagttc ccctaagttc ttagaggact 60
gctttgcctt ttgatctgag agttgcaaag ttccataaag aatggccctt gtggataagc 120
acaaagtcaa gagacagcga ttggacagaa tttgtgaaga tggagaaaac aaaggattca 180
gattgaagga ctgctcagac accctccgaa gaggtggccc tgcctgcgct cctcctggct 240
gcagagtacc ccaccagcgc gagatccagg gttgccagaa gacgagacaa ccgtgattgc 300
atgtgcggag gttcctcgat ggaagcgcag cccggcgcgc ccctcagctg gcctggccag 360
gccctatgaa ggtcacgcga aaaccctgct gcgggcttct tagcgaccgc attacgtgga 420
ctagcgggca agaaaagcct ggtcggcgct gccctcacag 460

<210> SEQ ID NO 62
<211> LENGTH: 622
<212> TYPE: DNA
<213> ORGANISM: Artificial Sequence
<220> FEATURE:
<223> OTHER INFORMATION: Synthetic polynucleotide

<400> SEQUENCE: 62
aggcgtctgg ccaggtggcg ctccgggcag gcctacttgg gtgtccccgc ctctgatacc 60
tccctgctgg aggaaacagc aggaaaagag aaccaggcag gcaggcagac atccccacgg 120
agcagcgttg ggcccccaag gtgcctgacc cacttcctag agtactgaac agtcccagag 180
tgtcacagct gatgtgcagg acagcctgga gctctcacct tcaacacggg gtgtacctga 240
gacttccagt ggatgagggt cagcctctgg agctgtgaaa acctgggccg acagcggagg 300
cagagctgca ctaatgttcc cacacgagtc cttcccaccc aacaccttgg tgcagggaga 360
cggaaggagc ctggagccag ggctagaaga agtcttcact tcccaggaga gccaaagcgt 420
gtctggccct aggtgggaaa agaactggct gtgacctttg ccctgacctg gaagggccca 480
gccttgggct gaatggcagc acccacgccc gcccgtccgg tgctgaccca cctgctggtg 540

-continued gctctcttcg gcatgggctc ctgggctgcg gtcaatggga tctgggtgga gctacctgtg 600
gtggtcaaag agcttccaga gg 622

<210> SEQ ID NO 63
<211> LENGTH: 1871
<212> TYPE: DNA
<213> ORGANISM: Artificial Sequence
<220> FEATURE:
<223> OTHER INFORMATION: Synthetic polynucleotide

<400> SEQUENCE: 63
ctctttctct tcctccagtt tccagtccag ccctgttggc tctcagaatg catcatcctt 60
ctccctgcag cgctctcact gaacatgctc aagcgcaagg aacttataat cttgtgttct 120
ctggattctg gatttagtaa tctgtattag tctgttctca cactgctaat aaagaaatac 180
ctgaggttgc ttccaagata gccaaatagg aacagctctg gtctgcagct cccagcaaga 240
tcgatgtaga agatgggtga tttctgcatt tccaactgag gtacctggtt catctcactg 300
ggactggttg gacagtgggt gcagcccatg gaaggtgagc tgaagcaagg tggggcgtca 360
cctcacccag gaagcacaag ggtcagggg atttaccttt cccagccaag ggaagccatg 420
acagactgta actggagaaa cggtacactc ctgaccaaat actgcacttt tcccacagtc 480
ttagcaactg gcagaccagg taatacccctc ccgtgcctgg ctcagtgggt tccatgccaa 540
cggagccttg ctcactgcta gcgcaacagt ctaagatcga cctgcgacgc tgcagcttga 600
tgcagggaga ggcatccaac attgctgagg cttgagtagc tcacagtgta agcaaagagg 660
cccggaagca caagttgggc agagctcatc gctgctcagc agggcctact gcctctatag 720
attccacctc tggaggcagg gcatggcaga aaaaaacgca gcagacagct tttgcagact 780
taaacgtccc tgtctgatgg ctctaaagag agcaatggtt ctctcagcat ggcattcgag 840
ctccaagaac agacagactg cctccccaag caggtccctg acccccatgt agctggactg 900
ggaaacacct ccccatcagg ggctgagaga tacctcaaac acgtgggtgc ccctctggga 960
cgaagcttcc agaggaagga tcaggcagca atatttgcta ttctgcagcc tttgctggtg 1020
atacccaggc aaacagattc tggagtggac ctccagcaaa ctccaacaaa cctgcagctg 1080
aggggtctga ctgtgggaag gaaaactaac aaagagaaag caatagcatc aacatcaaca 1140
aaaaggacat ccacaccaaa tccccatcta taggtcacca acatcaaaga ccaaaggtag 1200
ataaaaccac aaagatgggg agagaaacca gagcagaaaa gctgaaaatt ccaaaaaaca 1260
agcacctctt ctcctccaaa ggatcgcagc tccttgccag caagggaaca aaactagacg 1320
gagaatgagt ttgacaagtt gacagaagta ggcttcagaa ggttggtaat aacaaacttc 1380
tctgagctaa aggagcatct tctaacccat cgcaaagagg ctaaaaactg tggaaaaaaa 1440
aaaggttaga tgaatggcta actagaataa ccagtgtaga gaagacctca aatgacctga 1500
tgaagctgaa acccacagca caagaacttc gagactcatg cacaagcttc aatagccgat 1560
tcgatcaagt ggaagaaagg atatcagtga ttgaagatca aattaatgaa ataaagtgag 1620
aagaatgtct ggtgaagttc aagggcatct tgaacgtggt gcacttggag acagtgaggg 1680
aagcaggggt gaagtggctg ctacctgagt ccccttctgga gctccatttt gcttggtctt 1740
ggagaaggct tctcagctgc cctcccagct agtgagttac atctgctaac atgcttattt 1800
tcattcttcc ttcatctctt tatttaaaaa tcacagacca ggatggagat aaaggaactc 1860
aaagaatttg g 1871

<210> SEQ ID NO 64
<211> LENGTH: 457
<212> TYPE: DNA
<213> ORGANISM: Artificial Sequence
<220> FEATURE:
<223> OTHER INFORMATION: Synthetic polynucleotide

<400> SEQUENCE: 64
aaactgggca catttgggcc cctgcgctgc caggaggcat gggccctgga gcggctgctg 60
cgggaagccc gagtactgga ggcagtatgc gagttcagca ggcggtggga gatcccggcc 120
agctctgccc aggaagtggt gcagttctcg gcctctcggc ctggcttcct gaccttctgg 180
gaccagtgca cagagagact cagctgcttc ctctgcccgg tggagcgggt gcttctcacc 240
ttctgcaacc agtatggtgc ccgcctctcc ctgcgccagc caggcttggc tgaggctgtg 300
tgtgtgaagt tcctggagga tgccctgggg cagaagctgc ccagaaggcc ccagccaggg 360
cctggagagc agctcacagt cttccagttc tggagttttg tggaaacctt ggacagcccc 420
accatggagg cctacgtgac tgagaccgct gaggagg 457

<210> SEQ ID NO 65
<211> LENGTH: 427
<212> TYPE: DNA
<213> ORGANISM: Artificial Sequence
<220> FEATURE:
<223> OTHER INFORMATION: Synthetic polynucleotide

<400> SEQUENCE: 65
taatggaaac ttggaattag cagtggcttt ccttactgcg aagaatgcta agacccctca 60
gcaggaggag acaacttact accaaacagc acttcctggc aatgatagat acatcagtgt 120
gggaagccaa gcagatacaa atgtgattga tctcactgga gatgataaag atgatcttca 180
gagagcaatt gccttgagtt tggccgaatc aaacagggca ttcagggaga ctggaataac 240
tgatgaggaa caagccatta gcagagttct tgaagccagc atagcagaga ataaagcatg 300
tttgaagagg acacctacag aagtttggag ggattctcga aacccttatg atagaaaaag 360
acaggacaaa gctcccgttg ggctaaagaa tgttggcaat acttgttggt ttagtgctgt 420
tattcag 427

<210> SEQ ID NO 66
<211> LENGTH: 322
<212> TYPE: DNA
<213> ORGANISM: Artificial Sequence
<220> FEATURE:
<223> OTHER INFORMATION: Synthetic polynucleotide

<400> SEQUENCE: 66
aaccggatgc tacgggtgat gactgggagg aggagaaaaa ttacctcttt atcttgcatg 60
aacatcttaa ttttcagagt cttgctgcga cacccaggct ggagtgcaat ggcgctatct 120
cggctcactg caacctccgc ttcccggatt caagcgattc tcctgcctca gcctcccgag 180
taggtgggac tacaggacca gaggagcgag agcagcaaga accacaccca gcagcaatgt 240
cagcggaagt ggaaacctca gagggggtag acgagtcaga aaaaaagaac tctggggccc 300
tagaaaagga gaaccaaatg ag 322

<210> SEQ ID NO 67
<211> LENGTH: 491
<212> TYPE: DNA
<213> ORGANISM: Artificial Sequence
<220> FEATURE:

<223> OTHER INFORMATION: Synthetic polynucleotide

<400> SEQUENCE: 67
gggttgtgta taattacagt gcacatggtg tccagcgaga cggagaaggg tgggaagaga 60
gcataagcat cccattactg cagcccaaca tgtatggaat gatggagcaa tgggacaagt 120
acctggaaga cttctccacc tcgggggcct ggctgcctca cagagagtat gatggaaggt 180
ctgatcttca tgttggaata actaacacaa atggtataat gaggaaaagg aagtctccgg 240
aaacctcccc tagcattcca ggaggcgaaa gctatgcact gcgcagaggc tgggaaggct 300
ttaattaaat tcaaccactg tgagaaatac atctacagct tcagtgtgcc ccagtgctgc 360
cctctctgcc agcaggacct gggctcgagg aagctggagg acgcacctgt tagcatcgct 420
aatccattta ctaatggaca tcaagaaaaa tgttcattcc tcctcagacc aactcagggg 480
acatttctta g 491

<210> SEQ ID NO 68
<211> LENGTH: 431
<212> TYPE: DNA
<213> ORGANISM: Artificial Sequence
<220> FEATURE:
<223> OTHER INFORMATION: Synthetic polynucleotide

<400> SEQUENCE: 68
gtaaacaaat tgctcctgtg gagatgattg gcatcacatg gtgttttgag ctgatacacc 60
caacacttga gctcactgca acagtaccag attttcaccg ctatgcctcc tttcactctg 120
ggagtcttcc agaggtcttg cactcgggag agcatgctca ggtttcccca gctctacaaa 180
atcacccaga atgccaaaga cttcaacaca agggtaaata aggttgatct cagaattgtc 240
acctcaaaaa ggccctgcct tccactgttc agttctggtc atctgcctat gagatatctg 300
aagcttgaaa gagaacactt gaaaatcact gagaccgtga ctcccatccc agcacacaca 360
gcaagccaaa tactgtgttg accagtggtc atgccactgc ctgttgattt gttgaaaata 420
ttgtttacac g 431

<210> SEQ ID NO 69
<211> LENGTH: 752
<212> TYPE: DNA
<213> ORGANISM: Artificial Sequence
<220> FEATURE:
<223> OTHER INFORMATION: Synthetic polynucleotide

<400> SEQUENCE: 69
ttttaattga taaagaccag agtccaaaat ggaaaccagc tgatctaaaa gaagttactg 60
aggaagattt gaataatcac tttaagtctt tgggaagcag tgatttgaaa ttttgaggtg 120
acaggctttt aaggtatatt ttgtagcatg ggttggcaat ctacagcatg tgggccaaat 180
ccagcctgct gcctgttttt atataccctg taagctaaga atggtttccg catttttaaa 240
tggttgggaa aagaaatcaa agactaataa ttcatgacgt gaaaattatc agaattcaca 300
aataaagctt tattggaact agctatactc atctgtttat atattatctg tggctgcttt 360
gaaatgagta gttgcaatag agatggtaaa gcctacaaag cctaattatt tactgtctgg 420
tttttgtcag aaaaaagttt gtcaatcctt gttttagaag atggaaaaat gtgaagatct 480
ttggagattc tcttgagtgg tatatctaat tgaaatggga tcttcgtttg gcttgtatgt 540
tgatgaaatc aacttaggta tacaatataa aaaataaaga ccctgaaaat tgttttggag 600
aggtcatgac tttcatgaag gcgttagagc tggtaattaa taaaatgtct ccaacatctc 660
taaagatcac actaaggcaa ctcatggagg ggtcttcaaa gaccttgcaa gaagtactaa 720
ctatggagta tcggctaagt caagcttgta tg 752

<210> SEQ ID NO 70
<211> LENGTH: 297
<212> TYPE: DNA
<213> ORGANISM: Artificial Sequence
<220> FEATURE:
<223> OTHER INFORMATION: Synthetic polynucleotide

<400> SEQUENCE: 70
cgcgcggcac tggtcctggt ggtcctcctc atcgccgggg gtctcttcat gttcacctac 60
aagtccacac agttcaacgt ggagggcttc gccttggtgc tgggggcctc gttcatcggt 120
ggcattcgct ggaccctcac ccagatgctc ctgcagaagg ctgaactcgg accaaatcct 180
cagctgtcct cttcatcttg atcttctctc tgatcttcaa gctggaggag ctgctctggc 240
gacggcgctt gacgtgggct tgtccaactg gagcttcctg tatgtcaccg tctcgct 297

<210> SEQ ID NO 71
<211> LENGTH: 704
<212> TYPE: DNA
<213> ORGANISM: Artificial Sequence
<220> FEATURE:
<223> OTHER INFORMATION: Synthetic polynucleotide

<400> SEQUENCE: 71
ggatctgtga acaagaggaa cctcagcagc caggacaggc aggagcagtg gaatagctac 60
tatggcttct ggaatcctgg ttaatgtaaa ggaggaggtg acctgcccca tctgcctgga 120
actcctgaca caacccctga gcctggactg cggccacagc ttctgccaag catgcctcac 180
tgcaaaccac aagaagtcca tgctagacaa aggagagagt agctgccctg tgtgccggat 240
cagttaccag cctgagaaca tacggcctaa tcggcatgta gccaacatag tggagaagct 300
cagggaggtc aagttgagcc cagaggggca gaaagttgat cattgtgcac gccatggaga 360
gaaacttcta ctcttctgtc aggaggacgg gaaggtcatt tgctggcttt gtgagcggtc 420
tcaggagcac cgtggtcacc acacgttcct cacagaggag gttgcccggg agtaccaaga 480
tccaggcaat ctttccagac acatctactt cccagtaata tttccccgaa gagaaatatt 540
ggcagccgaa gacaccaaaa gcagaaaaat cacatggatt tgaattctta aatgtgcagc 600
aggtctaagg cccgcctgtt ctgtgccgtg acctgtgcta ccgaagtcat ctgttgctgt 660
agggaggcca gggactcagc cgatgcctca atggccaact gcag 704

<210> SEQ ID NO 72
<211> LENGTH: 688
<212> TYPE: DNA
<213> ORGANISM: Artificial Sequence
<220> FEATURE:
<223> OTHER INFORMATION: Synthetic polynucleotide

<400> SEQUENCE: 72
tcctcgcctc catcacctcc accgtagttg agccagcgat agtactgaga gtagggaaag 60
agcctccggt aataaagttt aagcagctcg ggcagctcgg tggggtcaaa cgtctccatt 120
gagcgcggaa ctcgccacgt aacagatctg attctgcagc tgatcaagga tgacactggt 180
gagaacccta tgagggagtg aagcagcctg gactcttacc acaagaggga ggtgttataa 240
gagcaatgca gaggttggag tgggcagcag ttggggcagg aggaagccga ctgctgcctg 300

```
gtctgcaaag aagtcctttc aagtctctag gactggactc ttcctaagca agtccgagaa    360

ggaagcaccc tcactatgtg gctctacctg gcggccttcg tgggcctgta ctaccttctg    420

cactggtacc gggagaggca ggtggtgagc cacctccaag acaagtatgt ctttatcacg    480

ggctgtgact cgggctttgg gaacctgctg gccagacagc tggatgcacg aggcttgaga    540

gtgctggctg cgtgtctgac ggagaagggg gccgagcagc tgaggggcca gacgtctgac    600

aggctggaga cggtgaccct ggatgttacc aagatggaga gcatcgctgc agctactcag    660

tgggtgaagg agcatgtggg ggacagag                                       688
```

<210> SEQ ID NO 73
<211> LENGTH: 99
<212> TYPE: DNA
<213> ORGANISM: Artificial Sequence
<220> FEATURE:
<223> OTHER INFORMATION: Synthetic polynucleotide

<400> SEQUENCE: 73

```
ggaacaacgg tggttggatg aacagcaaca gataatggaa tctcttaatg tactacacag     60

tgaattgaaa aataaggttg aaacattttc tgaatcaag                            99
```

<210> SEQ ID NO 74
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 74

```
catgttcaaa agaaagctgc agaatggaaa atcaagatag atattatagc ag             52
```

<210> SEQ ID NO 75
<211> LENGTH: 131
<212> TYPE: DNA
<213> ORGANISM: Artificial Sequence
<220> FEATURE:
<223> OTHER INFORMATION: Synthetic polynucleotide

<400> SEQUENCE: 75

```
ctttcattac tatgaatctt tttggccaga ccaccagtgt gtggataggt ttacaaaatg     60

atgattatga aacatggcta aatggaaagc ctgtggtata ttctaactgg tctccatttg    120

atataataaa t                                                         131
```

<210> SEQ ID NO 76
<211> LENGTH: 200
<212> TYPE: DNA
<213> ORGANISM: Artificial Sequence
<220> FEATURE:
<223> OTHER INFORMATION: Synthetic polynucleotide

<400> SEQUENCE: 76

```
cccaactgtt gtattttcag ttcttccagt gtgaatcagt taatattctc gggaacgagg     60

gagaggttga tcctatgagg aaatcaacca cagtgaaaag gcttgggccg cttttgtttt    120

cacctgcttt tgttgaacaa atttgatttc cggagtcagt cattttactg tcaagacatt    180

tcttcggcat tctgcaacag                                                200
```

<210> SEQ ID NO 77
<211> LENGTH: 180
<212> TYPE: DNA
<213> ORGANISM: Artificial Sequence -continued
<220> FEATURE:
<223> OTHER INFORMATION: Synthetic polynucleotide

<400> SEQUENCE: 77
ttcttccagt gtgaatcagt taatattctc gggaacgagg gagaggttga tcctatgagg 60
aaatcaacca cagtgaaaag gcttgggccg cttttgtttt cacctgcttt tgttgaacaa 120
atttgatttc cggagtcagt cattttactg tcaagacatt tcttcggcat tctgcaacag 180

<210> SEQ ID NO 78
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 78
tgtggtggcc gccggtggcg tggagaag 28

<210> SEQ ID NO 79
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 79
gctgcctaga ccacataatg aaatataaaa aaaagtgtgt caaggccg 48

<210> SEQ ID NO 80
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 80
agtttattaa ccacttaacc tctcagaact gaacaaagac aacattgttc ctggaacgcc 60
ctctttttaa aaaag 75

<210> SEQ ID NO 81
<211> LENGTH: 159
<212> TYPE: DNA
<213> ORGANISM: Artificial Sequence
<220> FEATURE:
<223> OTHER INFORMATION: Synthetic polynucleotide

<400> SEQUENCE: 81
atgacaacgg caacacgaca agaagtcctt ggcctctacc gcagcatttt caggcttgcg 60
aggaaatggc aggcgacatc agggcagatg gaagacacca tcaaagaaaa acagtacata 120
ctaaatgaag ccagaacgct gttccggaaa aacaaaaat 159

<210> SEQ ID NO 82
<211> LENGTH: 451
<212> TYPE: DNA
<213> ORGANISM: Artificial Sequence
<220> FEATURE:
<223> OTHER INFORMATION: Synthetic polynucleotide

<400> SEQUENCE: 82
ccattcgtta tctatgacat gaattcctta atgatgggag aagataaaat caagttcaaa 60
cacatcaccc ccctgcagga gcagagcaaa gaggtggcca tccgcatctt tcagggctgc 120

-continued

```
cagtttcgct ccgtggaggc tgtgcaggag atcacagagt atgccaaaag cattcctggt    180

tttgtaaatc ttgacttgaa cgaccaagta actctcctca aatatggagt ccacgagatc    240

atttacacaa tgctggcctc cttgatgaat aaagatgggg ttctcatatc cgagggccaa    300

ggcttcatga caagggagtt tctaaagagc ctgcgaaagc cttttggtga ctttatggag    360

cccaagtttg agtttgctgt gaagttcaat gcactggaat tagatgacag cgacttggca    420

atatttattg ctgtcattat tctcagtgga g                                   451
```

```
<210> SEQ ID NO 83
<211> LENGTH: 76
<212> TYPE: DNA
<213> ORGANISM: Artificial Sequence
<220> FEATURE:
<223> OTHER INFORMATION: Synthetic polynucleotide

<400> SEQUENCE: 83

cccggaggaa ccacccccgc cctcctcagc ctgatcctgg aagagactcg gggcccccca     60

gcctccgcca acccag                                                     76
```

```
<210> SEQ ID NO 84
<211> LENGTH: 73
<212> TYPE: DNA
<213> ORGANISM: Artificial Sequence
<220> FEATURE:
<223> OTHER INFORMATION: Synthetic polynucleotide

<400> SEQUENCE: 84

gatcccagga tgctggtatc ctgcatagat ttcaggtaca tcactgatgt cctgactgag     60

gaggatgccc tag                                                        73
```

```
<210> SEQ ID NO 85
<211> LENGTH: 260
<212> TYPE: DNA
<213> ORGANISM: Artificial Sequence
<220> FEATURE:
<223> OTHER INFORMATION: Synthetic polynucleotide

<400> SEQUENCE: 85

ggccagactt tggcagcgtg taaggtctga ggacaggggc accggaggcc gaggatgaga     60

ggccagtgcc tgtttccagg cagccagggc ctcagaaact ccggccggag cactcacccg    120

tcggtggagg ccgttaccag ggccacctta tttgcgagcg ggtcccggcg ggtcatcccg    180

gagctggcca tccgcaccga attccaagcc cgggcacaga ggcctagcag ccccgccttg    240

tgcatggatc agaccagcaa                                                260
```

```
<210> SEQ ID NO 86
<211> LENGTH: 375
<212> TYPE: DNA
<213> ORGANISM: Artificial Sequence
<220> FEATURE:
<223> OTHER INFORMATION: Synthetic polynucleotide

<400> SEQUENCE: 86

gaaaaatacc taggttagaa ttactaaatt aaaaaatgga cacttggggc caggcgcagt     60

ggcttacgcc tgtaattcca ccactttggg gagctgaggc gggcagatca cttgacatcg    120

agagttcaag accagcctga ccaacatgga gaaaccccgt ctctactaaa aatacaaaaa    180

attatccaga cgtagtggca catgcctgta atctcagcta cttgggaggc tgaggtagga    240

gaatcgcttg aacccgggag gcagaggttg tggtgagccg agatcatgcc attgaactcc    300
```

agcctgggca acaagagcga aactccgtct ccaaaaaaaa aaaaagacac ttatttaggc 360
tttccatata tcatg 375

<210> SEQ ID NO 87
<211> LENGTH: 202
<212> TYPE: DNA
<213> ORGANISM: Artificial Sequence
<220> FEATURE:
<223> OTHER INFORMATION: Synthetic polynucleotide

<400> SEQUENCE: 87
ctgggtgaag gggttggagc atgacaagca ggagacagac gttcacttca actccctgac 60
tggggagggg aacttcaatt ggcgctttgt gttccgcttt gactacctgc ccacggagcg 120
ggaggtgagc gtccggcgca ggtctggacc ctttgccctg gaggaggcgg agttccggca 180
gcctgcagtg ctggtcctgc ag 202

<210> SEQ ID NO 88
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 88
agaaccagag gacgaaaacg aagcttcgtt cctgaggaag aaaaacatga ggttggaata 60
ag 62

<210> SEQ ID NO 89
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 89
agaaccagag gacgaaaacg aagcttcgtt cctgaggaag aaaaacatga ggttggaata 60
a 61

<210> SEQ ID NO 90
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 90
gccagtgaca tatcaggcat ttcgggaatg tacactggag accacagttc atgccagcgg 60
ctggaataag 70

<210> SEQ ID NO 91
<211> LENGTH: 186
<212> TYPE: DNA
<213> ORGANISM: Artificial Sequence
<220> FEATURE:
<223> OTHER INFORMATION: Synthetic polynucleotide

<400> SEQUENCE: 91
gtcatccacc ggctgcccat gcccaacctg aaggacgagc tgcatcactc aggatggaac 60
acctgcagca gctgcttcgg tgatagcacc aagtcgcgca ccaagctggt gctgcccagt 120
ctcatctcct ctcgcatcta tgtggtggac gtgggctctg agccccgggc cccaaagctg 180
cacaag 186

<210> SEQ ID NO 92
<211> LENGTH: 91
<212> TYPE: DNA
<213> ORGANISM: Artificial Sequence
<220> FEATURE:
<223> OTHER INFORMATION: Synthetic polynucleotide

<400> SEQUENCE: 92
gaactcagag tggttttcca gatgggaatc acattgctct ctgtccctga gatcttgctg 60
gagacagggc tactcagtcc ctctttgcca g 91

<210> SEQ ID NO 93
<211> LENGTH: 101
<212> TYPE: DNA
<213> ORGANISM: Artificial Sequence
<220> FEATURE:
<223> OTHER INFORMATION: Synthetic polynucleotide

<400> SEQUENCE: 93
atggagaaaa caaaggattc agattgaagg actgctcaga caccctccga agaggtggcc 60
ctgcctgcgc tcctcctggc tgcagagtac cccaccagcg c 101

<210> SEQ ID NO 94
<211> LENGTH: 352
<212> TYPE: DNA
<213> ORGANISM: Artificial Sequence
<220> FEATURE:
<223> OTHER INFORMATION: Synthetic polynucleotide

<400> SEQUENCE: 94
gcctacttgg gtgtccccgc ctctgatacc tccctgctgg aggaaacagc aggaaaagag 60
aaccaggcag gcaggcagac atccccacgg agcagcgttg ggcccccaag gtgcctgacc 120
cacttcctag agtactgaac agtcccagag tgtcacagct gatgtgcagg acagcctgga 180
gctctcacct tcaacacggg gtgtacctga gacttccagt ggatgagggt cagcctctgg 240
agctgtgaaa acctgggccg acagcggagg cagagctgca ctaatgttcc cacacgagtc 300
cttcccaccc aacaccttgg tgcagggaga cggaaggagc ctggagccag gg 352

<210> SEQ ID NO 95
<211> LENGTH: 147
<212> TYPE: DNA
<213> ORGANISM: Artificial Sequence
<220> FEATURE:
<223> OTHER INFORMATION: Synthetic polynucleotide

<400> SEQUENCE: 95
gtctggtgaa gttcaagggc atcttgaacg tggtgcactt ggagacagtg agggaagcag 60
gggtgaagtg gctgctacct gagtcccttc tggagctcca ttttgcttgg tcttggagaa 120
ggcttctcag ctgccctccc agctagt 147

<210> SEQ ID NO 96
<211> LENGTH: 162
<212> TYPE: DNA
<213> ORGANISM: Artificial Sequence
<220> FEATURE:
<223> OTHER INFORMATION: Synthetic polynucleotide

<400> SEQUENCE: 96
tggtgcagtt ctcggcctct cggcctggct tcctgacctt ctgggaccag tgcacagaga 60
gactcagctg cttcctctgc ccggtggagc gggtgcttct caccttctgc aaccagtatg 120
gtgcccgcct ctccctgcgc cagccaggct tggctgaggc tg 162

<210> SEQ ID NO 97
<211> LENGTH: 124
<212> TYPE: DNA
<213> ORGANISM: Artificial Sequence
<220> FEATURE:
<223> OTHER INFORMATION: Synthetic polynucleotide

<400> SEQUENCE: 97
atgtgattga tctcactgga gatgataaag atgatcttca gagagcaatt gccttgagtt 60
tggccgaatc aaacagggca ttcagggaga ctggaataac tgatgaggaa caagccatta 120
gcag 124

<210> SEQ ID NO 98
<211> LENGTH: 118
<212> TYPE: DNA
<213> ORGANISM: Artificial Sequence
<220> FEATURE:
<223> OTHER INFORMATION: Synthetic polynucleotide

<400> SEQUENCE: 98
agtcttgctg cgacacccag gctggagtgc aatggcgcta tctcggctca ctgcaacctc 60
cgcttcccgg attcaagcga ttctcctgcc tcagcctccc gagtaggtgg gactacag 118

<210> SEQ ID NO 99
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 99
agagtatgat ggaaggtctg atcttcatgt tggaataact aacacaaatg 50

<210> SEQ ID NO 100
<211> LENGTH: 279
<212> TYPE: DNA
<213> ORGANISM: Artificial Sequence
<220> FEATURE:
<223> OTHER INFORMATION: Synthetic polynucleotide

<400> SEQUENCE: 100
attttcaccg ctatgcctcc tttcactctg ggagtcttcc agaggtcttg cactcgggag 60
agcatgctca ggtttcccca gctctacaaa atcacccaga atgccaaaga cttcaacaca 120
agggtaaata aggttgatct cagaattgtc acctcaaaaa ggccctgcct tccactgttc 180
agttctggtc atctgcctat gagatatctg aagcttgaaa gagaacactt gaaaatcact 240
gagaccgtga ctcccatccc agcacacaca gcaagccaa 279

<210> SEQ ID NO 101
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 101
agaggtcatg actttcatga aggcgttaga gctg 34

<210> SEQ ID NO 102
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 102
gaccaaatcc tcagctgtcc tcttcatctt gatcttctct ctgatcttca agctggagga 60
gctg 64

<210> SEQ ID NO 103
<211> LENGTH: 121
<212> TYPE: DNA
<213> ORGANISM: Artificial Sequence
<220> FEATURE:
<223> OTHER INFORMATION: Synthetic polynucleotide

<400> SEQUENCE: 103
gatccaggca atctttccag acacatctac ttcccagtaa tatttccccg aagagaaata 60
ttggcagccg aagacaccaa aagcagaaaa atcacatgga tttgaattct taaatgtgca 120
g 121

<210> SEQ ID NO 104
<211> LENGTH: 217
<212> TYPE: DNA
<213> ORGANISM: Artificial Sequence
<220> FEATURE:
<223> OTHER INFORMATION: Synthetic polynucleotide

<400> SEQUENCE: 104
taacagatct gattctgcag ctgatcaagg atgacactgg tgagaaccct atgagggagt 60
gaagcagcct ggactcttac cacaagaggg aggtgttata agagcaatgc agaggttgga 120
gtgggcagca gttggggcag gaggaagccg actgctgcct ggtctgcaaa gaagtccttt 180
caagtctcta ggactggact cttcctaagc aagtccg 217

<210> SEQ ID NO 105
<211> LENGTH: 210
<212> TYPE: DNA
<213> ORGANISM: Artificial Sequence
<220> FEATURE:
<223> OTHER INFORMATION: Synthetic polynucleotide

<400> SEQUENCE: 105
aatctttaat gaactgaaaa ctaaaatgct taatataaaa gaatataagg agaaactctt 60
gagtaccttg ggcgagtttc tagaagacca ttttcctctg cctgatagaa gtgttaaaaa 120
gaaaaagttc caaaagctga gacaagatct tgaaatggta ctgtccacta aggagtcaaa 180
gaatgaaaag ttaaaggaag acttagaaag 210

<210> SEQ ID NO 106
<211> LENGTH: 826
<212> TYPE: DNA
<213> ORGANISM: Artificial Sequence
<220> FEATURE:
<223> OTHER INFORMATION: Synthetic polynucleotide

<400> SEQUENCE: 106
aacttcgata tgacctgcca gcatcataca agtttcacaa aaagaaatca gtaagtctct 60
tgattttggc tggtctacat tcggtattga aaagctttct gggccggatg tggtggttca 120
tgcctgtaat cccagctact cgggaggctg aggcaagaga atcgcttgaa ctcaggaggc 180
agaggttgca gtgagctgag attgccccac tgaactccag cctgcgcgat aagagtgaga 240
ctcagtctcg aaaaagaaaa aaaaaggaaa gctttgtgac aagtaattat ttctagtgtt 300
accaactttc ctgtgtaaat atacaaagcc agcctaggag acaccataaa tggcctgtgg 360
gaaaggccca tcgtcaatag ctaatattct agttctttcc taaatgcttt gggtacaaaa 420
agaaaaaaaa aatcaaaaac tgtttttgct cttttcatat agtatatatt ttattagtta 480
gtttgtacta atacattctc atattacaaa ggcaatttaa tggaagaatc ttccttttga 540
tatttgaatc atctgaaata acacaaacag aacaatacat tcaaagaaat ctcatttgca 600
taacaaaaag acaagttaaa caacaaaaaa atttttcctt tctcacaggt ggacattgaa 660
gtggacctaa ttcggttttc cttttaaaag ccccgcaaac aaaagtcgtt taaaacctat 720
ttaaaatgaa taaaaaattg gttggacaga tatggctttt ctaaagactg ctttggaaat 780
ggcaagaaca gcagtatatt ccttacacaa atcctcaact agagaa 826

<210> SEQ ID NO 107
<211> LENGTH: 266
<212> TYPE: DNA
<213> ORGANISM: Artificial Sequence
<220> FEATURE:
<223> OTHER INFORMATION: Synthetic polynucleotide

<400> SEQUENCE: 107
attccaagtc acaataccac tgaagttcag aaacacattc ctctctgtgc cttactctca 60
agtaatccta attttcattt cactggaaaa tggtattttg aagactgtgg aaaggaaggc 120
tatgggtttg tttgtgaaaa aatgcaagtg ccttctgctg aatatcccca aagacccaag 180
cagttggaag aactggacgc atgctcaaca tttctgtgct gaagaagggg ggaccctggt 240
cgccattgaa agtgaggtgg agcaag 266

<210> SEQ ID NO 108
<211> LENGTH: 445
<212> TYPE: DNA
<213> ORGANISM: Artificial Sequence
<220> FEATURE:
<223> OTHER INFORMATION: Synthetic polynucleotide

<400> SEQUENCE: 108
agagagagag agagagagag gagaggaggg gcggggtggg ggaggagggg agtggggaga 60
gagaaagaga gaaacaccaa aaagacattt tcaaggaagg aagaaaatta gatggcaacc 120
ccctgtcccc tccccctaag aaaatcctct ctgagattaa actgtgtgaa gattagaggc 180
gtgtaggtca ggagcaggag gaagcccaac gctggactgt accagatcat ctaaaactgg 240
caattccagg cacagaaaac cagttcttca gaagcagaag ggtggtcagc caggggtga 300 aagggacagg ggtctcgcag ccagtttcca acatggctag atccatcaga aactgaagcc 360
gtggagaacg ctctcggggc ctttgccact tcttggagta gaagccgaca gagagctgtt 420
tggaaacttc tccttcacac accag 445

<210> SEQ ID NO 109
<211> LENGTH: 389
<212> TYPE: DNA
<213> ORGANISM: Artificial Sequence
<220> FEATURE:

<223> OTHER INFORMATION: Synthetic polynucleotide

<400> SEQUENCE: 109
gagagagaaa gagagaaaca ccaaaaagac attttcaagg aaggaagaaa attagatggc 60
aaccccctgt cccctccccc taagaaaatc ctctctgaga ttaaactgtg tgaagattag 120
aggcgtgtag gtcaggagca ggaggaagcc caacgctgga ctgtaccaga tcatctaaaa 180
ctggcaattc caggcacaga aaaccagttc ttcagaagca gaagggtggt cagccagggg 240
gtgaaaggga caggggtctc gcagccagtt tccaacatgg ctagatccat cagaaactga 300
agccgtggag aacgctctcg gggcctttgc cacttcttgg agtagaagcc gacagagagc 360
tgtttggaaa cttctccttc acacaccag 389

<210> SEQ ID NO 110
<211> LENGTH: 565
<212> TYPE: DNA
<213> ORGANISM: Artificial Sequence
<220> FEATURE:
<223> OTHER INFORMATION: Synthetic polynucleotide

<400> SEQUENCE: 110
gcctggcgct gctgctgccg cccgtcaccc tggcagccct ggtggacagc tggctccgag 60
aggactgccc agggctcaac tacgcagcct tggtcagcgg ggcaggcccc tcgcaggcgg 120
cgctgtgggc caaatcccct ggggtactgg cagggcagcc tttcttcgat gccatattta 180
cccaactcaa ctgccaagtc tcctggttcc tccccgaggg atcgaagctg gtgccggtgg 240
ccagagtggc cgaggtccgg ggccctgccc actgcctgct gctgggggaa cgggtggccc 300
tcaacacgct ggcccgctgc agtggcattg ccagtgctgc cgccgctgca gtggaggccg 360 ccagggggc cggctggact gggcacgtgg caggcacgag gaagaccacg ccaggcttcc 420
ggctggtgga gaagcggtgc gggcggccag acaggcggct gacttcactc tgaaggtgga 480
agtggaatgc agcagcctgc aggaggccgt gcaggcagct gaggctggtg ccgaccttgt 540
cctgctggac aacttcaagc cagag 565

<210> SEQ ID NO 111
<211> LENGTH: 270
<212> TYPE: DNA
<213> ORGANISM: Artificial Sequence
<220> FEATURE:
<223> OTHER INFORMATION: Synthetic polynucleotide

<400> SEQUENCE: 111
tggacatttt cctacatcgg cttccctgta gagctgaaca cagtctattt cattggggcc 60
cataatattc ctaatgcaaa tatgaatgaa gatggccctt ccatgtctgt gaatttcacc 120
tcaccaggaa gcctgtggga tccgaacatc actgcttgta agaagaatga ggagacagta 180
gaagtgaact tcacaaccac tcccctggga aacagataca tggctcttat ccaacacagc 240
actatcatcg ggttttctca ggtgtttgag 270

<210> SEQ ID NO 112
<211> LENGTH: 381
<212> TYPE: DNA
<213> ORGANISM: Artificial Sequence
<220> FEATURE:
<223> OTHER INFORMATION: Synthetic polynucleotide

<400> SEQUENCE: 112
aaagcataac ccctactgta gaactaaatg cactgtgcat gaaacttgga aaaaaaccaa 60
tgtataagcc tgttgaccct tactctcgga tgcagtccac ctataactac aacatgagag 120
gaggtgctta tcccccgagg ggctgcgggc gcctgagcgg ctcttcagcg tttgcgccgg 180
cggctgccgc gtctctctcg gctcccgctt cctttgaccg cctcccccccc ccggcccggc 240 ggcgcccgcc tcctccacgg ccactccgcc tcttccctcc cttcgtccct tcttcctctc 300 cctttttcc ttcttccttc ccctcctcgc cgccaccgcc caggaccgcc ggccggggga 360
cgagctcgga gcagcagcca g 381

<210> SEQ ID NO 113
<211> LENGTH: 325
<212> TYPE: DNA
<213> ORGANISM: Artificial Sequence
<220> FEATURE:
<223> OTHER INFORMATION: Synthetic polynucleotide

<400> SEQUENCE: 113
agagtaccca gagaaggaga agccagcaaa ggagacgaca cagacaagac ctcagagatc 60
aaaggaagag gccccttaat atcctggaat aatgggaccc atccccgtaa tcagtgaatc 120
tcatccaccc gcttgccagc ttctacccgc agcaagtaga agctaagtcc tggctcaaat 180
ctcttccctc cctccctctc ccagctgtca gtgcttttgg acttgtgctc agctcacgga 240
cacagaccta attaaacagt gtatagatga atgcacagcc aggattgaaa ttggactgca 300
ttacaagatt ccttacccaa ggcca 325

<210> SEQ ID NO 114
<211> LENGTH: 880
<212> TYPE: DNA
<213> ORGANISM: Artificial Sequence
<220> FEATURE:
<223> OTHER INFORMATION: Synthetic polynucleotide

<400> SEQUENCE: 114
ccatcaggtt tgggcggatg ccacaggccg agaaggagaa gctgttggcg gagatctcca 60
gtgatatcga ccagctgaat ccagagtccg ctgacctccg ggccctggca aaacatttgt 120
atgactcata cataaagtcc ttcccgctga ccaaagcaaa ggcgagggcg atcttgacag 180
gaaagacaac agacaaatca accgcccagg tttgctgaat gtgaagccca ttgaagacat 240
tcaagacaac ctgctacaag ccctggagct ccagctgaag ctgaaccacc ctgagtcctc 300
acagctgttt gccaagctgc tccagaaaat gacagacctc agacagattg tcacggaaca 360
cgtgcagcta ctgcaggtga tcaagaagac ggagacagac atgagtcttc acccgctcct 420
gcaggagatc tacaaggact tgtactagca gagagtcctg agccactgcc aacatttccc 480
ttcttccagt tgcactattc tgagggaaaa tctgacacct aagaaattta ctgtgaaaaa 540
gcattttaaa aagaaaaggt tttagaatat gatctatttt atgcatattg tttataaaga 600
cacatttaca atttactttt aatattaaaa attaccatat tatgaaattg ctgatagtat 660
ttgaagactg agtcttgtgt gtttcccacc ctagccccca ggctttcttt tttacccctt 720
ttccttctcc cctccctccc tccatccctc tcactcttcc tccctccctt ccctcctttc 780
cttcttcctt tatttttctt ttctttctta gacattttaa aatatgtgag tggaactgct 840
gatacacttt cattctcagt aaattaattt tttactcaat 880

<210> SEQ ID NO 115
<211> LENGTH: 194
<212> TYPE: DNA

-continued

<213> ORGANISM: Artificial Sequence
<220> FEATURE:
<223> OTHER INFORMATION: Synthetic polynucleotide

<400> SEQUENCE: 115
acaaagatca ttccactcag cctgggacga tggggaggaa aaaaatccag atctcccgca 60
tcctggacca aaggaatcgg cagcgccgtg aagaacctgg tggacagcag cgtctacttc 120
cgcagcgtgg agggtctgct caaacaggcc atcagcatcc gggaccatat gaatgccagt 180
gcccagggcc acag 194

<210> SEQ ID NO 116
<211> LENGTH: 110
<212> TYPE: DNA
<213> ORGANISM: Artificial Sequence
<220> FEATURE:
<223> OTHER INFORMATION: Synthetic polynucleotide

<400> SEQUENCE: 116
agaagcaaat gctggcacaa ggataccctg cttacacgac atcgtgcgcc tggctggggt 60
actcagatga cacgttgaag cagcctgtct ggaagttact tgtggacatg 110

<210> SEQ ID NO 117
<211> LENGTH: 1101
<212> TYPE: DNA
<213> ORGANISM: Artificial Sequence
<220> FEATURE:
<223> OTHER INFORMATION: Synthetic polynucleotide

<400> SEQUENCE: 117
gtgccacttc ggataaaccc tttggactcc taactccaat caggtgtctg ctttgttgag 60
gactcacaga cacagtctcc tttcttcaag atctttacaa tgcaagacct cactaacaca 120
cagggatggt ctcccagagg gtctgtgctg ttccttcact cagaacatca agatgcactg 180
aagtaaggat cctctattct acagttcctg ctagctgagc tattccatgg gggcttcagc 240
aggaaattcc aaggttggct ttgacaagct aaggccggct ggtggagcac atcgagttct 300
ggaggttcat gtgtgttttc atgaagatct gtctgcccgt agcagataaa gagttgttgc 360
cccactcctc ctggggtctt ctattttcct gggaggaatt tctggattaa ctgaacacac 420
acacacacac acacaccctt ttgaagcatc aacagtaatt ctgagttctt agggacaatg 480
cagattaaat ccacaataag aaagacaact atggccaggt gtggtggctc acgcctgtaa 540
tcccagaact ttgggaggct gaggcggatg gatcacctga ggtcaggagt tagagaccaa 600
cctgaccaac atggagaaac cccgtttcta ctaaaaatgc aaaattagcc gggcatggtg 660
gcaggcgcct gtaatcccaa atactcggga ggctgaggca ggagaatcac ttaaacccgg 720
gaggcagagg ttgcagtgag ccaagatcgc gccattgcac tccagcacat gggccccgtc 780
ctgggccaaa cgccgggcga tggcgaagcc gatcctgtga gcagaaagag acaaagactg 840
ctaaggcctg tgcaggggaa gaggtcgaca gtatgagctc tgaagttaag actgcccggg 900
tttgaattct ggctctttct ctatataacc cctacgtgtg cctactatgt gtaaaacagg 960
cttaatggca tggccatttt tggcattcct ttacttgttt ttattatgac ctggaccaca 1020
gcctcagttc ccaagaactg acatcacttt ctacagttcc caccatgggt gacaggcttc 1080
atcccctctt gggactgaga g 1101

<210> SEQ ID NO 118
<211> LENGTH: 408

<212> TYPE: DNA
<213> ORGANISM: Artificial Sequence
<220> FEATURE:
<223> OTHER INFORMATION: Synthetic polynucleotide

<400> SEQUENCE: 118
cgcagaatct aggcctgctc tggccagatc agtttcgaag accgtcgctc cgaaggaggc 60
acctctcgtt tcaagcctag tgacctcgat gcttttaggt tgcagcatac tggagagctc 120
tggcttgctt cgtgaaggct tagggagaac ttcattaggg ctggaaaagg gtggccaatg 180
tttgatttac tgcagttgtg ctttgcatat cggaaatgct ggctaaataa acggtatcaa 240
actaactctg aaagaacggc gccgcaaata acagcaccca attaaagaac cacaggattt 300
tagagattaa atgatctttt tgagatccaa gtacatctca tgggaagaca tgtaaggaat 360
ttgcataaga cagttatgca aaatggagct ggaggagctt tatttgtg 408

<210> SEQ ID NO 119
<211> LENGTH: 386
<212> TYPE: DNA
<213> ORGANISM: Artificial Sequence
<220> FEATURE:
<223> OTHER INFORMATION: Synthetic polynucleotide

<400> SEQUENCE: 119
gatccctgga gttgcagcta ccagacatgg tgcgtggggc ccggggcccc gagctctgct 60
ctgtgcagct ggcccgcaat ggggccgggc cgaggtgcaa tctgtttcgc tgctgccgcc 120
gcctgagggg ctggtggccg gtagtgaagc tgaaggaggc agaggacgtg gagcgggagg 180
cgcaggaggc tcaggctggc aagaagaagc gaaagcagag gaggaggaag ggccggccag 240
aagacctgga gttcacagac atgggtggca atgtgtacat cctcacgcta tgagctcaga 300
gttgtcatct ggaacacgga ggatgtggtt ctggacgacg agaatccact caccggagag 360
atgtcgagtg acatctatgt gaagag 386

<210> SEQ ID NO 120
<211> LENGTH: 1610
<212> TYPE: DNA
<213> ORGANISM: Artificial Sequence
<220> FEATURE:
<223> OTHER INFORMATION: Synthetic polynucleotide

<400> SEQUENCE: 120
gcagtgctcg gaatgtgacc aggcagggag cagtgacatg gaagcagata tggccatgga 60
aaccctacca gatggaacca aacgatcaag gaggcagatt aaggaaccag tgaaatttgt 120
tccacaggat gtgccaccag aacccaagaa gattccgata agaaacacgg aaagagttcc 180
tagagagaga agacaaagac agtctgtgtt gcaaaagaag cccaaggctg aagatttaag 240
aactgaatgt gcaacttgca agggaactgg agacaatgaa aatcttgtca ggtaagttgg 300
atgctaaaac cttgtcttta ggggatgaaa gttctatatt tattttctca tcacagaaaa 360
aatgaaaaaa caattgcagg ataagacctt tcttaaaata ttatatagtg gaaacagtac 420
tttagaaaca gatttcatcc acttcttaac ctctcacaca tggttatact ctggatttaa 480
atgtaaataa gagtgataat ctgcctgttt aacacaggga attatttttc tcttgacaag 540
agaaattgac agtgctctct atttagaggc catgaaagta atttgatcta aacactgtgt 600
actaagatta ttatgtttta tgtcagaaaa caataaagtt actaagctct gttagcatat 660
tctaaatgtt tgaaatttag aagcaatggt gagaagacag actttttatt gacaagaact 720

-continued

```
taattagcac tttcttattg cttatcaaaa caaatgtgtt aaatgcttct cccttacgaa    780

ataaagaaag gtgaaaagat ggcctaggtt gattttattt tttgttttgt ctttgtttct    840

ttgtttcgtt ttggtacttt attttttttt aatcagacat aatgctaatc agaaatctta    900

gctgatgctg cacattggct tttcccaacg gtccagaggc tgctaatttt agcggaaatg    960

aagacattga tcaaagctct ggtgagatgg gggagtgagt gtgtgaacaa aaagagagct   1020

aatttaaaag aggcatcaga ctttcaaagg acagtgtcac aaaagttctt acagttctta   1080

cagggacttt gtaagggaat ccattcttat ttctttaaaa aattgtcttc tggtaaagcc   1140

ctgttaaatt aactgaggac acagaaatta aacatttcaa aaagaataaa catattgata   1200

aaacaaatat attagtgttg ttgtatgttt ttaaatactt acttccaaat gatttaatct   1260

attttggtca ttaaaatatg tcttaatttc tcaaagaaag gcatgaagtc ttaaatttta   1320

tgagtttttt atgctatcaa tgagaaagat aaagtaaaaa ttacagtaga aaaagacaaa   1380

gtccttcaac aaagttaaga aagtttataa taattggcta atttttttga ggtagttcat   1440

gtagagtgtg ttgggagcta tcctgaaggt taagtttatt aaaatttagg gtaaagtagt   1500

aagtagttcc aagttcagga gatacacctg aataattctg accacagtat aaattttgca   1560

atatgtcgaa aatgaaatcc caagcataag cgtaacataa tggagtaaat              1610
```

<210> SEQ ID NO 121
<211> LENGTH: 291
<212> TYPE: DNA
<213> ORGANISM: Artificial Sequence
<220> FEATURE:
<223> OTHER INFORMATION: Synthetic polynucleotide

<400> SEQUENCE: 121

```
gcagtgctcg gaatgtgacc aggcagggag cagtgacatg gaagcagata tggccatgga     60

aaccctacca gatggaacca aacgatcaag gaggcagatt aaggaaccag tgaaatttgt    120

tccacaggat gtgccaccag aacccaagaa gattccgata agaaacacgg aaagagttcc    180

tagagagaga agacaaagac agtctgtgtt gcaaaagaag cccaaggctg aagatttaag    240

aactgaatgt gcaacttgca agggaactgg agacaatgaa aatcttgtca g             291
```

<210> SEQ ID NO 122
<211> LENGTH: 2565
<212> TYPE: DNA
<213> ORGANISM: Artificial Sequence
<220> FEATURE:
<223> OTHER INFORMATION: Synthetic polynucleotide

<400> SEQUENCE: 122

```
gggttcaact agatatagct tcacaatctc tggatcaaga aattttatta aaagttaaaa     60

ctgaaattga agaagagcta aaatctctgg acaaagaaat ttctgaaggg cactgtgttt    120

agtcttgagt cagaggagga ggaataccct ggaatcactg cagaagatag caatgacatt    180

tacatcctgc ccagcgacaa ctctggacaa gtcagtcccc cagagtctcc aactgtgacc    240

acttcctggc agtctgagag cttacctgtg tcactgtcag ctagccagag ttggcacaca    300

gaaagcctgc cagtgtcact aggccctgag tcctggcagc agattgcaat ggatcctgaa    360

gaagtgaaaa gcttagacag caacggagct ggagagaaga gtgagaacaa ctcctctaat    420

tctgacattg tgcacgtgga gaaagaagag gtgcccgagg gcatggaaga ggctgctgtg    480

gcttctgtgg tcttgccagc gcgggagctg caagaggcac ttcctgaagc cccagctccc    540

ttgcttccac atatcactgc cacctccctg ctggggacaa gggaacctga cacagaagtg    600
```

-continued atcacagttg agaaatccag ccctgctaca tctctgtttg tagaacttga tgaagaagag 660
gtgaaagcag caacaactga acctactgaa gtggaggagg tggtccccgc actggaaccc 720
acagaaacgc tgctgagtga gaaggagata aacgcaaggg aagagagcct tgtggaagag 780
ctgtcccctg ccagcgagaa gaagcccgtg ccgccgtctg agggcaagtc tagactgtcc 840
cccgccggtg agatgaagcc catgccgctg tctgagggca agtctatact gctgtttgga 900
ggggctgctg ctgttgccat cctggcagtg gccatcgggg tagccctggc tctgagaaag 960
aaataggagg cttttcagaa gagaaagaca gaaggatgta aggttggagt tgtattggct 1020
ggaatttgaa cctccagcag ctgtctggac atttgtggaa cactctggga taattgggga 1080
cttctgctca acatggcagt ggcatgttag gcatgttagg gcttgaggtg gggcattcac 1140
attcatctga ctgtaaatcc caagggcctc cgctcatgct aaattgagaa tcttaggggt 1200
aaagcacccc ctccaggacc gggtttctca gccttggcac tagtgctgtt ctgaccattc 1260
tctgtgttgg ggctgtcctg tgtgtggtgg gctccaccca ctagatgcca gtggcacccc 1320
ctcccagaga tgacaaacga aaatgtctct agacattgcc aaatgtcccg tgtgaacatc 1380
ccctattgag acccactgct ttagcgagag agggtttact taggaagaat tgggatagaa 1440
attcccagct gagagaactt agctgtgggc tcctcagcta ctgacttctt agctcttaat 1500
ccccttagaa tttcatcttt ctcgatgagc aggctctgca cccactcttt ttttgccccc 1560
cgccctcatc ctggagtgtg agggtgctcg cccgtactct cagctgcctc tcagggactg 1620
cactgttcct cttcaccccc aggttcctgc taagatccca cgggcgaggg cttgctctgg 1680
actcagtctg tcaagtcccc gaagcttcct gcagctccac cttgtaaaaa tgctgccttt 1740
gggaatcttc gaaatatgta cacagagaaa atcacatgaa ggagacctgg ggtccccact 1800
tgtgagtgca actgcaagta actctggcta gagagacaca tgtgtcttgt gtcaaggcag 1860
gaggataacc tggatgacct tctgaggtct cttcagccct tttcgctagt ggtcacccac 1920
caccatggtt acttgccagc aacatctcta ttgctggatg gtccctgtct ataaccttgg 1980
gctagtatat tttttccaat atgggacctt agtcttacta ctgatgagtt ctatgggtct 2040
cttgctaggg ggtaaggatt tttattcttg ggcttataga gccagttaga tcataattct 2100
tatgaaatag agagtgtcct aaatatcact gaaataaaaa gtaggaaaaa gaagcttgaa 2160
ttttaagact gaggctgctc tgcagattct agtttggctt tcagagttca agagtggtgg 2220
catcttcacc tgaattcttc aatgccaggg taataaacca aaatagtcct aatcagtata 2280
tgctagttga gcatcggcat aattttcttt cctctggctg atcccagccc taaaggaagg 2340
gtagacccgt gtctttccag ccctaaagga agggtagacc cgtgtctttc cagccctaaa 2400
ggaagggcag acccgtgtct ttccatgccc gagggccacg acgtcactat gcagggcaca 2460
cgtggcttgg tttaaaaagg tcatcttaga tttatcttag taaatgtaat aaattatttt 2520
ttagatcttg aaatttataa taaaaatact ttacctaccc tgatc 2565

<210> SEQ ID NO 123
<211> LENGTH: 178
<212> TYPE: DNA
<213> ORGANISM: Artificial Sequence
<220> FEATURE:
<223> OTHER INFORMATION: Synthetic polynucleotide

<400> SEQUENCE: 123
gtcattgagc ccaaggacat ccatgccaag tgcgaactgg cctttctcca caccagccac 60

-continued tgcctggcca gcggggaagt gatgatcagc tccctgggag acgtcaaggg caatggcaaa 120
gctacgaaat gtgggaattg tggacccggc tactccaccc ctctggaggc catgaaag 178

<210> SEQ ID NO 124
<211> LENGTH: 246
<212> TYPE: DNA
<213> ORGANISM: Artificial Sequence
<220> FEATURE:
<223> OTHER INFORMATION: Synthetic polynucleotide

<400> SEQUENCE: 124
gttgattcca taccctggct attgtgaata atgctgcagt gaacatggga gtacatacat 60
ctgtttgagg taatctgttc cagaagaaac atgtgtcgtt ctgactgagc ccctgcctgt 120
ctgtcacctt aagagccagt caattcatat ggtccccata tcaaagtctc ctgtgcccag 180
agagaggatt tcatttcaac catcaccatc accaccatca tcatcatcac caagagatgt 240
tgttga 246

<210> SEQ ID NO 125
<211> LENGTH: 359
<212> TYPE: DNA
<213> ORGANISM: Artificial Sequence
<220> FEATURE:
<223> OTHER INFORMATION: Synthetic polynucleotide

<400> SEQUENCE: 125
ggttcatagt ggcgtcatgc acgcagactc ctgcaagttc ccctaagttc ttagaggact 60
gctttgcctt ttgatctgag agttgcaaag ttccataaag aatggccctt gtggataagc 120
acaaagtcaa gagacagcga ttggacagaa tttgtgaagg agatccaggg ttgccagaag 180
acgagacaac cgtgattgca tgtgcggagg ttcctcgatg gaagcgcagc ccggcgcgcc 240
cctcagctgg cctggccagg ccctatgaag gtcacgcgaa aaccctgctg cgggcttctt 300
agcgaccgca ttacgtggac tagcgggcaa gaaaagcctg gtcggcgctg ccctcacag 359

<210> SEQ ID NO 126
<211> LENGTH: 270
<212> TYPE: DNA
<213> ORGANISM: Artificial Sequence
<220> FEATURE:
<223> OTHER INFORMATION: Synthetic polynucleotide

<400> SEQUENCE: 126
aggcgtctgg ccaggtggcg ctccgggcag ctagaagaag tcttcacttc ccaggagagc 60
caaagcgtgt ctggccctag gtgggaaaag aactggctgt gacctttgcc ctgacctgga 120
agggcccagc cttgggctga atggcagcac ccacgcccgc ccgtccggtg ctgacccacc 180
tgctggtggc tctcttcggc atgggctcct gggctgcggt caatgggatc tgggtggagc 240
tacctgtggt ggtcaaagag cttccagagg 270

<210> SEQ ID NO 127
<211> LENGTH: 1724
<212> TYPE: DNA
<213> ORGANISM: Artificial Sequence
<220> FEATURE:
<223> OTHER INFORMATION: Synthetic polynucleotide

<400> SEQUENCE: 127
ctctttctct tcctccagtt tccagtccag ccctgttggc tctcagaatg catcatcctt 60
ctccctgcag cgctctcact gaacatgctc aagcgcaagg aacttataat cttgtgttct 120
ctggattctg gatttagtaa tctgtattag tctgttctca cactgctaat aaagaaatac 180
ctgaggttgc ttccaagata gccaaatagg aacagctctg gtctgcagct cccagcaaga 240
tcgatgtaga agatgggtga tttctgcatt tccaactgag gtacctggtt catctcactg 300
ggactggttg gacagtgggt gcagcccatg gaaggtgagc tgaagcaagg tggggcgtca 360
cctcacccag gaagcacaag gggtcagggg atttaccttt cccagccaag ggaagccatg 420
acagactgta actggagaaa cggtacactc ctgaccaaat actgcacttt tcccacagtc 480
ttagcaactg gcagaccagg taatacccctc ccgtgcctgg ctcagtgggt tccatgccaa 540
cggagccttg ctcactgcta gcgcaacagt ctaagatcga cctgcgacgc tgcagcttga 600
tgcagggaga ggcatccaac attgctgagg cttgagtagc tcacagtgta agcaaagagg 660
cccggaagca caagttgggc agagctcatc gctgctcagc agggcctact gcctctatag 720
attccacctc tggaggcagg gcatggcaga aaaaaacgca gcagacagct tttgcagact 780
taaacgtccc tgtctgatgg ctctaaagag agcaatggtt ctctcagcat ggcattcgag 840
ctccaagaac agacagactg cctccccaag caggtccctg acccccatgt agctggactg 900
ggaaacacct ccccatcagg ggctgagaga tacctcaaac acgtgggtgc cctctggga 960 cgaagcttcc agaggaagga tcaggcagca atatttgcta ttctgcagcc tttgctggtg 1020
atacccaggc aaacagattc tggagtggac ctccagcaaa ctccaacaaa cctgcagctg 1080
aggggtctga ctgtgggaag gaaaactaac aaagagaaag caatagcatc aacatcaaca 1140
aaaaggacat ccacaccaaa tccccatcta taggtcacca acatcaaaga ccaaaggtag 1200
ataaaaccac aaagatgggg agagaaacca gagcagaaaa gctgaaaatt ccaaaaaaca 1260
agcacctctt ctcctccaaa ggatcgcagc tccttgccag caagggaaca aaactagacg 1320
gagaatgagt ttgacaagtt gacagaagta ggcttcagaa ggttggtaat aacaaacttc 1380
tctgagctaa aggagcatct tctaacccat cgcaaagagg ctaaaaactg tggaaaaaaa 1440
aaaggttaga tgaatggcta actagaataa ccagtgtaga gaagacctca aatgacctga 1500
tgaagctgaa acccacagca caagaacttc gagactcatg cacaagcttc aatagccgat 1560
tcgatcaagt ggaagaaagg atatcagtga ttgaagatca aattaatgaa ataaagtgag 1620
aagaatgagt tacatctgct aacatgctta ttttcattct tccttcatct ctttatttaa 1680
aaatcacaga ccaggatgga gataaaggaa ctcaaagaat ttgg 1724

<210> SEQ ID NO 128
<211> LENGTH: 295
<212> TYPE: DNA
<213> ORGANISM: Artificial Sequence
<220> FEATURE:
<223> OTHER INFORMATION: Synthetic polynucleotide

<400> SEQUENCE: 128
aaactgggca catttgggcc cctgcgctgc caggaggcat gggccctgga gcggctgctg 60
cgggaagccc gagtactgga ggcagtatgc gagttcagca ggcggtggga gatcccggcc 120
agctctgccc aggaagtgtg tgtgaagttc ctggaggatg ccctggggca gaagctgccc 180
agaaggcccc agccagggcc tggagagcag ctcacagtct tccagttctg gagttttgtg 240
gaaaccttgg acagccccac catggaggcc tacgtgactg agaccgctga ggagg 295

<210> SEQ ID NO 129
<211> LENGTH: 303
<212> TYPE: DNA

<213> ORGANISM: Artificial Sequence
<220> FEATURE:
<223> OTHER INFORMATION: Synthetic polynucleotide

<400> SEQUENCE: 129
taatggaaac ttggaattag cagtggcttt ccttactgcg aagaatgcta agacccctca 60
gcaggaggag acaacttact accaaacagc acttcctggc aatgatagat acatcagtgt 120
gggaagccaa gcagatacaa agttcttgaa gccagcatag cagagaataa agcatgtttg 180
aagaggacac ctacagaagt ttggagggat tctcgaaacc cttatgatag aaaaagacag 240
gacaaagctc ccgttgggct aaagaatgtt ggcaatactt gttggtttag tgctgttatt 300
cag 303

<210> SEQ ID NO 130
<211> LENGTH: 204
<212> TYPE: DNA
<213> ORGANISM: Artificial Sequence
<220> FEATURE:
<223> OTHER INFORMATION: Synthetic polynucleotide

<400> SEQUENCE: 130
aaccggatgc tacgggtgat gactgggagg aggagaaaaa ttacctcttt atcttgcatg 60
aacatcttaa ttttcaggac cagaggagcg agagcagcaa gaaccacacc cagcagcaat 120
gtcagcggaa gtggaaacct cagagggggt agacgagtca gaaaaaaaga actctggggc 180
cctagaaaag gagaaccaaa tgag 204

<210> SEQ ID NO 131
<211> LENGTH: 441
<212> TYPE: DNA
<213> ORGANISM: Artificial Sequence
<220> FEATURE:
<223> OTHER INFORMATION: Synthetic polynucleotide

<400> SEQUENCE: 131
gggttgtgta taattacagt gcacatggtg tccagcgaga cggagaaggg tgggaagaga 60
gcataagcat cccattactg cagcccaaca tgtatggaat gatggagcaa tgggacaagt 120
acctggaaga cttctccacc tcgggggcct ggctgcctca caggtataat gaggaaaagg 180
aagtctccgg aaacctcccc tagcattcca ggaggcgaaa gctatgcact gcgcagaggc 240
tgggaaggct ttaattaaat tcaaccactg tgagaaatac atctacagct tcagtgtgcc 300
ccagtgctgc cctctctgcc agcaggacct gggctcgagg aagctggagg acgcacctgt 360
tagcatcgct aatccattta ctaatggaca tcaagaaaaa tgttcattcc tcctcagacc 420
aactcagggg acatttctta g 441

<210> SEQ ID NO 132
<211> LENGTH: 152
<212> TYPE: DNA
<213> ORGANISM: Artificial Sequence
<220> FEATURE:
<223> OTHER INFORMATION: Synthetic polynucleotide

<400> SEQUENCE: 132
gtaaacaaat tgctcctgtg gagatgattg gcatcacatg gtgttttgag ctgatacacc 60
caacacttga gctcactgca acagtaccag atactgtgtt gaccagtggt catgccactg 120
cctgttgatt tgttgaaaat attgtttaca cg 152

<210> SEQ ID NO 133
<211> LENGTH: 718
<212> TYPE: DNA
<213> ORGANISM: Artificial Sequence
<220> FEATURE:
<223> OTHER INFORMATION: Synthetic polynucleotide

<400> SEQUENCE: 133
ttttaattga taaagaccag agtccaaaat ggaaaccagc tgatctaaaa gaagttactg 60
aggaagattt gaataatcac tttaagtctt tgggaagcag tgatttgaaa ttttgaggtg 120
acaggctttt aaggtatatt ttgtagcatg ggttggcaat ctacagcatg tgggccaaat 180
ccagcctgct gcctgttttt atataccctg taagctaaga atggtttccg catttttaaa 240
tggttgggaa aagaaatcaa agactaataa ttcatgacgt gaaaattatc agaattcaca 300
aataaagctt tattggaact agctatactc atctgtttat atattatctg tggctgcttt 360
gaaatgagta gttgcaatag agatggtaaa gcctacaaag cctaattatt tactgtctgg 420
tttttgtcag aaaaaagttt gtcaatcctt gttttagaag atggaaaaat gtgaagatct 480
ttggagattc tcttgagtgg tatatctaat tgaaatggga tcttcgtttg gcttgtatgt 540
tgatgaaatc aacttaggta tacaatataa aaaataaaga ccctgaaaat tgttttgggt 600
aattaataaa atgtctccaa catctctaaa gatcacacta aggcaactca tggaggggtc 660
ttcaaagacc ttgcaagaag tactaactat ggagtatcgg ctaagtcaag cttgtatg 718

<210> SEQ ID NO 134
<211> LENGTH: 233
<212> TYPE: DNA
<213> ORGANISM: Artificial Sequence
<220> FEATURE:
<223> OTHER INFORMATION: Synthetic polynucleotide

<400> SEQUENCE: 134
cgcgcggcac tggtcctggt ggtcctcctc atcgccgggg gtctcttcat gttcacctac 60
aagtccacac agttcaacgt ggagggcttc gccttggtgc tgggggcctc gttcatcggt 120
ggcattcgct ggaccctcac ccagatgctc ctgcagaagg ctgaactcgc tctggcgacg 180
gcgcttgacg tgggcttgtc caactggagc ttcctgtatg tcaccgtctc gct 233

<210> SEQ ID NO 135
<211> LENGTH: 583
<212> TYPE: DNA
<213> ORGANISM: Artificial Sequence
<220> FEATURE:
<223> OTHER INFORMATION: Synthetic polynucleotide

<400> SEQUENCE: 135
ggatctgtga acaagaggaa cctcagcagc caggacaggc aggagcagtg gaatagctac 60
tatggcttct ggaatcctgg ttaatgtaaa ggaggaggtg acctgcccca tctgcctgga 120
actcctgaca caacccctga gcctggactg cggccacagc ttctgccaag catgcctcac 180
tgcaaaccac aagaagtcca tgctagacaa aggagagagt agctgccctg tgtgccggat 240
cagttaccag cctgagaaca tacggcctaa tcggcatgta gccaacatag tggagaagct 300
cagggaggtc aagttgagcc cagaggggca gaaagttgat cattgtgcac gccatggaga 360
gaaacttcta ctcttctgtc aggaggacgg gaaggtcatt tgctggcttt gtgagcggtc 420
tcaggagcac cgtggtcacc acacgttcct cacagaggag gttgcccggg agtaccaaca 480
ggtctaaggc ccgcctgttc tgtgccgtga cctgtgctac cgaagtcatc tgttgctgta 540

-continued

```
gggaggccag ggactcagcc gatgcctcaa tggccaactg cag                  583


<210> SEQ ID NO 136
<211> LENGTH: 471
<212> TYPE: DNA
<213> ORGANISM: Artificial Sequence
<220> FEATURE:
<223> OTHER INFORMATION: Synthetic polynucleotide

<400> SEQUENCE: 136

tcctcgcctc catcacctcc accgtagttg agccagcgat agtactgaga gtagggaaag     60

agcctccggt aataaagttt aagcagctcg ggcagctcgg tggggtcaaa cgtctccatt    120

gagcgcggaa ctcgccacga gaaggaagca ccctcactat gtggctctac ctggcggcct    180

tcgtgggcct gtactacctt ctgcactggt accgggagag gcaggtggtg agccacctcc    240

aagacaagta tgtctttatc acgggctgtg actcgggctt tgggaacctg ctggccagac    300

agctggatgc acgaggcttg agagtgctgg ctgcgtgtct gacggagaag ggggccgagc    360

agctgagggg ccagacgtct gacaggctgg agacggtgac cctggatgtt accaagatgg    420

agagcatcgc tgcagctact cagtgggtga aggagcatgt gggggacaga g             471
```